US008361998B2

(12) United States Patent
Boström et al.

(10) Patent No.: US 8,361,998 B2
(45) Date of Patent: Jan. 29, 2013

(54) COMPOUNDS AND THEIR USE AS IKACH BLOCKERS

(75) Inventors: Jonas Boström, Mölndal (SE); Hans Emtenäs, Mölndal (SE); Kenneth Granberg, Mölndal (SE); Mickael Mogemark, Mölndal (SE); Antonio Llinas, Mölndal (SE)

(73) Assignee: AstraZeneca AB, Sodertalje ( * ) Notice: Subject to any disclaimer, the term of this patent is extended or adjusted under 35 U.S.C. 154(b) by 0 days.

(21) Appl. No.: 13/306,499

(22) Filed: Nov. 29, 2011

(65) Prior Publication Data
US 2012/0142659 A1 Jun. 7, 2012

Related U.S. Application Data

(60) Provisional application No. 61/417,996, filed on Nov. 30, 2010.

(51) Int. Cl.
A61K 31/397 (2006.01)
C07D 205/04 (2006.01)
(52) U.S. Cl. .................. 514/210.01; 548/950
(58) Field of Classification Search ............. 514/210.01; 548/950
See application file for complete search history.

(56) References Cited

U.S. PATENT DOCUMENTS
3,663,566 A   5/1972   Mauvernay et al.

FOREIGN PATENT DOCUMENTS
| DE | 2643252 | 3/1977 |
| EP | 0254545 | 10/1993 |
| WO | 2004011430 | 2/2004 |
| WO | 2006063722 | 6/2006 |
| WO | 2006073967 | 7/2006 |

OTHER PUBLICATIONS

Banitt et al, "Antiarrhythmics. N-(Aminoalkylene) trifluoroethoxyben zamides and N (aminoalkylene) trifluoroethoxynaphth-amides", Journal of Medicinal Chemistry, (1975), 18(11), 1130-4. ISSN: 0033-2623.
Cha TJ et al, "Kir3-based inward rectifier potassium current: potential role in atrial tachycardia remodeling effects on atrial repolarization and arrhythmias," Circulation (2006); 113:1730-1737.
Chiou CW et al, "Selective vagal denervation of the atria eliminates heart rate variability and baroreflex sensitivity while preserving ventricular innervation," Circulation (1997); 95:2573-2584.
Dobrev D et al, "The G protein-gated potassium current IKaCh is constitutively active in patients with chronic atrial fibrillation," Circulation (2005); 112:3697-3706.
Dobrzynsk H et al, "Distribution of the muscarinic K+ channel proteins Kir3.1 and Kir3.4 in the ventricle, atrium, and sinoatrial node of heart," J. Histochem. Cytochem. (2001); 49:1221-1234.
Ehrlich, J., "Inward rectifier potassium currents as a target for atrial fibrillation therapy," Cardiovasc Pharmacol. (2008), 52(2), 129-135.
Estes NA et al, "ACC/AHA/Physician consortium 2008 clinical performance measures for adults with nonvalvular atrial fibrillation or atrial flutter," J. Am. Coll. Cardiol. (2008); 51:865-884.
Fang MC et al, "Comparision of risk stratification schemes to predict thromboembolism in people with nonvalvular atrial fibrillation," J. Am. Coll. Cardiol. (2008); 51:810-815.
Galenko-Yaroshevskii et al, "Effect of befol and sufan on neurogenic atrial fibrillation," Bulletin of Exp. Biol. and Med., No. 4, 1998, Pharmacology and Toxicology, p. 355-357.
Grant AO, "Cardiac ion channels," Circ. Arrhythmia Electrophysiol. 2009; 2:185-194.
Krapivinsky G et al, "The G-protein-gated atrial K+ channel Ikach is a heteromultimer of two inwardly rectifying K+-channel proteins," Nature (1995); 374:135-141.
Li et al, "Antiarrhythmic drug therapy for atrial fibrillation: focus on atrial selectivity and safety," Cardiovascular & Hematological Agents in Medicinal Chemistry (2009), 7(1), 64-75.
Markides V et al, "Atrial fibrillation: classification, pathophysiology, mechanisms and drug treatment," Heart 2003; 89:939-943).
Poppe et al, "New aminocarboxamides with class III anti-arrhythmic activity", Archiv der Pharmazie (Weinheim, Germany) (1999), 332(7), 233-242. ISSN: 0365-6233.
Redfern WS et al, "Relationships between preclinical cardiac electrophysiology, clincal QT interval prolongation and torsade de pointes for a broad range of drugs: evidence for a provisional safety margin in drug development," Cardiovasc. Res. (2003); 58:32-45.
Schram G et al, Differential distribution of cardiac ion channel expression as a basis for regional specialization in electrical function, Circ. Res. (2002); 90:939-50.
Singh NN et al, Br. J. Pharmacol. (1970); 39:675-689. Tamargo et al., "Pharmacology of cardiac potassium channels," Cardiovascular Research (2004), 62, 9-33.
Thrall G et al, "Quality of life in patients with atrial fibrillation: a systematic review," Am. J. Med. (2006); 119:448e1-448e19.
Viswanathan et al., "Pharmacological therapy for atrial fibrillation: current options and new agents," Expert Opin. Investig. Drugs (2009) 18(4), 417-431.
Waldo et al, "Mechanisms of cardiac arrhythmias," Lancet (1993); 341:1189-1193.
Wang Z et al, "Sustained depolarization-induced outward current in human atrial myocytes . . . " Circ. Res. (1993); 73:1061-1076.

(Continued)

Primary Examiner — Rebecca Anderson
Assistant Examiner — Samantha Shterengarts
(74) Attorney, Agent, or Firm — David Gryte

(57) ABSTRACT

The invention relates to compounds according to Formula I:

Formula I

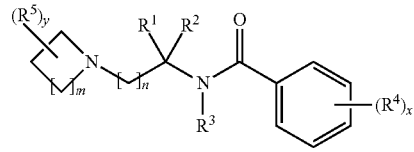

or a pharmaceutically acceptable salt thereof, wherein m, n, $R_1$, $R_2$, $R_3$, $R_4$, $R_5$, x and y are as defined herein. Compounds according to Formula I are pharmacologically effective as potassium channel inhibitors, in particular inhibitors of the acetylcholine operated inward rectifying potassium channel current (i.e. IKACh blockers), and are believed to be useful in the treatment of cardiac arrhythmias, in particular supraventricular tacharrhythmias, such as atrial fibrillation and atrial flutter.

7 Claims, 10 Drawing Sheets

OTHER PUBLICATIONS

Yung et al, "Potential antiarrhythmic agents. III. 4-Amino-N-[2-(substituted amino)ethyl]-2,6-dimethylbenzamides", Journal of Pharmaceutical Sciences (1972), 61(12), 1953-1956.ISSN: 0022-3549.

CASRN: (no bibliographic data from CA), 1184780-05-9; 1184681-20-6; 1184608-46-5; 1184212-47-2; 1184076-50-3; 1184013-46-4; 1183560-78-2; 1183429-13-1; 1183299-00-4; 1183247-54-2; 1183000-80-7; 1182764-19-7; 1182758-77-5; 1179946-23-6; 1179794-98-9; 1179306-12-7; 1179033-01-2; 1178826-29-3; 1178702-95-8; 1178642-86-8; 1178467-31-6; 1178356-44-9; 1178286-26-4; 1178182-93-8; 439215-16-4, 2012.

International Search Report issued for PCT/SE2011/051440 on Feb. 3, 2012.

COMPOUNDS AND THEIR USE AS IKACH BLOCKERS

CROSS-REFERENCE TO RELATED PATENT APPLICATION

This patent claims priority under 35 U.S.C. 119(e) to U.S. Provisional Patent Application No. 61/417,996 (filed 30 Nov. 2010). The entire text of the above patent application is incorporated by reference into this patent.

TECHNICAL FIELD

The present invention relates to a novel class of compounds which are pharmacologically effective as potassium channel inhibitors, in particular inhibitors of the acetylcholine operated inward rectifying potassium channel current, i.e. IKACh blockers.

The invention also relates to processes for preparing such compounds, to pharmaceutical compositions containing them, to the use of such compounds and to methods for their therapeutic use, particularly in the treatment of cardiac arrhythmias.

BACKGROUND

The normal electrophysiologic behaviour of the heart is determined by ordered propagation of excitatory stimuli that result in rapid depolarization of the cardiac cell, followed by a slower repolarization. The sum of these events creates the cardiac action potential in individual myocytes. Cardiac rhythm disturbances can be caused by abnormalities of impulse generation, propagation or the duration and configuration of such individual cardiac action potentials. The action potentials are generated by the integrated activity of specific ion currents through various transmembrane spanning ion channels with specific selectivity for individual ions (e.g. potassium, sodium, calcium, see Grant A O. Circ. Arrhythmia Electrophysiol. 2009; 2:185-194). The majority of these ion channels have been cloned and thus, their molecular components are known. This knowledge has enabled a more effective search for selective ion channel blockers, as specific ion channel targets can be recombinantly over-expressed in mammalian cells and be used for high capacity screening.

Electrophysiological studies in the early 1950s showed the importance of the movement of $K^+$ out of the cell to produce repolarization after the rapid depolarizing spike. Over the last 60 years, the introduction of single channel recording techniques and molecular cloning has resulted in a deeper understanding of cardiac repolarization and of the different potassium channels involved. Potassium channels are divided into:
 a. Voltage gated channels ($K_V$ 1-9)
 b. Calcium activated channels ($K_{Ca}$)
 c. Inward rectifier channels ($K_{ir}$ 1-6)
 d. Tandem pore domain channels (TWIK, TREK, TASK, TRAAK)

The pharmacology of cardiac potassium channels is disclosed in Tamargo et al., Cardiovascular Research (2004), 62, 9-33.

The expression of all these channels differs in various part of the cardiac muscle. Some channels are rather homogenously expressed, whereas some channels have a more chamber specific expression. Thus, the ultra rapid delayed rectifier ($K_V$1.5) and the acetylcholine operated inward rectifier ($K_{ir}$3.1/$K_{ir}$3.4) are shown to be rather atrial selective in their expression (Wang Z et al. Circ. Res. (1993); 73:1061-1076 and Schram G et al. Circ. Res. (2002); 90:939-50).

Compounds that block outwardly directed repolarizing potassium current will prolong the cardiac action potential duration (APD). An increase of APD prolongs the is corresponding effective refractory period (ERP), the time period during which the cell can not be re-exited to generate a new action potential (the so-called Class III antiarrhythmic action, see Singh B N et al. Br. J. Pharmacol. (1970); 39:675-689). As a group, such Class III compounds prevent cardiac tachyarrhythmia, such as atrial fibrillation (AF) based on so-called re-entrant mechanisms. In the normal myocardium, pacemaker cells of the sinoatrial node initiate the cardiac impulse. The cardiac impulse is then propagated to neighbouring excitable cells, and in this way depolarization spreads across the atria, through the atrioventricular node, and to the ventricles in a co-ordinated fashion. The impulse is unidirectional because of the refractoriness to depolarization of the preceding myocardial tissue. However, atrial re-entry circuits occur when the propagating impulse does not die out because it continues to encounter excitable atrial tissue, which it can depolarize. This occurs where there is an area of atrial refractory tissue encountered by the impulse that blocks its progress as a wave front. Following its circuit around this central area, the wave front may return to its point of origin after the ERP has finished and re-exited the atrial tissue, thereby forming a re-entrant circuit (Waldo A L. Lancet (1993); 341:1189-1193). Drugs that prolong the atrial ERP thus will minimize the risk for such re-excitation.

However, drugs that cause ERP prolongation by block of potassium current that exists in both atria and ventricle will prolong APD in both kind of myocardial tissue. Excessive APD prolongation in the ventricle or in the specialised conduction tissue, the so-called Purkinje Fibres, may increase the risk for a proarrhythmic event, i.e. the antiarrhythmic action is replaced by a situation in which arrhythmias may be created. A typical proarrhythmia caused by delay of ventricular repolarization is Torsades de pointes (TdP), which is a life threatening proarrhythmia, limiting the use of antiarrhythmic compounds of the Class III type. TdP is caused by so called early after depolarizations (EADs) defined as single or repetitive depolarizations originating from the AP plateau and which can propagate to and excite surrounding cardiac tissue. TdP is a life-threatening ventricular arrhythmia as it sometimes can transfer into ventricular fibrillation. Thus, the use of compounds which as antiarrhythmic mechanism delay cardiac repolarization in the ventricle, always carry a risk for such dangerous proarrhythmias and as a consequence, the development of several such compounds has been halted and some compounds which have is reached the market have been withdrawn (Redfern W S et al. Cardiovasc. Res. (2003); 58:32-45).

AF is the most common sustained cardiac arrhythmia and in 2008 10 million patients world-wide suffered from AF and this is estimated to grow to 13 million by 2020. The presence of AF is associated with a significant increase in the risk of adverse cardiovascular events and is an independent predictor of stroke and congestive heart failure (Estes N A et al. J. Am. Coll. Cardiol. (2008); 51:865-884; Fang M C et al. J. Am. Coll. Cardiol. (2008); 51:810-815). Moreover, patients quality of life is greatly reduced as a result of symptoms such as dizziness, palpitations, and reduced exercise capacity (Thrall G et al. Am. J. Med. (2006); 119:448e1-448e19).

The therapeutic goals in patients with AF are to reduce thromboembolic risk, to restore and maintain normal sinus rhythm and to control ventricular rate during AF. Thromboembolic risk is mostly reduced by anticoagulation therapy. Restoration and maintenance of sinus rhythm is obtained by using electrical or pharmacological cardioversion, or by ablation or surgery, followed by pharmacological control of sinus rhythm to prevent AF relapse. When AF is permanent and cardioversion is undoable, the arrhythmia has to be accepted and the main therapy is to control ventricular rate predominantly by drugs that delay AV nodal conduction, but also in some cases by AV nodal ablation and pacemaker implantation (Markides V et al. Heart 2003; 89:939-943).

Pharmacological therapy for atrial fibrillation is described in Expert Opin. Investig. Drugs (2009) 18 (4), 417-431. However, there is currently no optimal drug treatment for sinus rhythm maintenance available, and a novel compound with better efficacy for sinus rhythm maintenance and without limiting unacceptable ventricular side effects is urgently needed.

The parasympathetic nervous system acts through the vagus nerve to regulate the heart rate and the conduction properties of atrial, atrioventricular and ventricular tissue. In animal models, parasympathetic stimulation has been shown to predispose the atria to AF and attenuation of vagal effects has been shown to prevent AF induction (Chiou C W et al. Circulation (1997); 95:2573-2584). Parasympathetic effects to the heart are largely mediated through interaction with the acetylcholine operated inward rectifier channel (i.e. the KACh channel). The cardiac KACh channel is comprised of two homologous transmembrane spanning proteins—GIRK1 and GIRK 4 ($K_{ir}3.1$ and $K_{ir}3.4$) (Krapivinsky G et al. Nature (1995); 374:135-141), and both homomers are needed to build the functional channel. Increased activity of the KACh channel results in shortening of the atrial APD and ERP, thus favouring AF based on the re-entry mechanism. An interesting finding is that one of the pore forming homomers are prominently expressed in atrial muscle but are largely absent in ventricles (Dobyzynski H et al. J. Histochem. Cytochem. (2001); 49:1221-1234). This finding explain the fact that vagal stimulation in anaesthetized animals (dog, rabbit) causes substantial ERP shortening in the atria, whereas no such effects are noted in the ventricles, thus confirming the atrial selectivity of the KACh channel. Advantages of atrial selectivity in antiarrhythmic drug treatment of AF are discussed in Li et al., Cardiovascular & Hematological Agents in Medicinal Chemistry (2009), 7 (1), 64-75.

Another important finding is ionic remodelling induced by atrial pacing and induction of AF also results in increased constitutively active KACh channels by enhancing spontaneous channel openings, even in the absence of acetylcholine (Cha T J et al. Circulation (2006); 113:1730-1737). This finding also is shown in atrial muscle from AF patients (Dobra D et al. Circulation (2005); 112:3697-3706). Thus, block of IKACh will lead to atrial ERP prolongation in all AF patients, not only so in patients with AF of vagal origin. Ehrlich in J. Cardiovasc describes IKACh as a potential target for treatment of AF. Pharmacol. (2008), 52 (2), 129-135.

SUMMARY

It is an object of the present invention to provide novel compounds that are useful for the treatment (including prophylaxis) of diseases, disorders and/or conditions which is affected and/or mediated (fully or partially) by IKACh and where treatment by IKACh blockade is beneficial, in particular cardiac arrhythmias, and more specifically supraventricular tacharrhythmias, such as atrial fibrillation and atrial flutter; and therewith associated complications, such as congestive heart failure, ventricular fibrillation, and thromboembolic events.

According to a first aspect, the invention provides a compound of Formula I:

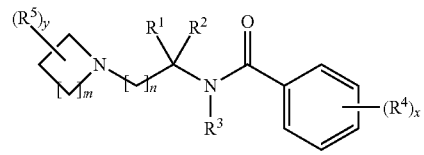

Formula I or a pharmaceutically acceptable salt thereof, wherein m, n, $R^1$, $R^2$, $R^3$, $R^4$, $R^5$, x and y, are as defined hereinafter.

It has been found that this group of compounds exhibit electrophysiological activity, in particular IKACh blocking activity. Thus, the compounds of the invention can be used as a medicament, and in particular the compounds are expected to be useful in the treatment of cardiac arrhythmias and therewith associated complications in a patient in need thereof (i.e. a person suffering from or susceptible to such a condition). The patient may be a human or non-human animal, in particular a human.

Compounds according to the invention are believed to be useful for restoration and maintenance of sinus rhythm, in particular maintenance of sinus rhythm. Compounds of the invention may have advantageous properties compared to compounds of the prior art, in particular enhanced potency, enhanced selectivity, and/or reduction of total clearance. These advantages may provide for corresponding useful properties in practice. For example, when used as pharmaceutical agents, compounds of the present invention may have a lower daily clinical dose, longer duration of action, and/or an improved side effect profile. In particular, the compounds according to the invention are atrial vs. ventricular selective inhibitors of the potassium channel function.

Compounds of the invention may also have the advantage that they may be more efficacious than, be less toxic than, have a broader range of activity than, be more potent than, be longer acting than, produce fewer side effects (including a lower incidence of proarrhythmias such as TdP and CNS effects) than, be more easily absorbed than, or that they may have other useful pharmacological properties than compounds known in the prior art.

According to a second aspect of the invention, there is provided a method of treating cardiac arrhythmias and/or cardiac diseases, disorders and/or conditions associated therewith by administering a therapeutically effective amount of a compound of the invention to a patient in need thereof.

According to a third aspect, there is provided a pharmaceutical composition comprising a compound of Formula I and a pharmaceutically acceptable carrier.

According to a fourth aspect of the invention, there is provided a process for preparing the compounds of the Formula I and salts thereof.

Other features and advantages of the present invention will become apparent from the following description of the invention.

DETAILED DESCRIPTION

Figure 1:
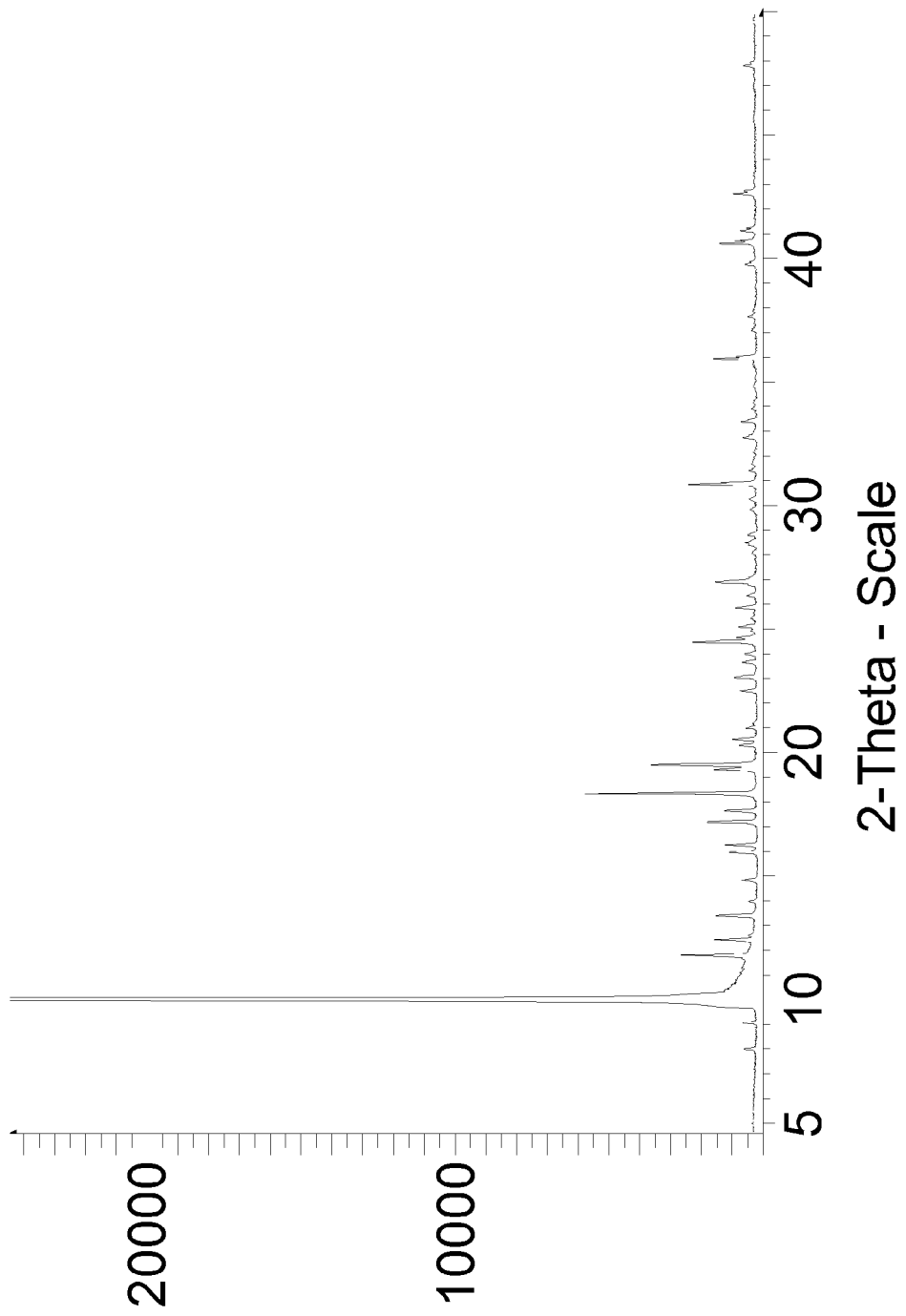
FIG. 1 shows the X-ray powder diffraction pattern for (S)-2-Chloro-4-fluoro-N-methyl-N-(3-methyl-1-(pyrrolidin-1-yl)butan-2-yl)benzamide (Example 1.17).
Figure 2:
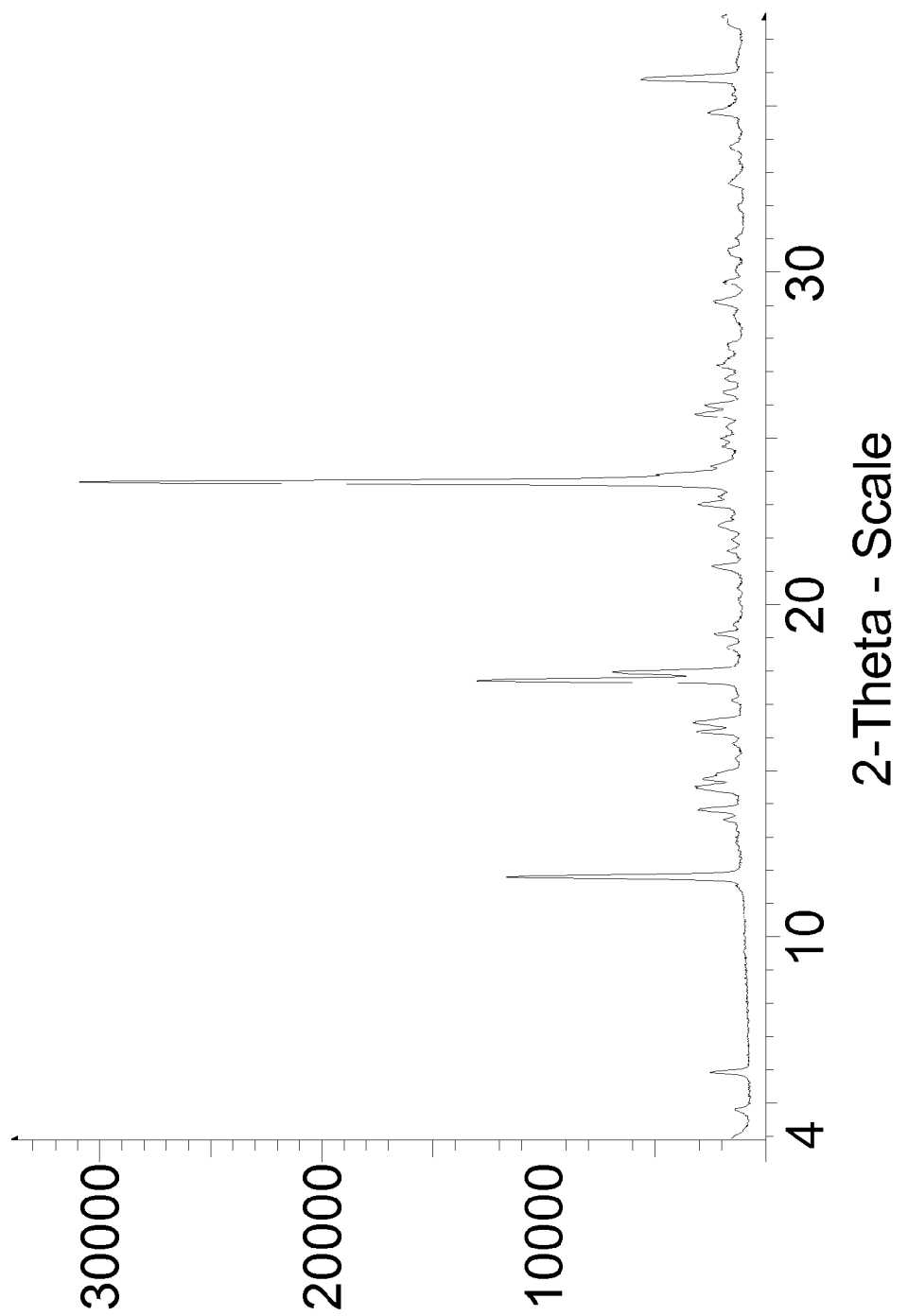
FIG. 2 shows the X-ray powder diffraction pattern for (S)-1-(2-(4-Bromo-N-methylbenzamido)-3-methylbutyl)azetidinium sulfate (Example 5.2B).
Figure 3:
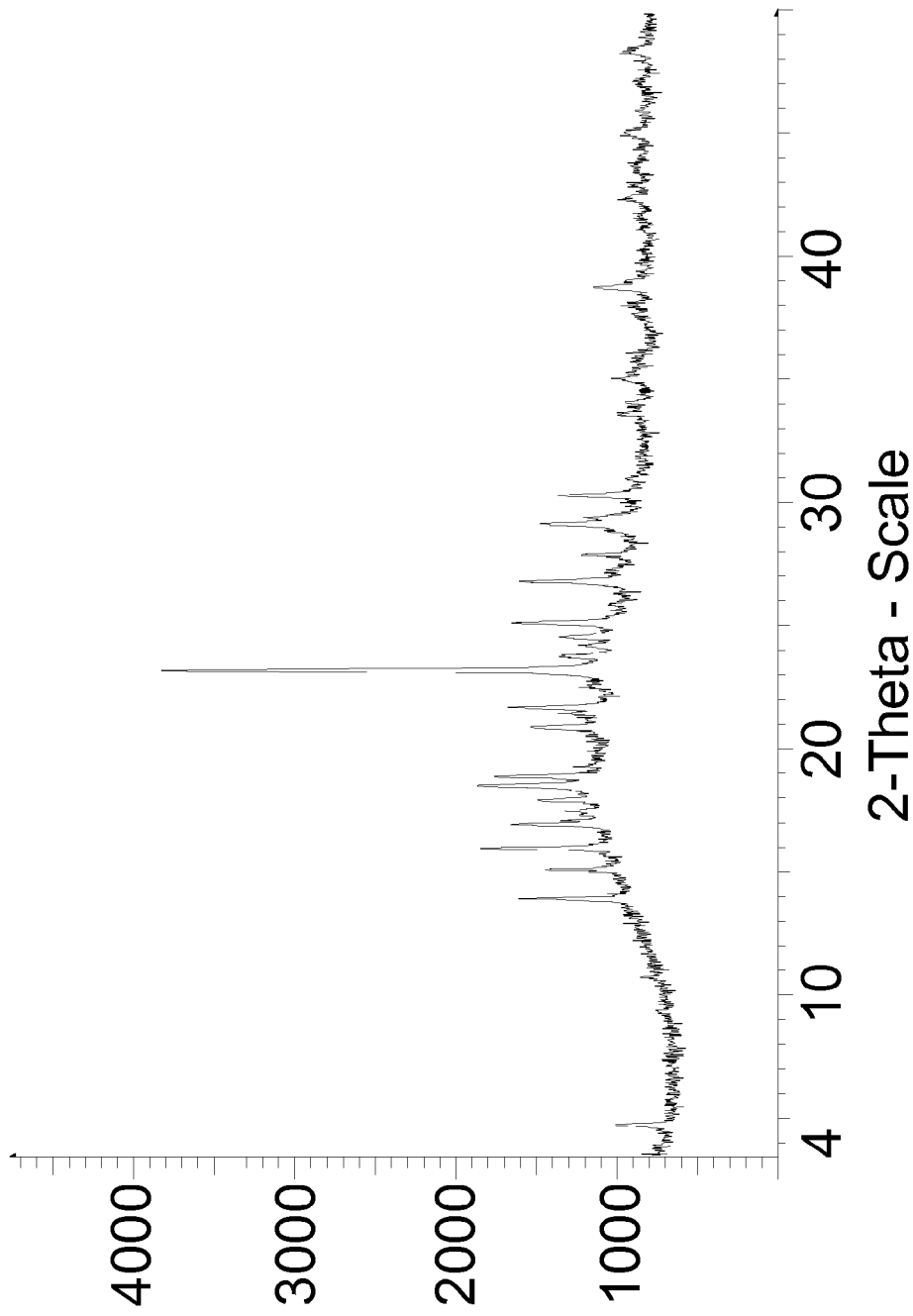
FIG. 3 shows the X-ray powder diffraction pattern for (S)-1-(2-(4-Bromo-N-methylbenzamido)-3-methylbutyl)azetidinium 2,3-dihydroxysuccinate (Example 5.2C).
Figure 4:
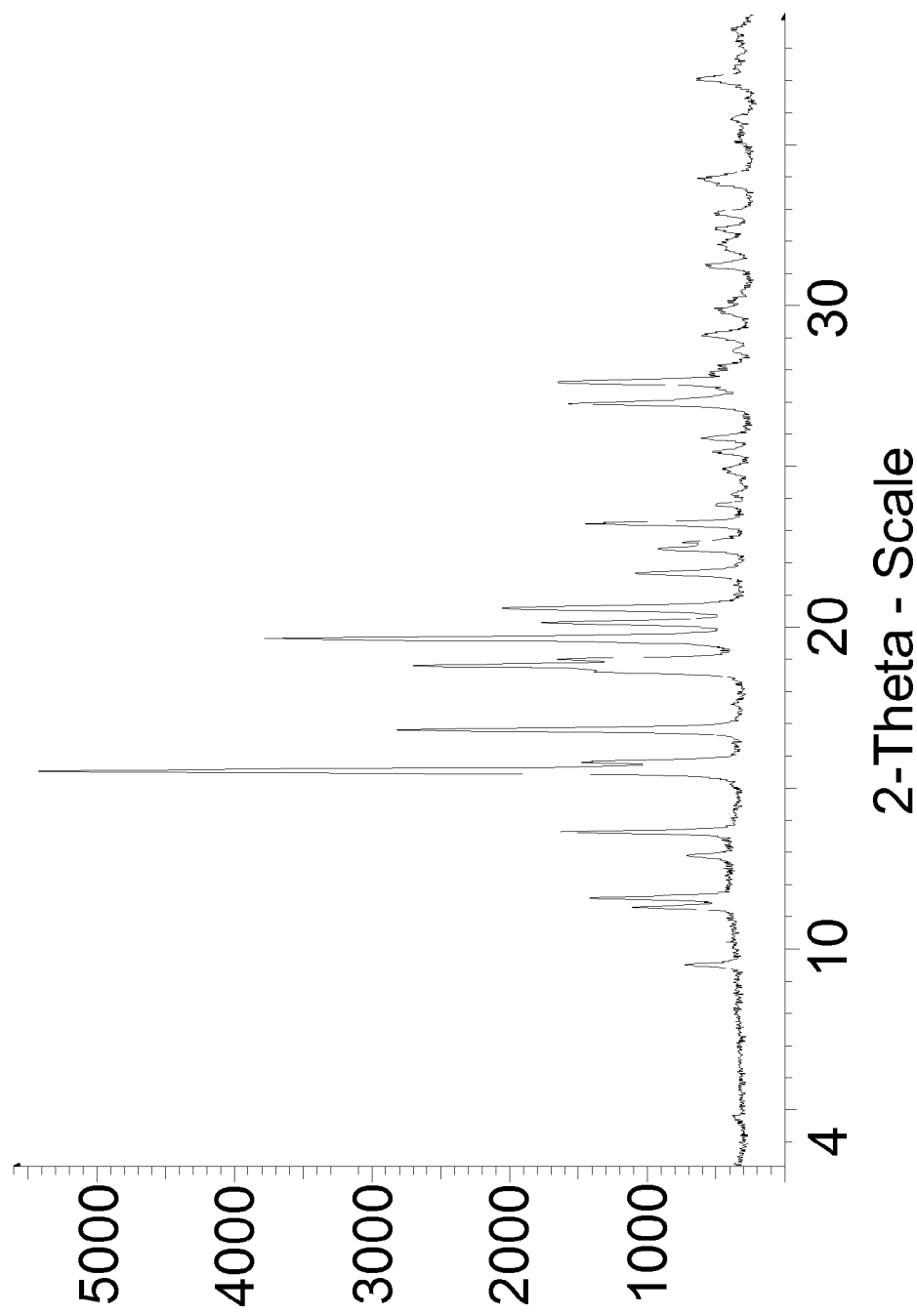
FIG. 4 shows the X-ray powder diffraction pattern for (S)-4-Fluoro-N-(1-(3-hydroxyazetidin-1-yl)-3-methylbutan-2-yl)-N,3-dimethylbenzamide (Example 6.1).
Figure 5:
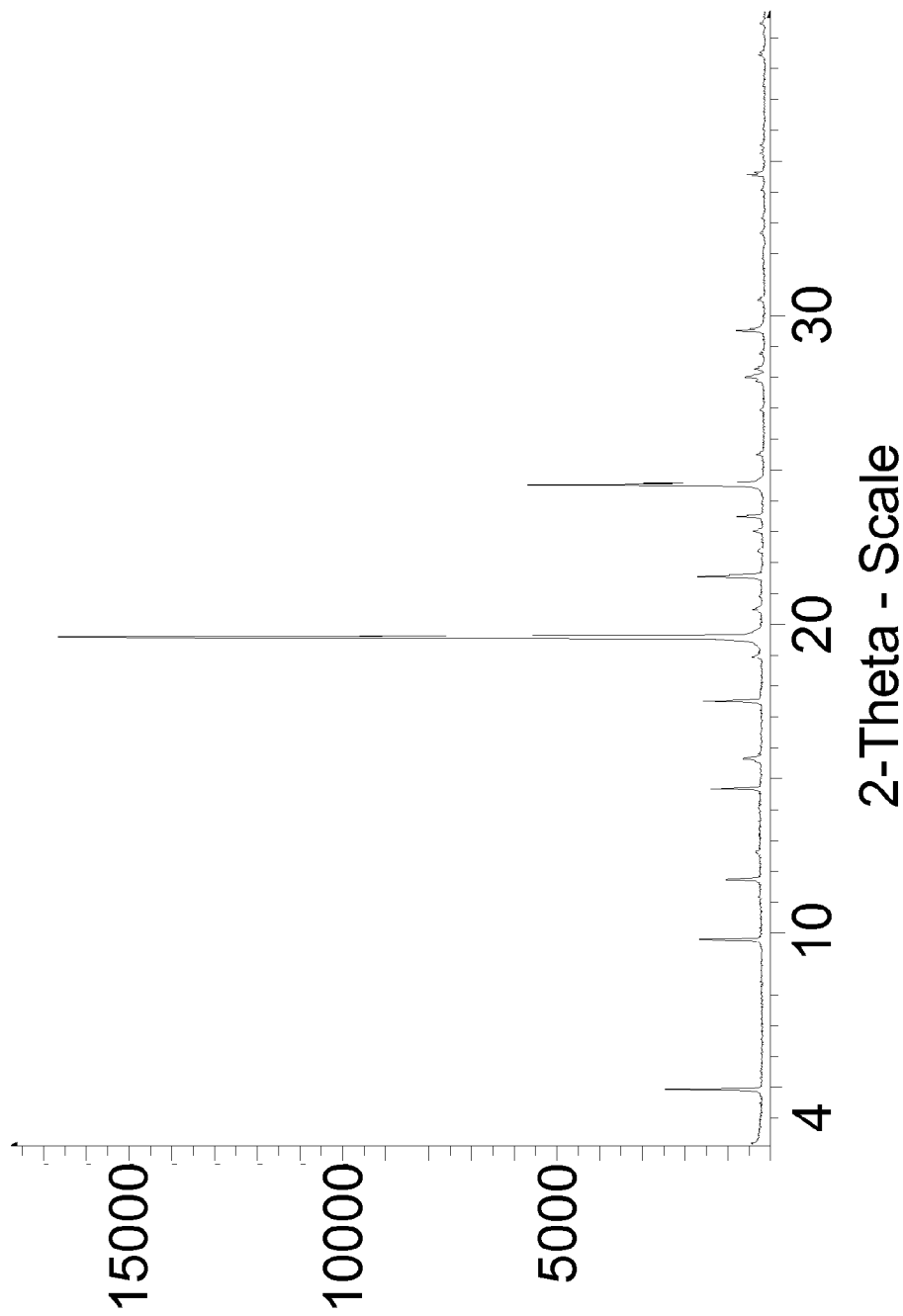
FIG. 5 shows the X-ray powder diffraction pattern for (S)-4-Chloro-N-(1-(3-hydroxyazetidin-1-yl)-3-methylbutan-2-yl)-N-methylbenzamide (Example 6.2).
Figure 6:
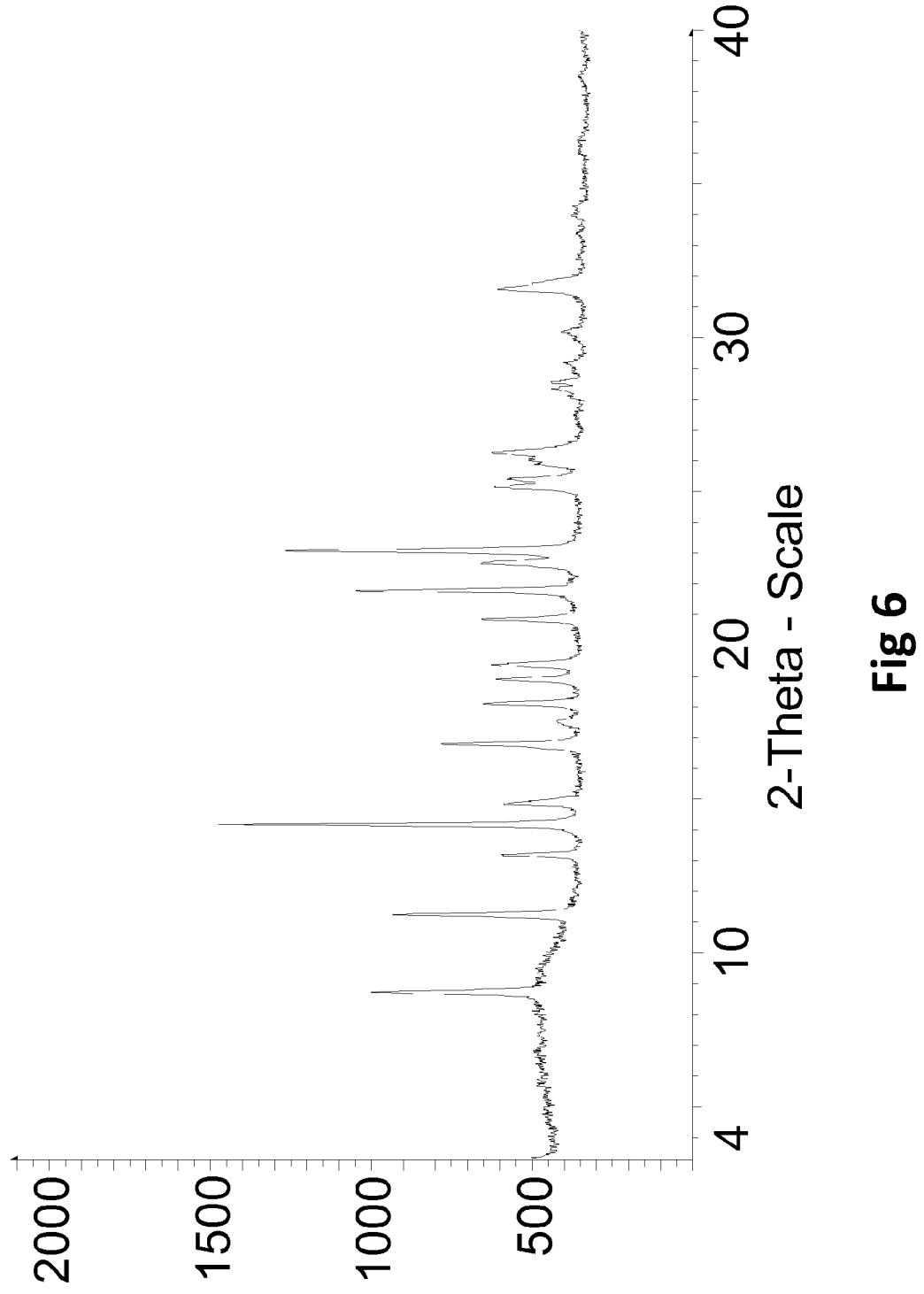
FIG. 6 shows the X-ray powder diffraction pattern for (S)-4-Chloro-N-(1-(3-hydroxyazetidin-1-yl)pentan-2-yl)-N-methylbenzamide hydrochloride (Example 8.2 B).
Figure 7:
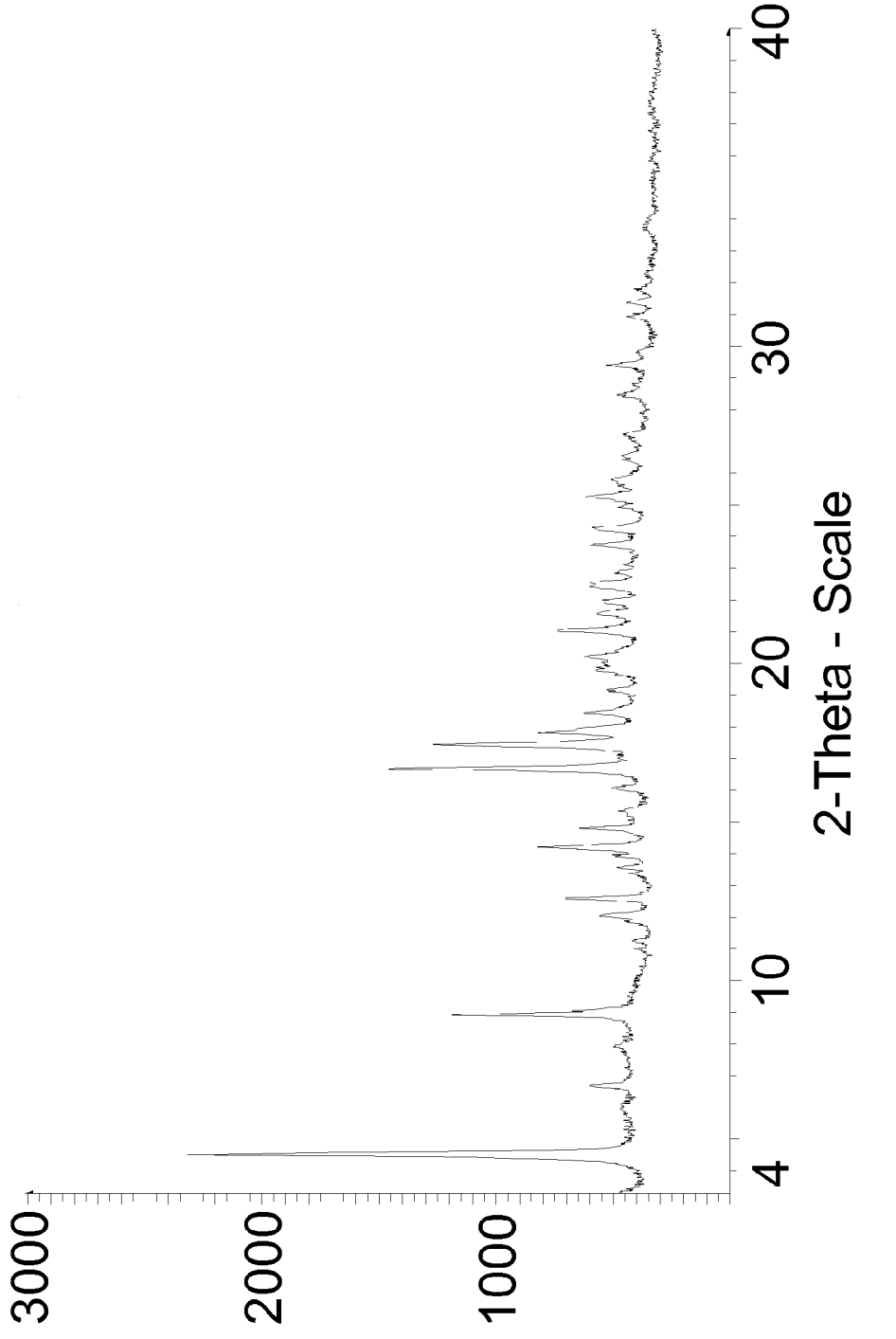
FIG. 7 shows the X-ray powder diffraction pattern for (S)-4-Chloro-N-(1-(3-hydroxyazetidin-1-yl)pentan-2-yl)-N-methylbenzamide tartrate (Example 8.2 C).
Figure 8:
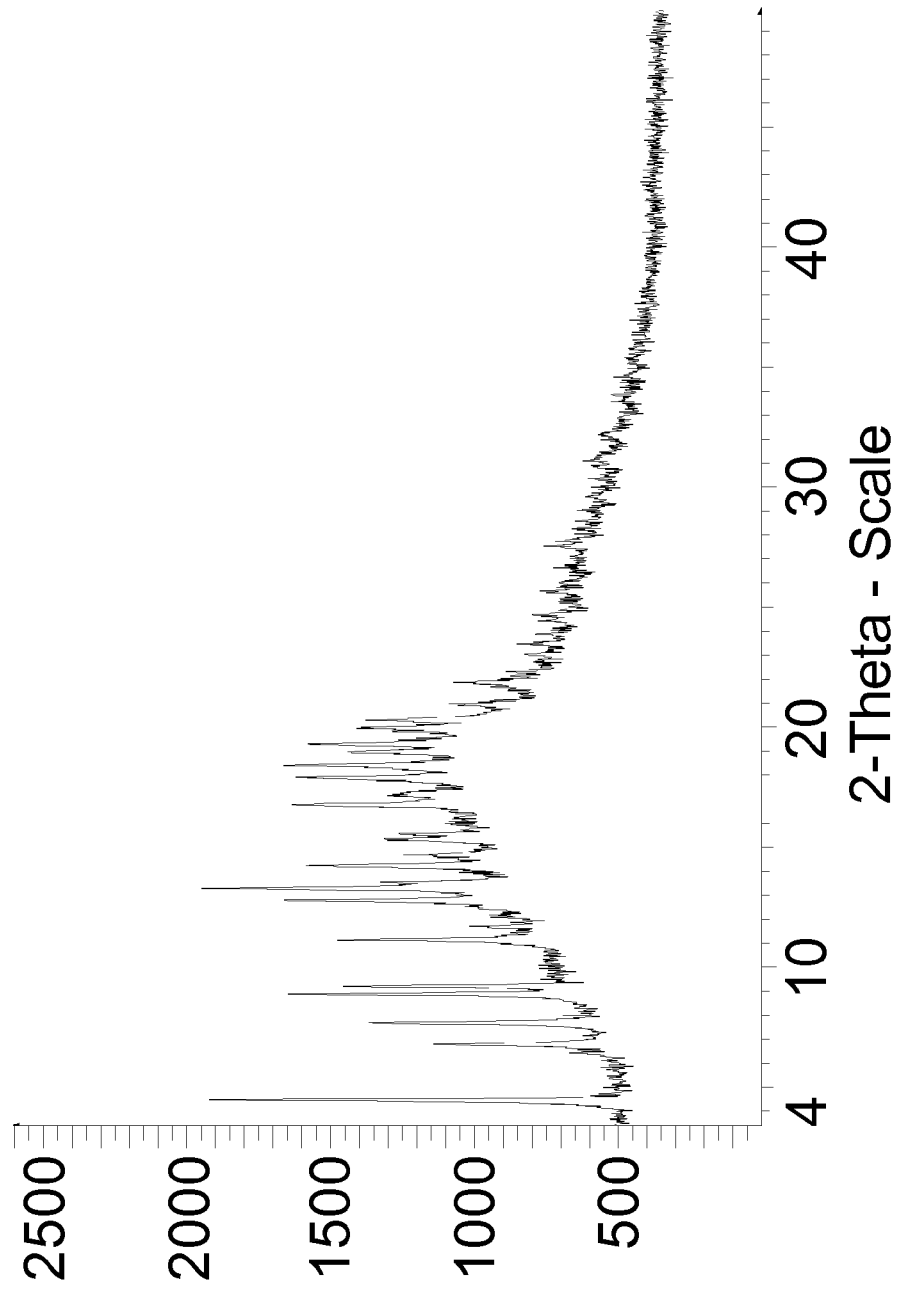
FIG. 8 shows the X-ray powder diffraction pattern for (S)-4-Fluoro-N,3-dimethyl-N-(3-methyl-1-(pyrrolidin-1-yl)butan-2-yl)benzamide-dihydroxysuccinate (Example 12.1).
Figure 9:
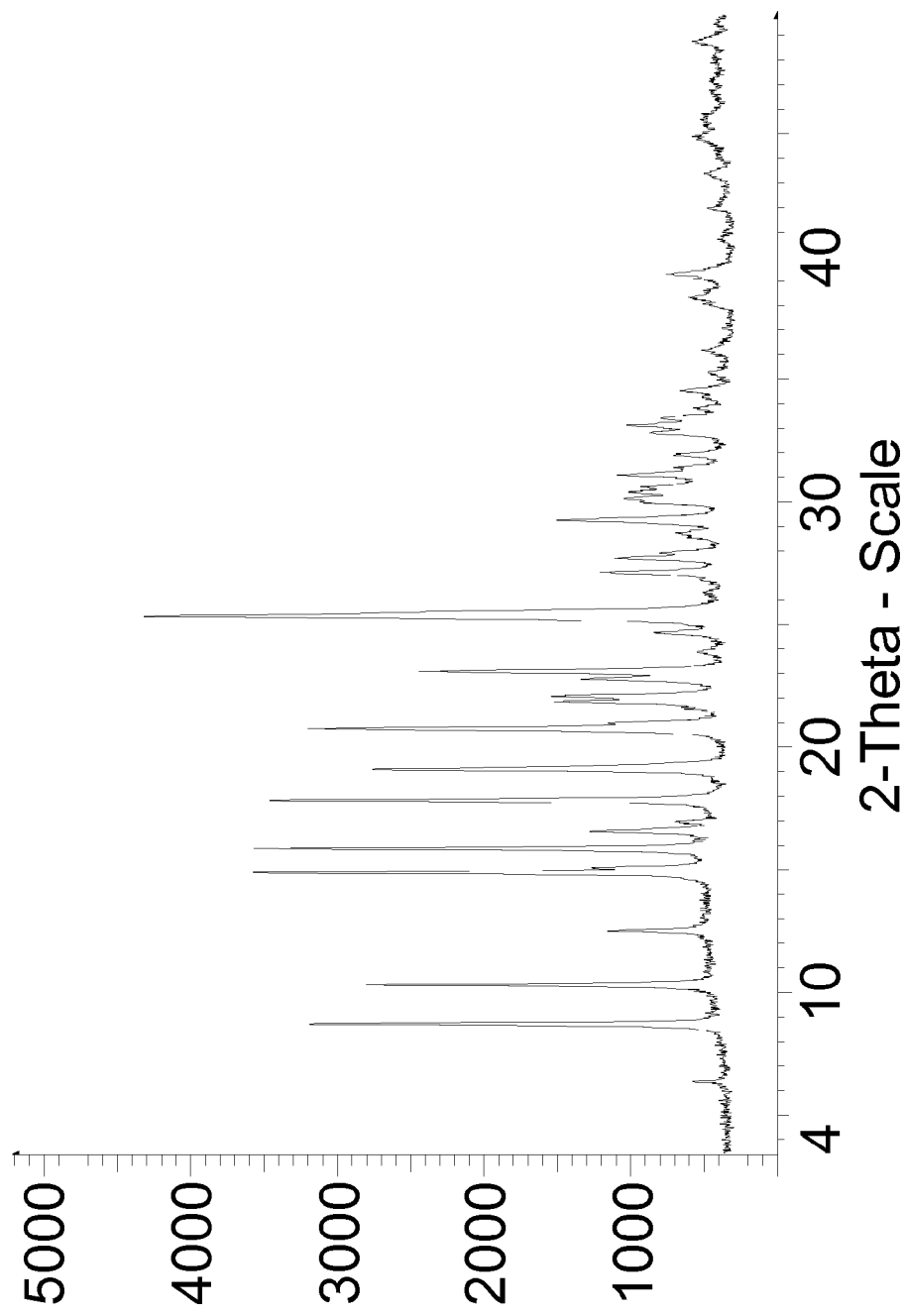
FIG. 9 shows the X-ray powder diffraction pattern for (S)-1-(2-(3-Chloro-4-fluoro-N-methylbenzamido)-3-methylbutyl)pyrrolidinium chloride (Example 16.55B).
Figure 10:
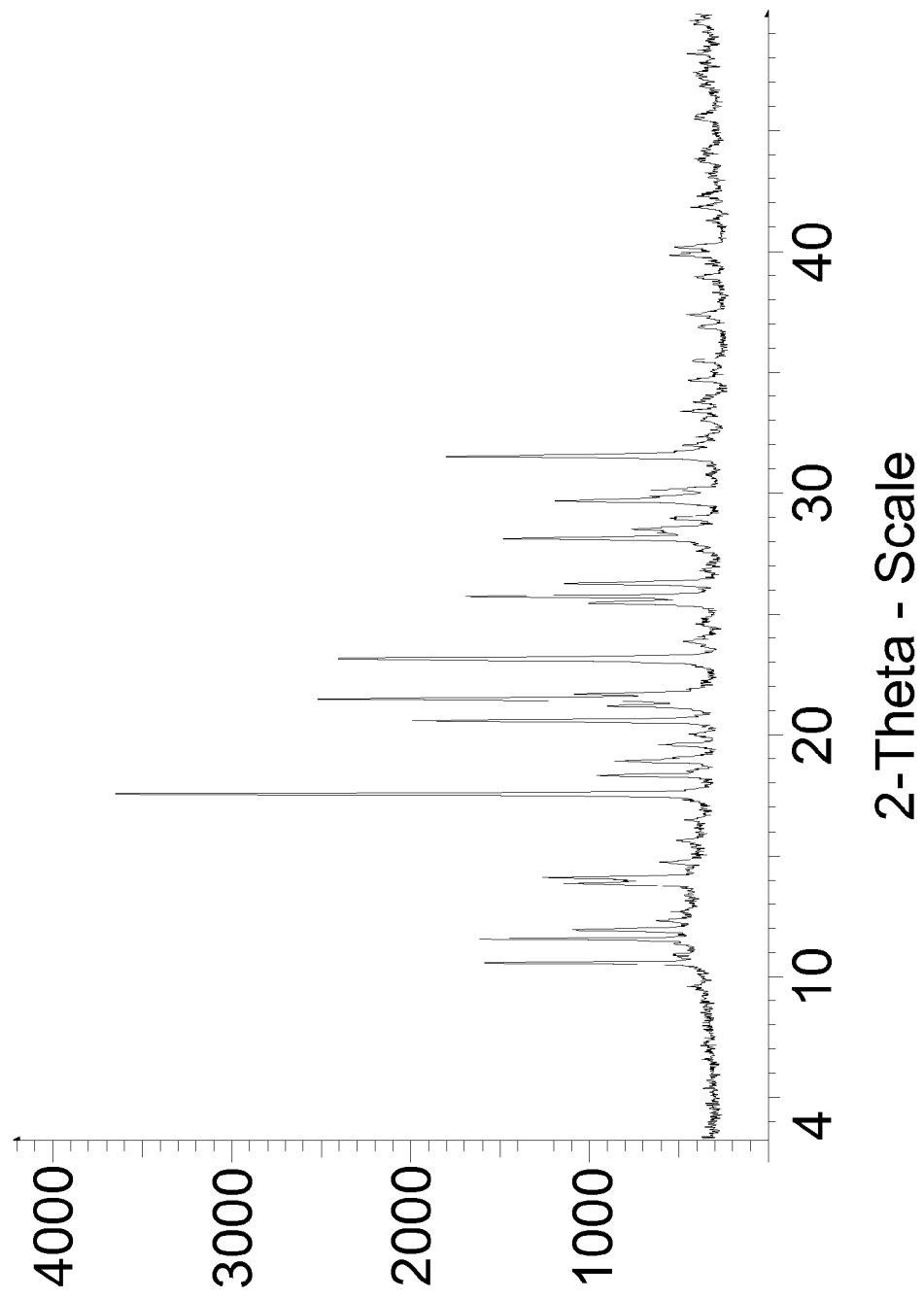
FIG. 10 shows the X-ray powder diffraction pattern for (S)-1-(2-(4-Chloro-N-methylbenzamido)-3-methylbutyl)pyrrolidinium chloride (Example 18).

The present invention relates to compounds of Formula I:

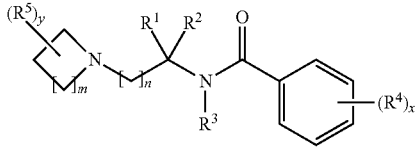

Formula I or a pharmaceutically acceptable salt thereof, wherein
each optional $R^5$ is independently selected from fluoro, nitrile, hydroxy, oxo, $C_{1-5}$ alkyl, $C_{3-5}$ cycloalkyl, $C_{1-5}$ alkoxy or $C_{1-5}$ alkoxyalkyl, wherein
  any alkyl, cycloalkyl or alkoxy group is substituted by 0, 1 or 2 substituents independently selected from fluoro, nitrile or hydroxy;
$R^1$ is selected from $C_{1-6}$ alkyl, $C_{3-6}$ cycloalkyl or $C_{1-6}$ alkoxyalkyl, wherein
  any alkyl, cycloalkyl or alkoxy group is substituted by 0, 1 or 2 substituents independently selected from fluoro or nitrile;
$R^2$ is selected from hydrogen or $C_{1-3}$ alkyl;
$R^3$ is selected from $C_{1-6}$ alkyl, $C_{3-6}$ cycloalkyl or $C_{1-6}$ alkoxyalkyl, wherein
  any alkyl or cycloalkyl group in these substituents is substituted by 0, 1 or 2 substituents independently selected from fluoro, nitrile or hydroxy;
each optional $R^4$ is independently selected from halo, nitrile, hydroxy, $C_{1-3}$ alkyl, $C_{1-3}$ alkoxy, $C_{1-3}$ alkoxyalkyl or $C_{1-3}$ alkylsulfide, wherein
  any alkyl or alkoxy group in these substituents is substituted by 0, 1, 2 or 3 substituents independently selected from halo, nitrile or hydroxy;

m is selected from 1, 2 or 3 (thus forming azetidinyl, pyrrolidinyl or piperidinyl);

n is selected from 1 or 2;

x is selected from 0, 1, 2, or 3; and y is selected from 0, 1, 2 or 3.

It may be noted that, as known to persons skilled in the art, an aliphatic carbon atom adjacent to a nitrogen atom, a sulphur atom or an oxygen atom is in general preferably not substituted with a hydroxy due to the potential chemical instability of such compounds.

Different isomers may have different biological activity. It may be the case that different compounds of Formula I may show the highest biological activity with different configurations.

In a particular embodiment of the invention, the compounds are represented by Formula Ia, or a pharmaceutically acceptable salt thereof, wherein m, n, $R^1$, $R^2$, $R^3$, $R^4$, $R_5$, x and y, are as defined above.

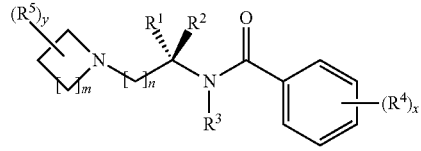

Formula Ia

In an embodiment of the invention, the compounds are represented by Formula I, or a pharmaceutically acceptable salt thereof, wherein y is 0, 1 or 2, and each $R^5$ is independently selected from fluoro, nitrile, hydroxy, $C_{1-5}$ alkyl, $C_{3-5}$ cycloalkyl, $C_{1-5}$ alkoxy or $C_{1-5}$ alkoxyalkyl, wherein
  any alkyl, cycloalkyl or alkoxy group is substituted by 0, 1 or 2 substituents independently selected from fluoro, nitrile or hydroxy, It shall be noted that $R^5$ may be linked to any of the ring carbon atoms of the N-containing heterocyclyl of Formula I, i.e. the azetidinyl, pyrrolidinyl or piperidinyl of Formula I. Moreover, two $R^5$ (same or different) may also be linked to the same ring carbon atom.

In a particular embodiment of the invention, the compounds are represented by Formula I, or a pharmaceutically acceptable salt thereof, wherein y is 0, 1 or 2, and each $R^5$ is independently selected from fluoro, nitrile, hydroxy, (unsubstituted) $C_{1-3}$ alkyl, (unsubstituted) cyclopropyl, (unsubstituted) $C_{1-3}$ alkoxy or (unsubstituted) $C_{1-3}$ alkoxyalkyl.

Non-limiting examples of $R^5$ are fluoro, nitrile, hydroxy, methyl, cyclopropyl, methoxy, ethoxy, 1-methylethoxy, cyanomethoxy or methoxymethyl.

In still another embodiment of the invention, the compounds are represented by Formula I, or a pharmaceutically acceptable salt thereof, wherein y is selected from 0, 1 or 2.

In a specific embodiment of the invention, the compounds are represented by Formula I, or a pharmaceutically acceptable salt thereof, wherein y is 1 and $R^5$ is hydroxy.

In another embodiment of the invention, the compounds are represented by Formula I, or a pharmaceutically acceptable salt thereof, wherein n is 1.

In a particular embodiment of the invention, the compounds are represented by Formula Ib, or a pharmaceutically acceptable salt thereof, wherein $R^1$, $R^2$, $R^3$, $R^4$, and x are as defined above.

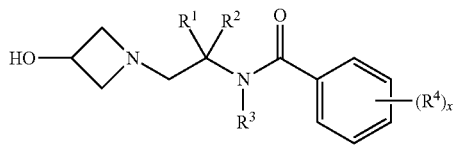
Formula Ib

In an embodiment of the invention, the compounds are represented by Formula I (or Formula Ib) or a pharmaceutically acceptable salt thereof, wherein $R^1$ is selected from (unsubstituted) $C_{1-6}$ alkyl, (unsubstituted) $C_{1-6}$ alkoxyalkyl or (unsubstituted) $C_{3-6}$ cycloalkyl.

Non-limiting examples of $R^1$ are methyl, ethyl, propyl, isopropyl, butyl, 1-methyl-propyl, 2-methyl-propyl, 1-methoxyethyl, 1-(1,1-dimethylethoxy)-ethyl, 1,1-dimethylethyl, cyclopropyl, cyclobutyl, cyclopentyl and cyclohexyl.

In a further embodiment of the invention, the compounds are represented by Formula I (or Formula Ib), or a pharmaceutically acceptable salt thereof, wherein $R^1$ is selected from (unsubstituted) $C_{1-4}$ alkyl, (unsubstituted) $C_{1-4}$ alkoxyalkyl, (unsubstituted) cyclopropyl or (unsubstituted) cyclobutyl, in particular (unsubstituted) $C_{1-4}$ alkyl, (unsubstituted) cyclopropyl or (unsubstituted) cyclobutyl, and more specifically (unsubstituted) $C_{2-4}$ alkyl (such as ethyl, propyl and isopropyl), cyclopropyl or cyclobutyl.

In a particular embodiment of the invention, the compounds are represented by Formula I (or Formula Ib), or a pharmaceutically acceptable salt thereof, wherein $R^2$ is selected from hydrogen or methyl, in particular hydrogen.

In a further embodiment of the invention, the compounds are represented by Formula I (or Formula Ib), or a pharmaceutically acceptable salt thereof, wherein $R^3$ is selected from (unsubstituted) $C_{1-6}$ alkyl, (unsubstituted) $C_{1-6}$ alkoxyalkyl or (unsubstituted) $C_{3-6}$ cycloalkyl.

Non-limiting examples of $R^3$ are methyl, ethyl, isopropyl, butyl, cyclopentyl, 2-methoxyethyl and 1-methyl-2-methoxyethyl.

In a particular embodiment of the invention, the compounds are represented by Formula I (or Formula Ib), or a pharmaceutically acceptable salt thereof, wherein $R^3$ is selected from (unsubstituted) $C_{1-3}$ alkyl or (unsubstituted) $C_{1-3}$ alkoxyalkyl, in particular (unsubstituted) $C_{1-3}$ alkyl, such as methyl.

In another embodiment of the invention, the compounds are represented by Formula I (or Formula Ib), or a pharmaceutically acceptable salt thereof, wherein x is 0, 1, 2 or 3 (in particular 0, 1 or 2) and each $R^4$ is independently selected from chloro, fluoro, bromo, nitrile, $C_{1-3}$ alkyl, $C_{1-3}$ alkoxy or $C_{1-3}$ alkylsulfide, wherein
any alkyl or alkoxy group in these substituents is substituted by 0, 1, 2 or 3 substituents selected from fluoro or nitrile.

In still another embodiment of the invention, the compounds are represented by Formula I (or Formula Ib), or a pharmaceutically acceptable salt thereof, wherein x is 0, 1, 2 or 3 (in particular 0, 1 or 2) and each $R^4$ is independently selected from chloro, fluoro, bromo, nitrile, $C_{1-3}$ alkyl or $C_{1-3}$ alkoxy, wherein
any alkyl or alkoxy group in these substituents is substituted by 0, 1, 2 or 3 substituents selected from fluoro or nitrile.

Non-limiting examples of $R^4$ are chloro, fluoro, bromo, nitrile, methyl, ethyl, isopropyl, difluoromethyl, trifluoromethyl, methoxy, hydroxy, difluoromethoxy, trifluoromethoxy, cyano-isopropyl and methylsulfide.

It shall be noted that $R^4$ may be linked to any of the ring carbon atoms of the phenyl group of Formula I.

In still another embodiment of the invention, the compounds are represented by Formula I (or Formula Ib), or a pharmaceutically acceptable salt thereof, wherein x is selected from 0, 1 or 2, in particular 1 or 2.

In still another embodiment of the invention, the compounds are represented by Formula I (or Formula Ib), or a pharmaceutically acceptable salt thereof, wherein x is 1 or 2 and $R^4$ is selected from chloro, fluoro, bromo, nitrile, methyl, ethyl, isopropyl, difluoromethyl, trifluoromethyl, methoxy, hydroxy, difluoromethoxy, trifluoromethoxy, cyano-isopropyl or methylsulfide, in particular chloro, fluoro, bromo, nitrile or methyl.

In a particular embodiment of the invention, the compounds are represented by Formula Ic, or a pharmaceutically acceptable salt thereof, wherein $R^1$, $R^4$, and x are as defined above.

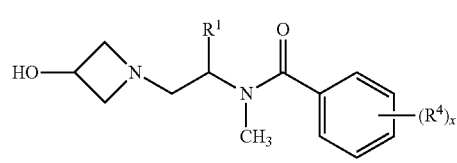
Formula Ic

One or more of the above embodiments may be combined to provide further specific embodiments of the invention.

Examples of specific compounds according to Formula I of the invention are:
(S)—N-(1-(Azetidin-1-yl)pentan-2-yl)-2,4-dichloro-N-methylbenzamide;
(S)—N-(1-(Azetidin-1-yl)pentan-2-yl)-4-chloro-N-methylbenzamide;
(S)—N-(1-(Azetidin-1-yl)pentan-2-yl)-4-bromo-N-methylbenzamide;
(S)—N-(1-(Azetidin-1-yl)pentan-2-yl)-4-fluoro-N,3-dimethylbenzamide;
(S)-4-Fluoro-N-(1-(3-fluoroazetidin-1-yl)-3-methylbutan-2-yl)-N,3-dimethylbenzamide;
(S)-4-Chloro-N-(1-(3-fluoroazetidin-1-yl)-3-methylbutan-2-yl)-N-methylbenzamide;
(S)-4-Bromo-N-(1-(3-fluoroazetidin-1-yl)-3-methylbutan-2-yl)-N-methylbenzamide;
(S)-3-Chloro-4-fluoro-N-(1-(3-fluoroazetidin-1-yl)-3-methylbutan-2-yl)-N-methylbenzamide;
(S)-4-Fluoro-N-(1-(3-fluoroazetidin-1-yl)-3-methylbutan-2-yl)-N-methyl-3-(trifluoromethyl)benzamide;
(S)—N-(1-(Azetidin-1-yl)-3-methylbutan-2-yl)-4-fluoro-N,3-dimethylbenzamide;
(S)—N-(1-(Azetidin-1-yl)-3-methylbutan-2-yl)-4-fluoro-N-methyl-3-(trifluoromethyl)benzamide;
(S)—N-(1-(Azetidin-1-yl)-3-methylbutan-2-yl)-3-chloro-4-fluoro-N-methylbenzamide;
(S)—N-(1-(Azetidin-1-yl)-3-methylbutan-2-yl)-3-chloro-N-methylbenzamide;
(S)—N-(1-(Azetidin-1-yl)-3-methylbutan-2-yl)-N-methylbenzamide;
(S)—N-(1-(Azetidin-1-yl)-3-methylbutan-2-yl)-N-methyl-3-(trifluoromethyl)benzamide;
(S)—N-(1-(Azetidin-1-yl)-3-methylbutan-2-yl)-N,3-dimethylbenzamide;

(S)-2-Chloro-4-fluoro-N-methyl-N-(3-methyl-1-(pyrrolidin-1-yl)butan-2-yl)benzamide;
(S)-3,4-Dichloro-N-(3,3-dimethyl-1-(pyrrolidin-1-yl)butan-2-yl)-N-methylbenzamide;
(S)-4-Bromo-N-(3,3-dimethyl-1-(pyrrolidin-1-yl)butan-2-yl)-N-methylbenzamide;
4-Chloro-N-methyl-N-((2S,3S)-3-methyl-1-(pyrrolidin-1-yl)pentan-2-yl)benzamide;
4-Bromo-N-methyl-N-((2S,3S)-3-methyl-1-(pyrrolidin-1-yl)pentan-2-yl)benzamide;
4-Fluoro-N,3-dimethyl-N-((2S,3S)-3-methyl-1-(pyrrolidin-1-yl)pentan-2-yl)benzamide;
2,4-Dichloro-N-methyl-N-((2S,3S)-3-methyl-1-(pyrrolidin-1-yl)pentan-2-yl)benzamide;
4-Fluoro-N-((2R,3R)-3-methoxy-1-(pyrrolidin-1-yl)butan-2-yl)-N,3-dimethylbenzamide;
N-((2R,3R)-3-Methoxy-1-(pyrrolidin-1-yl)butan-2-yl)-N,3-dimethylbenzamide
3-Chloro-4-fluoro-N-((2R,3R)-3-methoxy-1-(pyrrolidin-1-yl)butan-2-yl)-N-methylbenzamide;
4-Bromo-N-((2R,3R)-3-methoxy-1-(pyrrolidin-1-yl)butan-2-yl)-N-methylbenzamide;
4-Chloro-N-((2R,3R)-3-methoxy-1-(pyrrolidin-1-yl)butan-2-yl)-N-methylbenzamide;
(S)-4-Bromo-N-(1-(4-methoxypiperidin-1-yl)-3-methylbutan-2-yl)-N-methylbenzamide;
(S)-4-Chloro-N-(1-(4-methoxypiperidin-1-yl)-3-methylbutan-2-yl)-N-methylbenzamide;
(S)-4-Fluoro-N-(1-(4-methoxypiperidin-1-yl)-3-methylbutan-2-yl)-N,3-dimethylbenzamide;
(S)-3-Chloro-4-fluoro-N-(1-(4-methoxypiperidin-1-yl)-3-methylbutan-2-yl)-N-methylbenzamide;
(S)—N-(1-(4-Methoxypiperidin-1-yl)-3-methylbutan-2-yl)-N,3-dimethylbenzamide;
(S)-3-Methoxy-N-(1-(4-methoxypiperidin-1-yl)-3-methylbutan-2-yl)-N,4-dimethylbenzamide;
(S)—N-(1-(4-Methoxypiperidin-1-yl)-3-methylbutan-2-yl)-N,3,4-trimethylbenzamide;
(S)—N-(1-Cyclopropyl-2-(pyrrolidin-1-yl)ethyl)-4-fluoro-N,3-dimethylbenzamide;
(S)-4-Chloro-N-(1-cyclopropyl-2-(pyrrolidin-1-yl)ethyl)-N-methylbenzamide;
(S)-4-Bromo-N-(1-cyclopropyl-2-(pyrrolidin-1-yl)ethyl)-N-methylbenzamide;
(S)—N-(1-Cyclopropyl-2-(pyrrolidin-1-yl)ethyl)-3,4-difluoro-N-methylbenzamide;
(S)—N-(1-Cyclopropyl-2-(pyrrolidin-1-yl)ethyl)-N,3-dimethylbenzamide;
4-Methoxy-N—((S)-1-((S)-2-(methoxymethyl)pyrrolidin-1-yl)-3-methylbutan-2-yl)-N-methylbenzamide;
4-Chloro-N—((S)-1-((S)-2-(methoxymethyl)pyrrolidin-1-yl)-3-methylbutan-2-yl)-N-methylbenzamide;
4-Bromo-N—((S)-1-((S)-2-(methoxymethyl)pyrrolidin-1-yl)-3-methylbutan-2-yl)-N-methylbenzamide;
(S)—N-(2-(Azetidin-1-yl)-1-cyclopropylethyl)-4-fluoro-N,3-dimethylbenzamide;
(S)—N-(2-(Azetidin-1-yl)-1-cyclopropylethyl)-4-chloro-N-methylbenzamide;
(S)—N-(2-(Azetidin-1-yl)-1-cyclopropylethyl)-4-bromo-N-methylbenzamide;
(S)-4-Bromo-N-(1-cyclopropyl-2-(3-hydroxyazetidin-1-yl)ethyl)-N-methylbenzamide
(S)—N-(1-(Azetidin-1-yl)-3-methylbutan-2-yl)-4-chloro-N-methylbenzamide;
(S)—N-(1-(Azetidin-1-yl)-3-methylbutan-2-yl)-4-bromo-N-methylbenzamide;
(S)-4-Fluoro-N-(1-(3-hydroxyazetidin-1-yl)-3-methylbutan-2-yl)-N,3-dimethylbenzamide;
(S)-4-Chloro-N-(1-(3-hydroxyazetidin-1-yl)-3-methylbutan-2-yl)-N-methylbenzamide;
(S)-4-Bromo-N-(1-(3-hydroxyazetidin-1-yl)-3-methylbutan-2-yl)-N-methylbenzamide;
(S)—N-(1-Cyclopropyl-2-(3-hydroxyazetidin-1-yl)ethyl)-4-fluoro-N,3-dimethylbenzamide;
(S)-4-Chloro-N-(1-cyclopropyl-2-(3-hydroxyazetidin-1-yl)ethyl)-N-methylbenzamide;
(S)-3-Chloro-N-(1-cyclopropyl-2-(3-hydroxyazetidin-1-yl)ethyl)-4-fluoro-N-methylbenzamide;
(S)—N-(1-Cyclopropyl-2-(3-hydroxyazetidin-1-yl)ethyl)-4-fluoro-N-methylbenzamide;
(S)—N-(1-Cyclopropyl-2-(3-hydroxyazetidin-1-yl)ethyl)-4-fluoro-N-methyl-3-(trifluoromethyl)benzamide;
(S)-3,4-Difluoro-N-(1-(3-hydroxyazetidin-1-yl)pentan-2-yl)-N-methylbenzamide;
(S)-4-Chloro-N-(1-(3-hydroxyazetidin-1-yl)pentan-2-yl)-N-methylbenzamide;
(S)-3-Chloro-4-fluoro-N-(1-(3-hydroxyazetidin-1-yl)pentan-2-yl)-N-methylbenzamide;
(S)-4-Chloro-N-(1-(3-hydroxyazetidin-1-yl)pentan-2-yl)-N,3-dimethylbenzamide;
(S)-4-Fluoro-N-(1-(3-hydroxyazetidin-1-yl)pentan-2-yl)-N-methyl-3-(trifluoromethyl)benzamide;
(S)-4-Fluoro-N-(1-(3-hydroxyazetidin-1-yl)pentan-2-yl)-N-methylbenzamide;
(S)-4-Bromo-N-(1-(3-hydroxyazetidin-1-yl)pentan-2-yl)-N-methylbenzamide;
(S)—N-(1-(3-Hydroxyazetidin-1-yl)pentan-2-yl)-N-methyl-3-(trifluoro-methyl)benzamide;
(S)-4-Cyano-N-(1-(3-hydroxyazetidin-1-yl)pentan-2-yl)-N-methylbenzamide;
(S)—N-(1-(3-Hydroxyazetidin-1-yl)pentan-2-yl)-N,3-dimethylbenzamide;
(S)-4-Fluoro-N-(1-(3-hydroxyazetidin-1-yl)pentan-2-yl)-N,3-dimethylbenzamide;
N—((S)-1-((3S,4S)-3,4-Dihydroxypyrrolidin-1-yl)-3-methylbutan-2-yl)-4-fluoro-N,3-dimethylbenzamide;
4-Chloro-N—((S)-1-((3S,4S)-3,4-dihydroxypyrrolidin-1-yl)-3-methylbutan-2-yl)-N,3-dimethylbenzamide;
4-Chloro-N—((S)-1-((3S,4S)-3,4-dihydroxypyrrolidin-1-yl)-3-methylbutan-2-yl)-N-methylbenzamide;
4-Chloro-N—((S)-1-((3S,4S)-3,4-dihydroxypyrrolidin-1-yl)-3-methylbutan-2-yl)-3-fluoro-N-methylbenzamide;
4-Chloro-N—((S)-1-((3R,4R)-3,4-dihydroxypyrrolidin-1-yl)-3-methylbutan-2-yl)-N,3-dimethylbenzamide;
(S)-4-Fluoro-N-(1-(3-hydroxyazetidin-1-yl)butan-2-yl)-N,3-dimethylbenzamide;
(S)—N-(1-Cyclopropyl-2-(3-cyclopropyl-3-hydroxyazetidin-1-yl)ethyl)-4-fluoro-N,3-dimethylbenzamide;
(S)-3-Chloro-N-(1-cyclopropyl-2-(3-cyclopropyl-3-hydroxyazetidin-1-yl)ethyl)-4-fluoro-N-methylbenzamide;
(S)—N-(1-Cyclopropyl-2-(3-cyclopropyl-3-hydroxyazetidin-1-yl)ethyl)-3,4-difluoro-N-methylbenzamide;
(S)-4-Cyano-N-(1-cyclopropyl-2-(3-cyclopropyl-3-hydroxyazetidin-1-yl)ethyl)-N-methylbenzamide;
(S)—N-(1-Cyclopropyl-2-(3-cyclopropyl-3-hydroxyazetidin-1-yl)ethyl)-N,3,4-trimethylbenzamide;
(S)-4-Bromo-N-(1-(3-hydroxy-3-methylazetidin-1-yl)-3-methylbutan-2-yl)-N-methylbenzamide;
(S)-4-Chloro-N-(1-(3-hydroxy-3-methylazetidin-1-yl)-3-methylbutan-2-yl)-N-methylbenzamide;
(S)-4-Fluoro-N-(1-(3-hydroxy-3-methylazetidin-1-yl)-3-methylbutan-2-yl)-N-methyl-3-(trifluoromethyl)benzamide;

(S)—N-(1-Cyclopropyl-2-(3-hydroxyazetidin-1-yl)ethyl)-3,4-difluoro-N-methylbenzamide;
N-[(1S)-2-(azetidin-1-yl)-1-cyclopropylethyl]-N,3,4-trimethylbenzamide;
(S)—N-(2-(Azetidin-1-yl)-1-cyclopropylethyl)-3,4-difluoro-N-methylbenzamide;
2-Chloro-4-fluoro-N—((S)-1-((S)-3-hydroxypyrrolidin-1-yl)-3-methylbutan-2-yl)-N-methylbenzamide;
4-Chloro-N—((S)-1-((S)-3-hydroxypyrrolidin-1-yl)-3-methylbutan-2-yl)-N-methylbenzamide;
(S)—N-(1-(Azetidin-1-yl)-3-methylbutan-2-yl)-4-chloro-N-ethylbenzamide;
(S)-4-Fluoro-N,3-dimethyl-N-(3-methyl-1-(pyrrolidin-1-yl)butan-2-yl)benzamide;
(S)—N,3-Dimethyl-N-(3-methyl-1-(pyrrolidin-1-yl)butan-2-yl)benzamide;
(S)-3-Chloro-N-(1-cyclopropyl-2-(pyrrolidin-1-yl)ethyl)-4-fluoro-N-methyl-benzamide;
(S)—N-(1-Cyclopropyl-2-(pyrrolidin-1-yl)ethyl)-N,3,4-trimethylbenzamide;
(R)-3-Chloro-N-methyl-N-(4-methyl-1-(pyrrolidin-1-yl)pentan-3-yl)benzamide;
(R)-4-Fluoro-N,3-dimethyl-N-(4-methyl-1-(pyrrolidin-1-yl)pentan-3-yl)benzamide;
N-((2R,3R)-3-Tert-butoxy-1-(pyrrolidin-1-yl)butan-2-yl)-4-fluoro-N,3-dimethylbenzamide;
(S)-4-Bromo-N-ethyl-N-(3-methyl-1-(pyrrolidin-1-yl)butan-2-yl)benzamide;
(S)—N-Ethyl-4-fluoro-3-methyl-N-(3-methyl-1-(pyrrolidin-1-yl)butan-2-yl)benzamide;
(S)-4-Chloro-N-ethyl-N-(3-methyl-1-(pyrrolidin-1-yl)butan-2-yl)benzamide;
(S)-4-Chloro-N-(2-methoxyethyl)-N-(3-methyl-1-(pyrrolidin-1-yl)butan-2-yl)benzamide;
(S)-4-Bromo-N-(2-methoxyethyl)-N-(3-methyl-1-(pyrrolidin-1-yl)butan-2-yl)benzamide;
(S)-3-Chloro-N-(1-(3,3-difluoropiperidin-1-yl)-3-methylbutan-2-yl)-4-fluoro-N-methylbenzamide;
(S)—N-(1-(3,3-Difluoropiperidin-1-yl)-3-methylbutan-2-yl)-4-fluoro-N-methyl-3-(trifluoromethyl)benzamide;
(S)—N-(1-(3,3-Difluoropiperidin-1-yl)-3-methylbutan-2-yl)-N,3,4-trimethylbenzamide;
(S)—N-(1-(3,3-Difluoropiperidin-1-yl)-3-methylbutan-2-yl)-3-methoxy-N,4-dimethylbenzamide;
(S)-4-Bromo-N-(1-(3,3-difluoropiperidin-1-yl)-3-methylbutan-2-yl)-N-methyl-benzamide;
4-Chloro-N-methyl-N-(2-methyl-1-(pyrrolidin-1-yl)propan-2-yl)benzamide;
4-Bromo-N-methyl-N-(2-methyl-1-(pyrrolidin-1-yl)propan-2-yl)benzamide;
(S)-3-Fluoro-N-methyl-N-(3-methyl-1-(pyrrolidin-1-yl)butan-2-yl)-5-(trifluoromethyl)benzamide;
(S)-2,3,5-Trifluoro-N-methyl-N-(3-methyl-1-(pyrrolidin-1-yl)butan-2-yl)benzamide;
(S)—N-Methyl-N-(3-methyl-1-(pyrrolidin-1-yl)butan-2-yl)-3-(trifluoromethyl)benzamide;
(S)-4-Fluoro-3-methoxy-N-methyl-N-(3-methyl-1-(pyrrolidin-1-yl)butan-2-yl)benzamide;
(S)-3,5-Difluoro-N-methyl-N-(3-methyl-1-(pyrrolidin-1-yl)butan-2-yl)benzamide;
(S)-3-Fluoro-N,2-dimethyl-N-(3-methyl-1-(pyrrolidin-1-yl)butan-2-yl)benzamide;
(S)—N,4-Dimethyl-N-(3-methyl-1-(pyrrolidin-1-yl)butan-2-yl)benzamide;
(S)—N-Methyl-N-(3-methyl-1-(pyrrolidin-1-yl)butan-2-yl)-4-(tri-fluoromethoxy)benzamide;
(S)—N-Methyl-N-(3-methyl-1-(pyrrolidin-1-yl)butan-2-yl)-3-(tri-fluoromethoxy)benzamide;
(S)-3-Chloro-2-fluoro-N-methyl-N-(3-methyl-1-(pyrrolidin-1-yl)butan-2-yl)benzamide;
(S)-2-Fluoro-N-methyl-N-(3-methyl-1-(pyrrolidin-1-yl)butan-2-yl)benzamide;
(S)-2-Fluoro-N-methyl-N-(3-methyl-1-(pyrrolidin-1-yl)butan-2-yl)-6-(trifluoromethyl)benzamide;
(S)—N-Methyl-N-(3-methyl-1-(pyrrolidin-1-yl)butan-2-yl)-2-(trifluoromethyl)benzamide;
(S)-3,4,5-Trifluoro-N-methyl-N-(3-methyl-1-(pyrrolidin-1-yl)butan-2-yl)benzamide;
(S)-2,5-Difluoro-N-methyl-N-(3-methyl-1-(pyrrolidin-1-yl)butan-2-yl)benzamide;
(S)-4-Fluoro-N-methyl-N-(3-methyl-1-(pyrrolidin-1-yl)butan-2-yl)-2-(trifluoromethyl)benzamide;
2,6-Difluoro-N-methyl-N-[(1S)-2-methyl-1-(pyrrolidin-1-ylmethyl)propyl]benzamide;
4-Chloro-N,3-dimethyl-N-[(1S)-2-methyl-1-(piperidin-1-ylmethyl)propyl]benzamide;
2-Chloro-4-fluoro-N-methyl-N-[(1S)-2-methyl-1-(piperidin-1-yl-methyl)propyl]benzamide;
4-Bromo-N-methyl-N-[(1S)-2-methyl-1-(piperidin-1-ylmethyl)propyl]benzamide;
3,4-Dichloro-N-methyl-N-[(1S)-2-methyl-1-(piperidin-1-ylmethyl)propyl]benzamide;
N,3-Dimethyl-N-[(1S)-2-methyl-1-(piperidin-1-ylmethyl)propyl]benzamide;
2,4-Dichloro-N-methyl-N-[(1S)-2-methyl-1-(piperidin-1-ylmethyl)propyl]benzamide;
4-Chloro-2-fluoro-N-methyl-N-[(1S)-2-methyl-1-(piperidin-1-ylmethyl)propyl]-benzamide;
N-Methyl-N-[(1S)-2-methyl-1-(piperidin-1-ylmethyl)propyl]-3-(trifluoromethyl)-benzamide;
3-Chloro-4-fluoro-N-methyl-N-[(1S)-2-methyl-1-(piperidin-1-ylmethyl)propyl]-benzamide;
4-Chloro-N-methyl-N-[(1S)-2-methyl-1-(piperidin-1-ylmethyl)propyl]benzamide;
(S)-3-Bromo-N-methyl-N-(3-methyl-1-(piperidin-1-yl)butan-2-yl)benzamide;
(S)-4-Bromo-3-fluoro-N-methyl-N-(3-methyl-1-(piperidin-1-yl)butan-2-yl)benzamide;
(S)-3-Chloro-N-methyl-N-(3-methyl-1-(piperidin-1-yl)butan-2-yl)benzamide;
(S)-3-Fluoro-N,2-dimethyl-N-(3-methyl-1-(piperidin-1-yl)butan-2-yl)benzamide;
3-Chloro-2-fluoro-N-[(1S)-1-{[(3S)-3-hydroxypyrrolidin-1-yl]methyl}-2-methylpropyl]-N-methylbenzamide;
4-Fluoro-N-[(1S)-1-{[(3S)-3-hydroxypyrrolidin-1-yl]methyl}-2-methylpropyl]-N,3-dimethylbenzamide;
N-[(1S)-1-{[(3S)-3-Hydroxypyrrolidin-1-yl]methyl}-2-methylpropyl]-N-methyl-4-(trifluoromethoxy)benzamide;
N-[(1S)-1-{[(3S)-3-Hydroxypyrrolidin-1-yl]methyl}-2-methylpropyl]-N-methyl-3-(tri-fluoromethoxy)benzamide;
N-[(1S)-1-{[(3S)-3-Hydroxypyrrolidin-1-yl]methyl}-2-methylpropyl]-N,4-dimethylbenzamide;
3-Fluoro-N-[(1S)-1-{[(3S)-3-hydroxypyrrolidin-1-yl]methyl}-2-methylpropyl]-N-methyl-5-(trifluoromethyl)benzamide;
3-Fluoro-N—((S)-1-((S)-3-hydroxypyrrolidin-1-yl)-3-methylbutan-2-yl)-N,2-dimethylbenzamide;
4-Fluoro-N—((S)-1-((S)-3-hydroxypyrrolidin-1-yl)-3-methylbutan-2-yl)-N-methyl-2-(trifluoromethyl)benzamide;
(S)-2,4-Dichloro-N-methyl-N-(3-methyl-1-(pyrrolidin-1-yl)butan-2-yl)benzamide;
(S)-3-Chloro-N-methyl-N-(3-methyl-1-(pyrrolidin-1-yl)butan-2-yl)benzamide;

(S)-4-Isopropyl-N-methyl-N-(3-methyl-1-(pyrrolidin-1-yl)butan-2-yl)benzamide;
(S)-4-Chloro-N,3-dimethyl-N-(3-methyl-1-(pyrrolidin-1-yl)butan-2-yl)benzamide;
(S)-3,4-Dichloro-N-methyl-N-(3-methyl-1-(pyrrolidin-1-yl)butan-2-yl)benzamide;
(S)-4-Bromo-3-fluoro-N-methyl-N-(3-methyl-1-(pyrrolidin-1-yl)butan-2-yl)benzamide;
(S)-4-Chloro-2-fluoro-N-methyl-N-(3-methyl-1-(pyrrolidin-1-yl)butan-2-yl)benzamide;
(S)-2-(Difluoromethoxy)-N-methyl-N-(3-methyl-1-(pyrrolidin-1-yl)butan-2-yl)benzamide;
(S)-3-Chloro-4-fluoro-N-methyl-N-(3-methyl-1-(pyrrolidin-1-yl)butan-2-yl)benzamide;
(R)-3,4-Dichloro-N-methyl-N-(3-methyl-1-(pyrrolidin-1-yl)butan-2-yl)benzamide;
(R)-4-Bromo-N-methyl-N-(3-methyl-1-(pyrrolidin-1-yl)butan-2-yl)benzamide;
(R)-2,4-Dichloro-N-methyl-N-(3-methyl-1-(pyrrolidin-1-yl)butan-2-yl)benzamide;
(R)-4-Chloro-2-fluoro-N-methyl-N-(3-methyl-1-(pyrrolidin-1-yl)butan-2-yl)benzamide;
(R)-4-Bromo-3-fluoro-N-methyl-N-(3-methyl-1-(pyrrolidin-1-yl)butan-2-yl)benzamide;
(S)-4-Bromo-N-methyl-N-(1-(pyrrolidin-1-yl)butan-2-yl)benzamide;
(S)-3,4-Dichloro-N-methyl-N-(1-(pyrrolidin-1-yl)butan-2-yl)benzamide;
4-Fluoro-N—((S)-1-((R)-3-hydroxypyrrolidin-1-yl)-3-methylbutan-2-yl)-N,3-dimethylbenzamide;
4-Chloro-N—((S)-1-((R)-3-hydroxypyrrolidin-1-yl)-3-methylbutan-2-yl)-N-methylbenzamide;
4-Bromo-N—((S)-1-((R)-3-hydroxypyrrolidin-1-yl)-3-methylbutan-2-yl)-N-methylbenzamide;
3-Chloro-4-fluoro-N—((S)-1-((R)-3-hydroxypyrrolidin-1-yl)-3-methylbutan-2-yl)-N-methylbenzamide;
4-Fluoro-N—((S)-1-((R)-3-hydroxypyrrolidin-1-yl)-3-methylbutan-2-yl)-N-methyl-3-(trifluoromethyl)benzamide;
(S)-4-Chloro-N-methyl-N-(3-methyl-1-(pyrrolidin-1-yl)butan-2-yl)benzamide;
(S)-4-Bromo-N-methyl-N-(3-methyl-1-(pyrrolidin-1-yl)butan-2-yl)benzamide;
(S)-4-Chloro-N-cyclopentyl-N-(3-methyl-1-(pyrrolidin-1-yl)butan-2-yl)benzamide;
(S)—N-(1-(3,3-Difluoropyrrolidin-1-yl)-3-methylbutan-2-yl)-N,3,4-trimethylbenzamide;
(S)-4-Fluoro-N-(1-(3-hydroxyazetidin-1-yl)-2,3-dimethylbutan-2-yl)-N,3-dimethylbenzamide;
(S)—N-(1-(3-Hydroxyazetidin-1-yl)pentan-2-yl)-N,3,4-trimethylbenzamide;
(S)-4-Fluoro-N-(1-(4-hydroxypiperidin-1-yl)-3-methylbutan-2-yl)-N,3-dimethylbenzamide;
(R)-4-Fluoro-N-(1-(4-hydroxypiperidin-1-yl)-3-methylbutan-2-yl)-N,3-dimethylbenzamide;
(S)—N-(1-(4-Cyanopiperidin-1-yl)-3-methylbutan-2-yl)-4-fluoro-N,3-dimethylbenzamide;
(S)-4-Chloro-N-(1-(4-hydroxypiperidin-1-yl)-3-methylbutan-2-yl)-N-methylbenzamide;
(S)-3,4-Difluoro-N-(1-(3-(methoxymethyl)azetidin-1-yl)-3-methylbutan-2-yl)-N-methylbenzamide;
3,4-Difluoro-N-((2S,3S)-1-(3-hydroxyazetidin-1-yl)-3-methylpentan-2-yl)-N-methylbenzamide;
4-Chloro-N-((2S,3S)-1-(3-hydroxyazetidin-1-yl)-3-methylpentan-2-yl)-N-methylbenzamide;
4-Ethyl-N-((2S,3S)-1-(3-hydroxyazetidin-1-yl)-3-methylpentan-2-yl)-N-methylbenzamide;
N-((2S,3S)-1-(3-Hydroxyazetidin-1-yl)-3-methylpentan-2-yl)-N-methylbenzamide;
4-Cyano-N-((2S,3S)-1-(3-hydroxyazetidin-1-yl)-3-methylpentan-2-yl)-N-methylbenzamide;
N-((2S,3S)-1-(3-Hydroxyazetidin-1-yl)-3-methylpentan-2-yl)-4-methoxy-N-methylbenzamide;
4-Cyano-2-fluoro-N-((2S,3S)-1-(3-hydroxyazetidin-1-yl)-3-methylpentan-2-yl)-N-methylbenzamide;
N-((2S,3S)-1-(3-Hydroxyazetidin-1-yl)-3-methylpentan-2-yl)-2-methoxy-N,5-dimethylbenzamide;
5-Chloro-N-((2S,3S)-1-(3-hydroxyazetidin-1-yl)-3-methylpentan-2-yl)-2-methoxy-N-methylbenzamide;
4-Chloro-N-((2R,3R)-1-(3-hydroxyazetidin-1-yl)-3-methoxybutan-2-yl)-N-methylbenzamide;
(S)-4-Chloro-N-(1-(3-ethoxyazetidin-1-yl)pentan-2-yl)-N-methylbenzamide;
(S)-4-Chloro-N-(1-(3-methoxyazetidin-1-yl)pentan-2-yl)-N-methylbenzamide;
4-Chloro-N-{(2S)-1-[3-(cyanomethoxy)azetidin-1-yl]pentan-2-yl}-N-methylbenzamide;
4-Chloro-N-methyl-N-{(2S)-1-[3-(propan-2-yloxy) azetidin-1-yl]pentan-2-yl}benzamide;
(R)—N-(1-Cyclopentyl-2-(3-hydroxyazetidin-1-yl)ethyl)-3,4-difluoro-N-methylbenzamide;
(S)—N-(1-Cyclopentyl-2-(3-hydroxyazetidin-1-yl)ethyl)-3,4-difluoro-N-methylbenzamide;
(R)—N-[1-Cyclopentyl-2-(3-hydroxyazetidin-1-yl)ethyl]-4-methoxy-N-methylbenzamide;
(S)—N-[1-Cyclopentyl-2-(3-hydroxyazetidin-1-yl)ethyl]-4-methoxy-N-methylbenzamide;
(R)-4-Chloro-N-[1-cyclopentyl-2-(3-hydroxyazetidin-1-yl)ethyl]-N-methylbenzamide;
(S)-4-Chloro-N-[1-cyclopentyl-2-(3-hydroxyazetidin-1-yl)ethyl]-N-methylbenzamide;
(R)—N-[1-Cyclopentyl-2-(3-hydroxyazetidin-1-yl)ethyl]-4-fluoro-N,3-dimethylbenzamide;
(S)—N-[1-Cyclopentyl-2-(3-hydroxyazetidin-1-yl)ethyl]-4-fluoro-N,3-dimethylbenzamide;
(R)-4-Cyano-N-[1-cyclopentyl-2-(3-hydroxyazetidin-1-yl)ethyl]-N-methylbenzamide;
(S)-4-Cyano-N-[1-cyclopentyl-2-(3-hydroxyazetidin-1-yl)ethyl]-N-methylbenzamide;
(R)-2-Chloro-N-[1-cyclopentyl-2-(3-hydroxyazetidin-1-yl)ethyl]-4-fluoro-N-methylbenzamide;
(S)-2-Chloro-N-[1-cyclopentyl-2-(3-hydroxyazetidin-1-yl)ethyl]-4-fluoro-N-methylbenzamide;
(R)-3-Chloro-N-[1-cyclopentyl-2-(3-hydroxyazetidin-1-yl)ethyl]-4-fluoro-N-methylbenzamide;
(S)-3-Chloro-N-[1-cyclopentyl-2-(3-hydroxyazetidin-1-yl)ethyl]-4-fluoro-N-methylbenzamide;
(S)-4-Chloro-N-(1-(3-hydroxyazetidin-1-yl)hexan-2-yl)-N-methylbenzamide;
3,4-Difluoro-N-[(2S)-1-(3-hydroxyazetidin-1-yl)hexan-2-yl]-N-methylbenzamide;
4-Cyano-2-fluoro-N-[(2S)-1-(3-hydroxyazetidin-1-yl)hexan-2-yl]-N-methylbenzamide;
4-Cyano-N-[(2S)-1-(3-hydroxyazetidin-1-yl)hexan-2-yl]-N-methylbenzamide;
N-[(2S)-1-(3-Hydroxyazetidin-1-yl)hexan-2-yl]-N-methylbenzamide;
4-Hydroxy-N-[(2S)-1-(3-hydroxyazetidin-1-yl)hexan-2-yl]-N-methylbenzamide;
4-Fluoro-N-[(2S)-1-(3-hydroxyazetidin-1-yl)hexan-2-yl]-N-methylbenzamide;
3-Chloro-4-fluoro-N-[(2S)-1-(3-hydroxyazetidin-1-yl)hexan-2-yl]-N-methylbenzamide;

2,5-Difluoro-N-[(2S)-1-(3-hydroxyazetidin-1-yl)hexan-2-yl]-N-methylbenzamide;
3-(Difluoromethyl)-N-[(2S)-1-(3-hydroxyazetidin-1-yl)hexan-2-yl]-N-methylbenzamide;
4-Chloro-N-[(2S)-1-(3-hydroxyazetidin-1-yl)pentan-2-yl]-N-(propan-2-yl)benzamide;
3,4-Difluoro-N-[(2S)-1-(3-hydroxyazetidin-1-yl)pentan-2-yl]-N-(propan-2-yl)benzamide;
4-Chloro-N-[(1R)-1-cyclobutyl-2-(3-hydroxyazetidin-1-yl)ethyl]-N-methylbenzamide;
4-Cyano-N-[(1R)-1-cyclobutyl-2-(3-hydroxyazetidin-1-yl)ethyl]-N-methylbenzamide;
N-[(1R)-1-Cyclobutyl-2-(3-hydroxyazetidin-1-yl)ethyl]-4-(difluoromethoxy)-N-methylbenzamide;
N-[(1R)-1-Cyclobutyl-2-(3-hydroxyazetidin-1-yl)ethyl]-4-fluoro-N,3-dimethylbenzamide;
N-[(1R)-1-Cyclobutyl-2-(3-hydroxyazetidin-1-yl)ethyl]-4-fluoro-N-methylbenzamide;
2-Chloro-N-[(1R)-1-cyclobutyl-2-(3-hydroxyazetidin-1-yl)ethyl]-4-fluoro-N-methylbenzamide;
N-[(1R)-1-Cyclobutyl-2-(3-hydroxyazetidin-1-yl)ethyl]-3,4-difluoro-N-methylbenzamide;
N-[(1R)-1-Cyclobutyl-2-(3-hydroxyazetidin-1-yl)ethyl]-3-(difluoromethyl)-N-methylbenzamide;
3-Cyano-N-[(1R)-1-cyclobutyl-2-(3-hydroxyazetidin-1-yl)ethyl]-4-fluoro-N-methylbenzamide;
N-[(1R)-1-Cyclobutyl-2-(3-hydroxyazetidin-1-yl)ethyl]-2,4-difluoro-N-methylbenzamide;
3-Chloro-N-[(1R)-1-cyclobutyl-2-(3-hydroxyazetidin-1-yl)ethyl]-2-fluoro-N-methylbenzamide;
N-[(1R)-1-Cyclobutyl-2-(3-hydroxyazetidin-1-yl)ethyl]-2-fluoro-4-methoxy-N-methylbenzamide;
N-[(1R)-1-Cyclobutyl-2-(3-hydroxyazetidin-1-yl)ethyl]-3-fluoro-4-methoxy-N-methylbenzamide;
N-[(1R)-1-Cyclobutyl-2-(3-hydroxyazetidin-1-yl)ethyl]-N-methylbenzamide;
4-Cyano-N-[(1S)-1-cyclohexyl-2-(3-hydroxyazetidin-1-yl)ethyl]-N-methylbenzamide;
4-Chloro-N-[(1S)-1-cyclohexyl-2-(3-hydroxyazetidin-1-yl)ethyl]-N-methylbenzamide;
3-Cyano-N-[(1S)-1-cyclohexyl-2-(3-hydroxyazetidin-1-yl)ethyl]-N-methylbenzamide;
4-Cyano-N-[(1S)-1-cyclohexyl-2-(3-hydroxyazetidin-1-yl)ethyl]-2-fluoro-N-methylbenzamide;
4-(2-Cyanopropan-2-yl)-N-[(1S)-1-cyclohexyl-2-(3-hydroxyazetidin-1-yl)ethyl]-N-methylbenzamide;
3-Cyano-N-[(1S)-1-cyclohexyl-2-(3-hydroxyazetidin-1-yl)ethyl]-5-fluoro-N-methylbenzamide;
N-[(1S)-1-Cyclohexyl-2-(3-hydroxyazetidin-1-yl)ethyl]-4-fluoro-N-methylbenzamide;
N-[(1S)-1-Cyclohexyl-2-(3-hydroxyazetidin-1-yl)ethyl]-N-methylbenzamide;
4-Chloro-N-[(2R)-1-(3-hydroxyazetidin-1-yl)pentan-2-yl]-N-methylbenzamide;
3,4-Difluoro-N-[(2S)-1-(3-hydroxyazetidin-1-yl)-4-methylpentan-2-yl]-N-methylbenzamide;
4-Chloro-N-[(2S)-1-(3-hydroxyazetidin-1-yl)-4-methylpentan-2-yl]-N-methylbenzamide;
4-Ethyl-N-[(2S)-1-(3-hydroxyazetidin-1-yl)-4-methylpentan-2-yl]-N-methylbenzamide;
3-(Difluoromethyl)-N-[(2S)-1-(3-hydroxyazetidin-1-yl)-4-methylpentan-2-yl]-N-methylbenzamide;
4-Fluoro-N-[(2S)-1-(3-hydroxyazetidin-1-yl)-4-methylpentan-2-yl]-3-methoxy-N-methylbenzamide;
4-Cyano-2-fluoro-N-[(2S)-1-(3-hydroxyazetidin-1-yl)-4-methylpentan-2-yl]-N-methylbenzamide;
4-Chloro-N-[(2S)-1-(3-hydroxyazetidin-1-yl)-4-methylpentan-2-yl]-2-methoxy-N-methylbenzamide;
N-[(2S)-1-(3-Hydroxyazetidin-1-yl)-4-methylpentan-2-yl]-N-methyl-4-(methylsulfanyl)benzamide;
(S)-2-chloro-N-(1-cyclobutyl-2-(3-hydroxyazetidin-1-yl)ethyl)-4-fluoro-N-methylbenzamide;
(S)-4-Cyano-N-(1-cyclobutyl-2-(3-hydroxyazetidin-1-yl)ethyl)-N-methylbenzamide;
(S)—N-(1-Cyclobutyl-2-(3-hydroxyazetidin-1-yl)ethyl)-3,4-difluoro-N-methylbenzamide;
(S)—N-(1-Cyclobutyl-2-(3-hydroxyazetidin-1-yl)ethyl)-2,4-difluoro-N-methylbenzamide;
(S)—N-(1-Cyclobutyl-2-(3-hydroxyazetidin-1-yl)ethyl)-2-fluoro-4-methoxy-N-methylbenzamide;
(S)—N-(1-Cyclobutyl-2-(3-hydroxyazetidin-1-yl)ethyl)-3-fluoro-4-methoxy-N-methylbenzamide;
(S)—N-(1-Cyclobutyl-2-(3-hydroxyazetidin-1-yl)ethyl)-N-methylbenzamide;
(S)—N-(1-Cyclobutyl-2-(3-hydroxyazetidin-1-yl)ethyl)-N-methyl-4-(trifluoromethyl)benzamide;
(S)—N-(1-Cyclobutyl-2-(3-hydroxyazetidin-1-yl)ethyl)-4-methoxy-N,3-dimethylbenzamide;
(S)—N-(1-Cyclobutyl-2-(3-hydroxyazetidin-1-yl)ethyl)-2-fluoro-N,5-dimethylbenzamide;
(S)-4-Chloro-3-fluoro-N-(1-(3-hydroxyazetidin-1-yl)butan-2-yl)-N-methylbenzamide;
(S)-4-Chloro-N-(1-(3-hydroxyazetidin-1-yl)butan-2-yl)-N-methylbenzamide;
(S)—N-(1-Cyclobutyl-2-(3-hydroxyazetidin-1-yl)ethyl)-4-fluoro-N-methylbenzamide;
(S)-4-Chloro-N-(1-cyclobutyl-2-(3-hydroxyazetidin-1-yl)ethyl)-N-methylbenzamide;
(S)—N-(1-Cyclobutyl-2-(3-hydroxyazetidin-1-yl)ethyl)-3-(difluoromethyl)-N-methylbenzamide;
(S)—N-(1-Cyclobutyl-2-(3-hydroxyazetidin-1-yl)ethyl)-4-fluoro-N,3-dimethylbenzamide
(S)-4-Chloro-N-(1-(3-hydroxyazetidin-1-yl)propan-2-yl)-N-methylbenzamide;
(S)—N-(1-(3-Hydroxyazetidin-1-yl)propan-2-yl)-N,3,4-trimethylbenzamide;
(S)-4-Chloro-3-fluoro-N-(1-(3-hydroxyazetidin-1-yl)propan-2-yl)-N-methylbenzamide;
(S)-4-Chloro-N-(1-(3-hydroxyazetidin-1-yl)propan-2-yl)-N,3-dimethylbenzamide;
(S)-4-Bromo-N-(1-(3-hydroxyazetidin-1-yl)propan-2-yl)-N-methylbenzamide;
(S)-4-Bromo-N-(1-(3-hydroxyazetidin-1-yl)butan-2-yl)-N-methylbenzamide;
4-Chloro-N—((S)-1-((2S,3R)-3-hydroxy-2-methylazetidin-1-yl)pentan-2-yl)-N-methylbenzamide;
4-Chloro-N—((S)-1-((2R,3S)-3-hydroxy-2-methylazetidin-1-yl)pentan-2-yl)-N-methylbenzamide;
4-Fluoro-N—((S)-1-((2R*,3S*)-3-hydroxy-2-methylazetidin-1-yl)pentan-2-yl)-N-methylbenzamide;
3,4-Difluoro-N—(S)-1-((2R*,3S*)-3-hydroxy-2-methylazetidin-1-yl)pentan-2-yl)-N-methylbenzamide;
4-Chloro-N—((S)-1-((2S,3S)-3-hydroxy-2-methylazetidin-1-yl)pentan-2-yl)-N-methylbenzamide;
4-Chloro-N—((S)-1-((2R,3R)-3-hydroxy-2-methylazetidin-1-yl)pentan-2-yl)-N-methylbenzamide;
3,4-Difluoro-N—((S)-1-((2S,3S)-3-hydroxy-2-methylazetidin-1-yl)pentan-2-yl)-N-methylbenzamide;
3,4-Difluoro-N—((S)-1-((2R,3R)-3-hydroxy-2-methylazetidin-1-yl)pentan-2-yl)-N-methylbenzamide;
4-Fluoro-N—((S)-1-((2S,3S)-3-hydroxy-2-methylazetidin-1-yl)pentan-2-yl)-N-methylbenzamide;

4-Fluoro-N—((S)-1-((2R,3R)-3-hydroxy-2-methylazetidin-1-yl)pentan-2-yl)-N-methylbenzamide;
(S)-4-Chloro-N-(1-(4-hydroxypiperidin-1-yl)pentan-2-yl)-N-methylbenzamide;
(S)-4-Chloro-N-(1-(4-methoxypiperidin-1-yl)pentan-2-yl)-N-methylbenzamide;
4-Cyano-N—((S)-1-((S)-3-hydroxypyrrolidin-1-yl)pentan-2-yl)-N-methylbenzamide;
4-Chloro-N—((S)-1-((S)-3-hydroxypyrrolidin-1-yl)pentan-2-yl)-N-methylbenzamide,
or a pharmaceutically acceptable salt of any of the forgoing compounds. It shall be noted that any one or more of these specific compounds may be disclaimed from any of the herein mentioned embodiments of the invention.

In a further specific embodiment of the invention, the compounds are represented by Formula I, or a pharmaceutically acceptable salt thereof, wherein each optional $R^5$ is independently selected from fluoro, nitrile, hydroxy, $C_{1-3}$ alkyl, cyclopropyl, $C_{1-3}$ alkoxy or $C_{1-3}$ alkoxyalkyl;
$R^1$ is selected from $C_{1-6}$ alkyl, $C_{1-6}$ alkoxyalkyl or $C_{3-6}$ cycloalkyl;
$R^2$ is hydrogen;
$R^3$ is selected from $C_{1-6}$ alkyl, $C_{1-6}$ alkoxyalkyl or $C_{3-6}$ cycloalkyl;
each $R^4$ is independently selected from chloro, fluoro, bromo, nitrile, $C_{1-3}$ alkyl, $C_{1-3}$ alkoxy or $C_{1-3}$ alkylsulfide, wherein
  any alkyl or alkoxy group in these substituents is substituted by 0, 1, 2 or 3 substituents independently selected from fluoro or nitrile;
M is selected from 1, 2 or 3;
n is 1;
y is selected from 0, 1 or 2; and
x is selected from 1 or 2.

In a still further specific embodiment of the invention, the compounds are represented is by Formula I, or a pharmaceutically acceptable salt thereof, wherein $R^5$ is hydroxy;
$R^1$ is selected from $C_{1-6}$ alkyl, $C_{1-6}$ alkoxyalkyl or $C_{3-6}$ cycloalkyl;
$R^2$ is hydrogen;
$R^3$ is selected from $C_{1-6}$ alkyl, $C_{1-6}$ alkoxyalkyl or $C_{3-6}$ cycloalkyl;
each $R^4$ is independently selected from chloro, fluoro, bromo, nitrile, methyl, difluoromethyl, trifluoromethyl, methoxy, hydroxy, difluoromethoxy, trifluoromethoxy or methylsulfide;
m is 1 (thus forming azetidinyl);
n is 1;
y is selected from 0, 1 or 2; and
x is selected from 1 or 2.

In a still further specific embodiment of the invention, the compounds are represented by Formula Ic, or a pharmaceutically acceptable salt thereof, wherein

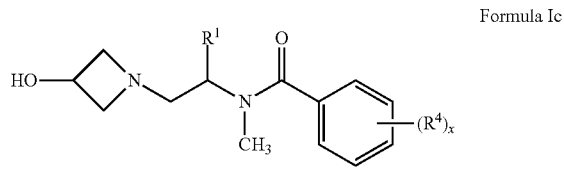

Formula Ic $R^1$ is selected from $C_{1-6}$ alkyl, $C_{1-6}$ alkoxyalkyl or $C_{3-6}$ cycloalkyl;

each $R^4$ is independently selected from chloro, fluoro, bromo, nitrile, methyl, difluoromethyl, trifluoromethyl or methoxy, in particular chloro, fluoro, bromo, nitrile or methyl; and
x is selected from 0, 1 or 2.

In a further specific embodiment of the invention, the compounds are represented by Formula Ic, or a pharmaceutically acceptable salt thereof, wherein
$R^1$ is selected from $C_{2-4}$ alkyl or $C_{3-6}$ cycloalkyl, such as ethyl, propyl, isopropyl, butyl, 1-methyl-propyl, 2-methyl-propyl, cyclopropyl, cyclobutyl, cyclopentyl or cyclohexyl;
each $R^4$ is independently selected from chloro, fluoro, bromo, nitrile, methyl, difluoromethyl, trifluoromethyl or methoxy; and
x is selected from 0, 1 or 2.

In a more specific embodiment of the invention, the compounds are represented by Formula Ic, or a pharmaceutically acceptable salt thereof, wherein
$R^1$ is selected from $C_{2-4}$ alkyl or $C_{3-6}$ cycloalkyl, such as ethyl, propyl, isopropyl, butyl, 1-methyl-propyl, 2-methyl-propyl, cyclopropyl, cyclobutyl, cyclopentyl or cyclohexyl;
each $R^4$ is independently selected from chloro, fluoro, bromo, nitrile or methyl; and
x is selected from 1 or 2.

In a further specific embodiment of the invention, the compounds are represented by Formula Id, or a pharmaceutically acceptable salt thereof, wherein

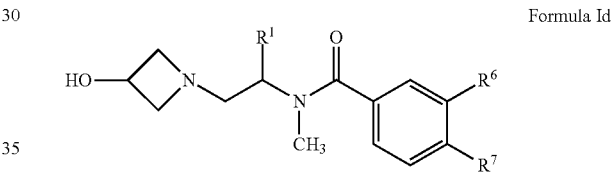

Formula Id $R^1$ is selected from ethyl, propyl, isopropyl, butyl, 1-methyl-propyl, 2-methyl-propyl, cyclopropyl, cyclobutyl, cyclopentyl or cyclohexyl;
$R^6$ is selected from hydrogen, chloro, fluoro or methyl; and
$R^7$ is selected from chloro, fluoro, bromo, nitrile or methyl, in particular chloro, fluoro, bromo or nitrile.

Examples of specific compounds according to Formula Id of the invention are:
4-Bromo-N-(1-cyclopropyl-2-(3-hydroxyazetidin-1-yl)ethyl)-N-methylbenzamide;
4-Fluoro-N-(1-(3-hydroxyazetidin-1-yl)-3-methylbutan-2-yl)-N,3-dimethylbenzamide;
4-Chloro-N-(1-(3-hydroxyazetidin-1-yl)-3-methylbutan-2-yl)-N-methylbenzamide;
4-Bromo-N-(1-(3-hydroxyazetidin-1-yl)-3-methylbutan-2-yl)-N-methylbenzamide;
N-(1-Cyclopropyl-2-(3-hydroxyazetidin-1-yl)ethyl)-4-fluoro-N,3-dimethylbenzamide;
4-Chloro-N-(1-cyclopropyl-2-(3-hydroxyazetidin-1-yl)ethyl)-N-methylbenzamide;
3-Chloro-N-(1-cyclopropyl-2-(3-hydroxyazetidin-1-yl)ethyl)-4-fluoro-N-methylbenzamide;
N-(1-Cyclopropyl-2-(3-hydroxyazetidin-1-yl)ethyl)-4-fluoro-N-methylbenzamide;
3,4-Difluoro-N-(1-(3-hydroxyazetidin-1-yl)pentan-2-yl)-N-methylbenzamide;
4-Chloro-N-(1-(3-hydroxyazetidin-1-yl)pentan-2-yl)-N-methylbenzamide;
3-Chloro-4-fluoro-N-(1-(3-hydroxyazetidin-1-yl)pentan-2-yl)-N-methylbenzamide;

4-Chloro-N-(1-(3-hydroxyazetidin-1-yl)pentan-2-yl)-N,3-dimethylbenzamide;
4-Fluoro-N-(1-(3-hydroxyazetidin-1-yl)pentan-2-yl)-N-methylbenzamide;
4-Bromo-N-(1-(3-hydroxyazetidin-1-yl)pentan-2-yl)-N-methylbenzamide;
4-Cyano-N-(1-(3-hydroxyazetidin-1-yl)pentan-2-yl)-N-methylbenzamide;
4-Fluoro-N-(1-(3-hydroxyazetidin-1-yl)pentan-2-yl)-N,3-dimethylbenzamide;
4-Fluoro-N-(1-(3-hydroxyazetidin-1-yl)butan-2-yl)-N,3-dimethylbenzamide;
N-(1-Cyclopropyl-2-(3-hydroxyazetidin-1-yl)ethyl)-3,4-difluoro-N-methylbenzamide;
N-(1-(3-Hydroxyazetidin-1-yl)pentan-2-yl)-N,3,4-trimethylbenzamide;
3,4-Difluoro-N-(1-(3-hydroxyazetidin-1-yl)-3-methylpentan-2-yl)-N-methylbenzamide;
4-Chloro-N-(1-(3-hydroxyazetidin-1-yl)-3-methylpentan-2-yl)-N-methylbenzamide;
4-Cyano-N-(1-(3-hydroxyazetidin-1-yl)-3-methylpentan-2-yl)-N-methylbenzamide;
N-(1-Cyclopentyl-2-(3-hydroxyazetidin-1-yl)ethyl)-3,4-difluoro-N-methylbenzamide;
4-chloro-N-[1-cyclopentyl-2-(3-hydroxyazetidin-1-yl)ethyl]-N-methylbenzamide;
N-[1-cyclopentyl-2-(3-hydroxyazetidin-1-yl)ethyl]-4-fluoro-N,3-dimethylbenzamide;
4-cyano-N-[1-cyclopentyl-2-(3-hydroxyazetidin-1-yl)ethyl]-N-methylbenzamide;
3-chloro-N-[1-cyclopentyl-2-(3-hydroxyazetidin-1-yl)ethyl]-4-fluoro-N-methylbenzamide;
4-chloro-N-(1-(3-hydroxyazetidin-1-yl)hexan-2-yl)-N-methylbenzamide;
3,4-Difluoro-N-[1-(3-hydroxyazetidin-1-yl)hexan-2-yl]-N-methylbenzamide;
4-Cyano-N-[1-(3-hydroxyazetidin-1-yl)hexan-2-yl]-N-methylbenzamide;
4-Fluoro-N-[1-(3-hydroxyazetidin-1-yl)hexan-2-yl]-N-methylbenzamide;
3-Chloro-4-fluoro-N-[1-(3-hydroxyazetidin-1-yl)hexan-2-yl]-N-methylbenzamide;
4-Chloro-N-[1-cyclobutyl-2-(3-hydroxyazetidin-1-yl)ethyl]-N-methylbenzamide;
4-Cyano-N-[1-cyclobutyl-2-(3-hydroxyazetidin-1-yl)ethyl]-N-methylbenzamide;
N-[1-Cyclobutyl-2-(3-hydroxyazetidin-1-yl)ethyl]-4-fluoro-N,3-dimethylbenzamide;
N-[1-Cyclobutyl-2-(3-hydroxyazetidin-1-yl)ethyl]-4-fluoro-N-methylbenzamide;
N-[1-Cyclobutyl-2-(3-hydroxyazetidin-1-yl)ethyl]-3,4-difluoro-N-methylbenzamide;
4-cyano-N-[1-cyclohexyl-2-(3-hydroxyazetidin-1-yl)ethyl]-N-methylbenzamide;
4-Chloro-N-[1-cyclohexyl-2-(3-hydroxyazetidin-1-yl)ethyl]-N-methylbenzamide;
N-[1-Cyclohexyl-2-(3-hydroxyazetidin-1-yl)ethyl]-4-fluoro-N-methylbenzamide;
4-Chloro-N-[1-(3-hydroxyazetidin-1-yl)pentan-2-yl]-N-methylbenzamide;
3,4-Difluoro-N-[1-(3-hydroxyazetidin-1-yl)-4-methylpentan-2-yl]-N-methylbenzamide;
4-Chloro-N-[1-(3-hydroxyazetidin-1-yl)-4-methylpentan-2-yl]-N-methylbenzamide;
4-Cyano-N-(1-cyclobutyl-2-(3-hydroxyazetidin-1-yl)ethyl)-N-methylbenzamide;
N-(1-Cyclobutyl-2-(3-hydroxyazetidin-1-yl)ethyl)-3,4-difluoro-N-methylbenzamide;
4-Chloro-3-fluoro-N-(1-(3-hydroxyazetidin-1-yl)butan-2-yl)-N-methylbenzamide;
4-Chloro-N-(1-(3-hydroxyazetidin-1-yl)butan-2-yl)-N-methylbenzamide;
N-(1-Cyclobutyl-2-(3-hydroxyazetidin-1-yl)ethyl)-4-fluoro-N-methylbenzamide;
4-Chloro-N-(1-cyclobutyl-2-(3-hydroxyazetidin-1-yl)ethyl)-N-methylbenzamide;
N-(1-Cyclobutyl-2-(3-hydroxyazetidin-1-yl)ethyl)-4-fluoro-N,3-dimethylbenzamide;
4-Bromo-N-(1-(3-hydroxyazetidin-1-yl)butan-2-yl)-N-methylbenzamide;
or a pharmaceutically acceptable salt of any of the foregoing compounds.

In a further specific embodiment of the invention, the compounds are represented by Formula Id, or a pharmaceutically acceptable salt thereof, wherein
$R^1$ is selected from ethyl, propyl, isopropyl, cyclopropyl or cyclobutyl;
$R^6$ is selected from hydrogen, chloro, fluoro or methyl; and
$R^7$ is selected from chloro, fluoro, bromo or nitrile.

In a still further specific embodiment of the invention, the compounds are represented by Formula Ie, or a pharmaceutically acceptable salt thereof, wherein

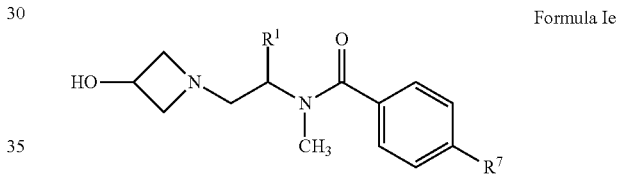

Formula Ie $R^1$ is selected from ethyl, propyl, isopropyl, butyl, 1-methyl-propyl, 2-methyl-propyl, cyclopropyl, cyclobutyl, cyclopentyl or cyclohexyl, in particular ethyl, propyl, isopropyl, cyclopropyl or cyclobutyl; and
$R^7$ is selected from chloro, fluoro, bromo, nitrile or methyl.

In a still further specific embodiment of the invention, the compounds are represented by Formula Ie, or a pharmaceutically acceptable salt thereof, wherein
$R^1$ is selected from ethyl, propyl, isopropyl, butyl, 1-methyl-propyl, 2-methyl-propyl, in particular ethyl, propyl or isopropyl; and
$R^7$ is selected from chloro, fluoro, bromo or nitrile.

In a still further specific embodiment of the invention, the compounds are represented by Formula Ie, or a pharmaceutically acceptable salt thereof, wherein
$R^1$ is selected from cyclopropyl, cyclobutyl, cyclopentyl or cyclohexyl, in particular cyclopropyl or cyclobutyl; and
$R^7$ is selected from chloro, fluoro, bromo or nitrile.

It shall be understood that as used herein all references to compounds according to the invention, including a specific chemical formula or name, are intended to include all pharmaceutically acceptable salts, co-crystals, solvates, hydrates, polymorphs, stereoisomers, and tautomeric isomers thereof.

The following definitions shall apply throughout the specification and the appended claims.

As used herein "pharmaceutically acceptable salt", where such salts are possible, includes salts prepared from pharmaceutically acceptable non-toxic inorganic or organic bases or acids, i.e. pharmaceutically acceptable acid and base addition salts (see "Handbook of Pharmaceutical Salts: Properties, Selection and Use", P. H. Stahl, P. G. Wermuth, IUPAC, Wiley-VCH, 2002).

Acid addition salts are formed from inorganic or organic acids. Examples of suitable non-toxic acid addition salts are acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Hemisalts of the acids may also be formed, for example, hemisulphate.

Base-addition salts are formed from inorganic or organic bases. Examples of suitable non-toxic base-addition salts are salts derived from aluminum, ammonium, calcium, copper, ferric, ferrous, lithium, magnesium, manganic salts, manganous, potassium, sodium, zinc, primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, TEA, trimethylamine, tripropylamine, and tromethamine.

In a salt, proton transfer occurs between the compound of Formula I and the counter ion of the salt. However, in some cases there is no or only partial proton transfer and the solid is therefore not a true salt. It is accepted that the proton transfer is in fact a continuum, and can change with temperature, and therefore the point at which a salt is better described as a "co-crystal" may be subjective. The term "co-crystal" as used herein refers to a multicomponent system in which there exist a host API (active pharmaceutical ingredient) molecule or molecules and a guest (or co-former) molecule or molecules. The guest or co-former is defined as existing as a solid at room temperature in order to distinguish the co-crystal from solvates (including hydrates). However, a co-crystal may itself form solvates (including hydrates). In a co-crystal there is generally predominance for interaction through non-ionic forces such as hydrogen bonding.

It is also to be understood that certain compounds of the Formula I can exist in solvated forms, including solvates of the free compounds or solvates of a salt of the compound, as well as unsolvated forms.

The term "solvate" is used herein to describe a molecular complex comprising the compound of the invention and one or more pharmaceutically acceptable solvent molecules, for example, ethanol. The term "hydrate" is employed when said solvent is water.

The compounds of the invention may exist in a continuum of solid states ranging from fully amorphous to fully crystalline. Thus, it is to be understood that all polymorphs, including mixtures of different polymorphs, are included within the scope of the claimed compounds.

Throughout the specification and the appended claims, a given chemical formula or name shall encompass, where possible, all stereoisomers and tautomeric isomers thereof, including compounds exhibiting more than one type of isomerism, and mixtures of one or more thereof.

The compounds of the invention include, where possible, all stereoisomers, such as diastereomers (including cis-trans isomers, formerly called 'geometric isomers'), enantiomers (optical isomers), including racemates as well as mixtures in different proportions of the separate enantiomers, and conformational isomers (including rotamers). Stereoisomers may be separated using conventional techniques, e.g. chromatography or fractional crystallisation. The enantiomers may be isolated by separation of racemate for example by fractional crystallisation with a chiral counterion, resolution or chiral HPLC. The diastereomers may be isolated by separation of isomer mixtures for instance by fractional crystallisation, fractional salt crystallisation, chiral HPLC and/or achiral HPLC or flash chromatography. Alternatively the stereoisomers may be made by chiral synthesis from chiral starting materials under conditions that will not cause racemisation or epimerisation, or by derivatisation, with a chiral reagent.

The compounds of the invention also include, where possible, all tautomeric isomers thereof, such as prototropic tautomerism (e.g. hydroxypyridine—pyridone, ketone—enol, amide—imidic acid, amine—imine), annular tautomerism, ring-chain tautomerism and valence tautomerism.

The compounds of the invention also encompasses isotopically-labelled compounds of Formula I wherein one or more atoms are replaced by atoms having the same atomic number, but an atomic mass or mass number different from the atomic mass or mass number usually found in nature. Examples of isotopes that can be incorporated include isotopes of hydrogen, carbon, nitrogen and oxygen, such as $^2$H, $^3$H, $^{14}$C, $^{13}$C, $^{11}$C, $^{15}$N, $^{18}$O, $^{17}$O or $^{19}$F. The invention also encompasses the use of these isotopically labelled compounds for pharmacological and metabolic studies. Without being bound by any theory, substitution with heavier isotopes, such as substitution of one or more hydrogen atoms with deuterium ($^2$H), might provide pharmacological advantages in some instances, such as increased metabolic stability.

In addition, compounds of Formula I may be administered in the form of a prodrug. A prodrug is a compound, which may have little or no pharmacological activity itself, but when such a compound is administered into or onto the body, it is converted into a compound of Formula I having the desired activity. Various prodrugs are known within the art (see Rautio et al, "Prodrugs: design and clinical applications", Nature Reviews, Drug Discovery, 255, vol 7, March 2008).

Also included within the scope of the invention are metabolites of compounds of Formula I, that is compounds formed in vivo upon administration of the drug.

As used herein, the term "leaving group" refers to a moiety that can be displaced by another moiety, such as by nucleophilic attack, during a chemical reaction. Leaving groups are well known in the art and include, for example, halogen, hydroxy, alkoxy, —O(C=O)$R_a$, —OSO$_2$—$R_b$, and —OSi($R_c$)$_3$ wherein $R_a$ can be $C_{1-8}$ alkyl, $C_{3-7}$ cycloalkyl, aryl, heteroaryl, or heterocycloalkyl, wherein $R_b$ can be $C_{1-8}$ alkyl, aryl, or heteroaryl, and wherein $R_c$ can be $C_{1-8}$ alkyl. Examples of leaving groups include, but are not limited to, fluoro, chloro, bromo, 4-nitrophenyloxy, mesylate, tosylate, trimethylsilyloxy, and the like.

As used herein, the terms "treating", "treat", or "treatment" are intended to embrace therapeutic (curative), prophylactic (preventing), controlling and palliative treatment of the indicated diseases, disorders and/or conditions.

As used herein, the term "IC$_{50}$" refers to the effectiveness of a compound in inhibiting a biological or biochemical function. $IC_{50}$ represents the concentration of a drug that is required for 50% inhibition in vitro.

As used herein, the term "pharmacologically effective amount" (including "therapeutically effective amount") means an amount of a compound or pharmaceutical composition according to the invention that is sufficient to induce the desired therapeutic or biological effect.

As used herein, the term "alkyl" means a straight or branched chain saturated aliphatic hydrocarbon group. $C_{1-6}$ alkyl means an alkyl having from 1 to 6 carbon atoms. Non-limiting examples of $C_{1-6}$ alkyl are methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, iso-butyl, t-butyl, pentyl, iso-pentyl, neo-pentyl, hexyl, isohexyl and the like.

As used herein, the term "cycloalkyl" represents a saturated monocyclic aliphatic ring system containing from 3 to 7 ring carbon atoms. Examples of 3 to 6-membered cycloalkyl include, but are not limited to cyclopropyl, cyclobutyl, cyclohexyl, and cyclopentyl.

As used herein, the term "alkoxy" denotes —O-alkyl wherein alkyl is as defined above. $C_{1-6}$ alkoxy includes an alkyl having from 1 to 6 carbon atoms. Non-limiting examples of $C_{1-6}$ alkoxy are methoxy, ethoxy, n-propyloxy, iso-propyloxy, 2-methyl-1-propyloxy, 2-methyl-2-propyloxy, 2-methyl-1-butyloxy, 3-methyl-1-butyloxy, 2-methyl-3-butyloxy, 2,2-dimethyl-1-propyloxy, 2-methyl-1-pentyloxy, 3-methyl-1-pentyloxy, 4-methyl-1-pentyloxy, 2-methyl-2-pentyloxy, 3-methyl-2-pentyloxy, 4-methyl-2-pentyloxy, 2,2-dimethyl-1-butyloxy, 3,3-dimethyl-1-butyloxy, 2-ethyl-1-butyloxy, butyloxy, iso-butyloxy, t-butyloxy, pentyloxy, iso-pentyloxy, neo-pentyloxy, hexyloxy, and the like.

As used herein, the term "alkoxyalkyl" means -alkyl-O-alkyl, wherein alkyl is as defined above. $C_{1-6}$ alkoxyalkyl includes a total of from 1 to 6 carbon atoms.

As used herein, the term "alkylsulfide" denotes —S-alkyl, wherein alkyl is as defined above. $C_{1-3}$ alkylsulfide includes an alkyl having from 1 to 3 carbon atoms. Non-limiting examples of $C_{1-3}$ alkylsulfide are methylsulfide, ethylsulfide and propylsulfide.

As used herein, the term "halo" refers to fluoro, chloro, bromo and iodo.

As used herein, the term "hydroxy" refers to —OH.

As used herein, the term "carboxy" refers to —COOH.

As used herein, the term "nitrile" (sometimes also called "cyano") refers to —CN.

As used herein, the term "oxo" refers to =O.

Unless otherwise indicated, the term "substituted" means substituted by one or more defined groups.

As used herein, the term "protecting group" means temporary substituents which protect a potentially reactive functional group from undesired chemical transformations. Protecting groups may also be used to obtain a certain selectivity in a reaction. Examples of such protecting groups include esters of carboxylic acids, silyl ethers of alcohols, and acetals and ketals of aldehydes and ketones respectively (see "Protective Groups in Organic Synthesis", 4th edition, T. W. Greene & P. G. M Wutz, Wiley-Interscience (2007)). The protecting groups may be removed at any convenient stage in the synthesis using conventional techniques well known in the art.

Certain of the above defined terms may occur more than once in the formulae herein and upon such occurrence each term shall be defined independently of the other.

Pharmacological Properties

Compounds of Formula I have been found to exhibit potassium channel inhibiting activity, especially inhibiting activity of the acetylcholine operated inward rectifying potassium channel, for example as demonstrated in the test described below. In particular, compounds of Formula I are believed to be useful in treating cardiac arrhythmias, in particular supraventricular tacharrhythmias, such as atrial fibrillation and atrial flutter, and therewith associated complications (e.g. congestive heart failure, ventricular fibrillation, and thromboembolic events).

According to a further aspect of the invention, there is provided a compound of Formula I as previously defined for use as a medicament.

In another aspect, the invention provides the use of a compound of Formula I for treatment of cardiac arrhythmias and therewith associated complications.

In a further aspect, the invention provides the use of a compound of Formula I in the preparation of a medicament for treatment of cardiac arrhythmias, and more specifically supraventricular tacharrhythmias, such as atrial fibrillation and atrial flutter, and therewith associated complications, such as congestive heart failure, ventricular fibrillation, and thromboembolic events.

In a still further aspect, the invention provides a method of treating diseases, disorders and/or conditions which is affected and/or mediated (fully or partially) by IKACh and where treatment by IKACh blockade is beneficial, in particular cardiac arrhythmias and therewith associated complications, comprising administering a pharmacologically effective amount of a compound of Formula I to a patient in need thereof.

It is believed that compounds of Formula I may possess satisfactory pharmacological profile and promising biopharmaceutical properties, such as toxicological profile, metabolism and pharmacokinetic properties, solubility, and permeability, in particular for providing a satisfactory bioavailability upon oral administration of a pharmacologically effective amount of the compound. It will be understood that determination of appropriate biopharmaceutical properties is within the knowledge of a person skilled in the art.

It is further believed that compounds of Formula I may also possess satisfactory selectivity profile over other ion channels as exemplified by, but not limited to, Nav1.2, Nav1.3, Nav1.7, Nav1.5, Kv1.5, hERG, Kv4.3, KvLQT1, Cav1.2, Cav3.2 and HCN4.

Pharmaceutical Compositions

The compounds of the invention can be administered to a non-human or human mammal, in particular man, via any route possible, such as the oral, topical, intradermal, transdermal, parenteral (including intravenous, intraarterial, intraperitoneal, intrathecal, intraventricular, intraurethral, intrasternal, intracranial, intramuscular, intrasynovial and subcutaneous), ocular (ophthalmic), buccal, lingual, sublingual, rectal, vaginal, pulmonary (nasal or buccal inhalation) and/or intranasal route, in the form of a pharmaceutical composition comprising (a pharmacologically effective amount of) the active compound according to the invention and one or more pharmaceutically acceptable carrier.

When formulated with a pharmaceutically acceptable carrier, the compound of the invention may be present in the pharmaceutical composition in a concentration from 0.1 to 99.5%, such as from 0.5 to 95%, by weight of the total composition.

The choice of carrier is within the knowledge of a person skilled in the art and depends on, for instance, the mode of administration, the dosage form, and the physical properties of the active compound, such as solubility and stability. The term "carrier" as used herein relates to a therapeutically inactive ingredient.

The dosage form may be a solid, semi-solid or liquid system. The formulation may be an immediate and/or modified release, including delayed-, sustained-, pulsed-, controlled-, targeted and programmed release formulation.

Examples of dosage forms are tablets, pills, troches, powders, granules, dispersions, suspensions, solutions, capsules (containing particulates, powders, or liquids), gels, creams, lotions, ointments, aerosols, suppository, pessary, enema, and the like. Since tablets, pills and capsules are easy to administer, these dosage forms generally represent the most advantageous oral delivery forms.

Examples of carriers are pharmaceutically acceptable diluents, bulking agents, binders, disintegrating agents, lubricants, anti-oxidants, preservatives, coatings, surface active agents, sweetening and flavoring agents, taste-masking agents, colorants, emollients, anti-foaming agents, adjuvants, enhancers, and other excipients.

Thus, according to a further aspect of the invention there is also provided a pharmaceutical composition comprising a compound of Formula I as an active therapeutic ingredient and a pharmaceutically acceptable carrier. The composition of the invention may optionally also contain one or more other therapeutic ingredients as described hereinafter.

The compositions of the invention may be administered at varying doses of active compound depending upon the particular compound employed, the route of administration, the patient (including weight, sex, health condition, and diet), drug mixing, and the condition being treated and the severity thereof.

Suitable doses of the compounds of the invention in the treatment of humans are believed to be from about 0.001 to about 1000 mg/kg, such as from about 0.01 to about 100 mg/kg, body weight, given in a single dose or in divided daily doses. The dosage regimen may be adjusted to provide the optimal therapeutic response.

Combination Therapy

One or more compounds of the invention may be combined with at least one other pharmacologically active agent that is useful in the treatment of cardiac arrhythmias and/or any other cardiovascular disorders.

According to an additional aspect of the invention there is provided a combination treatment comprising the administration of a pharmacologically effective amount of a compound of Formula I, or a pharmaceutically acceptable salt thereof, optionally together with a pharmaceutically acceptable diluent or carrier, with the simultaneous, sequential or separate administration of one or more of the following agents:

any other antiarrhythmic agent, such as Class I agents (e.g. quinidine, lidocaine, and propafenone), Class II agents (e.g. propranolol), Class III agents (e.g. sotalol, dofetilide, amiodarone, dronedarone, budiodarone, azimilide and ibutilide), Class IV agents (e.g. diltiazem and verapamil), "Class V agents" (e.g. adenosine), and cardiac glycosides (e.g. digitalis and ouabain);

haemostasis modulators, including antithrombotics such as activators of fibrinolysis; thrombin inhibitors; factor VIIa inhibitors; anticoagulants, such as vitamin K antagonists (e.g. warfarin), heparin and low molecular weight analogues thereof (e.g. dalteparin), factor Xa inhibitors (e.g. rivaroxaban and apixaban), and direct thrombin inhibitors (e.g. argatroban); antiplatelet agents, such as cyclooxygenase inhibitors (e.g. aspirin and NSAIDs), adenosine diphosphate (ADP) receptor inhibitors (e.g. clopidogrel), phosphodiesterase inhibitors (e.g. cilostazol), glycoprotein IIB/IIA inhibitors (e.g. tirofiban), and adenosine reuptake inhibitors (e.g. dipyridamole);

anti-dyslipidemia agents, such as HMG-CoA reductase inhibitors (statins) and other cholesterol-lowering agents; PPARα agonists (fibrates, e.g. gemfibrozil and fenofibrate); bile acid sequestrants (e.g. cholestyramine); cholesterol absorption inhibitors (e.g. plant sterols (i.e. phytosterols), synthetic inhibitors); cholesteryl ester transfer protein (CETP) inhibitors; inhibitors of the ileal bile acid transport system (IBAT inhibitors); bile acid binding resins; nicotinic acid (niacin) and analogues thereof; anti-oxidants; and omega-3 fatty acids;

antihypertensive agents, including adrenergic receptor antagonists, such as beta blockers (e.g. atenolol), alpha blockers (e.g. doxazosin), and mixed alpha/beta blockers (e.g. labetalol); adrenergic receptor agonists, including alpha-2 agonists (e.g. clonidine); angiotensin converting enzyme (ACE) inhibitors (e.g. lisinopril), calcium channel blockers, such as dihydropyridines (e.g. nifedipine), phenylalkylamines (e.g. verapamil), and benzothiazepines (e.g. diltiazem); angiotensin II receptor antagonists (e.g. losartan); aldosterone receptor antagonists (e.g. eplerenone); centrally acting adrenergic drugs, such as central alpha agonists (e.g. clonidine); and diuretic agents (e.g. furosemide);

anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyltransferase (DGAT) inhibitors, and cannabinoid (CB1) receptor antagonists (e.g. rimonabant);

insulin and insulin analogues;

insulin secretagogues, including sulphonylureas (e.g. glipizide) and prandial glucose regulators (sometimes called "short-acting secretagogues"), such as meglitinides (e.g. repaglinide and nateglinide);

agents that improve incretin action, for example dipeptidyl peptidase IV (DPP-4) inhibitors (e.g. vildagliptin, and sitagliptin), and glucagon-like peptide-1 (GLP-1) agonists (e.g. exenatide);

insulin sensitising agents including peroxisome proliferator activated receptor gamma (PPARγ) agonists, such as thiazolidinediones (e.g. pioglitazone and rosiglitazone), and agents with any combination of PPAR alpha, gamma and delta activity;

agents that modulate hepatic glucose balance, for example biguanides (e.g. metformin), fructose 1,6-bisphosphatase inhibitors, glycogen phopsphorylase inhibitors, glycogen synthase kinase inhibitors, and glucokinase activators;

agents designed to reduce/slow the absorption of glucose from the intestine, such as alpha-glucosidase inhibitors (e.g. miglitol and acarbose);

agents which antagonise the actions of or reduce secretion of glucagon, such as amylin analogues (e.g. pramlintide);

agents that prevent the reabsorption of glucose by the kidney, such as sodium-dependent glucose transporter 2 (SGLT-2) inhibitors;

or a pharmaceutically acceptable salt, solvate, solvate of such a salt or a prodrug thereof, optionally together with a pharmaceutically acceptable carrier to a mammal, such as man, in need of such therapeutic treatment.

In an additional aspect of the invention, there is provided a method of treating cardiac arrhythmias and therewith associated complications in a mammal, such as man, in need of such treatment which comprises administering to said animal a pharmacologically effective amount of a compound of Formula I, or a pharmaceutically acceptable salt thereof, optionally together with a pharmaceutically acceptable carrier, in simultaneous, sequential or separate administration with a pharmacologically effective amount of a compound from one of the other classes of compounds described in this combination section, or a pharmaceutically acceptable salt, solvate, solvate of such a salt or a prodrug thereof, optionally together with a pharmaceutically acceptable carrier.

According to a further aspect of the invention there is provided a pharmaceutical composition which comprises a compound of Formula I, or a pharmaceutically acceptable salt thereof, and a compound from one of the other classes of compounds described in this combination section or a pharmaceutically acceptable salt, solvate, solvate of such a salt or a prodrug thereof, in association with a pharmaceutically acceptable carrier.

According to a further aspect of the present invention there is provided a kit comprising a compound of Formula I, or a pharmaceutically acceptable salt thereof, and a compound from one of the other classes of compounds described in this combination section or a pharmaceutically acceptable salt, solvate, solvate of such a salt or a prodrug thereof.

According to a further aspect of the present invention there is provided a kit comprising:

a) a compound of Formula I, or a pharmaceutically acceptable salt thereof, together with a pharmaceutically acceptable carrier, in a first unit dosage form;

b) a compound from one of the other classes of compounds described in this combination section or a pharmaceutically acceptable salt, solvate, solvate of such a salt or a prodrug thereof, together with a pharmaceutically acceptable carrier, in a second unit dosage form; and c) container means for containing said first and second dosage forms.

According to another aspect of the invention there is provided the use of a compound of the Formula I, or a pharmaceutically acceptable salt thereof, and one of the other compounds described in this combination section, or a pharmaceutically acceptable salt, solvate, solvate of such a salt or a prodrug thereof, (in the manufacture of a medicament for use) in the treatment of cardiac arrhythmias and/or its associated complications in a mammal, such as man.

According to a further aspect of the present invention there is provided a combination treatment comprising the administration of a pharmacologically effective amount of a compound of the Formula I, or a pharmaceutically acceptable salt thereof, optionally together with a pharmaceutically acceptable carrier, with the simultaneous, sequential or separate administration of a pharmacologically effective amount of one of the other compounds described in this combination section, or a pharmaceutically acceptable salt, solvate, solvate of such a salt or a prodrug thereof, optionally together with a pharmaceutically acceptable carrier to a mammal, such as man in need of such therapeutic treatment.

Compounds in the invention can also be administered as the sole active ingredient but in combination with the use of a pacemaker or defribillator device.

Preparation of the Compounds

The compounds of Formula I and their salts can be prepared according to the any one more of procedures of the following schemes and examples or any process known to be applicable to the preparation of chemically related compounds. Those skilled in the art will readily understand that known variations of the conditions and processes of the following preparative procedures can be used to prepare these compounds.

Compounds of Formula I may be prepared by the following processes a1) to a4).

a1) Compounds of Formula If (i.e. compounds according to Formula I wherein $R_3$ is methyl) in which $R_1$, $R_2$, $R_4$ and $R_5$ are defined as above and i is 0 or 1 may be prepared according to Scheme 1.

Scheme 1

II

III

IV

If

Carboxylic acids of Formula II can be transformed into amides of Formula III by reacting with the appropriate amine and a coupling reagent. One skilled in the art understands that there exists a multitude of suitable methods for this type of conversion. In one such method carboxlic acids of Formula II are first activated with a coupling reagent such as TBTU, EDC or HATU, in the presence of a suitable base, for example NMM, DIPEA or TEA in a solvent such as DCM or DMF. The activated acid may then be reacted with the appropriate amine to give amides of Formula III.

Amides of Formula III can be transformed into amines of Formula IV using, for example, a reducing agent such as LAH in a suitable solvent such as THF, dioxane or diethyl ether at either rt or an elevated temperature. Amines of Formula IV may be converted into compounds of Formula If by reacting the amine, carboxylic acid and a coupling reagent such as TBTU, EDC or HATU, in the presence of a base such as NMM, DIPEA or TEA in a solvent such as DCM or DMF. An alternative route to obtain amides of Formula If is via acylation of amines of Formula IV with a suitable acid chloride in the presence of a base, for example NMM, DIPEA or TEA in a solvent such as DCM or DMF.

a2) Compounds of Formula I may also be prepared according to Scheme 2, wherein i represents 0 or 1.

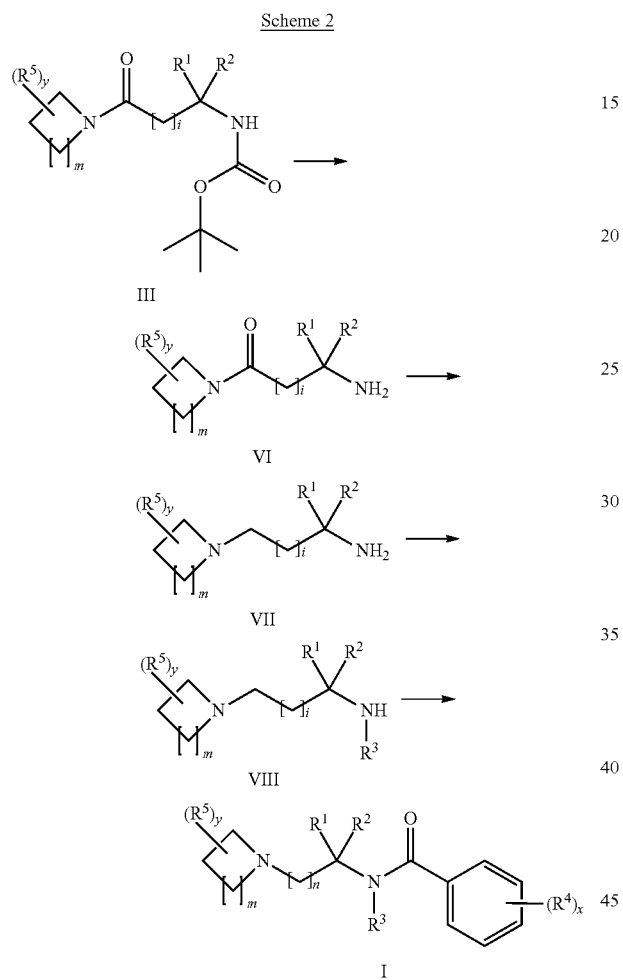

Scheme 2

The t-butoxycarbonyl group of compounds of Formula III may be removed, for example, by treatment with a suitable acid such as hydrochloric, sulphuric or phosphoric acid or TFA to form amines of Formula VI. Compounds of Formula VI can be transformed into amines of Formula VII using, for example, a reducing agent such as LAH in a suitable solvent such as THF, dioxane or diethyl ether at either rt or at an elevated temperature. To convert amines of Formula VII to compounds of Formula VIII, one skilled in the art can understand there exists a large variety of suitable methods for such transformations. For example, reductive amination were the amines of Formula VII are reacted with the appropriate aldehyde in the presence of a suitable reducing agent, for example $NaBH_4$, $NaBH_3CN$ or $NaBH(OCOCH_3)_3$, in the presence or absence of a base or acid may give compounds of Formula VIII. Alternatively, alkylation of amines of Formula VII through treatment with a base, for example TEA, and addition of an appropriate electrophile, for example alkyl halides or acyl halides may give compounds of Formula VIII. Amines of Formula VIII may be transformed into amides of Formula I by reacting the amines with suitable carboxylic acids and a coupling reagent such as TBTU, EDC or HATU, in the presence of a suitable base, for example NMM, DIPEA or TEA in a solvent such as DCM or DMF. An alternative route to obtain amides of Formula I may be through acylation of an amine of Formula VIII with the appropriate acid chloride in the presence of a base, for example NMM, DIPEA or TEA, in a solvent such as DCM or DMF.

a3) Compounds of Formula I may also be prepared according to Scheme 3.

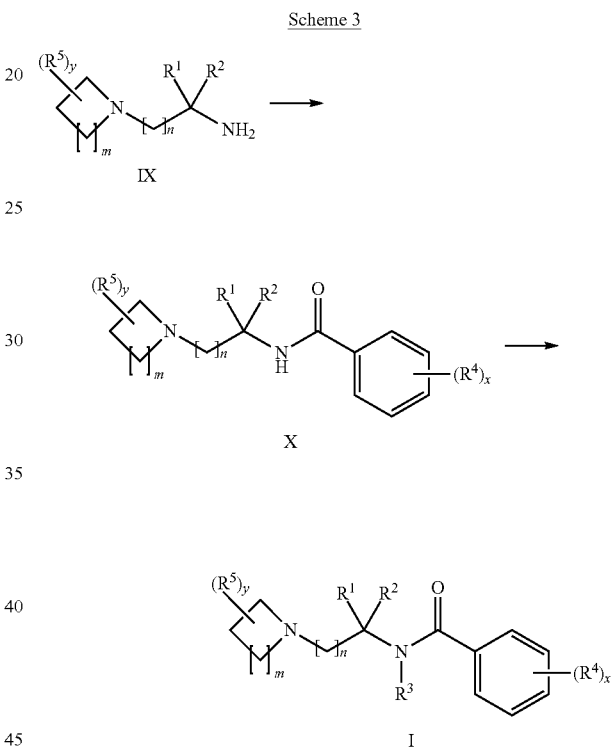

Scheme 3

Those skilled in the art will readily understand that there exists a multitude of suitable methods for the formation of amides of Formula X. Compounds of Formula X can, for example be obtained by reacting amines of Formula IX with the appropriate acid chloride in the presence of a base, for example NMM, DIPEA or TEA in a solvent such as DCM or DMF. Alternatively, amides of Formula X may be formed through activation of the appropriate carboxylic acid with a coupling reagent such as TBTU, EDC or HATU, in the presence of a base such as NMM, DIPEA or TEA in a solvent such as DCM or DMF. The activated acid can then be reacted with a suitable amine (of Formula IX) to form amides of Formula X. Alkylation of amides of Formula X may be performed by treatment with a base, for example NaH, and addition of the appropriate electrophile, for example alkyl halides or acyl halides to give compounds of Formula I.

a4) Compounds of Formula If (i.e. compounds according to Formula I wherein $R_3$ is methyl), wherein i represents 0 or 1, may also be prepared according to Scheme 4.

Scheme 4

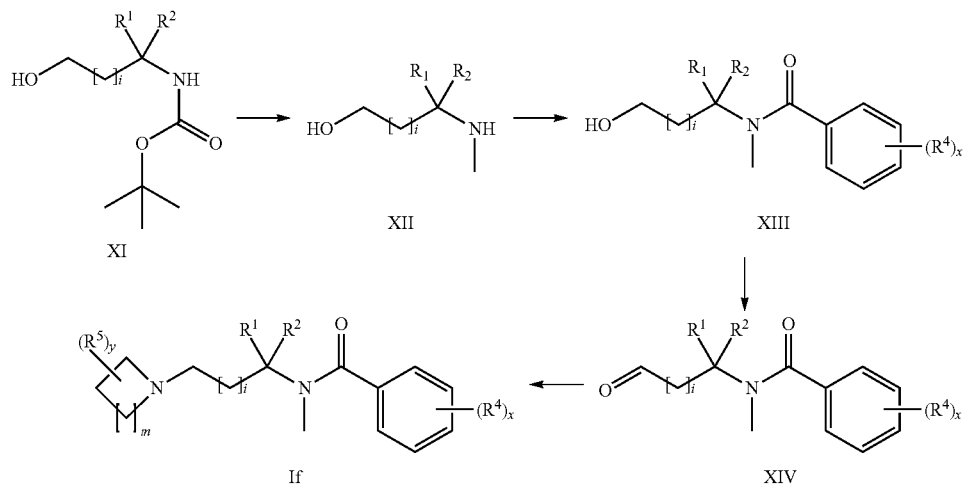

Treatment of amines of Formula XI with a reducing agent such as LAH can in a suitable solvent such as THF, dioxane or diethyl ether at either rt or an elevated temperature give compounds of Formula XII. Compounds of Formula XIII may be obtained by reacting the appropriate amine (Formula XII), carboxylic acid and a coupling reagent such as TBTU, EDC or HATU, in the presence of a base such as NMM, DIPEA or TEA in a solvent such as DCM or DMF. One skilled in the art understands that there exists a multitude of suitable methods for the formation of aldehydes of Formula XIV. In one such method alcohols of Formula XIII may be transformed in to aldehydes of Formula XIV by treatment with Dess-Martin periodinane. An alternative route to obtain aldehydes of Formula XIV may be through Swern oxidation of alcohols of Formula XIII using, for example oxalylchloride or trifluoroacetic anhydride together with DMSO in the presence of a base such as TEA or DIPEA. Reacting the appropriate amine with aldehydes of Formula XIV in the presence of a suitable reducing agent, for example $NaBH_4$, $NaBH_3CN$ or $NaBH(OCOCH_3)_3$, in the presence or absence of a base or acid can give compounds of Formula I.

During the amide formation step in Scheme 1-4, diacylation may occur in reactions where a hydroxyl group are present in the reacting amine. To obtain the monoacylated product hydrolysis of the formed ester may be performed using, for example NaOH in a solvent such as MeOH or $H_2O$.

After completion of any one of processes a1) to a4), if necessary, one or more of the following may be performed:
 converting a compound of Formula I into another compound of Formula I;
 removing any protecting groups, and/or;
 forming a pharmaceutically acceptable salt or a prodrug thereof.

For the avoidance of doubt it is to be understood that where in this specification a group is qualified by "defined as above" the said group encompasses the first occurring and broadest definition as well as each and all of the particular definitions for that group.

The compounds of Formula I prepared by the process of the invention can be converted to its salts by conventional method.

The compounds of the invention and intermediates may be isolated from their reaction mixtures, and if necessary further purified, by using standard technique, for example, chromatography, recrystallization, etc.

Intermediate compounds may also exist in enantiomeric forms and may be used as purified enantiomers, diastereomers, racemates or mixtures.

If not commercially available, the necessary starting materials for the procedures such as those described above may be made by procedures which are selected from standard organic chemical techniques, techniques which are analogous to the synthesis of known, structurally similar compounds, techniques which are described or illustrated in the references given above, or techniques which are analogous to the above described procedure or the procedures described in the examples.

Persons skilled in the art will appreciate that, in order to obtain compounds of the invention in an alternative, and on some occasions, more convenient manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art.

Further features of the invention are the compounds obtainable by the processes disclosed herein.

The naming of compounds in this patent application was made using the software package ACD/Name 10.06 (or 12.01) from ACD/Labs or a Struct=Name Pro 9.0.7 (or 11.0.1 or 11.0.2) software package from Cambridgesoft.

The invention will now be illustrated by means of non-limiting examples, in which the following general experimental procedures were used:
  (i) Phase Separators used in the experimental are ISO-LUTE® Phase Separator Columns.
  (ii) Straight phase flash chromatography was performed using SP1™ Purification System from Biotage™ using normal phase silica FLASH+™ (40M, 25M or 12M) or SNAP™ KP-Sil Cartridges (340, 100, 50 or 10).
  (iii) Purification by preparative reverse-phase HPLC was preformed using one of the following methods:
  (iv) Method A: Purification by preparative reverse-phase HPLC with mass triggered fraction collector, equipped with a XBridge Prep C18 5 μm OBD 150×19 mm column, using a gradient of MeCN in H₂O/MeCN/NH₃ 95/5/0.2, pH 10 as mobile phase.
    Method B: Purification by preparative reverse-phase HPLC using XBridge Prep C18 10 μm OBD 250×19 mm column, using a gradient of MeCN in H₂O/MeCN/NH₃ 95/5/0.2, pH 10 as mobile phase.
    Method C: Purification by preparative reverse-phase HPLC using XBridge Prep C18 10 μm 250×50 mm column, using a gradient of MeCN in H₂O/MeCN/NH₃ 95/5/0.2, pH 10 as mobile phase.
    Method D: Purification by preparative reverse-phase HPLC with mass triggered fraction collector, equipped with a Gemini-NX prep C18 5 μm 110A AXIA 21.2×150 mm column, using a linear gradient of 5-95% MeCN in H₂O/MeCN/NH₃ 95/5/0.2, pH 10 as mobile phase.
    Method E: Purification by preparative reverse-phase HPLC with mass triggered fraction collector, equipped with a Sunfire Prep C18 5 μm OBD 19×150 mm column, using a linear gradient of 5-95% MeCN in H₂O/MeCN/FA 95/5/0.2, pH 3 as mobile phase.
    Method F: Purification by preparative reverse-phase HPLC using Kromasil Prep C8 10 μm OBD 250×20 mm column, using a gradient of MeCN in H₂O/MeCN/HOAc 95/5/0.2, pH 4 as mobile phase.
    Method G: Purification by preparative reverse-phase HPLC using Kromasil Prep C8 10 μm 250×50 mm column, using a gradient of MeCN in H₂O/MeCN/HOAc 95/5/0.2, pH 4 as mobile phase.
  (v) $^1$H NMR measurements were performed on Varian INOVA 400, 500 and 600 spectrometers or Bruker Avance 400, 500 and 600 spectrometers, operating at $^1$H frequencies of 400, 500 and 600 MHz respectively. Chemical shifts are given in ppm with the solvent as internal standard unless noted. Protons on heteroatoms such as NH and OH protons are only reported when detected in NMR. The NMR experiments were performed at a temperature of 25° C.
  (vi) #WET1D experiments: The solutions for the $^1$H NMR spectra are taken from a concentrated sample dissolved in $(CH_3)_2SO$ and are diluted with $(CD_3)_2SO$. Since a substantial amount of $(CH_3)_2SO$ is present in the sample, first a pre-scan is run and analysed to automatically suppress the $(CH_3)_2SO$ (2.54 ppm) and $H_2O$ (3.3 ppm) peaks. This means that the intensity of peaks that reside in these areas around 3.3 ppm and 2.54 ppm is reduced. Furthermore impurities are seen in the spectrum which gives rise to a triplet at 1.12 ppm, a singlet at 2.96 ppm and two multiplets between 2.76-2.70 ppm and 2.61-2.55 ppm. Most probably these impurities are dimethylsulfone and diethylsulfoxide. Because of that some signals from the compound around these frequencies may have been omitted and the omitted area is indicated in the NMR report.
  (vii) Mass spectra were recorded on a Water SQD mass spectormeter equipped with acquity HPLC and an electrospray interface (LC-MS) or LC-MS system consisting of a Waters ZQ or 3100 using a LC-Agilent 1100/1200 LC system.
  (viii) Accurate mass (HRMS) spectral data were obtained using TOF-MS on a Waters LCT, Waters LCTP, Agilent 6530 QTOF system, Waters Xevo QTOF or Waters QTOF Micro.
  (ix) Syringe filter from Advantec MFS Inc. with a pore size of 0.5 μm was used.
  (x) The X-ray diffraction analysis was performed according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-ray Diffraction Procedures, John Wiley & Sons, New York. X-ray powder diffraction data were measured without any internal reference. The X-ray powder diffraction (referred to herein as XRPD) pattern was determined by mounting a sample on a zero background holder, single silicon crystal, and spreading out the sample into a thin layer. Using a Bruker D8 Advance theta-2 theta diffractometer with a Position sensitive detector (PSD), Lynx-Eye, the sample was spun (to improve counting statistics) and irradiated with X-rays generated by a copper tube operated at 30 kV and 50 mA with a wavelength of 1.5406 angstroms. Automatic variable divergence slits were used. The X-ray powder diffraction (XRPD) patterns in this were obtained in Bragg-Brentano geometry. Persons skilled in the art of X-ray powder diffraction will realise that the relative intensity of peaks can be affected by, for example, grains above 30 microns in size and non-unitary aspect ratios that may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures). Generally, a measurement error of a diffraction angle in an X-ray powder diffractogram may be approximately plus or minus 0.2° 2-theta, and such a degree of a measurement error should be taken into account when considering the X-ray powder diffraction data. Furthermore, it should be understood that intensities might fluctuate depending on experimental conditions and sample preparation (e.g. preferred orientation). The following definitions have been used for the relative intensity (%): 81-100%, vs (very strong); 41-80%, str (strong); 21-40%, med (medium); 10-20%, w (weak); 1-9%, vw (very weak).

(xi) Yields, where present, are not necessarily the maximum attainable.
(xii) The following abbreviations are used:
C Celsius
DCE 1,2-dichloroethane
DCM dichloromethane
DIPEA N,N-diisopropylethylamine
DMF N,N'-dimethylformamide
DMSO dimethylsulfoxide
EDC N1-((ethylimino)methylene)-N3,N3-dimethyl-propane-1,3-diamine hydrochloride
Ee enantiomeric excess
ESI electrospray ionization
ES electrospray
EtOAc ethyl acetate
EtOH ethanol
Et$_2$O diethylether
FA formic acid
HATU 2-(7-aza-1H-benzotriazole-1-yl)-1,1,3,3-tetramethyluronium hexafluorophosphate)
HPLC high performance liquid chromatography
HRMS high resolution mass spectrometry
IPA 2-propanol
LAH lithium aluminium hydride
LC liquid chromatography
MeCN acetonitrile
MeI iodomethane
MeOH methanol
M molar
MS mass spectroscopy
MTBE 2-methoxy-2-methylpropane
NMM N-methyl morpholine
NMR nuclear magnetic resonance
TBTU 2-(1H-benzo[d][1,2,3]triazol-1-yl)-1,1,3,3-tetramethyliso uronium tetrafluoroborate
TEA triethylamine
TFA trifluoroacetic acid
THF tetrahydrofuran
TOF time of flight
QTOF quadrupole time of flight
aq aqueous
rt room temperature
h hour(s)
min minutes
br broad
s singlet
d doublet
t triplet
m multiplet
dd double doublet
td triple doublet It will be understood that those chemicals referred to below for which no manufacturing process are disclosed are either common chemicals which are commercially available or may easily be prepared by a person skilled in the art from commercially available chemicals.

Intermediates described hereinafter were used in the Examples below. These intermediates may be prepared by using the reactions described below, but other procedures and reactions may be used as well as appreciated by those skilled in the art.

Compound A1: (S)-Tert-butyl 1-(3-hydroxyazetidin-1-yl)-3-methyl-1-oxobutan-2-ylcarbamate (S)-2-(Tert-butoxycarbonylamino)-3-methylbutanoic acid (30.00 g, 138.08 mmol), which is commercially available, and TBTU (48.8 g, 151.9 mmol) was mixed in DCM (400 mL). The mixture was cooled to 0° C. and NMM (45.5 mL, 414.2 mmol) and DMF (100 mL) was added. After 30 min at rt was azetidin-3-ol hydrochloride (18.15 g, 165.7 mmol) added. The resultant mixture was stirred at rt over night. The mixture was washed with NaHCO$_3$ (saturated, 2×300 mL) and brine (300 mL), filtered through a phase separator and concentrated under reduced pressure to give the title compound (35 g, 93%). The obtained crude product was used without further purification. $^1$H NMR (400 MHz, CD$_3$OD) δ 0.74-1.10, 1.45, 1.67-2.14, 3.58-3.91, 3.92-4.34, 4.37-4.52, 4.52-4.72. Total no of protons: 23. LCMS (M+H)$^+$: 273.

In a similar manner the following compound was synthesized:

| Compound | Name | $^1$H NMR | Yield |
|---|---|---|---|
| A2 | (S)-Tert-butyl 1-(3-hydroxyazetidin-1-yl)-1-oxopentan-2-ylcarbamate | $^1$H NMR (600 MHz, DMSO-d6) δ 0.89-0.96, 1.26-1.62, 3.66-3.80, 3.92-4.24, 4.38-4.44, 4.52-4.63. Total no of protons: 22 | 3.97 g 96% |

Compound B1: (S)-Tert-butyl 2-(azetidin-1-yl)-1-cyclopropyl-2-oxoethylcarbamate (S)-2-(Tert-butoxycarbonylamino)-2-cyclopropylacetic acid (2.0 g, 9.30 mmol), which is commercially available, and NMM (3.07 mL, 27.9 mmol) was mixed in DMF (20 mL). The mixture was cooled to 0° C. and TBTU (3.34 g, 10.42 mmol) was added. After 10 min at rt was azetidine (1.6 mL, 23.7 mmol) added. The resultant mixture was stirred at rt over night. The mixture was concentrated and the residue dissolved in DCM (300 mL). The organic phase was washed with NaHCO$_3$ (saturated, 150 mL) and brine (150 mL), filtered through a phase separator and concentrated under reduced pressure to give the title compound (2.04 g, 86%). The obtained crude product was used without further purification. $^1$H NMR (400 MHz, CD$_3$OD) δ 0.39, 0.44-0.63, 1.09, 1.43, 2.31, 3.84, 3.93-4.46, 5.30. Total no of protons: 22.

In a similar manner the following compound was synthesized:

| Compound | Name | $^1$H NMR | Yield |
|---|---|---|---|
| B2 | (S)-Tert-butyl 1-cyclopropyl-2-(3-cyclopropyl-3-hydroxyazetidin-1-yl)-2-oxoethylcarbamate | $^1$H NMR (400 MHz, CD$_3$OD) δ 0.28-0.68, 1.09, 1.24, 1.43, 3.74-3.84, 3.88, 3.95-4.09, 4.17, 5.25. Total no of protons: 24 | 1.18 g, 82% |
| B3 | Tert-butyl (S)-1-((3R,4R)-3,4-dihydroxypyrrolidin-1-yl)-3-methyl-1-oxobutan-2-ylcarbamate | 1H NMR (400 MHz, CD$_3$OD) δ 0.91-1.02, 1.4-1.49, 1.92-2.04, 3.47-3.6, 3.89-3.95, 4.05-4.17. Total number of protons: 23. | 2.70 g, 97%, 76% pure |

Compound C1: (S)-Tert-butyl 1-(3-hydroxy-3-methylazetidin-1-yl)-3-methyl-1-oxobutan-2-ylcarbamate (S)-2-(Tert-butoxycarbonylamino)-3-methylbutanoic acid (5.30 g, 24.4 mmol), and TBTU (9.40 g, 29.3 mmol) was mixed in DMF (50 mL). To the mixture was NMM (6.70 mL, 60.99 mmol) added. After 30 min at rt was 3-methylazetidin-3-ol hydrochloride (3.01 g, 24.39 mmol) added. The resultant mixture was stirred at rt over night. The mixture was concentrated and the residue dissolved in DCM (200 mL). The organic phase was washed with NaHCO$_3$ (saturated, 2×150 mL) and brine (150 mL), filtered through a phase separator and concentrated under reduced pressure to give the title compound (7.00 g, quant. yield). The obtained crude product was used without further purification. $^1$H NMR (400 MHz, CD$_3$OD) δ 0.76-1.07, 1.31-1.56, 1.78-2.04, 2.55-2.73, 3.64-3.98, 4.04-4.42, 6.52-6.84.

In a similar manner the following compounds were synthesized:

| Compound | Name | $^1$H NMR and LCMS | Yield |
|---|---|---|---|
| C2 | (S)-Tert-butyl 1-cyclopropyl-2-(3-hydroxyazetidin-1-yl)-2-oxoethyl-carbamate | $^1$H NMR (400 MHz, CD$_3$OD) δ 0.16-0.76, 0.92-1.19, 1.20-1.69, 2.44, 3.34-4.80. LCMS (M + H)$^+$: 271. | 7.79 g 89% |
| C3 | (S)-Tert-butyl 1-(3-fluoroazetidin-1-yl)-3-methyl-1-oxobutan-2-yl-carbamate | $^1$H NMR (400 MHz, CD$_3$OD) δ 0.75-1.09, 1.44, 1.80-2.11, 3.56-4.79, 5.14-5.46. Total no of protons: 22. LCMS (M + H)$^+$: 275. | 6.0 g quant. yield |
| C4 | Tert-butyl (S)-1-((3S,4S)-3,4-dihydroxypyrrolidin-1-yl)-3-methyl-1-oxobutan-2-ylcarbamate | Mixture of rotamers: (400 MHz, CD$_3$OD) δ 0.91-1, 1.41-1.49, 1.91-2.01, 3.39-3.45, 3.59-3.66, 3.7-3.83, 4.05-4.15. LCMS (M + H)$^+$: 303. | 208 mg, 75% |

Compound D: (S)-Tert-butyl 1-(azetidin-1-yl)-3-methyl-1-oxobutan-2-ylcarbamate (S)-2-(Tert-butoxycarbonylamino)-3-methylbutanoic acid (50.0 g, 230.1 mmol), EDC hydrochloride (52.9 g, 276.2 mmol) and 1-hydroxypyrrolidine-2,5-dione (39.7 g, 345.2 mmol) was mixed in DCM (180 mL). The mixture was cooled to 0° C. and DIPEA (160 mL, 920.6 mmol) was added. After 1 h at 0° C. was azetidine (18.62 mL, 276.2 mmol) added. The resultant mixture was stirred at rt over night. The mixture was concentrated and the residue dissolved in DCM (200 mL). The organic phase was washed with NaHCO$_3$ (saturated, 2×150 mL), HCl (1M aq. solution, 2×200 mL) and brine (150 mL), filtered through a phase separator and concentrated under reduced pressure to give the title compound (42 g, 71%). The obtained crude product was used without further purification.

$^1$H NMR (400 MHz, CDCl$_3$) δ 0.86, 1.75-1.90, 1.94-2.18, 2.18-2.36, 2.38, 2.99-3.29.

Total no of protons: 19. LCMS (M+H)$^+$: 257.

Compound E: (S)-Tert-butyl 1-(azetidin-1-yl)-1-oxopentan-2-ylcarbamate (S)-2-(Tert-butoxycarbonylamino)pentanoic acid (17.0 g, 78.25 mmol), which is commercially available, and EDC hydrochloride (18.00 g, 93.90 mmol) was mixed in DCM (300 mL). To the mixture was NMM (20.65 mL, 187.79 mmol) added. The mixture was cooled to 0° C. and azetidine (6.33 mL, 93.90 mmol) was added. The resultant mixture was stirred at 0° C. for 30 min. and at rt over night. The reaction mixture was washed with NaHCO$_3$ (saturated, 2×300 mL) and brine (300 mL), filtered through a phase separator and concentrated under reduced pressure. The residue was purified via Biotage (gradient; DCM/iso-propanol, 99:1 to 90:10, KP-SIL 340 g column). The solvent was removed under reduced pressure to give the title compound (12.0 g, 60%). $^1$H NMR (400 MHz, CD$_3$OD) δ 0.92, 1.20-1.76, 2.30, 3.89-4.26, 4.26-4.46, 5.16. LCMS (M+H)$^+$: 257.

Compound F1: (S)-Tert-butyl 3,3-dimethyl-1-oxo-1-(pyrrolidin-1-yl)butan-2-ylcarbamate (S)-2-(Tert-butoxycarbonylamino)-3-methylbutanoic acid (7.00 g, 30.3 mmol) and TBTU (9.72 g, 30.27 mmol) was mixed in DMF (70 mL). The mixture was cooled to 0° C. and NMM (3.99 mL, 36.3 mmol) was added. After 10 min was pyrrolidine (3.00 mL, 36.32 mmol) added. The resultant mixture was stirred at 0° C. for 30 min. and at rt over night. The mixture was concentrated and the residue dissolved in DCM (250 mL). The organic phase was washed with NaHCO$_3$ (saturated, 2×200 mL) and brine (200 mL), filtered through a phase separator and concentrated under reduced pressure. The residue was purified via Biotage (gradient; DCM/iso-propanol, 99:1 to 90:10, KP-SIL 340 g column). The solvent was removed under reduced pressure to give the title compound (6.4 g, 74%). $^1$H NMR (400 MHz, CDCl$_3$) δ 0.99, 1.43, 1.80-2.01, 3.31-3.45, 3.47-3.59, 3.67-3.79, 4.29, 5.28. Total no of protons: 27. LCMS (M+H)$^+$: 285.

In a similar manner the following compounds were synthesized:

| Compound | Name | $^1$H NMR and LCMS | Yield |
|---|---|---|---|
| F2 | Tert-butyl (2S,3S)-3-methyl-1-oxo-1-(pyrrolidin-1-yl)pentan-2-ylcarbamate | $^1$H NMR (400 MHz, CDCl$_3$) δ 0.76-0.95, 0.97-1.14, 1.40, 1.48-1.61, 1.63-1.76, 1.77-2.00, 3.32-3.58, 3.60-3.76, 4.18-4.31, 5.23. Total no of protons: 28. LCMS (M + H)$^+$: 285. | 5.72 g 93% |
| F3 | (S)-Tert-butyl 1-cyclopropyl-2-oxo-2-(pyrrolidin-1-yl)ethylcarbamate | $^1$H NMR (400 MHz, CDCl$_3$) δ 0.25-0.60, 1.15, 1.43, 1.81-2.03, 3.34-3.58, 3.64, 4.27, 5.42. Total no of protons: 24. | 1.51 g 96% |
| F4 | Tert-butyl (S)-1-((R)-3-hydroxypyrrolidin-1-yl)-3-methyl-1-oxobutan-2-ylcarbamate | $^1$H NMR (400 MHz, CD$_3$OD) δ 0.85-1.04, 1.43, 1.80-2.21, 3.36-3.80, 3.83-4.21, 4.29-4.50, 6.36-6.74. | 4.2 g quant. yield |
| F5 | Tert-butyl 2-methyl-1-oxo-1-(pyrrolidin-1-yl)propan-2-ylcarbamate | $^1$H NMR (400 MHz, CDCl$_3$) δ 1.42, 1.50, 1.84, 3.54, 4.51, 5.17. Total no of protons: 24. LCMS (M + H)$^+$: 257. | 5.08 g 79% |
| F6 | (S)-Tert-butyl 1-oxo-1-(pyrrolidin-1-yl)butan-2-ylcarbamate | $^1$H NMR (400 MHz, CDCl$_3$) δ 0.92, 1.41, 1.48-1.64, 1.65-2.06, 3.32-3.46, 3.46-3.56, 3.56-3.72, 4.34, 5.34. Total no of protons: 24. LCMS (M + H)$^+$: 257. | 5.88 g 67% |
| F7 | Tert-butyl (S)-1-((S)-2-(methoxymethyl)pyrrolidin-1-yl)-3-methyl-1-oxo-butan-2-ylcarbamate | LCMS (M + H)$^+$: 315. | 2.25 g 49% |
| F8 | (R)-Tert-butyl 4-methyl-1-oxo-1-(pyrrolidin-1-yl)pentan-3-ylcarbamate | $^1$H NMR (400 MHz, CDCl$_3$) δ 0.90, 0.93, 1.42, 1.79-1.88, 1.90-2.07, 2.40-2.60, 3.38-3.50, 3.54-3.71, 5.51-5.63. Total no of protons: 28. LCMS (M + H)$^+$: 285. | 3.40 g 92% |

Compound G1: Tert-butyl (2S,3R)-3-methoxy-1-oxo-1-(pyrrolidin-1-yl)butan-2-ylcarbamate (2S,3R)-2-(Tert-butoxycarbonylamino)-3-methoxybutanoic acid (643 mg, 2.76 mmol), which is commercially available, and DIPEA (1.440 mL, 8.27 mmol) was mixed in DCM (10 mL). The mixture was cooled to 0° C. TBTU (974 mg, 3.03 mmol) was added and the mixture stirred at rt for 10 min. Pyrrolidine (0.274 mL, 3.31 mmol) was added and the resultant mixture was stirred at rt for 16 h. The mixture was diluted with DCM (10 mL). The organic phase was washed with NaHCO$_3$ (8% in aq. solution) and brine, filtered through a phase separator and concentrated under reduced pressure. The residue was purified via Biotage (gradient; DCM/isopropanol, 99:1 to 95:5, KP-SIL 340 g column). The solvent was removed under reduced pressure to give the title compound (0.704 g, 95%). $^1$H NMR (400 MHz, CD$_3$OD) δ 1.15, 1.44, 1.82-2.05, 3.33, 3.35-3.52, 3.54-3.65, 3.66-3.79, 4.36. Total no of protons: 25. LCMS (M+H)$^+$: 287.

In a similar manner the following compound was synthesized:

| Compound | Name | $^1$H NMR | Yield |
|---|---|---|---|
| G2 | Tert-butyl (2S,3R)-3-tert-butoxy-1-oxo-1-(pyrrolidin-1-yl)butan-2-yl-carbamate | $^1$H NMR (400 MHz, CDCl$_3$) δ 1.12, 1.19, 1.43, 1.80-1.98, 3.36-3.45, 3.48-3.61, 3.74, 3.82-3.90, 4.39. Total no of protons: 31 | 2.60 g quant. yield |

Compound H: (S)-Tert-butyl 1-(3,3-difluoropyrrolidin-1-yl)-3-methyl-1-oxobutan-2-ylcarbamate (S)-2-(Tert-butoxycarbonylamino)-3-methylbutanoic acid (1.1 g, 5.06 mmol), which is commercially available, and TBTU (1.63 g, 5.06 mmol) was mixed in DMF (10 mL). The mixture was cooled to 0° C. and TEA (2.105 mL, 15.19 mmol) was added. After 10 min was 3,3-difluoropyrrolidine hydrochloride (0.872 g, 6.08 mmol) added. The resultant mixture was stirred at rt over night. The mixture was concentrated and the residue dissolved in DCM (50 mL). The organic phase was washed with HCl (1M aq. solution, 100 mL), NaHCO$_3$ (saturated, 2×100 mL) and brine (100 mL), filtered through a phase separator and concentrated under reduced pressure to give the title compound (1.54 g, 99%). The obtained crude product was used without further purification. $^1$H NMR (400 MHz, CD$_3$OD) δ 0.77-1.09, 1.21, 1.43, 1.84-2.08, 2.22-2.69, 3.52-4.40. Total no of protons: 24. LCMS (M+H)$^+$: 307.

Compound H: (S)-Tert-butyl 1-(4-methoxypiperidin-1-yl)-3-methyl-1-oxobutan-2-ylcarbamate (S)-2-(Tert-butoxycarbonylamino)-3-methylbutanoic acid (2.0 g, 9.21 mmol) and TBTU (2.96 g, 9.21 mmol) were mixed in DMF (20 mL). The mixture was cooled to 0° C. and NMM (1.518 mL, 13.81 mmol) was dropwise added. After stirring for 10 min was 4-methoxypiperidine (1.272 g, 11.05 mmol) added. The resultant mixture was stirred at rt over night. The mixture was concentrated and the residue dissolved in DCM (50 mL). The organic layer was washed with HCl (1M aq. solution, 100 mL), NaHCO$_3$ (saturated, 2×100 mL) and brine (100 mL), filtered through a phase separator and concentrated under reduced pressure. The residue was purified via Biotage (isocratic; DCM/MeOH, 95:5, KP-SIL 100 g column). The solvent was removed under reduced pressure to give the title compound (1.75 g, 60%). $^1$H NMR (400 MHz, CD$_3$OD) δ 0.69-1.09, 1.24-1.71, 1.72-2.10, 3.09-3.27, 3.36, 3.39-3.60, 3.60-4.15, 4.20-4.49. Total no of protons: 30.

In a similar manner the following compound was synthesized:

| Compound | Name | $^1$H NMR and LCMS | Yield |
|---|---|---|---|
| I2 | (S)-Tert-butyl 1-(3,3-difluoropiperidin-1-yl)-3-methyl-1-oxobutan-2-yl-carbamate | $^1$H NMR (400 MHz, CD$_3$OD) δ 0.79-1.05, 1.46, 1.56-2.23, 3.45-4.04, 4.21-4.42. Total no of protons: 25. LCMS (M + H)$^+$: 321. | 3.40 g quant. yield |

Compound J1: (S)-1-(Azetidin-1-yl)-N-methylpentan-2-amine

To a 1M solution of LAH in THF (31.2 mL, 31.2 mmol) was (S)-tert-butyl 1-(azetidin-1-yl)-1-oxopentan-2-ylcarbamate (Compound E) (2.0 g, 7.80 mmol) dropwise added (over approximately 60 min) as a solution in THF (40 mL) under a nitrogen atmosphere. The resultant mixture was stirred at rt for 30 min and heated at 55° C. over night. The reaction mixture was cooled to 0° C. Water (1.5 mL) was slowly added, followed by THF (10 mL), 15% aq. NaOH (1.5 mL) and additional water (4 mL). The reaction mixture was warmed to rt and stirred for 1 h. The mixture was filtered and the solid was washed with THF. The filtrate was dried (Na$_2$SO$_4$) and concentrated under reduced pressure to give the title compound (1.22 g, quant. yield). The obtained crude product was used without further purification. $^1$H NMR (400 MHz, CH$_3$OD) δ 0.90, 1.13-1.41, 2.04, 2.23-2.43, 3.08-3.24. Total no of protons: 19. LCMS (M+H)$^+$: 157.

In a similar manner the following compounds were synthesized:

| Compound | Name | $^1$H NMR and LCMS | Yield |
|---|---|---|---|
| J2 | (S)-3-Methyl-1-(3-methyl-2-(methylamino)butyl)azetidin-3-ol | $^1$H NMR (400 MHz, CD$_3$OD) δ 0.76-1.02, 1.44, 1.70-1.98, 2.12-2.20, 2.29-2.50, 2.83-3.09, 3.22-3.31. Total no of protons: 20. | 4.25 g 93% |
| J3 | (S)-1-(2-Cyclopropyl-2-(methylamino)ethyl)azetidin-3-ol | $^1$H NMR (400 MHz, CD$_3$OD) δ 0.07-0.68, 1.47-1.60, 2.41, 2.47-2.70, 2.74-3.00, 3.56-3.76, 4.20-4.37. | 1.30 g 74% |
| J4 | (S)-1-(2-(Methylamino)pentyl)azetidin-3-ol | $^1$H NMR (600 MHz, CD$_3$OD) δ 0.87-0.96, 1.23-1.43, 2.24-2.35, 2.31, 2.37-2.47, 2.77-2.82, 2.85-2.92, 3.54-3.67, 4.29. Total no of protons: 18. | 1.89 g 76% |
| J5 | (S)-1-(3-Fluoroazetidin-1-yl)-N,3-dimethylbutan-2-amine | $^1$H NMR (400 MHz, CD$_3$OD) δ 0.57-1.12, 1.79-1.94, 2.11-2.21, 2.31-2.39, 2.41-2.55, 2.99-3.27, 3.47-3.84, 4.96-5.33. LCMS (M + H)$^+$: 175 | 2.60 g 66% |
| J6 | (S)-1-(2-(Methylamino)pentyl)piperidin-4-ol | 1H NMR (400 MHz, CDCl3) δ 0.85-0.94, 1.12-1.38, 1.39-1.60, 1.77-2.01, 2.17-2.26, 2.36-2.40, 2.40-2.53, 2.56-2.65, 2.74-2.82, 3.23-3.30, 3.58-3.69, 3.69-3.76. | 2.63 g 71% |

-continued

| Compound | Name | $^1$H NMR and LCMS | Yield |
|---|---|---|---|
| J7 | (S)-1-((S)-2-(Methyl-amino)pentyl)pyrrolidin-3-ol | 1H NMR (400 MHz, DMSO-d6) δ 0.65-0.77, 1.03-1.26, 1.31-1.41, 1.47, 1.74-1.86, 1.98-2.09, 2.11, 2.14-2.27, 2.34-2.37, 2.40-2.47, 2.51-2.62, 3.02-3.34, 3.95-4.08, 4.50. | 4.6 g 89% |
| J8 | (3S,4S)-1-((S)-3-Methyl-2-(methyl-amino)butyl)pyrrolidine-3,4-diol | 1H NMR (400 MHz, CD3OD) δ 0.84-0.99, 1.85-1.96, 2.28-2.35, 2.37-2.43, 2.48-2.55, 2.8-2.87, 3.96-4.04. | 108 mg 69% |

Compound K1: (S)-1-(Azetidin-1-yl)-N,3-dimethylbutan-2-amine

A solution of (S)-tert-butyl 1-(azetidin-1-yl)-3-methyl-1-oxobutan-2-ylcarbamate (Compound D) (20 g, 78 mmol) in THF (200 mL) was dropwise charged (over approximately 90 min) to a jacketed reactor containing a 1M solution of LAH in THF (200 mL, 200 mmol) under a nitrogen atmosphere. The resultant mixture was heated at 60° C. over night. The reaction was cooled to −5° C. and H$_2$O (7.6 mL) was slowly added. The mixture was diluted with THF (200 mL). A 15% aq. NaOH (7.6 mL) solution and additional H$_2$O (22.8 mL) were added. The mixture was warmed to 25° C. and stirred for 1 h. The slurry was filtered and solids were washed with THF. The filtrate was concentrated under reduced pressure to give the title compound (1.7 g, 79%). The obtained crude product was used without further purification. $^1$H NMR (400 MHz, CH$_3$OD) δ 0.86, 1.75-1.90, 1.94-2.18, 2.18-2.36, 2.38, 2.99-3.29. Total no of protons: 19.

In a similar manner the following compound was synthesized:

| Compound | Name | $^1$H NMR and LCMS | Yield |
|---|---|---|---|
| K2 | (S)-1-(3-Methyl-2-(methylamino)butyl)-azetidin-3-ol | 1H NMR (400 MHz, CD$_3$OD) δ 0.66-1.06, 1.74-2.02, 2.06-2.26, 2.41, 2.65-3.02, 3.52-3.73, 4.17-4.46. Total no of protons: 18. | 20.20 g 80% |

Compound L1: (S)-2-(Azetidin-1-yl)-1-cyclopropyl-N-methylethanamine

To a solution of (S)-tert-butyl 2-(azetidin-1-yl)-1-cyclopropyl-2-oxoethylcarbamate (Compound B1) (1.4 g, 5.50 mmol) in THF (40 mL) was a 1M solution of LAH in THF (16 mL, 16.0 mmol) dropwise added (over approximately 10 min) at −20° C. under a nitrogen atmosphere. The resultant mixture was stirred at rt for 1 h and heated at 60° C. over night. The reaction was cooled to −5° C. and Na$_2$SO$_4$×10H$_2$O (ca 5 g) and NaOH (2M, 2 mL) was added. The mixture was diluted with EtOH (100 mL) and the resultant mixture was warmed to rt and stirred for 1 h. The mixture was filtered and the solid was washed with THF. The filtrate was concentrated under reduced pressure to give the title compound (0.31 g, 37%). The obtained crude product was used without further purification. $^1$H NMR (400 MHz, CDCl$_3$) δ 0.03, 0.26, 0.33-0.46, 0.50-0.64, 1.51, 2.00-2.12, 2.42-2.48, 2.49, 2.56, 3.19. Total no of protons: 17. LCMS (M+H)$^+$: 155.

In a similar manner the following compounds were synthesized:

| Compound | Name | $^1$H NMR and LCMS | Yield |
|---|---|---|---|
| L2 | (S)-3-Cyclopropyl-1-(2-cyclopropyl-2-(methyl-amino)ethyl)azetidin-3-ol | $^1$H NMR (400 MHz, CD$_3$OD) δ 0.02, 0.26, 0.32-0.64, 1.08-1.22, 1.47, 2.43-2.55, 2.62, 2.94, 3.05, 3.16. Total no of protons: 20. LCMS (M + H)$^+$: 211 | 0.73 g 91% |

Compound M1: (S)—N,3,3-Trimethyl-1-(pyrrolidin-1-yl)butan-2-amine

To a 1M solution of LAH in THF (28.1 mL, 28.1 mmol) was (S)-tert-butyl 3,3-dimethyl-1-oxo-1-(pyrrolidin-1-yl)butan-2-ylcarbamate (Compound F1) (2.0 g, 7.03 mmol) dropwise added (over approximately 60 min) as a solution in THF (40 mL) under a nitrogen atmosphere. The resultant mixture was stirred at rt for 30 min and heated at 55° C. over night. The reaction mixture was cooled to 0° C. Water (1.5 mL) was slowly added, followed by THF (10 mL), 15% aq. NaOH (1.5 mL) and additional water (4 mL). The reaction mixture was warmed to rt and stirred for 1 h. The mixture was filtered and the solid was washed with THF. The filtrate was dried (Na$_2$SO$_4$) and concentrated under reduced pressure to give the title compound (1.24 g, 96%). The obtained crude product was used without further purification. $^1$H NMR (400 MHz, CDCl$_3$) δ 0.90, 1.72-1.81, 2.08, 2.26, 2.32-2.48, 2.50, 2.53-2.68. Total no of protons: 23. LCMS (M+H)$^+$: 185.

In a similar manner the following compounds were synthesized:

| Compound | Name | $^1$H NMR and LCMS | Yield |
|---|---|---|---|
| M2 | (2S,3S)-N,3-Dimethyl-1-(pyrrolidin-1-yl)pentan-2-amine | $^1$H NMR (400 MHz, CDCl$_3$) δ 0.82, 0.92, 1.10-1.26, 1.26-1.40, 1.53-1.66, 1.69-1.77, 2.04-2.16, 2.29-2.47, 2.47-2.61. Total no of protons: 23. | 1.24 g 95% |
| M3 | (S)-1-Cyclopropyl-N-methyl-2-(pyrrolidin-1-yl)ethanamine | $^1$H NMR (400 MHz, CDCl$_3$) δ 0.03, 0.31, 0.41, 0.52-0.67, 1.62-1.82, 2.38, 2.48-2.64, 2.72-2.85. Total no of protons: 19. LCMS (M + H)$^+$: 169. | 0.83 g 94% |
| M4 | (R)-1-((S)-3-Methyl-2-(methylamino)butyl)-pyrrolidin-3-ol | $^1$H NMR (400 MHz, CD$_3$OD) δ 0.80-1.03, 1.60-1.76, 1.80-2.00, 2.05-2.42, 2.44-2.79, 4.19-4.40. LCMS (M + H)$^+$: 187. | 1.87 g 68.4% |
| M5 | (S)-N-Methyl-1-(pyrrolidin-1-yl)butan-2-amine | $^1$H NMR (400 MHz, CDCl$_3$) δ 0.88, 1.18-1.39, 1.45-1.62, 1.69-1.81, 2.14-2.31, 2.31-2.47, 2.47-2.62. Total no of protons: 19. | 1.11 g 91% |
| M6 | (2R,3R)-3-Methoxy-N-methyl-1-(pyrrolidin-1-yl)butan-2-amine | $^1$H NMR (400 MHz, CD$_3$OD) δ 1.12, 1.83-1.73, 2.63-2.38, 3.33, 3.41-3.34. Total no of protons: 21 | 0.42 g 92% |
| M7 | (2R,3R)-3-Tert-butoxy-N-methyl-1-(pyrrolidin-1-yl)butan-2-amine | $^1$H NMR (400 MHz, CD$_3$OD) δ 1.06, 1.20, 1.71-1.85, 2.43, 2.43-2.63, 3.81-3.88. Total no of protons: 27 LCMS (M + H)$^+$: 229 | 1.49 g 83% |

-continued

| Compound Name | | ¹H NMR and LCMS | Yield |
|---|---|---|---|
| M8 | (S)-1-((S)-2-(Methoxymethyl)pyrrolidin-1-yl)-N,3-dimethylbutan-2-amine | (The obtained crude product was used in the next step without characterization.) | 0.27 g 17% |
| M9 | (R)-N,4-Dimethyl-1-(pyrrolidin-1-yl)pentan-3-amine | ¹H NMR (400 MHz, CDCl₃) δ 0.88, 1.44-1.55, 1.57-1.66, 1.72-1.88, 2.19-2.25, 2.39, 2.41-2.59. Total no of protons: 23. | 2.1 g 93% |
| M10 | (R)-N,3-Dimethyl-1-(pyrrolidin-1-yl)butan-2-amine | ¹H NMR (500 MHz, CDCl₃) δ 0.85, 0.90, 1.69-1.91, 2.13-2.19, 2.29-2.42, 2.46-2.57. Total no of protons: 22. | 0.68 g 53% |
| M11 | (S)-1-(2-(Methylamino)propyl)azetidin-3-ol | (The obtained crude product was used in the next step without characterization.) | 1.80 g 71%, 50% pure |
| M12 | (S)-1-(2-(Methylamino)butyl)azetidin-3-ol | ¹H NMR (400 MHz, CD₃OD) δ 0.87-0.95, 1.30-1.56, 2.23-2.30, 2.33, 2.42-2.49, 2.78-2.85, 2.88-2.93, 3.59-3.68, 4.29-4.39. Total no of protons: 16. | 1.80 g 71%, 50% pure |
| M13 | (3R,4R)-1-((S)-3-Methyl-2-(methylamino)butyl)pyrrolidine-3,4-diol | ¹H NMR (400 MHz, CD₃OD) δ 0.87, 0.95, 1.84-1.96, 2.33-2.52, 2.96-3.05, 3.96-4.01. Total no of protons: 19. | 0.61 g 36%, 80% pure |

Compound N:
N,2-Dimethyl-1-(pyrrolidin-1-yl)propan-2-amine

To a solution of tert-butyl 2-methyl-1-oxo-1-(pyrrolidin-1-yl)propan-2-ylcarbamate (Compound F5) (2.696 g, 10.52 mmol) in THF (20 mL) was a 1M LAH in THF (42.1 mL, 42.07 mmol) solution dropwise added (over approximately 10 min) at 0° C. under a nitrogen atmosphere. The resultant mixture was stirred at rt for 1 h and heated at 40° C. over night. The reaction was cooled to 0° C. and Na₂SO₄×10H₂O followed by NaOH (2M, 2 mL) was added. The mixture was diluted with Et₂O (100 mL) and the resultant mixture was filtered. The solids were washed with Et₂O (3×50 mL). To the filtrate was HCl (1.25 N aq. solution, 15 mL) in EtOH added. The filtrate was concentrated and the residue mixed with EtOH (60 mL). The EtOH was removed under reduced pressure. IPA (30 mL) was added and the mixture sonicated for 2 min. After filtration was the title compound (1.89 g, 96%) obtained as a HCl salt. ¹H NMR (400 MHz, CDCl₃) δ 1.00, 1.71, 2.29, 2.41, 2.63. Total no of protons: 19.

Compound O: (S)-1-(3,3-Difluoropyrrolidin-1-yl)-3-methylbutan-2-amine

To a 1M solution of LAH in THF (9.89 mL, 9.89 mmol) was (S)-2-amino-1-(3,3-difluoropyrrolidin-1-yl)-3-methylbutan-1-one (1.02 g, 4.95 mmol) dropwise added (over approximately 60 min) as a solution in THF under a nitrogen atmosphere. The mixture was stirred at rt for 30 min and heated at 70° C. over night. The reaction was cooled to 0° C. Water (0.5 mL) was slowly added, followed by 15% aq. NaOH (0.5 mL), THF (10 mL) and additional water (2 mL). The reaction mixture was warmed to rt and stirred for 1 h. The mixture was filtered and the solid washed with THF. The filtrate was dried (Na₂SO₄) and concentrated under reduced pressure to give the title compound (0.67 g, 70.6%). The obtained crude product was used without further purification. ¹H NMR (400 MHz, CH₃OD) δ 0.87-0.99, 1.52-1.65, 2.12-2.48, 2.59-2.87, 2.92-3.07, 3.31-3.67.
Total no of protons: 16. LCMS (M+H)⁺: 193.

Compound P: (S)—N-(1-(3,3-Difluoropyrrolidin-1-yl)-3-methylbutan-2-yl)-3,4-dimethylbenzamide 3,4-Dimethylbenzoic acid (130 mg, 0.87 mmol) and TBTU (279 mg, 0.87 mmol) was mixed in DMF (1.5 mL). The mixture was cooled to 0° C. and NMM (0.287 mL, 2.61 mmol) was dropwise added. After 10 min at 0° C. was (S)-1-(3,3-difluoropyrrolidin-1-yl)-3-methylbutan-2-amine (Compound O) (167 mg, 0.87 mmol) added. The resultant mixture was stirred at rt over night. The mixture was concentrated and the residue dissolved in DCM (5 mL). The organic phase was washed with HCl (1M aq. solution, 5 mL), NaHCO₃ (saturated, 2×5 mL) and brine (5 mL), and filtered through a phase separator and concentrated under reduced pressure. The residue was purified by preparative HPLC to give the title compound (143 mg, 51%). ¹H NMR (400 MHz, DMSO-d6) δ 0.65-1.03, 1.61-1.92, 2.00-2.21, 2.23, 2.53-3.03, 3.66-4.22, 7.19, 7.55, 7.61, 7.87. Total no of protons: 26.
LCMS (M+H)⁺: 325

Compound Q: (S)-4-Chloro-N-(3-methyl-1-(pyrrolidin-1-yl)butan-2-yl)benzamide

4-Chlorobenzoic acid (1.061 g, 6.78 mmol), TBTU (2.25 g, 7.01 mmol) and DIPEA (20.3 mmol) was mixed in DMF (25 mL). After 10 min was (S)-3-methyl-1-(pyrrolidin-1-yl)butan-2-amine (0.962 g, 6.16 mmol), which is commercially available, added. The resultant mixture was stirred at rt over night. The mixture was concentrated and the residue was purified by preparative HPLC to give the title compound (1.48 g, 82%). ¹H NMR (400 MHz, CDCl₃) δ 0.97, 1.80, 1.94-2.32, 2.47-2.76, 2.80-3.01, 4.13, 6.66, 7.41, 7.80. Total no of protons: 23. LCMS (M+H)⁺: 295.

Compound R: (S)—N-(2-Methoxyethyl)-3-methyl-1-(pyrrolidin-1-yl)butan-2-amine (S)-3-Methyl-1-(pyrrolidin-1-yl)butan-2-amine (0.24 g, 1.54 mmol), which is commercially available, and potassium carbonate (0.139 mL, 2.30 mmol) was slurried in MeCN. 1-Bromo-2-methoxyethane (0.147 mL, 1.54 mmol) was added and the reaction was stirred at rt for 2 h. LMCS showed only traces of the desired product. DIPEA (0.535 mL, 3.07 mmol) was added and the resultant mixture was stirred at rt over night and heated at 60° C. for 4 h. The mixture was cooled to rt and diluted with water (50 mL) and DCM (50 mL). The two layers were separated and the water layer was extracted with DCM (3×100 mL). The organic layers were combined and washed with brine (100 mL), passed through phase separator and concentrated under reduced pressure to give the title compound (0.31 g, 97%). The obtained crude product was used without further purification. LCMS (M+H)⁺: 215.

Compound S1: (S)-1-(4-Methoxypiperidin-1-yl)-N,3-dimethylbutan-2-amine

To a 1M solution of LAH in THF (22.26 mL, 22.26 mmol) was (S)-tert-butyl 1-(4-methoxypiperidin-1-yl)-3-methyl-1-oxobutan-2-ylcarbamate (Compound I1) (1.75 g, 5.57 mmol) dropwise added (over approximately 60 min) as a solution in THF (20 mL) under a nitrogen atmosphere. The resultant mixture was stirred at rt for 30 min and heated at 70° C. over night. The reaction was cooled to 0° C. Water (1 mL) was slowly added, followed by 15% aq. NaOH (1 mL), THF (20 mL) and additional water (2 mL). The reaction mixture was warmed to rt and stirred for 1 h. The mixture was filtered and the solid was washed with THF. The filtrate was dried (Na$_2$SO$_4$) and concentrated under reduced pressure to give the title compound (0.95 g, 80%). The obtained crude product was used without further purification. $^1$H NMR (400 MHz, CH$_3$OD) δ 0.90, 1.44-1.69, 1.74-1.98, 1.98-2.12, 2.32, 2.53-2.71, 2.71-2.93, 3.15-3.29, 3.30. LCMS (M+H)$^+$: 215.

In a similar manner the following compound was synthesized:

| Compound | Name | $^1$H NMR and LCMS | Yield |
|---|---|---|---|
| S2 | (S)-1-(3,3-Difluoro-piperidin-1-yl)-N,3-dimethylbutan-2-amine | $^1$H NMR (400 MHz, CD$_3$OD) δ 0.83-0.98, 1.63-2.00, 2.14-2.63, 2.66-2.81, 3.35-3.81. Total no of protons: 21. LCMS (M + H)$^+$: 221 | 1.65 g, 71% |

Compound T: (S)-2-Amino-1-(azetidin-1-yl)-3-methylbutan-1-one (S)-Tert-butyl 1-(azetidin-1-yl)-3-methyl-1-oxobutan-2-ylcarbamate (Compound D) (23.56 g, 90.07 mmol) was stirred in 4M HCl in dioxane (56.3 mL, 225 mmol) for 30 min. Additional dioxane and MeOH was added until the reaction mixture became a clear solution. The solvent was removed under reduced pressure and conc. HCl (3.00 mL, 30.4 mmol) was added. The mixture was stirred for 5 h before the solvent was removed. The residue was purified via Biotage (gradient; EtOAc:MeOH (2% TEA), 99:1 to 90:10, then EtOAc:MeOH (2% TEA) 90:10 to 0/100 KP-SIL 340 g. The solvent was removed under reduced pressure to give the title compound (10.3 g, 70.3%). $^1$H NMR (600 MHz, CH$_3$OD) δ 1.03, 1.06, 2.07-2.16, 2.33-2.41, 3.71, 3.99-4.07, 4.07-4.14, 4.25-4.33, 4.33-4.41. Total no of protons: 14. LCMS (M+H)$^+$: 157.

Compound U: (S)-1-(Azetidin-1-yl)-3-methylbutan-2-amine

To a 1M solution of LAH in THF (19.2 mL, 19.2 mmol) was (S)-2-amino-1-(azetidin-1-yl)-3-methylbutan-1-one (Compound T) (2 g, 12.8 mmol) in THF (12.8 mL) added (over approximately 30 min) at 0° C. under a nitrogen atmosphere. The resultant mixture was stirred at rt for 1 h and heated at 60° C. for 6 h. The reaction was cooled to 0° C. Water (0.73 mL) was slowly added, followed by 15% aq. NaOH (0.73 mL) and additional water (2.2 mL). The reaction mixture was warmed to rt and stirred for 1 h. Celite and Na$_2$SO$_4$ were added. The mixture was filtered and the filtrate concentrated under reduced pressure to give the title compound (1.14 g, 63%). $^1$H NMR (400 MHz, CDCl$_3$) δ 3.29-3.04, 2.51-2.39, 2.37-2.21, 2.14-1.96, 1.60-1.47, 1.34, 0.94-0.76. Total no of protons: 18.

Compound V: (S)-1-(Azetidin-1-yl)-N-ethyl-3-methylbutan-2-amine (S)-1-(Azetidin-1-yl)-3-methylbutan-2-amine (Compound U) (0.420 g, 2.95 mmol) and acetaldehyde (0.166 mL, 2.95 mmol) was mixed in DCM (10 mL). Sodium triacetoxyhydroborate (0.813 g, 3.84 mmol) was added in small portions and the resultant mixture was stirred at rt for 5 h. Water was added and the pH was adjusted to pH9. The water phase was extracted with DCM (4×50 mL). The combined organic layers were combined and washed with brine, passed through phase separator and evaporated under reduced pressure to give the title compound (0.1 g, 20%). The obtained crude product was used without further purification. LCMS (M+H)$^+$: 171.

Compound X: (S)-Tert-butyl 1-(3-hydroxyazetidin-1-yl)-2,3-dimethyl-1-oxobutan-2-ylcarbamate HATU (1.854 g, 4.88 mmol) and azetidin-3-ol hydrochloride (0.534 g, 4.88 mmol) was added to (S)-2-(tert-butoxycarbonylamino)-2,3-dimethylbutanoic acid (0.94 g, 4.06 mmol), which is commercially available, and DIPEA (2 mL, 11.45 mmol) in DMF (10 mL). The resultant mixture was stirred at rt over night. The mixture was concentrated and the residue dissolved in DCM. The organic phase was washed with NaHCO$_3$ (saturated) and brine (200 mL). The filtrate was dried (Na$_2$SO$_4$) and concentrated under reduced pressure. The residue was purified via Biotage (gradient; DCM/MeOH, 98:2 to 90:10, KP-SIL 100 g column) to give the title compound (1.1 g, 93%).

Compound Y: (S)-1-(2,3-Dimethyl-2-(methylamino)butyl)azetidin-3-ol

To a solution of (S)-tert-butyl 1-(3-hydroxyazetidin-1-yl)-2,3-dimethyl-1-oxobutan-2-ylcarbamate (Compound X) (1.07 g, 3.74 mmol) in THF (50 mL) was a 1M solution of LAH in THF (16 ml, 16.00 mmol) dropwise added (over approximately 2 min) at −20° C. under a nitrogen atmosphere. The resultant mixture was stirred at rt for 30 min and heated at 60° C. over night. Additional LAH in THF (1M solution, 2 mL, 2 mmol) was added and the mixture was heated at 70° C. over night. The solvent was removed. 1,4-Dioxane (60 mL) and a 0.5M solution of LAH in ethylene glycol dimethyl ether (10 mL) was added to the residue. The resultant mixture was heated at 100° C. over night. The mixture was diluted with diethyl ether (150 mL) and the reaction was quenched with Na$_2$SO$_4$×10H$_2$O. The mixture was filtered and the filtrate was concentrated under reduced pressure to give the title compound (0.8 g, quant.yield). The obtained crude product was used without further purification. LCMS (M+H)+: 187.

Compound Z: (S)-4-Fluoro-N-(1-hydroxy-3-methylbutan-2-yl)-N,3-dimethylbenzamide TEA (1.774 mL, 12.80 mmol) was added to (S)-3-methyl-2-(methylamino)butan-1-ol (Compound B2.1) (0.5 g, 4.3 mmol) in DCM (5 mL). The mixture was cooled on an ice-bath and 4-fluoro-3-methylbenzoyl chloride (1.27 mL, 8.96 mmol) in DCM (5 mL) was dropwise (over 5 min) added. The resultant mixture was stirred at rt over night. Additional TEA (0.414 mL, 2.99 mmol) and 4-fluoro-3-methylbenzoyl chloride (0.368 g, 2.13 mmol) was added and the stirring was continued for 3 h. Water (12 mL) was added to the mixture. The organic layer was dried though a phase separator and concentrated. THF (15 mL) and NaOH was added to the residue and the resulting mixture was stirred over night. The mixture was neutralized by the addition of acetic acid. The solvent was removed and DCM (50 mL) was added. The organic phase was washed with Na$_2$CO$_3$ (saturated, 2×30 mL) and brine (30 mL), filtered through a phase separator and concentrated under reduced pressure to give the title compound (0.91 g, 85%). The obtained crude product was used without further purification. Mixture of rotamers: (600 MHz, CD$_3$OD) δ 0.77-0.82, 0.95, 1.02, 1.74-1.83, 1.89-1.97, 2.23-2.31, 2.83, 2.92, 3.37-3.44, 3.58-3.74, 3.79-3.86, 4.23-4.31, 7.01-7.11, 7.18-7.36. Ratio major:minor:1:0.6. Total no of protons: 19.

Compound A2.1: (S)-4-Fluoro-N,3-dimethyl-N-(3-methyl-1-oxobutan-2-yl)benzamide

Dess-Martin periodinane (0.25 g, 0.59 mmol) was added to (S)-4-fluoro-N-(1-hydroxy-3-methylbutan-2-yl)-N,3-dimethylbenzamide (Compound Z) (0.1 g, 0.39 mmol) in DCM (3 mL) at rt. The resultant mixture was stirred at rt for 2 h. An aqueous NaHCO$_3$ (8 wt %) solution containing sodium pyrosulphite (0.059 mL, 0.43 mmol) was added and the resultant mixture was stirred vigorously for 15 min. The organic phases was washed with Na$_2$CO$_3$ (8 wt %), filtered through a phase separator and dried using Na$_2$SO$_4$. The solvent was removed under reduced pressure to give the title compound (93 mg, 94%). The obtained crude product was used without further purification. LCMS (M+H)$^+$: 252.

The following compounds were prepared, in a manner essentially similar to that described for A2.1:

| Example | Name | $^1$H NMR and/or LCMS | Yield |
|---|---|---|---|
| A2.2 | (S)-4-Chloro-N-methyl-N-(3-methyl-1-oxobutan-2-yl)benzamide | LCMS (M + H)$^+$: 254. | 0.86 g, 96% |
| A2.3 | (S)-3,4-Difluoro-N-methyl-N-(3-methyl-1-oxobutan-2-yl)benzamide | LCMS (M + H)$^+$: 256. | 2.17 g, quant. yield |

Compound B2.1: (S)-3-Methyl-2-(methylamino)butan-1-ol

A 1M solution of LAH in THF (16 mL, 16.0 mmol) was heated to 55° C. (S)-2-(Tert-butoxycarbonylamino)-3-methylbutanoic acid (14 g, 64.4 mmol), which is commercially available, dissolved in THF (30 mL) was added (over approximately 45 min). The resultant mixture was stirred at 55° C. Additional LAH in THF (1M solution, 40 mL, 2 mmol) was added and the stirring was continued for 4 h. The reaction was quenched with Na$_2$SO$_4$×10H$_2$O and celite and the resultant mixture was stirred for 2 days. The mixture was filtered and the filtrate was concentrated under reduced pressure to give the title compound (7.0 g, 93%). The obtained crude product was used without further purification.

$^1$H NMR (400 MHz, CD$_3$OD) δ 0.87-0.99, 1.81-1.94, 2.28, 2.38, 3.46, 3.62. Total no of protons: 13.

The following compound was prepared, in a manner essentially similar to that described for B2.1:

| Example | Name | $^1$H NMR and/or LCMS | Yield |
|---|---|---|---|
| B2.2 | (1-((2R,3R)-3-Methoxy-2-(methylamino)butyl)azetidin-3-ol | $^1$H NMR (600 MHz, CDCl$_3$) δ 1.10, 2.31-2.36, 2.41, 2.43-2.47, 2.84-2.89, 2.89-2.97, 3.32, 3.33-3.38, 3.55-3.67, 4.33-4.45. | 0.72 g, 72% |

Compound C2.1: (S)-2-(4-Chloro-N-methylbenzamido)-3-methylbutyl 4-chlorobenzoate TEA (4.73 mL, 34.1 mmol) was added to (S)-3-methyl-2-(methylamino)butan-1-ol (Compound B2.1) (1 g, 8.5 mmol) in DCM (10 mL). The mixture was cooled on an ice-bath and 4-chlorobenzoyl chloride (3.14 g, 17.9 mmol) in DCM (10 mL) was dropwise (over 10 min) added. The resultant mixture was stirred at rt for 2 h. The organic phase was washed with Na$_2$CO$_3$ (8 wt %, 40 mol) and concentrated under reduced pressure to give the title compound (3.3 g, 98%). The obtained crude product was used without further purification. LCMS (M+H)$^+$: 394. Mixture of rotamers: $^1$H NMR (600 MHz, CD$_3$OD) δ 0.93-1.04 (m), 1.13 (d), 1.98-2.13 (m), 2.87 (s), 3.02 (s), 3.60-3.74 (m), 4.43-4.73 (m), 7.16-7.64 (m), 7.87-8.19 (m). Total number of protons: 21.

The following compound was prepared, in a manner essentially similar to that described for C2.1:

| Example | Name | $^1$H NMR and/or LCMS | Yield |
|---|---|---|---|
| C2.2 | (S)-2-(3,4-Difluoro-N-methylbenzamido)-3-methylbutyl 3,4-difluorobenzoate | Mixture of rotamers: $^1$H NMR (600 MHz, CD$_3$OD) δ 0.95-0.98 (m), 1.02 (d), 1.14 (d), 2.01-2.14 (m), 2.89 (s), 3.02 (s), 3.64-3.74 (m), 4.46-4.72 (m), 7.04-7.56 (m), 7.83-7.95 (m), 8.00-8.12 (m). Total no of protons: 19 LCMS (M + H)$^+$: 398. | 4.05 g, quant. yield |

Compound D2.1: (S)-4-Chloro-N-(1-hydroxy-3-methylbutan-2-yl)-N-methylbenzamide

NaOH (2.35 ml, 8.93 mmol) was added to (S)-2-(4-chloro-N-methylbenzamido)-3-methylbutyl 4-chlorobenzoate (Compound C2.1) (3.2 g, 8.12 mmol) in MeOH. The resultant mixture was stirred at rt for 20 min. Additional NaOH (1.07 ml, 4.06 mmol) was added and the stirring continued for 1 h. To the mixture was water (5 mol) added and the resultant mixture was stirred for 2 h. The mixture was neutralized by the addition of acetic acid. The solvent was removed and DCM (50 mL) was added. The organic phase was washed with NaHCO$_3$ (saturated, 3×50 mL), filtered through a phase separator and concentrated under reduced pressure to give the title compound (1.47 g, 71%). The obtained crude product was used without further purification. Mixture of rotamers: (600 MHz, CD$_3$OD) δ 0.78-0.85, 0.95-0.99, 1.02-1.07, 1.78-1.86, 1.90-1.98, 2.84, 2.95, 3.35-3.40, 3.59-3.66, 3.68-3.77, 3.83-3.88, 4.28-4.34, 7.39-7.48. Total no of protons: 17. LCMS (M+H)$^+$: 256.

Compound E2.1: (S)-3,4-Difluoro-N-(1-hydroxy-3-methylbutan-2-yl)-N-methylbenzamide LiOH (25.7 mL, 12.83 mmol) was added to (S)-2-(3,4-difluoro-N-methylbenzamido)-3-methylbutyl 3,4-difluorobenzoate (Compound C2.2) (4 g, 8.56 mmol) in MeOH (40 mL). The resultant mixture was stirred at rt over night. Additional LiOH (10.27 mL, 10.27 mmol) was added and the stirring continued for 2 h. The mixture was neutralized by the addition of acetic acid. The solvent was removed and DCM (50 mL) was added. The organic phase was washed with NaHCO$_3$ (saturated, 1×50 mol, 2×30 mL), dried (Na$_2$SO$_4$) and concentrated under reduced pressure to give the title compound (2.18 g, 99%). The obtained crude product was used without further purification.

Mixture of rotamers: $^1$H NMR (600 MHz, CD$_3$OD) δ 0.78-0.84 (m), 0.97 (d), 1.04 (d), 1.77-1.86 (m), 1.90-1.98 (m), 2.85 (s), 2.94 (s), 3.34-3.40 (m), 3.60-3.66 (m), 3.70-3.76 (m), 3.83-3.88 (m), 4.26-4.33 (m), 7.22-7.44 (m). Total no of protons: 16. LCMS (M+H)$^+$: 258.

Compound F2.1: Tert-butyl (2S,3S)-1-(3-hydroxyazetidin-1-yl)-3-methyl-1-oxopentan-2-ylcarbamate NMM (6.12 mL, 55.6 mmol) in DMF (5 mL) was added to (2S,3S)-2-(tert-butoxycarbonylamino)-3-methylpentanoic acid (4.15 g, 17.9 mmol), which is commercially available, in DCM (45 mL) under a nitrogen atmosphere. TBTU was added portionwise and the resultant mixture was stirred at rt for 15 min. Azetidin-3-ol hydrochloride (2.359 g, 21.53 mmol) was added and the stirring continued for 20 h. The mixture was diluted with DCM, washed with NaHCO$_3$ and brine, filtered through a phase separator and concentrated under reduced pressure. The residue was dissolved in Et$_2$O, washed with water, filtered through a phase separator and concentrated under reduced pressure to give the title compound (5 g, 97%). The obtained crude product was used without further purification. $^1$H NMR (600 MHz, CDCl$_3$) δ 0.81-0.95, 1.04-1.16, 1.35-1.48, 1.48-1.70, 3.79-4.09, 4.14-4.24, 4.25-4.42, 4.52-4.74, 5.05-5.16.

The following compounds were prepared, in a manner essentially similar to that described for Compound F2.1:

| Example | Name | $^1$H NMR and/or LCMS | Yield |
|---|---|---|---|
| F2.2 | Tert-butyl (2S,3R)-1-(3-hydroxyazetidin-1-yl)-3-methoxy-1-oxobutan-2-ylcarbamate | $^1$H NMR (600 MHz, CDCl$_3$) δ 1.10, 2.31-2.36, 2.41, 2.43-2.47, 2.84-2.89, 2.89-2.97, 3.32, 3.33-3.38, 3.55-3.67, 4.33-4.45. | 1.93 g, 84% |
| F2.3 | (S)-Tert-butyl 1-(3-hydroxyazetidin-1-yl)-1-oxohexan-2-ylcarbamate | LCMS (M + H)$^+$: 287 | 10.34 g, 77% |
| F2.4 | (S)-Tert-butyl 1-cyclohexyl-2-(3-hydroxyazetidin-1-yl)-2-oxoethylcarbamate | $^1$H NMR (400 MHz, CD$_3$OD) δ 0.86-1.32 (m, 5H), 1.43 (s, 9H), 1.50-1.90 (m, 6H), 3.70-3.89 (m, 2H), 3.98-4.06 (m, 1H), 4.11-4.26 (m, 1H), 4.45 (t, 1H), 4.49-4.65 (m, 2H). LCMS (M + H)$^+$: 313.5 | 11.30 g, 121% |
| F2.5 | (S)-Tert-butyl 1-(3-hydroxyazetidin-1-yl)-4-methyl-1-oxopentan-2-ylcarbamate | $^1$H NMR (600 MHz, CDCl$_3$) δ 0.92, 1.30-1.53, 1.65, 2.63, 3.83, 3.91, 4.00, 4.14-4.38, 4.53-4.74, 5.04. | 24.7 g, 100% |
| F2.6 | (R)-Tert-butyl 1-(3-hydroxyazetidin-1-yl)-1-oxopentan-2-ylcarbamate | $^1$H NMR (400 MHz, CDCl$_3$) δ 0.80, 1.02-1.62, 2.10-2.26, 2.29-2.46, 3.72, 3.80, 3.89, 3.95-4.15, 4.15-4.32, 4.36-4.48, 4.49-4.70, 4.99. LCMS (M + H)$^+$: 285. | 1.050 g, 44.1% |
| F2.7 | (R)-Tert-butyl 1-cyclobutyl-2-(3-hydroxyazetidin-1-yl)-2-oxoethylcarbamate | | 7.5 g, 121%, 69% pure |

Compound G2.1: 1-((2S,3S)-3-Methyl-2-(methylamino)pentyl)azetidin-3-ol

To LAH (1 M solution in THF) (69.8 mL, 69.84 mmol) was added a solution of tert-butyl (2S,3S)-1-(3-hydroxyazetidin-1-yl)-3-methyl-1-oxopentan-2-ylcarbamate (Compound F2.1) (5 g, 17.5 mmol) in anhydrous THF (24 mL) dropwise (1 h) under nitrogen. The reaction mixture was stirred at rt for 1 h and then heated at 60° C. over night. The reaction mixture was cooled to 0° C. Water (3.5 ml) was added dropwise, followed by 15% aq. NaOH (3.5 ml), THF (50 ml) and water (7.5 ml). The mixture was allowed to reach rt and stirred for 30 min. The solids were filtered off and washed with THF. The filtrate was dried over Na$_2$SO$_4$ and concentrated under reduced pressure to give the title compound as colorless oil (2.8 g, 86%). The product was used in the next step without further purification. $^1$H NMR (600 MHz, CDCl$_3$) δ 0.80 (d, 3H), 0.91 (t, 3H), 1.10-1.23 (m, 1H), 1.25-1.38 (m, 1H), 1.53-1.63 (m, 1H), 2.15-2.30 (m, 3H), 2.36 (s, 3H), 2.38-2.47 (m, 2H), 2.77-2.84 (m, 1H), 2.89-2.97 (m, 1H), 3.50-3.64 (m, 2H), 4.33-4.44 (m, 1H).

The following compounds were prepared, in a manner essentially similar to that described for Compound G2.1:

| Example | Name | $^1$H NMR and/or LCMS | Yield |
|---|---|---|---|
| G2.2 | (S)-1-(2-(Methylamino)hexyl)azetidin-3-ol | Mixture of rotamers: $^1$H NMR (600 MHz, CD$_3$OD) δ 0.87-0.97 (m, 3H), 1.23-1.50 (m, 7H), 2.27-2.37 (m, 4H), 2.39-2.49 (m, 2H), 2.79-2.84 (m, 1H), 2.88-2.94 (m, 1H), 3.56-3.67 (m, 2H), 4.26-4.36 (m, 1H). Total number of protons in spectrum: 20 | 5.04 g, 77%, 89% pure |
| G2.3 | (S)-1-(2-Cyclohexyl-2-(methylamino)ethyl)azetidin-3-ol | $^1$H NMR (400 MHz, CD$_3$OD) δ 0.94-1.34, 1.45-1.82, 2.10-2.18, 2.34, 2.40-2.47, 2.75-2.82, 2.85-2.93, 3.54-3.66, 4.24-4.36. | 5.40 g, 70%, 75% pure |
| G2.4 | (S)-1-(4-Methyl-2-(methylamino)pentyl)azetidin-3-ol | $^1$H NMR (600 MHz, CD$_3$OD) δ 0.89-0.94, 1.11-1.18, 1.26-1.32, 1.63-1.71, 2.32, 2.35-2.49, 2.82, 2.91, 3.59-3.66, 4.28-4.34. Total number of protons: 20 (expected 22, NH and OH protons exchanged with solvent). LCMS (M + H)$^+$: 187. | 12.8 g, 80%, 90% pure |
| G2.5 | (R)-1-(2-(Methylamino)pentyl)azetidin-3-ol | $^1$H NMR (400 MHz, CDCl$_3$) δ 0.87-1.00, 1.16-1.51, 1.94-2.13, 2.25-2.54, 2.80-2.90, 2.90-2.98, 3.60-3.77, 4.39-4.50. Total number of protons: 20. | 0.586 g, 88% |
| G2.6 | (R)-1-(2-Cyclobutyl-2-(methylamino)ethyl)azetidin-3-ol | $^1$H NMR (400 MHz, CD$_3$OD) δ 1.76-2.00, 2.06-2.18, 2.23-2.44, 2.37-2.40, 2.80-2.98, 3.57-3.71, 4.30-4.40. | 3.85 g, 93%, 52% pure |

Compound H2.1: 2-Cyclopentyl-3-ethoxy-3-oxopropanoic acid

KOH (3.42 g, 61.0 mmol) in water (10 mL) was slowly added (over 1 h) to diethyl 2-cyclopentylmalonate (12.12 g, 53.09 mmol) in ethanol (30 mL) at 0° C. The resultant mixture was stirred at 0° C. for 2 h and at rt over night. The mixture was freezing-dried, and the residue partitioned between $Et_2O$ and water. The aqueous layer was washed with $Et_2O$. The combined organic layers were washed with brine, dried ($Na_2SO_4$) and concentrated under reduce pressure to recover unreacted diethyl cyclopentylmalonate (1.94 g, 8.5 mmol). The aqueous layer was cooled to −10° C. and the pH was adjusted to 1 using HCl (conc.). The water layer was extracted with $Et_2O$ (6×50 mL), dried ($MgSO_4$) and concentrated under reduce pressure to give the title compound (10.2 g, 96%). The obtained crude product was used without further purification. $^1H$ NMR (400 MHz, $CDCl_3$) δ 1.21-1.38, 1.47-1.75, 1.76-1.97, 2.37-2.55, 3.24, 4.14-4.31. Total no of protons: 15.

Compound I2.1: Ethyl 2-cyclopentyl-2-(methoxycarbonylamino)acetate

TEA (5.74 mL, 41.2 mmol) was added to 2-cyclopentyl-3-ethoxy-3-oxopropanoic acid (Compound H2.1) (7.5 g, 37.46 mmol) and diphenyl phosphorazidate (9.42 mL, 43.7 mmol) in toluene (25 mL) at rt under a nitrogen atmosphere. The mixture was heated at 80° C. for 30 min. The temperature was adjusted to 75° C. and MeOH (50.0 mL) was added. The resultant mixture was heated at 75° C. for 5 h and in a microwave reactor at 100° C. for 10 min. The solvent was removed under reduced pressure. The residue was diluted with EtOAc and the organic phase was washed with 5% citric acid, $NaHCO_3$ (saturated) and NaCl (saturated). The organic phase was dried ($MgSO_4$), filtered and concentrated under reduce pressure. The residue was purified via Biotage (DCM/MeOH, KP-SIL 100 g column) to give the title product (8.14 g, 95%). $^1H$ NMR (400 MHz, $CDCl_3$) δ 1.28, 1.31-1.46, 1.46-1.81, 2.21, 3.68, 4.13-4.24, 4.24-4.33, 5.15. Total no of protons: 19.

Compound J2.1: 2-Cyclopentyl-2-(methoxycarbonylamino)acetic acid

KOH (3.87 g, 69.0 mmol) in water (50 mL) was added to ethyl 2-cyclopentyl-2-(methoxycarbonylamino)acetate (Compound I2.1) (7.6 g, 33.2 mmol) in ethanol (20 mL). The resultant mixture was stirred at rt for 5 h. Part of the solvent was removed under reduce pressure. The remaining mixture was extracted with $Et_2O$ (2×50 mL). The pH of the water layer was acidified by additions of HCl (1N, 20 mL) and the resultant mixture was extracted with DCM (3×50 mL), dried ($MgSO_4$) and concentrated under reduce pressure. The residue was purified via Biotage (gradient: 10-80% of DCM/MeOH/HOAc (1: 0.05: 0.01) in DCM, KP-SIL 340 g column), KP-SIL 340 g column) to give the title product (5.95 g, 85%). $^1H$ NMR (600 MHz, $CDCl_3$) 1.26-1.48, 1.49-1.68, 1.68-1.85, 2.28, 3.69, 4.31, 5.12. Total no of protons: 14.

Compound K2.1: Methyl 1-cyclopentyl-2-(3-hydroxyazetidin-1-yl)-2-oxoethylcarbamate TBTU (0.373 g, 1.16 mmol) was added to azetidin-3-ol hydrochloride (1.960 g, 17.89 mmol), 2-cyclopentyl-2-(methoxycarbonylamino)acetic acid (Compound J2.1) (3 g, 14.91 mmol) and DIPEA (10 mL, 57.3 mmol) in DCM (60 mL) at rt. The resultant mixture was stirred for 2 h. Additional azetidin-3-ol hydrochloride (0.45 g, 4.11 mmol) was added and the mixture was heated at 50° C. for 1.5 h. The mixture was cooled to rt and the pH was adjusted to 2 using $KHSO_4$ (1.5 M). The mixture was extracted with DCM and the combined DCM layers were washed with brine and concentrated under reduced pressure. The residue was diluted with MeOH (15 mL) and KOH (1.56 g) in water (30 mL) was added. The resultant mixture was stirred at rt for 5 h. Part of the solvent was removed under reduce pressure. The remaining mixture was diluted with water and extracted with DCM. The organic layer was washed with brine, dried ($MgSO_4$) and concentrated under reduce pressure. The residue was purified via Biotage (gradient: 10-100% of DCM/MeOH (1:0.05) in DCM, KP-SIL 100 g column) to give the title product (5.95 g, 50%). $^1H$ NMR (600 MHz, $CDCl_3$) 1.15-1.40, 1.45-1.81, 2.04-2.20, 2.33, 2.50, 3.65, 3.84, 3.92, 4.04, 4.14-4.28, 4.32, 4.37-4.44, 4.65, 5.25. Total no of protons: 20.

Compound L2.1: 1-(2-Cyclopentyl-2-(methylamino)ethyl)azetidin-3-ol

To a solution of methyl 1-cyclopentyl-2-(3-hydroxyazetidin-1-yl)-2-oxoethylcarbamate (Compound K2.1) (1.89 g, 7.37 mmol) in THF (50 mL) was a 1M solution of LAH in THF (30 mL, 30.0 mmol) dropwise added (over approximately 5 min) at rt under a nitrogen atmosphere. The resultant mixture was stirred at rt for 30 min and heated at 45° C. over night. Additional LAH in THF (1M solution, 10 mL) was added and the mixture was heated at 65° C. for 1 day. The mixture was diluted with $Et_2O$ (150 mL) and the reaction was quenched with $Na_2SO_4×10H_2O$. The mixture was filtered and a HCl solution in EtOH was added (1.25N, 15 mL) to the filtrate. The filtrate was concentrated under reduced pressure and the residue was co-evaporated with MeOH to give the title compound (1.5 g, 75.0%). The obtained crude product was used without further purification. LCMS $(M+H)^+$: 199.

Compound M2.1: (S)-2-Amino-1-(3-hydroxyazetidin-1-yl)pentan-1-one

To a solution of (S)-tert-butyl 1-(3-hydroxyazetidin-1-yl)-1-oxopentan-2-ylcarbamate (Compound A2) (3.5 g, 12.8 mmol) in anhydrous DCM (50 mL) was added TFA (18 mL, 242 mmol) dropwise at 0° C. under $N_{2(g)}$. The reaction mixture was stirred at r.t for 2 h and then concentrated under reduced pressure. The residue was dissolved in DCM and concentrated under reduced pressure to remove the residue of TFA. This procedure was repeated twice with DCM and twice with MeOH. To the residue was added diethyl ether and decanted (×2). The crude product was dried in vacuo give the title compound (3.88 g) used in the next step without further purification. LCMS $(M+H)^+$: 173.1

Compound N2.1: (S)-1-(3-Hydroxyazetidin-1-yl)-2-(propan-2-ylideneamino)pentan-1-one A solution of (S)-2-amino-1-(3-hydroxyazetidin-1-yl)pentan-1-one (Compound M2.1) (1.9 g, 11.0 mmol) in propan-2-one (40 mL, 544 mmol) was stirred at rt for 48 h. The reaction mixture was then concentrated in vacuo until 10 mL remained. To the mixture was added Me-THF (40 mL) and then mixture was again reduced in vacuo until 10 mL remained. This procedure was repeated three times and the remaining mixture (11 mL) was used in the next step without further treatment. LCMS $(M+H)^+$: 213.1.

Compound O2.1: (S)-1-(2-(Isopropylamino)pentyl)azetidin-3-ol

A solution of (S)-1-(3-hydroxyazetidin-1-yl)-2-(propan-2-ylideneamino)pentan-1-one (Compound N2.1) (2.34 g, 11.0 mmol) in Me-THF (11 Ml) was added to aluminum(III) lithium hydride (1.0 M solution in THF) (44.0 mL, 44.00 mmol) dropwise under $N_2$. The reaction mixture was stirred at rt for 40 min and then heated at 60° C. overnight. The reaction mixture was cooled to 0° C. Water (2.25 mL) was added dropwise, followed by 15% aq. NaOH (2.25 mL), THF (35 mL) and water (4.82 mL). The mixture was allowed to reach rt and stirred for 30 min. The mixture was filtered and the solid washed with THF and the filtrate was dried over Na2SO4 and concentrated in vacuo to give the title compound (2.8 g), which was used in the next step without further purification. LCMS (M+H)$^+$: 201.1

Compound S2.1: (2S,3R)-1-Benzhydryl-2-methylazetidin-3-yl benzoate and (2R,3S)-1-benzhydryl-2-methylazetidin-3-yl benzoate Benzoic anhydride (1.61 g, 7.11 mmol) was added to a stirred mixture of (2S,3R)-1-benzhydryl-2-methylazetidin-3-ol and (2R,3S)-1-benzhydryl-2-methylazetidin-3-ol (1.2 g, 4.74 mmol) and N,N-dimethylpyridin-4-amine (1.16 g, 9.47 mmol) in DCM (25 mL), and the resulting mixture was stirred over the weekend. 8% NaHCO$_3$ (25 mL) was added and the stirring continued for 30 min. Phases were separated on a phase separator and the aqueous layer extracted with DCM (25 mL). The combined organic layers were concentrated and purified on a 20 g Isolute Flash Si column eluted with heptane/EtOAc 6:1 to yield the title compound (1.69 g, 100%).
$^1$H NMR (400 MHz, CDCl$_3$) δ 0.88, 2.83, 3.36, 3.84, 4.43, 4.89, 7.16-7.33, 7.39-7.49, 7.56, 8.02. Total no of protons: 23. LCMS (M+H)$^+$: 358.3.

Compound T2.1: (2S,3R)-2-Methylazetidin-3-yl benzoate and (2R,3S)-2-methylazetidin-3-yl benzoate (2S,3R)-1-Benzhydryl-2-methylazetidin-3-yl benzoate and (2R,3S)-1-benzhydryl-2-methylazetidin-3-yl benzoate (Compound S2.1) (1.69 g, 4.73 mmol) was dissolved in EtOH (25 mL) and added to Pd(OH)$_2$ (20% wt Pd, 50% wet, 200 mg). The mixture was hydrogenated at 8 bar pressure over night. The catalyst was filtered off and washed with EtOH, and the combined filtrates were concentrated to yield the title compound as a 1:1 mixture of title compound and diphenylmethane (1.54 g, 90%). $^1$H NMR (400 MHz, CDCl$_3$) δ 1.41, 3.64, 3.81, 4.06, 5.06, 7.46, 7.58, 8.06. Total no of protons: 12. LCMS (M+H)$^+$: 192.1.

Compound U2.1: (2S,3R)-1-(S)-2-(Tert-butoxycarbonylamino)pentanoyl)-2-methylazetidin-3-yl benzoate and (2R,3S)-1-(S)-2-(tert-butoxycarbonylamino)pentanoyl)-2-methylazetidin-3-yl benzoate NMM (0.939 mL, 8.54 mmol) and TBTU (2.06 g, 6.40 mmol) were added to a stirred solution of (S)-2-(tert-butoxycarbonylamino)pentanoic acid (1.21 g, 5.55 mmol), which is commercially available, and (2S,3R)-2-methylazetidin-3-yl benzoate and (2R,3S)-2-methylazetidin-3-yl benzoate (Compound T2.1) (1.54 g, 53% purity, 4.27 mmol) in DCM (15 mL), and the resulting mixture was stirred for 2 h. 8% NaHCO$_3$ (20 mL) was added and the phases separated on a phase separator. The aqueous layer was extracted with DCM (20 mL) and the combined organic layers washed with 8% NaHCO$_3$ (2×20 mL). The organic layer was passed through a phase separator and concentrated. The residue was purified by preparative HPLC to yield the title compound as a 1:1 mixture of (2S,3R)-1-((S)-2-(tert-butoxycarbonylamino) pentanoyl)-2-methylazetidin-3-yl benzoate and (2R,3S)-1-(S)-2-(tert-butoxycarbonylamino)pentanoyl)-2-methylazetidin-3-yl benzoate (1.40 g, 84%). $^1$H NMR (400 MHz, CD$_3$OD) δ 0.89-1.00, 1.27-1.78, 3.88-4.88, 4.95-5.05, 7.50, 7.64, 8.05. Total no of protons: 29. LCMS (M+H)$^+$: 391.3.

The following Compound U2.2 was prepared, in a manner essentially similar to that described for Compound U2.1

| Example | Name | $^1$H NMR and/or LCMS | Yield |
| --- | --- | --- | --- |
| U2.2 | Tert-butyl (S)-1-((S)-3-hydroxypyrrolidin-1-yl)-1-oxopentan-2-ylcarbamate | LCMS (M + H)$^+$: 287. | 9.11 g, quant. yield |

Compound V2.1: (2S,3R)-2-Methyl-1-((S)-2-(methylamino)pentyl)azetidin-3-ol and (2R,3S)-2-methyl-1-((S)-2-(methylamino)pentyl)azetidin-3-ol A solution of a 1:1 mixture of (2S,3R)-1-((S)-2-(tert-butoxycarbonylamino)-pentanoyl)-2-methylazetidin-3-yl benzoate and (2R,3S)-1-(S)-2-(tert-butoxycarbonyl-amino)pentanoyl)-2-methylazetidin-3-yl benzoate (Compound U2.1) (1.40 g, 3.58 mmol) in dry THF (15 mL) was added dropwise to a stirred solution of 1M LiAlH$_4$ in THF (21.5 mL, 21.5 mmol) under a N$_2$ atmosphere. The reaction mixture was stirred at room temperature for 30 min, and at 60° C. over night. The mixture was cooled to 0° C. in an ice-bath and aqueous NaHCO$_3$ (8%, 5.1 mL) was added dropwise (10 mL THF was added to facilitate stirring), and the stirring was continued for an additional 1 h at rt. The mixture was diluted with DCM, the white precipitate filtered off and washed with DCM. The filtrate was concentrated to yield the title compound as a 1:1 mixture of (2S,3R)-2-methyl-1-((S)-2-(methylamino)pentyl)azetidin-3-ol and (2R,3S)-2-methyl-1-((S)-2-(methylamino)pentyl)azetidin-3-ol, containing 1 eq of BnOH (1.00 g, 95%). $^1$H NMR (400 MHz, CD$_3$OD) δ 0.94, 1.14-1.53, 2.28-2.43, 2.48-2.61, 2.68, 2.88, 3.65, 3.77. Total no of protons: 20. LCMS (M+H)$^+$: 187.2.

Compound X2.1: (2S,3S)-2-Methyl-1-((S)-2-(methylamino)pentyl)azetidin-3-ol and (2R,3R)-2-methyl-1-((S)-2-(methylamino)pentyl)azetidin-3-ol A 1:1 mixture of (2S,3S)-2-methyl-1-((S)-2-(methylamino)pentyl)azetidin-3-ol and (2R,3R)-2-methyl-1-((S)-2-(methylamino)pentyl)azetidin-3-ol, containing 1 eq of BnOH (728 mg, 60%) was prepared from (2S,3S)-1-benzhydryl-2-methylazetidin-3-ol and (2R,3R)-1-benzhydryl-2-methylazetidin-3-ol (1.05 g, 4.14 mmol) in 4 steps by the same method as for Compound V2.1. $^1$H NMR (400 MHz, CD$_3$OD) δ 0.93, 1.10, 1.15, 1.18-1.51, 2.21-2.58, 3.02, 3.17-3.31 (partially obscured by solvent peak), 4.26. Total no of protons: 20. LCMS (M+H)$^+$: 187.2.

Compound Y2.1: (S)-Tert-butyl 1-cyclobutyl-2-(3-hydroxyazetidin-1-yl)-2-oxoethylcarbamate NMM (4.26 mL, 38.8 mmol) was added to a mixture of (S)-2-(tert-butoxycarbonylamino)-2-cyclobutylacetic acid (4.04 g, 17.6 mmol), which is commercially available, in DCM (45 mL) and DMF (14 mL). The mixture was cooled to 0° C. and TBTU (5.66 g, 17.6 mmol) was added. After 10 min was azetidin-3-ol hydrochloride (2.40 g, 21.9 mmol) added.

The resultant mixture was stirred at rt over night. The mixture was washed with NaHCO$_3$ (8% aq., 30 mL). A second wash with NaHCO$_3$ (8% aq., 30 mL) resulted in an emulsion. The emulsion was diluted with DCM (50 mL) and NaHCO$_3$ (8% aq., 30 mL), mixed well and left to separate. The organic layer was dried (Na$_2$SO$_4$) and concentrated under reduced pressure. The residue was co-evaporated with toluene to give the title compound (4.10 g, 82%) as a solid. The obtained crude product was used without further purification. $^1$H NMR (400 MHz, CD$_3$OD) δ 1.44 (9H), 1.76-2.09 (6H), 2.51-2.65 (1H), 3.67-3.82 (1H), 3.97-4.27 (3H), 4.45-4.69 (2H). Expected Number of protons: 24. OH- and NH-protons are exchanged with CD$_3$OD.

Compound Z2.1: (S)-1-(2-Cyclobutyl-2-(methylamino)ethyl)azetidin-3-ol

A 1 M solution of LAH in THF (66.8 mL, 66.8 mmol) under nitrogen was heated to 45° C. A solution of (S)-tert-butyl 1-cyclobutyl-2-(3-hydroxyazetidin-1-yl)-2-oxoethylcarbamate (Compound Y2.1) (3.80 g, 13.4 mmol) in THF (20 mL) was added dropwise over 30 min. The resultant mixture was stirred at 47° C. over night. The mixture was cooled on an ice-bath and NaHCO$_3$ (8% aq., 16 mL) was carefully added dropwise. The stirring was continued for 2 h at rt. The precipitate was filtered off and washed with DCM. The filtrate was concentrated and the residue dissolved in DCM and filtered through a 0.45 μm syringe filter. The filtrate was concentrated to give the title compound (2.23 g, 91%, 92% pure) as an oil. $^1$H NMR (400 MHz, CD$_3$OD) δ 1.69-2.13 (6H), 2.2-2.38 (7H), 2.79 (1H), 2.89 (1H), 3.56-3.66 (2H), 4.26-4.34 (1H). Expected Number of protons: 20. OH- and NH-protons are exchanged with CD$_3$OD.

Compound A3.1: (S)-Tert-butyl 1-(3-hydroxyazetidin-1-yl)-1-oxopropan-2-ylcarbamate DIPEA (8.53 mL, 49.0 mmol) was added to a mixture of (S)-2-(tert-butoxycarbonylamino)propanoic acid (3.089 g, 16.33 mmol), which is commercially available, and TBTU (5.24 g, 16.33 mmol) in DCM (30 mL). Upon stirring at rt the mixture gradually became a clear solution. Azetidin-3-ol hydrochloride (2.68 g, 24.5 mmol) was added and the mixture was stirred over night. NaHCO$_3$ (8% aq., 20 mL) was added. The organic layer was washed with NaHCO$_3$ (8% aq., 3×60 mL). DCM (100 mL) was used for back extraction of the combined aqueous phases. Toluene was added and the combined organic layers were concentrated on the rotavapor over night (45° C. in waterbath) to give the title product (3.35 g, 84%,) as a transparent oil which solidified upon standing. Mixture of rotamers: $^1$H NMR (500 MHz, CD$_3$OD) δ 1.21-1.27, 1.41-1.49, 3.7-3.83, 3.98-4.27, 4.41-4.47, 4.56-4.64.

The following Compound A3.2 was prepared in a manner essentially similar to that described for Compound A3.1.

| Example | Name | $^1$H NMR and/or LCMS | Yield |
|---|---|---|---|
| A3.2 | (S)-Tert-butyl 1-(3-hydroxyazetidin-1-yl)-1-oxobutan-2-ylcarbamate | $^1$H NMR (400 MHz, CD$_3$OD) δ0.9-1, 1.4-1.5, 1.52-1.74, 3.7-4.05, 4.13-4.28, 4.41-4.48, 4.53-4.65. | 8.08 g, 110%. 61% pure |

Compound B3.1: Tert-butyl 1,1,1-trifluoro-3-(3-hydroxyazetidin-1-yl)-3-oxopropan-2-ylcarbamate TBTU (6.87 g, 21.4 mmol) was added to a stirred suspension of 2-(tert-butoxycarbonylamino)-3,3,3-trifluoropropanoic acid, which is commercially available, in DCM (50 mL). NMM (4.4 mL, 40 mmol) and 3-hydroxyazetidinol hydrochloride (2.48 g, 22.6 mmol) were added. The mixture was stirred at rt for 4 h. The turbid solution was diluted with DCM (70 mL) and washed with NaHCO$_3$ solution (saturated, 1×100, 2×20 mL). After drying (Na$_2$SO$_4$) the solvent was evaporated under reduced pressure. The residue was stirred at rt with isohexanes (60 mL) to yield the title product (3.97 g, 97%) as a colourless powder. $^1$H NMR (500 MHz, DMSO-d6) δ 7.86-8.05 (1H), 5.71-5.87 (1H), 4.86-5.03 (1H), 4.27-4.54 (2H), 4.04-4.15 (1H), 3.78-3.97 (1H), 3.56-3.68 (1H), 1.38-1.4 (9H). Ratio of rotamers ~6:4.

Compound C3.1: 1-(3,3,3-Trifluoro-2-(methylamino)propyl)azetidin-3-ol

Tert-butyl 1,1,1-trifluoro-3-(3-hydroxyazetidin-1-yl)-3-oxopropan-2-ylcarbamate (Compound B3.1) (3.97 gg, 13.3 mmol) was added under argon in portions to 1M solution of LAH in THF (53 mL, 53 mmol) over 15 min. The mixture was heated under argon to reflux for 7 h. After additional standing for 15 h at rt EtOAc (10 mL) was added dropwise under ice cooling, followed by addition of water/THF (1:1, 12 mL). The mixture was diluted with DCM (120 mL). Celite was added and the suspension was stirred for 10 min. The mixture was filtered, the solids washed with DCM (2×50 mL). The combined filtrates were dried (Na$_2$SO$_4$) and concentrated under reduced pressure to give the title compound (2.39 g, 91%). The obtained crude product was used in the next step without characterization.

Compound D3.1: 1-(3,3,3-Trifluoro-2-(methylamino)propyl)azetidin-3-yl benzoate A solution of benzoyl fluoride (1.37 mL, 12.6 mmol) in DCM (5 mL) was added dropwise under argon to an ice cooled solution of 1-(3,3,3-trifluoro-2-(methylamino)propyl)azetidin-3-ol (Compound C3.1) (2.28 g, 11.5 mmol) and TEA (3.21 mL, 23 mmol) in DCM (45 mL). The stirring was continued at rt for 2.5 h. NaHCO$_3$ (saturated, 20 mL) was added and the mixture was stirred vigorously for 40 min. The layers were separated, the aqueous layer was extracted with DCM, and the combined organic layers were washed with NaHCO$_3$ (saturated), dried (Na$_2$SO$_4$) and concentrated under reduced pressure. The residue was purified by preparative HPLC. After concentrating the fractions to approximately 30 mL the aqueous emulsion was extracted DCM (×2). The combined organic layers were dried (Na$_2$SO$_4$) and concentrated under reduced pressure to give the title product (1.54 g, 44%.) as a colourless oil. $^1$H NMR (500 MHz, DMSO-d6) δ 7.97 (2H), 7.67 (1H), 7.53 (2H), 5.16 (1H), 3.7-3.79 (2H), 3.25 (1H), 3.18 (1H), 2.92-3.02 (1H), 2.66 (1H), 2.59 (1H), 2.38 (3H), 1.99-2.06 (1H).

Compound E3.1: (S)-Tert-butyl 1-(4-hydroxypiperidin-1-yl)-1-oxopentan-2-ylcarbamate TBTU (7.09 g, 22.09 mmol) was added to a solution of (S)-2-(tert-butoxycarbonylamino)pentanoic acid (4 g, 18.41 mmol), which is commercially available, and piperidin-4-ol (2.235 g, 22.09 mmol) in DCM (50 mL). The reaction was stirred for 3 h and was then quenched by addition of NaHCO3 (aq., 8%, 25 mL). The aqueous phase was extracted with DCM. The organic phases were combined, dried (MgSO$_4$), filtered and evaporated. The residue was added H$_3$PO$_4$ (aq) (1 M, 25 mL) and the aqueous phase was extracted with Et$_2$O.

The organic phases were pooled, dried (MgSO₄), filtered and evaporated to give the title product (5.86 g, 106%) as a yellow oil. The obtained crude product was used in the next step without characterization.

It may be noted that certain intermediates disclosed herein for preparation of compounds of Formula I are believed to be novel and therefore comprise an independent aspect of the invention.

It shall be noted that if the intermediate/compound was prepared as a specific isomer (e.g. 3R,4S), the chemical name of the intermediate/compound reflects that.

Example 1.1

(S)—N-(1-(Azetidin-1-yl)pentan-2-yl)-2,4-dichloro-N-methylbenzamide

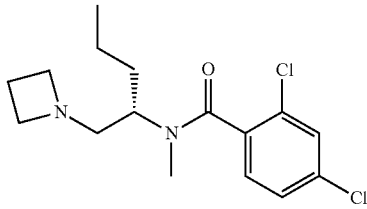 [SMILES: CCC[C@@H](CN1CCC1)N(C)C(=O)c1ccc(Cl)cc1Cl]

2,4-Dichlorobenzoic acid (92 mg, 0.48 mmol) and TBTU (162 mg, 0.50 mmol) was mixed in DMF (1.5 mL). The mixture was cooled to 0° C. and NMM (0.063 mL, 0.58 mmol) was dropwise added. After 10 min at 0° C. was (S)-1-(azetidin-1-yl)-N-methyl-pentan-2-amine (Compound J1) (75 mg, 0.48 mmol) added. The resultant mixture was stirred at 0° C. for 30 min and at rt for 16 h. The mixture was concentrated and the residue dissolved in DCM (5 mL). The organic phase was washed with NaHCO₃ (saturated, 2×5 mL), filtered through a phase separator and concentrated under reduced pressure. The residue was purified by preparative HPLC to give the title compound (98 mg, 62%). Mixture of rotamers: ¹H NMR (400 MHz, DMSO-d6): 0.59-0.87, 0.90, 0.98-1.66, 1.72-2.11, 2.22-2.47, 2.5, 2.78, 4.26-4.70, 7.24-7.36, 7.43-7.64, 7.65-7.79. Total no of protons: 22. HRMS (M+H)⁺: calculated 329.1187. found 329.1161

The compounds according to Examples 1.2-1.17 were prepared, from appropriate intermediates, by analogy with the method described for Example 1.1 hereinbefore.

| Example | Name | Yield |
|---|---|---|
| 1.2 | (S)-N-(1-(Azetidin-1-yl)pentan-2-yl)-4-chloro-N-methylbenzamide | 87 mg, 62% |
| ¹H NMR and HRMS | Mixture of rotamers: (400 MHz, DMSO-d6) δ 0.62-1.11, 1.15-1.80, 2.41, 3.00-3.22, 3.3 (overlaps with the H₂O peak), 3.42-3.73, 4.55-4.76, 7.10-7.71. Ratio major:minor: 3:2. Total no of protons: 23. HRMS (M + H)⁺: calculated found 295.1563. The compound was 295.1577; found to be amorphous by XRPD. | |
| 1.3 | (S)-N-(1-(Azetidin-1-yl)pentan-2-yl)-4-bromo-N-methylbenzamide | 88 mg, 54% |
| ¹H NMR and HRMS | Mixture of rotamers: (400 MHz, DMSO-d6) δ 0.58-0.98, 0.93-1.65, 1.79-1.98, 2.20-2.37, 2.5 (overlaps with the DMSO peak), 2.56-2.79, 2.83-3.03, 3.03-3.17, 3.3 (overlaps with the H₂O peak), 4.46, 7.12-7.72. Ratio major:minor: 7:3. Total no of protons: 23. HRMS (M + H)⁺: calculated 339.1072; found 339.1067 | |
| 1.4 | (S)-N-(1-(Azetidin-1-yl)pentan-2-yl)-4-fluoro-N,3-dimethyl-benzamide | 77 mg, 55% |
| ¹H NMR and HRMS | Mixture of rotamers: (400 MHz, DMSO-d6) δ 0.47-1.65, 1.74-2.01, 2.26, 2.30-2.41, 2.5 (overlaps with the DMSO peak), 2.67, 2.86-3.06, 3.05-3.21, 3.36-3.54, 4.47, 6.82-7.56. Total no of protons: 25. HRMS (M + H)⁺: calculated 293.2029; found 293.2017 | |
| 1.5 | (S)-4-Fluoro-N-(1-(3-fluoroazetidin-1-yl)-3-methylbutan-2-yl)-N,3-dimethylbenzamide | 35 mg, 20% |
| ¹H NMR and HRMS | Mixture of rotamers: (400 MHz, CD₃OD) δ 0.75-1.13, 1.65-1.99, 2.30, 2.55-2.98, 3.05-3.29, 3.39-3.80, 4.28, 4.95-5.28, 7.03-7.16, 7.21-7.52. Total no of protons: 24. HRMS (M + H)⁺: calculated 311.1935; found 311.1930 | |
| 1.6 | (S)-4-Chloro-N-(1-(3-fluoroazetidin-1-yl)-3-methylbutan-2-yl)-N-methylbenzamide | 36 mg, 20% |
| ¹H NMR and HRMS | Mixture of rotamers: (400 MHz, CD₃OD) δ 0.74-1.13, 1.66-1.96, 2.51-3.00, 3.05-3.27, 3.42-3.82, 4.29, 4.95-5.28, 7.31-7.63. Total no of protons: 22. HRMS (M + H)⁺: calculated 313.1483; found 313.1486 | |
| 1.7 | (S)-4-Bromo-N-(1-(3-fluoroazetidin-1-yl)-3-methylbutan-2-yl)-N-methylbenzamide | 41 mg, 20% |
| ¹H NMR and HRMS | Mixture of rotamers: (400 MHz, CD₃OD) δ 0.77-1.11, 1.66-1.99, 2.56-2.80, 2.81-2.97, 3.06-3.28, 3.38-3.76, 4.28, 4.94-5.26, 7.30-7.51, 7.54-7.68. Total no of protons: 22. HRMS (M + H)⁺: calculated 357.0978; found 357.0975 | |
| 1.8 | (S)-3-Chloro-4-fluoro-N-(1-(3-fluoroazetidin-1-yl)-3-methylbutan-2-yl)-N-methylbenzamide | 34 mg, 18% |
| ¹H NMR and HRMS | NMR (400 MHz, CD₃OD) δ 0.60-1.27, 1.61-2.01, 2.44-3.01, 3.04-3.42, 3.43-3.82, 4.07-4.44, 4.94-5.30, 7.23-7.85. Total no of protons: 21. HRMS (M + H)⁺: calculated 331.1389; found 331.1394 | |
| 1.9 | (S)-4-Fluoro-N-(1-(3-fluoroazetidin-1-yl)-3-methyl-butan-2-yl)-N-methyl-3-(trifluoromethyl)benzamide | 31 mg, 15% |
| ¹H NMR and HRMS | NMR (400 MHz, CD₃OD) δ 0.56-1.27, 1.61-2.02, 2.48-3.06, 3.09-3.41, 3.43-3.97, 4.16-4.41, 4.97-5.32, 7.27-7.57, 7.63-8.17. Total no of protons: 21. HRMS (M + H)⁺: calculated 365.1652; found 365.1658 | |
| 1.10 | (S)-N-(1-(Azetidin-1-yl)-3-methylbutan-2-yl)-4-fluoro-N,3-dimethylbenzamide | 47 mg, 53% |
| ¹H NMR and HRMS | Mixture of rotamers: (600 MHz, DMSO-d6) δ 0.70, 0.81, 0.93, 1.57-1.79, 1.84-1.99, 2.23, 2.14-2.69 (omitted signals), 2.70, 2.92-3.17, 3.3-3.4 (omitted signals), 7.11-7.19, 7.23, 7.33, 7.39. HRMS (M + H)⁺: calculated 293.2029; found 293.1999 | |
| 1.11 | (S)-N-(1-(Azetidin-1-yl)-3-methylbutan-2-yl)-4-fluoro-N-methyl-3-(trifluoromethyl)benzamide | 39 mg, 17% |
| ¹H NMR and HRMS | Mixture of rotamers: (400 MHz, CD₃OD) δ 0.47-1.22, 1.67-1.94, 1.96-2.25, 2.50-2.68, 2.72, 2.87, 3.04-3.24, 3.25-3.40, 4.29, 7.28-7.57, 7.59-8.05, 8.04-8.26. Ratio major:minor: 7:3. Total no of protons: 22. HRMS (M + H)⁺: calculated 347.1747; found 347.1757 | |
| 1.12 | (S)-N-(1-(Azetidin-1-yl)-3-methylbutan-2-yl)-3-chloro-4-fluoro-N-methylbenzamide | 28 mg, 14% |
| HRMS | HRMS (M + H)⁺: calculated 313.1483; found 313.1473 | |
| 1.13 | (S)-N-(1-(Azetidin-1-yl)-3-methylbutan-2-yl)-3-chloro-N-methylbenzamide | 23 mg, 12% |
| HRMS | HRMS (M + H)⁺: calculated 295.1577; found 295.1592 | |
| 1.14 | (S)-N-(1-(Azetidin-1-yl)-3-methylbutan-2-yl)-N-methylbenzamide | 1.8 mg, 1% |
| HRMS | HRMS (M + H)⁺: calculated 261.1967; found 261.1958 | |
| 1.15 | (S)-N-(1-(Azetidin-1-yl)-3-methylbutan-2-yl)-N-methyl-3-(trifluoromethyl)benzamide | 3.8 mg, 1.8% |
| HRMS | HRMS (M + H)⁺: calculated 329.1841; found 329.1832 | |

-continued

| Example | Name | Yield |
|---|---|---|
| 1.16 | (S)-N-(1-(Azetidin-1-yl)-3-methylbutan-2-yl)-N,3-dimethyl-benzamide | 3.8 mg, 1.8% |
| HRMS | HRMS (M + H)$^+$: calculated 275.2123; found 275.2113 | |
| 1.17 | (S)-2-Chloro-4-fluoro-N-methyl-N-(3-methyl-1-(pyrrolidin-1-yl)butan-2-yl)benzamide | 2.62 g, 89% |
| $^1$H NMR. HRMS and XRPD | Mixture of rotamers: (400 MHz, CD$_3$OD) δ 0.70-1.19, 1.52-2.03, 2.21-3.21, 4.25-4.62, 6.99-7.46, 7.62-7.77. Total no of protons: 24. HRMS (M + H)$^+$: calculated 327.1639; found 327.1629. XRPD pattern d (Å) 8.9 (vs), 7.5 (vw), 6.6 (vw), 5.2 (vw), 5.0 (vw), 4.84 (vw), 4.56 (vw), 3.63 (vw), 3.31 (vw), 2.90 (vw)) | |

Example 2.1

(S)-3,4-Dichloro-N-(3,3-dimethyl-1-(pyrrolidin-1-yl)butan-2-yl)-N-methylbenzamide

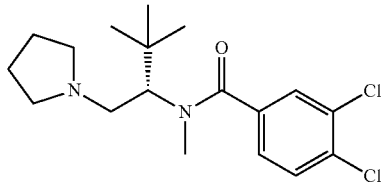 [SMILES: CN(C(=O)c1ccc(Cl)c(Cl)c1)[C@H](CN1CCCC1)C(C)(C)C]

To a solution of (S)—N,3,3-trimethyl-1-(pyrrolidin-1-yl)butan-2-amine (Compound M1) (75 mg, 0.41 mmol) in DMF (1.5 mL) was NMM (0.049 mL, 0.45 mmol) and 3,4-dichlorobenzoyl chloride (0.074 mL, 0.53 mmol) added. The resultant mixture was stirred at rt overnight. The mixture was concentrated and the residue dissolved in DCM (5 mL). The organic phase was washed with NaHCO$_3$ (saturated, 5 mL), filtered through a phase separator and concentrated under reduced pressure. The residue was purified by preparative HPLC to give the title compound (109 mg, 75%). Mixture of rotamers: $^1$H NMR (400 MHz, DMSO-d6) δ 0.97, 1.35-1.99, 2.07-2.43, 2.52-2.73, 2.93-3.18, 4.57, 6.86-7.18, 7.18-7.37, 7.37-7.61, 7.61-7.88. Total no of protons: 26. HRMS (M+H)$^+$: calculated 357.1500. found 357.1470.

The compounds according to Examples 2.2-2.6 were prepared, from appropriate intermediates, by analogy with the method described for Example 2.1 hereinbefore.

| Example | Name | Yield |
|---|---|---|
| 2.2 | (S)-4-Bromo-N-(3,3-dimethyl-1-(pyrrolidin-1-yl)butan-2-yl)-N-methylbenzamide | 78 mg, 52% |
| $^1$H NMR and HRMS | Mixture of rotamers: (400 MHz, DMSO-d6) δ 0.90, 1.55-1.76, 2.16-2.43, 2.71, 2.87, 2.93-3.11, 3.34-3.44, 4.48-4.72, 7.23-7.32, 7.35-7.43, 7.43-7.53. Ratio major:minor: 7:3. Total no of protons: 27. HRMS (M + H)$^+$: calculated 367.1385; found 367.1376 | |
| 2.3 | 4-Chloro-N-methyl-N-((2S,3S)-3-methyl-1-(pyrrolidin-1-yl)pentan-2-yl)benzamide | 74 mg, 56% |
| $^1$H NMR and HRMS | Mixture of rotamers: (400 MHz, CD$_3$OD) δ 0.71-1.09, 1.10-1.30, 1.41-1.97, 2.32-3.05, 3.37-3.52, 4.40-4.71, 7.14-7.76. Total no of protons: 27. HRMS (M + H)$^+$: calculated 323.1890; found 323.1984 | |
| 2.4 | 4-Bromo-N-methyl-N-((2S,3S)-3-methyl-1-(pyrrolidin-1-yl)pentan-2-yl)benzamide | 64 mg, 43% |
| $^1$H NMR and HRMS | Mixture of rotamers: (400 MHz, CD$_3$OD) δ 0.65-1.08, 1.06-1.31, 1.37-1.59, 1.59-1.97, 2.34-3.03, 3.36-3.46, 4.31-4.71, 7.16-7.45, 7.45-7.76. Total no of protons: 27. HRMS (M + H)$^+$: calculated 367.1385; found 367.1360 | |
| 2.5 | 4-Fluoro-N,3-dimethyl-N-((2S,3S)-3-methyl-1-(pyrrolidin-1-yl)pentan-2-yl)benzamide | 87 mg, 67% |
| $^1$H NMR and HRMS | Mixture of rotamers: (400 MHz, CD$_3$OD) δ 0.59-1.09, 1.08-1.30, 1.37-1.97, 2.07-3.05, 3.42-3.63, 4.40-4.70, 6.96-7.19, 7.19-7.51. Total no of protons: 29. HRMS (M + H)$^+$: calculated 321.2342; found 321.2343 | |
| 2.6 | 2,4-Dichloro-N-methyl-N-((2S,3S)-3-methyl-1-(pyrrolidin-1-yl)pentan-2-yl)benzamide | 68 mg, 47% |
| $^1$H NMR and HRMS | Mixture of rotamers: (400 MHz, CD$_3$OD) δ 0.71-1.13, 1.11-1.34, 1.77, 2.24-2.59, 2.59-2.79, 2.79-3.03, 4.28-4.71, 7.12-7.74. Total no of protons: 26. HRMS (M + H)$^+$: calculated 357.1500; found 357.1473 | |

Example 3.1

4-Fluoro-N-((2R,3R)-3-methoxy-1-(pyrrolidin-1-yl)butan-2-yl)-N,3-dimethylbenzamide

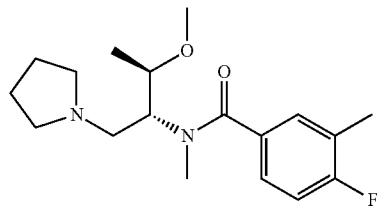 [SMILES: CO[C@H](C)[C@@H](CN1CCCC1)N(C)C(=O)c1ccc(F)c(C)c1]

To a solution of (2R,3R)-3-methoxy-N-methyl-1-(pyrrolidin-1-yl)butan-2-amine (Compound M6) (80 mg, 0.43 mmol) in DCM (1.5 mL) was DIPEA (0.090 mL, 0.52 mmol) and 4-fluoro-3-methylbenzoyl chloride (0.061 mL, 0.43 mmol) added. The resultant mixture was stirred at rt overnight. The mixture was diluted with DCM (5 mL), washed with NaHCO3 (saturated, 5 mL), filtered through a phase separator and concentrated under reduced pressure. The residue was purified by preparative HPLC to give the title compound (102 mg, 74%).

Mixture of rotamers: $^1$H NMR (400 MHz, CD$_3$OD) δ 1.09, 1.22, 1.53-1.94, 2.17-2.40, 2.40-2.49, 2.50-2.63, 2.63-2.76, 2.76-2.86, 2.89, 2.97, 3.19, 3.31, 3.37-3.44, 3.52-3.66, 3.65-3.81, 6.87-7.15, 7.17-7.57. Ratio major:minor:3:2. Total no of protons in spectrum: 27. HRMS (M+H)$^+$: calculated 323.2135. found 323.2139.

The compounds according to Examples 3.2-3.20 were prepared, from appropriate intermediates, by analogy with the method described for Example 3.1 hereinbefore.

| Example | Name | Yield |
|---|---|---|
| 3.2 | N-((2R,3R)-3-Methoxy-1-(pyrrolidin-1-yl)butan-2-yl)-N,3-dimethylbenzamide | 84 mg, 64% |
| $^1$H NMR and HRMS | Mixture of rotamers: (400 MHz, CD$_3$OD) δ 1.08, 1.25, 1.55-2.03, 2.17-2.42, 2.42-2.53, 2.53-2.64, 2.65-2.76, 2.76-2.84, 2.84, 3.01, 3.14-3.24, 3.34, 3.36-3.46, 3.54-3.67, 3.67-3.79, 7.01-7.55. Ratio major:minor: 3:2. | |

-continued

| Example | Name | Yield |
|---|---|---|
| | Total no of protons: 28. HRMS (M + H)⁺: calculated 305.2229; found 305.2216 | |
| 3.3 | 3-Chloro-4-fluoro-N-((2R,3R)-3-methoxy-1-(pyrrolidin-1-yl)butan-2-yl)-N-methylbenzamide | 79 mg, 53% |
| ¹H NMR and HRMS | Mixture of rotamers: (400 MHz, CD₃OD) δ 1.09, 1.24, 1.50-2.02, 2.22-2.50, 2.48-2.65, 2.65-2.80, 2.79, 3.19-3.28, 3.34, 3.37-3.46, 3.50-3.76, 7.23-7.38, 7.38-7.52, 7.54-7.71. Ratio major:minor: 55:45. Total no of protons: 24. HRMS (M + H)⁺: calculated 343.1588; found 343.1567 | |
| 3.4 | 4-Bromo-N-((2R,3R)-3-methoxy-1-(pyrrolidin-1-yl)butan-2-yl)-N-methylbenzamide | 101 mg, 64% |
| ¹H NMR and HRMS | Mixture of rotamers: (400 MHz, CD₃OD) δ 0.95-1.37, 1.60-1.93, 2.24-2.38, 2.38-2.49, 2.49-2.64, 2.64-2.77, 2.77-2.87, 2.90, 2.97, 3.16-3.25, 3.34, 3.40, 3.51-3.72, 7.28-7.50, 7.60. Ratio major:minor: 3:2. Total no of protons: 25. HRMS (M + H)⁺: calculated 369.1177; found 369.1188 | |
| 3.5 | 4-Chloro-N-((2R,3R)-3-methoxy-1-(pyrrolidin-1-yl)butan-2-yl)-N-methylbenzamide | 73 mg, 53% |
| ¹H NMR and HRMS | Mixture of rotamers: (400 MHz, CD₃OD) δ 1.09, 1.22, 1.56-2.03, 2.21-2.38, 2.38-2.50, 2.50-2.62, 2.64-2.76, 2.78-2.87, 2.88, 2.98, 2.99, 3.20, 3.34, 3.40, 3.53-3.72, 7.21-7.65. Ratio major:minor: 3:2. Total no of protons: 25. HRMS (M + H)⁺: calculated 325.1683; found 325.1672 | |
| 3.6 | (S)-4-Bromo-N-(1-(4-methoxypiperidin-1-yl)-3-methylbutan-2-yl)-N-methylbenzamide | 132 mg, 75% |
| ¹H NMR and HRMS | Mixture of rotamers: (400 MHz, CD₃OD) δ 0.69-1.19, 1.33-1.66, 1.66-2.08, 2.11-2.22, 2.24-2.51, 2.51-2.71, 2.72, 2.91, 2.93-3.07, 3.12-3.27, 3.33, 4.49, 7.25-7.38, 7.37-7.56, 7.56-7.79. Ratio major:minor: 7:3. Total no of protons: 29. HRMS (M + H)⁺: calculated 397.1490; found 397.1479 | |
| 3.7 | (S)-4-Chloro-N-(1-(4-methoxypiperidin-1-yl)-3-methylbutan-2-yl)-N-methylbenzamide | 108 mg, 69% |
| ¹H NMR and HRMS | Mixture of rotamers: (400 MHz, CD₃OD) δ 0.70-1.15, 1.35-1.66, 1.68-2.07, 2.11-2.22, 2.23-2.51, 2.51-2.70, 2.74, 2.91, 2.94-3.05, 3.12-3.28, 3.33, 4.49, 7.29-7.43, 7.43-7.53. Ratio major:minor: 7:3. Total no of protons: 29. HRMS (M + H)⁺: calculated 353.1996; found 353.1976 | |
| 3.8 | (S)-4-Fluoro-N-(1-(4-methoxypiperidin-1-yl)-3-methylbutan-2-yl)-N,3-dimethylbenzamide | 79 mg, 51% |
| ¹H NMR and HRMS | Mixture of rotamers: (400 MHz, CD₃OD) δ 0.63-1.24, 1.35-1.64, 2.22-2.49, 2.50-2.81, 2.81-3.06, 3.11-3.28, 3.33, 3.37-3.48, 4.48, 7.00-7.17, 7.18-7.44. Ratio major:minor: 7:3. Total no of protons: 31. HRMS (M + H)⁺: calculated 351.2448; found 351.2447 | |
| 3.9 | (S)-3-Chloro-4-fluoro-N-(1-(4-methoxypiperidin-1-yl)-3-methylbutan-2-yl)-N-methylbenzamide | 107 mg, 65% |
| ¹H NMR and HRMS | Mixture of rotamers: (400 MHz, CD₃OD) δ 0.69-1.17, 1.37-1.67, 1.68-2.14, 2.14-2.25, 2.27-2.55, 2.54-2.71, 2.75, 2.90, 2.93-3.05, 3.17-3.28, 3.33, 4.46, 7.27-7.42, 7.42-7.49, 7.49-7.58, 7.61-7.71. Ratio major:minor: 7:3. Total no of protons: 28. HRMS (M + H)⁺: calculated 371.1902; found 371.1882 | |
| 3.10 | (S)-N-(1-(4-Methoxypiperidin-1-yl)-3-methylbutan-2-yl)-N,3-dimethylbenzamide | 94 mg, 64% |
| ¹H NMR and HRMS | Mixture of rotamers: (400 MHz, CD₃OD) δ 0.67-1.18, 1.38-1.65, 1.65-2.07, 2.09-2.20, 2.23-2.51, 2.63, 2.90, 2.94-3.10, 3.17-3.28, 3.33, 3.37-3.47, 4.50, 7.12-7.22, 7.22-7.37. Ratio major:minor: 7:3. Total no of protons: 32. HRMS (M + H)⁺: calculated 333.2542; found 333.2537 | |
| 3.11 | (S)-3-Methoxy-N-(1-(4-methoxypiperidin-1-yl)-3-methylbutan-2-yl)-N,4-dimethylbenzamide | 124 mg, 77% |
| HRMS | HRMS (M + H)⁺: calculated 363.2648; found 363.2641 | |
| 3.12 | (S)-N-(1-(4-Methoxypiperidin-1-yl)-3-methylbutan-2-yl)-N,3,4-trimethylbenzamide | 100 mg, 65% |
| HRMS | HRMS (M + H)⁺: calculated 347.2698; found 347.2685 | |
| 3.13 | (S)-N-(1-Cyclopropyl-2-(pyrrolidin-1-yl)ethyl)-4-fluoro-N,3-di-methylbenzamide | 107 mg, 59% |
| ¹H NMR and HRMS | Mixture of rotamers: (400 MHz, DMSO-d6) δ 0.06-0.63, 0.90-1.03, 1.54-1.72, 2.13-2.62, 2.70-3.03, 3.82-3.97, 7.07-7.31. Ratio major:minor: 1:0.7. Total no of protons: 25. HRMS (M + H)⁺: calculated 305.2029; found 305.2014 | |
| 3.14 | (S)-4-Chloro-N-(1-cyclopropyl-2-(pyrrolidin-1-yl)ethyl)-N-methylbenzamide | 86 mg, 47% |
| ¹H NMR and HRMS | Mixture of rotamers: (600 MHz, DMSO-d6) δ 0.02-0.72, 0.88-1.09, 1.51-1.80, 2.06-2.58, 2.70-3.12, 3.78-4.05, 7.24-7.37, 7.38-7.59. Ratio: 1:1. Total no of protons: 23 HRMS (M + H)⁺: calculated 307.1577; found 307.1572 | |
| 3.15 | (S)-4-Bromo-N-(1-cyclopropyl-2-(pyrrolidin-1-yl)ethyl)-N-methylbenzamide | 81 mg, 39% |
| ¹H NMR and HRMS | Mixture of rotamers: (400 MHz, DMSO-d6) δ 0.02-0.72, 0.88-1.09, 1.51-1.80, 2.06-2.58, 2.70-3.12, 3.78-4.05, 7.24-7.37, 7.38-7.59. Ratio: 1:1. Total no of protons: 23. HRMS (M + H)⁺: calculated 351.1072; found 351.1055 | |
| 3.16 | (S)-N-(1-Cyclopropyl-2-(pyrrolidin-1-yl)ethyl)-3,4-difluoro-N-methylbenzamide | 121 mg, 66% |
| ¹H NMR and HRMS | Mixture of rotamers: (600 MHz, DMSO-d6) δ 0.05-0.68, 0.89-1.08, 1.55-1.76, 2.12-2.65, 2.69-3.08, 3.78-3.96, 7.12-7.22, 7.31-7.58. Total no of protons: 22. HRMS (M + H)⁺: calculated 309.1778; found 309.1760 | |
| 3.17 | (S)-N-(1-Cyclopropyl-2-(pyrrolidin-1-yl)ethyl)-N,3-dimethyl-benzamide | 142 mg, 83% |
| ¹H NMR and HRMS | Mixture of rotamers: (600 MHz, DMSO-d6) δ 0.09-0.68, 0.90-1.05, 1.53-1.77, 2.11-2.63, 2.69-3.04, 3.84-3.98, 6.97-7.38. Ratio major:minor: 1:0.7. Total no of protons: 26. HRMS (M + H)⁺: calculated 287.2123; found 287.2118 | |
| 3.18 | 4-Methoxy-N-((S)-1-((S)-2-(methoxy-methyl)pyrrolidin-1-yl)-3-methylbutan-2-yl)-N-methylbenzamide | 3.3 mg, 2.7% |
| HRMS | HRMS (M + H)⁺: calculated 349.2491; found 349.2481 | |
| 3.19 | 4-Chloro-N-((S)-1-((S)-2-(methoxy-methyl)pyrrolidin-1-yl)-3-methylbutan-2-yl)-N-methylbenzamide | 121 mg, 66% |
| ¹H NMR and HRMS | Mixture of rotamers: (600 MHz, DMSO-d6, (CH₃)₂SO#) δ 0.74, 0.82, 0.96, 1.23-1.48, 1.55-1.84, 2.56-2.70, 2.73, 2.8-4.2 (omitted signals), 7.23-7.32, 7.38-7.51. Ratio major:minor: 3:2. HRMS (M + H)⁺: calculated 353.1996; found 353.2000 | |
| 3.20 | 4-Bromo-N-((S)-1-((S)-2-(methoxy-methyl)pyrrolidin-1-yl)-3-methylbutan-2-yl)-N-methylbenzamide | 8.8 mg, 6.3% |
| HRMS | HRMS (M + H)⁺: calculated 397.1490; found 397.1479 | |

Example 4.1

(S)—N-(2-(Azetidin-1-yl)-1-cyclopropylethyl)-4-fluoro-N,3-dimethylbenzamide

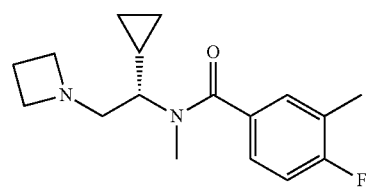 [SMILES: Cc1cc(C(=O)N(C)[C@H](CN2CCC2)C2CC2)ccc1F]

To a mixture of 4-fluoro-3-methylbenzoic acid (330 mg, 2.14 mmol) and DIPEA (0.508 mL, 2.92 mmol) in DCM (3 mL) was TBTU (687 mg, 2.14 mmol) added. After 10 min was a solution of (S)-2-(azetidin-1-yl)-1-cyclopropyl-N-methylethanamine (Compound L1) (300 mg, 1.94 mmol) in DCM (3 mL) added. The resultant mixture was stirred at r.t for 6 h. The mixture was washed with NaHCO$_3$ (8% aq., 5 mL), filtered through a phase separator and concentrated under reduced pressure. The residue was purified by preparative HPLC to give the title compound (353 mg, 63%). Mixture of rotamers: $^1$H NMR (600 MHz, CD$_3$OD) δ 0.04-0.14, 0.31-0.40, 0.40-0.48, 0.48-0.57, 0.59-0.66, 0.67-0.75, 0.92-1.06, 2.01-2.07, 2.07-2.16, 2.29, 2.30, 2.56-2.65, 2.76-2.88, 2.90, 2.94-3.00, 3.02, 3.09-3.21, 3.26-3.37, 3.80-3.91, 7.04-7.14, 7.22-7.40. Total no of protons: 23. HRMS (M+H)$^+$: calculated 291.1873. found 291.1865.

The compounds according to Examples 4.2-4.4 were prepared, from appropriate intermediates, by analogy with the method described for Example 4.1 hereinbefore.

| Example | Name | Yield |
|---|---|---|
| 4.2 | (S)-N-(2-(Azetidin-1-yl)-1-cyclopropylethyl)-4-chloro-N-methylbenzamide | 77 mg, 55% |
| $^1$H NMR and HRMS | Mixture of rotamers: (400 MHz, CD$_3$OD) δ 0.23-1.11, 1.82-2.22, 2.78, 3.3, 3.60-3.94, 6.96-7.60. Total no of protons: 21. HRMS (M + H)$^+$: calculated 293.1421; found 293.1427 | |
| 4.3 | (S)-N-(2-(Azetidin-1-yl)-1-cyclopropylethyl)-4-bromo-N-methylbenzamide | 99 mg, 60% |
| $^1$H NMR and HRMS | Mixture of rotamers: (400 MHz, CD$_3$OD) δ 0.04-0.25, 0.25-0.83, 0.86-1.22, 1.71-2.29, 2.49-2.71, 2.71-3.23, 3.3, 3.64-4.11, 7.14-7.50, 7.48-7.92. Total no of protons: 21. HRMS (M + H)$^+$: calculated 337.0915; found 337.0898 | |
| 4.4 | (S)-4-Bromo-N-(1-cyclopropyl-2-(3-hydroxyazetidin-1-yl)ethyl)-N-methylbenzamide | 670 mg, 43% |
| $^1$H NMR and HRMS | Mixture of rotamers: (600 MHz, CD$_3$OD) δ 0.04-0.15, 0.29-0.76, 0.92-1.07, 2.58-2.66, 2.75-3.08, 3.39-3.45, 3.51-3.57, 3.64-3.76, 3.81-3.90, 4.24-4.39, 4.24-4.37, 7.32-7.41, 7.58-7.65. Total no of protons: 20. HRMS (M + H)$^+$: calculated 353.0865; found 353.0881 | |

Example 5.1 A (S)—N-(1-(Azetidin-1-yl)-3-methylbutan-2-yl)-4-chloro-N-methylbenzamide

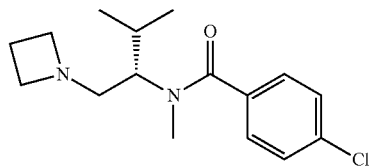 [SMILES: CC(C)[C@@H](CN1CCC1)N(C)C(=O)c1ccc(Cl)cc1]

4-Chlorobenzoic acid (1.300 mL, 12.80 mmol) and TBTU (4.31 g, 13.44 mmol) was mixed in DMF (35 mL). The mixture was cooled to 0° C. and NMM (1.689 mL, 15.36 mmol) was dropwise added. After 10 min at 0° C. was (S)-1-(azetidin-1-yl)-N-methylpentan-2-amine (Compound J1) (2 g, 12.80 mmol) added. The resultant mixture was stirred at 0° C. for 30 min and at rt for 16 h. The mixture was concentrated and the residue dissolved in DCM (25 mL). The organic phase was washed with NaHCO$_3$ (saturated, 2×50 mL), and brine (50 mL), filtered through a phase separator and concentrated under reduced pressure. The residue was purified by preparative HPLC to give the title compound (2.49 g, 66%).

Mixture of rotamers: $^1$H NMR (400 MHz, CD$_3$OD) δ 0.73-1.18, 1.65-1.91, 1.95-2.25, 2.69, 3.04-3.23, 3.23-3.37, 7.27-7.75. Ratio major:minor:7:3. Total number of protons: 23. HRMS (M+H)$^+$: calculated 295.1577. found 295.1570.

Example 5.1 B (S)-1-(2-(4-Chloro-N-methylbenzamido)-3-methylbutyl)azetidinium 2,3-dihydroxysuccinate The title compound of Example 5.1 A was dissolved in MeCN (10 mL) and a solution of DL-tartaric acid (659 mg, 4.39 mmol) in water (15 mL) was added. The resulting mixture was filtered and the solution freeze dried in vacuo to give the title product (3.13 g, 66%). Mixture of rotamers: $^1$H NMR (400 MHz, DMSO-d6) δ 0.42-1.25, 1.52-1.86, 1.86-2.01, 2.01-2.24, 2.5-2.54, 2.64, 2.77, 2.84-3.23, 3.40-3.82, 3.95, 4.10-4.35, 7.10-7.71. Ratio major:minor:6:4. The compound was found to be amorphous by XRPD.

The compound according to Examples 5.2 A-C was prepared, from appropriate intermediates, by analogy with the methods described for Examples 5.1 A and 5.1 B hereinbefore.

| Example | Name | Yield |
|---|---|---|
| 5.2 A | (S)-1-(2-(4-Bromo-N-methylbenzamido)-3-methylbutyl)azetidinium 3-carboxypropanoate | 4.37 g, 83% |
| $^1$H NMR, HRMS and XRPD | Mixture of rotamers: (400 MHz, DMSO-d6) δ 0.82, 1.56-1.87, 1.88-2.01, 2.02-2.22, 2.5, 2.64, 2.72, 2.82-3.21, 3.96, 4.11-4.37, 7.33, 7.41, 7.63. Ratio major:minor: 3:2. HRMS (M + H)$^+$: calculated 339.1072; found 339.1055. The compound was found to be amorphous by XRPD. | |
| | Example 5.2 B: (S)-1-(2-(4-Bromo-N-methylbenzamido)-3-methylbutyl)azetidinium sulfate (S)-N-(1-(Azetidin-1-yl)-3-methylbutan-2-yl)-4-bromo-N-methylbenzamide (95 mg, 0.28 mmol) was mixed in MeCN (0.5 mL) and water (1 mL). Sulfuric acid (14.30 mg, 0.14 mmol) in water (1 mL) was dropwise added and the resultant mixture freeze dried in vacuo to give the title compound (107 mg, 98%). XRPD pattern d (Å) 15.0 (vw), 7.5 (med), 6.4 (vw), 6.1 (vw), 5.4 (vw), 4.99 (med), 4.20 (vw), 3.86 (vw), 3.75 (vs), 3.45 (vw), 2.57 (vw), 2.50 (w), 2.21 (vw). | |
| | Example 5.2 C: (S)-1-(2-(4-Bromo-N-methylbenzamido)-3-methylbutyl)azetidinium 2,3-dihydroxysuccinate (S)-N-(1-(Azetidin-1-yl)-3-methylbutan-2-yl)-4-bromo-N-methylbenzamide (89 mg, 0.26 mmol) was mixed in MeCN (0.5 mL) and water (1 mL). Succinic acid (15.49 mg, 0.13 mmol) was added and the resultant mixture freeze dried to give the title compound (119 mg, 99%). XRPD pattern d (Å) 6.4 (med), 5.9 (w), 5.6 (med), 5.2 (w), 4.80 (med), 4.70 (med), 4.25 (w), 4.10 (med), 3.83 (vs), 3.54 (med), 3.33 (med), 3.06 (w), 2.95 (w). | |

Example 6.1

(S)-4-Fluoro-N-(1-(3-hydroxyazetidin-1-yl)-3-methylbutan-2-yl)-N,3-dimethylbenzamide

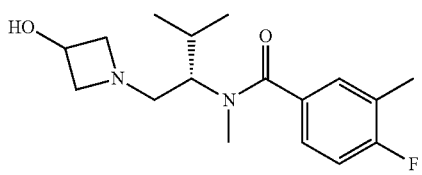 [SMILES: Cc1cc(C(=O)N(C)[C@H](CN2CC(O)C2)C(C)C)ccc1F]

4-Fluoro-3-methylbenzoic acid (0.089 g, 0.58 mmol) and TBTU (0.196 g, 0.61 mmol) was mixed in DMF (1.5 mL). The mixture was cooled to 0° C. and NMM (0.070 mL, 0.64 mmol) was dropwise added. After 40 min at 0° C. was (S)-1-(3-methyl-2-(methylamino)butyl)azetidin-3-ol (Compound K2) (0.1 g, 0.58 mmol) added. The resultant mixture was stirred at 0° C. for 30 min and at rt for 16 h. NaOH (aq., 3.8 M, 0.5 mL), water (0.5 mL) and dioxane (1 mL) was added and the resultant mixture was stirred at rt overnight. To the mixture was water (2 mL) and DMSO (4 mL) added. The residue was purified by preparative HPLC to give the title compound (121 mg, 68%). Mixture of rotamers: $^1$H NMR (400 MHz, CD$_3$OD) δ 0.80-0.87, 0.94, 1.05, 1.68-1.93, 2.25-2.34, 2.54-3.00, 3.26-3.34, 3.39-3.46, 3.55-3.61, 3.62-3.75, 4.19-4.43, 7.02-7.49. Ratio major:minor:1:0.5. Total no of protons: 24. HRMS (M+H)$^+$: calculated 309.1978. found 309.1949. XRPD pattern d (Å) 9.3 (vw), 7.8 (w), 7.6 (w), 6.5 (med), 5.7 (vs), 5.3 (str), 4.71 (str), 4.52 (str), 4.40 (med), 4.31 (med), 3.83 (med), 3.30 (med), 3.22 (med). The compound was found to be a hydrate (most likely a monohydrate).

Example 6.2

(S)-4-Chloro-N-(1-(3-hydroxyazetidin-1-yl)-3-methylbutan-2-yl)-N-methylbenzamide

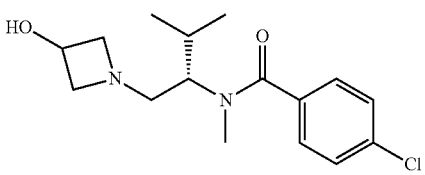 [SMILES: CC(C)[C@@H](CN1CC(O)C1)N(C)C(=O)c1ccc(Cl)cc1]

(S)-1-(3-Methyl-2-(methylamino)butyl)azetidin-3-ol (Compound K2) (1.0 g, 3.48 mmol) was dissolved in DCM (13.3 mL), DIPEA (1.82 mL, 10.4 mmol), 4-chlorobenzoic acid (0.654 g, 4.18 mmol), and TBTU (1.45 g, 4.53 mmol) were added. The reaction was stirred for 2 h at rt whereupon saturated NaHCO$_3$ (aq.) was added. The organic layer was separated and evaporated in vacuo. The residue was redissolved in THF/water and 3.8 M NaOH was added (1.2 mL) the reaction mixture was stirred for 15 min whereupon water was added and some of the organics was evaporated. The water phase was extracted with DCM, separated using a phase-separator and evaporated. The residue was evaporated and redissolved in DMSO and purified by preparative HPLC on a XBridge C18 column (10 µm 250×50 ID mm) using a gradient of 15-55% Acetonitrile in H$_2$O/ACN/NH$_3$ 95/5/0.2 buffer over 30 minutes with a flow of 100 mL/min. The compounds were detected by UV at 220 nm to give the target compound pooling of pure fractions and evaporation of solvents in vacuo gave (S)-4-chloro-N-(1-(3-hydroxyazetidin-1-yl)-3-methylbutan-2-yl)-N-methylbenzamide (0.67 g, 62%). Mixture of rotamers: $^1$H NMR (600 MHz, CD$_3$OD) δ 0.81-0.88, 0.99, 1.09, 1.72-2.00, 1.95, 2.63-2.76, 2.80, 2.85-2.97, 3.12-3.19, 3.26-3.35, 3.46-3.67, 4.10-4.19, 4.28-4.56, 7.44-7.54. Ratio major:minor:1:0.2. Total no of protons: 27.3 (5.3 from CH$_3$CO$_2$H). HRMS (M+H)$^+$: calculated 311.1526. found 311.1528.

A solution of (S)-4-chloro-N-(1-(3-hydroxyazetidin-1-yl)-3-methylbutan-2-yl)-N-methylbenzamide (0.20 g, 0.64 mmol) in ethanol (0.2 mL) was added to water (1.8 mL) in a test tube containing a broken glass rod. The test tube was put in a water bath with ultra sonic waves. After approximately 10 min the milky mixture became white and thick. The formed crystals were filtered off (P3-filter) and washed with a cold ethanol (10% in water). The crystals were air dried to give the product (S)-4-chloro-N-(1-(3-hydroxyazetidin-1-yl)-3-methylbutan-2-yl)-N-methylbenzamide (0.12 g, 60%) as white crystals. This material was used further for crystallization experiments.

To a solution of (S)-4-chloro-N-(1-(3-hydroxyazetidin-1-yl)-3-methylbutan-2-yl)-N-methylbenzamide (0.040 g, 0.13 mmol) in ethanol (2 mL) in an open test tube was added water (6 mL). After ten days crystals had formed:

a) One crystal (approximately 3 mm) was seen at the top of the solvent and was specifically picked out and analyzed by thermoanalysis, which showed only one thermal event at high temperature indicating no solvation that this crystalline form is likely to be anhydrous.

b) The crystals which precipitated were filtered off and air-dried before they were further dried under vacuo over night to give the product (S)-4-chloro-N-(1-(3-hydroxyazetidin-1-yl)-3-methylbutan-2-yl)-N-methylbenzamide (0.106 g, 44%) as white crystals. The compound was found to be a monohydrate. XRPD pattern d (Å), 18.0 (w), 9.0 (vw), 7.6 (vw), 6.0 (vw), 5.1 (vw), 4.52 (str), 4.11 (w), 3.78 (vw), 3.62 (vw).

The compound according to Example 6.3 was prepared, from appropriate intermediates, by analogy with the method described for Example 6.1 hereinbefore.

| Example | Name | Yield |
|---|---|---|
| 6.3 | (S)-4-Bromo-N-(1-(3-hydroxyazetidin-1-yl)-3-methylbutan-2-yl)-N-methylbenzamide | 62 mg, 26% |
| $^1$H NMR and HRMS | Mixture of rotamers: (600 MHz, CD$_3$OD) δ 0.79-0.88, 0.98, 1.08 1.72-1.98, 1.95, 2.61-3.24, 3.37-3.64, 3.95-4.10, 4.27-4.53, 7.38-7.48, 7.57-7.70. Ratio major:minor: 1:0.3. Total no of protons: 25 (3 from CH$_3$CO$_2$H). HRMS (M + H)$^+$: calculated 355.1021; found 355.1036 | |

Example 7.1

(S)—N-(1-Cyclopropyl-2-(3-hydroxyazetidin-1-yl)ethyl)-4-fluoro-N,3-dimethylbenzamide

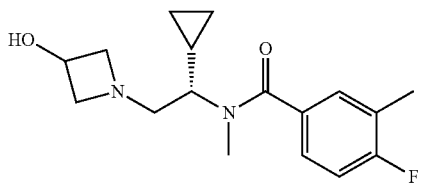 [SMILES: Cc1cc(C(=O)N(C)[C@H](CN2CC(O)C2)C2CC2)ccc1F]

4-Fluoro-3-methylbenzoic acid (0.095 g, 0.62 mmol), TBTU (0.226 g, 0.70 mmol) and 4-methylmorpholine (0.194 mL, 1.76 mmol) was mixed in DMF (2 mL). After 30 min at rt was (S)-1-(2-cyclopropyl-2-(methylamino)ethyl)azetidin-3-ol (Compound J3) (0.1 g, 0.59 mmol) added. The resultant mixture was stirred at rt overnight. Analysis by LCMS indicated formation of both mono and diacylated product. Additional TBTU (0.189 g, 0.59 mmol), 4-fluoro-3-methylbenzoic acid (0.091 g, 0.59 mmol) and NMM (0.129 mL, 1.17 mmol) were added to drive the reaction towards the diacylated product. The resultant mixture was stirred at rt overnight. The mixture was diluted with DCM (5 mL) and the organic phase was washed with NaHCO$_3$ (saturated, 5 mL), filtered through a phase separator and concentrated under reduced pressure. The residue was dissolved in a mixture of MeOH (3 mL) and NaOH (aq. 3 mL, 1M) and the resultant mixture stirred at rt for 30 min. The solvents were evaporated and the crude mixture purified by preparative HPLC to give the title compound (54 mg, 30%). Mixture of rotamers: $^1$H NMR (400 MHz, CD$_3$OD) δ –0.13-1.25, 2.01-2.48, 2.60-2.65, 2.73-3.22, 3.39-4.02, 4.21-4.45, 6.96-7.45. Total no of protons: 22. HRMS (M+H)$^+$: calculated 307.1822. found 307.1827.

The compounds according to Examples 7.2-7.5 were prepared, from appropriate intermediates, by analogy with the method described for Example 7.1 hereinbefore.

| Example | Name | Yield |
|---|---|---|
| 7.2 | (S)-4-Chloro-N-(1-cyclopropyl-2-(3-hydroxyazetidin-1-yl)ethyl)-N-methylbenzamide | 27 mg, 15% |
| $^1$H NMR and HRMS | Mixture of rotamers: (400 MHz, CD$_3$OD) δ –0.43-1.29, 2.43-3.11, 3.30-3.89, 4.10-4.35, 7.14-7.56. Total number of protons: 20. HRMS (M + H)$^+$: calculated 309.1370; found 309.1371 | |
| 7.3 | (S)-3-Chloro-N-(1-cyclopropyl-2-(3-hydroxyazetidin-1-yl)ethyl)-4-fluoro-N-methylbenzamide | 78 mg, 41% |
| $^1$H NMR and HRMS | Mixture of rotamers: (400 MHz, CD$_3$OD) δ –0.42-1.52, 2.57-2.64, 2.76-3.14, 3.40-3.95, 4.16-4.52, 7.21-7.76. Total number of protons: 19. HRMS (M + H)$^+$: calculated 327.1275; found 327.1273 | |
| 7.4 | (S)-N-(1-Cyclopropyl-2-(3-hydroxyazetidin-1-yl)ethyl)-4-fluoro-N-methylbenzamide | 54 mg, 31% |
| $^1$H NMR and HRMS | Mixture of rotamers: (400 MHz, CD$_3$OD) δ –0.24-1.27, 2.51-2.73, 2.85, 2.92-3.15, 3.37-4.05, 4.20-4.50, 6.95-7.70. Total number of protons: 20. HRMS (M + H)$^+$: calculated 293.1665; found 293.1642 | |
| 7.5 | (S)-N-(1-Cyclopropyl-2-(3-hydroxyazetidin-1-yl)ethyl)-4-fluoro-N-methyl-3-(trifluoromethyl)benzamide | 88 mg, 42% |
| $^1$H NMR and HRMS | Mixture of rotamers: (400 MHz, CD$_3$OD) δ –0.32-1.42, 2.53-2.64, 2.74-3.16, 3.37-4.07, 4.12-4.49, 7.20-7.55, 7.61-8.02. Total number of protons: 19. HRMS (M + H)$^+$: calculated 361.1539; found 361.1533 | |

Example 8.1

(S)-3,4-Difluoro-N-(1-(3-hydroxyazetidin-1-yl)pentan-2-yl)-N-methylbenzamide

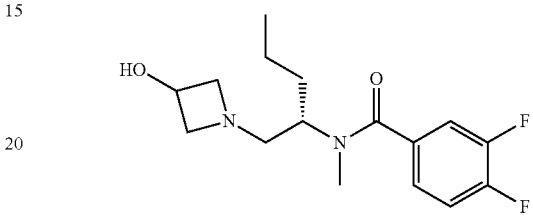

3,4-Difluorobenzoic acid (0.184 g, 1.16 mmol), TBTU (0.373 g, 1.16 mmol) and DIPEA (0.303 mL, 1.74 mmol) was stirred in DCM (2 mL) for 40 min before (S)-1-(2-(methylamino)pentyl)azetidin-3-ol (Compound J4) (0.1 g, 0.58 mmol) was added. The resultant mixture was stirred at rt overnight. The solvent was removed under reduced pressure and the residue dissolved in a mixture of MeOH (3 mL) and NaOH (aq. 1 mL, 1M). The resultant mixture was stirred at rt for 90 min before the MeOH was removed on a vacuum centrifuge. The crude product was extracted with DCM and concentrated under reduced pressure. The residue was purified by preparative HPLC to give the title compound (102 mg, 56%). Mixture of rotamers: (600 MHz, DMSO-d6) δ 0.67-0.76, 0.79-0.91, 0.92-1.04, 1.06-1.48, 2.30-2.76, 3.23-3.42, 3.43-3.53, 4.05-4.17, 4.37-4.47, 5.17-5.26, 7.14-7.27, 7.36-7.56. Total no of protons: 22. HRMS (M+H)$^+$: calculated 313.1728. found 313.1714.

Example 8.2 A

(S)-4-Chloro-N-(1-(3-hydroxyazetidin-1-yl)pentan-2-yl)-N-methyl-benzamide

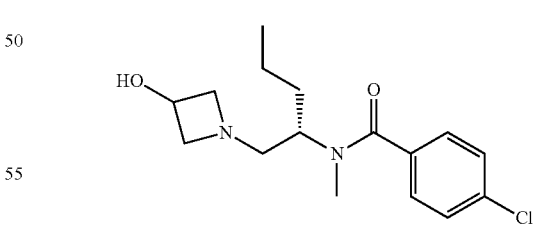

N-ethyl-N-isopropylpropan-2-amine (1.580 mL, 9.07 mmol) was added to a stirred suspension of 4-chlorobenzoic acid (0.473 g, 3.02 mmol) and TBTU (0.971 g, 3.02 mmol) in DCM (10 mL) at rt. The suspension was stirred for about 5 min before a solution of (S)-1-(2-(methylamino)pentyl)azetidin-3-ol (Compound J4) (0.62 g, 3.02 mmol) in DCM (3 mL) was added. The reaction was stirred at rt overnight. The reaction mixture was washed with an 8% aq. sol. of NaHCO$_3$ (20 mL). The organic layer was dried through a phase separator and concentrated on the rotary evaporator. The residue was purified by preparative HPLC affording the title compound (0.760 g, 81%) as an oil. Mixture of rotamers: $^1$H NMR (400 MHz, CD$_3$OD) δ 0.80-0.88, 0.94-1.01, 1.09-1.65, 2.39-2.53, 2.62-2.99, 3.28-3.62, 3.65-3.76, 4.22-4.39, 4.64-4.76, 7.39-7.52. HRMS (M+H)$^+$: calculated 311.1526. found 311.1539.

Example 8.2 B (S)-4-Chloro-N-(1-(3-hydroxyazetidin-1-yl)pentan-2-yl)-N-methyl-benzamide hydrochloride A solution of hydrochloric acid in MeOH (0.1 M, 0.48 ml) was added (S)-4-Chloro-N-(1-(3-hydroxyazetidin-1-yl)pentan-2-yl)-N-methylbenzamide (Example 8.2A) (15 mg, 48 μmol) and allowed to evaporate. The product was dissolved in EtOAc (1 mL) and allowed to evaporate until dry.

XRPD pattern d (Å) 10.16 (str), 7.88 (str), 6.72 (str), 6.25 (vs), 5.28 (str), 4.9 (str), 4.69 (str), 4.58 (str), 4.26 (str), 4.08 (str), 3.92 (str), 3.85 (vs), 3.54 (str), 3.39 (str), 2.83 (str).

Example 8.2 C (S)-4-Chloro-N-(1-(3-hydroxyazetidin-1-yl)pentan-2-yl)-N-methyl-benzamide tartrate A solution of tartaric acid in MeOH (0.1 M, 0.48 ml) was added to (S)-4-Chloro-N-(1-(3-hydroxyazetidin-1-yl)pentan-2-yl)-N-methylbenzamide (Example 8.2A) (15 mg, 48 μmol) and allowed to evaporate. The product was dissolved in EtOAc (1 mL) and allowed to evaporate until dry.

XRPD pattern d (Å) 19.7 (vs), 9.95 (str), 9.8 (med), 7.04 (med), 6.25 (med), 5.32 (str), 5.09 (str), 4.97 (med), 4.22 (med).

The compounds according to Examples 8.3-8.11 were prepared, from appropriate intermediates, by analogy with the method described for Example 8.1 hereinbefore.

The compounds according to Examples 8.12-8.17 were prepared, from appropriate intermediates, by analogy with the method described for Example 8.2 A hereinbefore.

| Example | Name | Yield |
|---|---|---|
| 8.3 | (S)-3-Chloro-4-fluoro-N-(1-(3-hydroxyazetidin-1-yl)pentan-2-yl)-N-methylbenzamide | 110 mg, 58% |
| $^1$H NMR and HRMS | Mixture of rotamers: (600 MHz, DMSO-d6) δ 0.66-0.91, 0.92-1.49, 2.30-2.75, 3.20-3.41, 3.43-3.53, 4.05-4.18, 4.37-4.47, 5.12-5.32, 7.17-7.79. Total no of protons: 22. HRMS (M + H)$^+$: calculated 329.1432; found 329.1454 | |
| 8.4 | (S)-4-Chloro-N-(1-(3-hydroxyazetidin-1-yl)pentan-2-yl)-N,3-di-methylbenzamide | 96 mg, 51% |
| $^1$H NMR and HRMS | Mixture of rotamers: (400 MHz, DMSO-d6) δ 0.71-0.78, 0.86-0.92, 0.96-1.50, 2.32-2.40, 2.47-2.65, 42.68-2.76, 3.25-3.42, 3.46-3.55, 4.06-4.19, .42-4.51, 5.23, 7.12-7.16, 7.19-7.23, 7.28-7.32, 7.35-7.38, 7.43-7.47. Total no of protons: 25. HRMS (M + H)$^+$: calculated 325.1683; found 325.1680 | |
| 8.5 | (S)-4-Fluoro-N-(1-(3-hydroxyazetidin-1-yl)pentan-2-yl)-N-methyl-3-(trifluoromethyl)benzamide | 129 mg, 61% |
| $^1$H NMR and HRMS | Mixture of rotamers: (600 MHz, DMSO-d6) δ 0.66-0.74, 0.84-0.91, 0.93-1.50, 2.31-2.39, 2.44-2.76, 3.21-3.42, 3.44-3.53, 4.01-4.20, 4.36-4.52, 5.15-5.33, 7.47-7.97. Total no of protons: 22. HRMS (M + H)$^+$: calculated 363.1696; found 363.1686 | |
| 8.6 | (S)-4-Fluoro-N-(1-(3-hydroxyazetidin-1-yl)pentan-2-yl)-N-methylbenzamide | 96 mg, 56% |
| $^1$H NMR and HRMS | Mixture of rotamers: (600 MHz, DMSO-d6) δ 0.70-0.77, 0.79-0.92, 0.95-1.51, 2.23-2.75, 3.22-3.56, 4.02-4.19, 4.42-4.52, 5.23, 7.21-7.29, 7.35-7.48. Total no of protons: 23. HRMS (M + H)$^+$: calculated 295.1822; found 295.1844 | |
| 8.7 | (S)-4-Bromo-N-(1-(3-hydroxyazetidin-1-yl)pentan-2-yl)-N-methylbenzamide | 105 mg, 51% |
| $^1$H NMR and HRMS | Mixture of rotamers: (600 MHz, DMSO-d6) δ 0.71-0.78, 0.86-0.92, 0.96-1.52, 2.33-2.39, 2.46-2.64, 2.67-2.75, 3.24-3.41, 3.45-3.54, 4.06-4.19, 4.43-4.52, 5.23, 7.25-7.29, 7.31-7.35, 7.61-7.65. Total no of protons: 23. HRMS (M + H)$^+$: calculated 355.1021; found 355.1027 | |
| 8.8 | (S)-N-(1-(3-Hydroxyazetidin-1-yl)pentan-2-yl)-N-methyl-3-(tri-fluoromethyl)benzamide | 104 mg, 52% |
| $^1$H NMR and HRMS | Mixture of rotamers: (600 MHz, DMSO-d6) δ 0.66-0.75, 0.85-0.91, 0.93-1.51, 2.27-2.79, 3.16-3.56, 4.00-4.21, 4.39-4.53, 5.16-5.30, 7.53-7.87. Total no of protons: 23. HRMS (M + H)$^+$: calculated 345.1790; found 345.1768 | |
| 8.9 | (S)-4-Cyano-N-(1-(3-hydroxyazetidin-1-yl)pentan-2-yl)-N-methylbenzamide | 90 mg, 51% |
| $^1$H NMR and HRMS | Mixture of rotamers: (600 MHz, DMSO-d6) δ 0.68-0.76, 0.84-0.90, 0.93-1.50, 2.30-2.79, 3.17-3.55, 4.02-4.22, 4.38-4.53, 5.17-5.27, 7.42-7.58, 7.82-7.95. Total no of protons: 23. HRMS (M + H)$^+$: calculated 302.1868; found 302.1857 | |
| 8.10 | (S)-N-(1-(3-Hydroxyazetidin-1-yl)pentan-2-yl)-N,3-dimethyl-benzamide | 95 mg, 56% |
| $^1$H NMR and HRMS | Mixture of rotamers: (600 MHz, DMSO-d6) δ 0.64-1.50, 2.18-2.75, 3.09-3.62, 4.03-4.17, 4.41-4.52, 5.12-5.30, 6.96-7.38. Total no of protons: 26. HRMS (M + H)$^+$: calculated 291.2072; found 291.2053 | |
| 8.11 | (S)-4-Fluoro-N-(1-(3-hydroxyazetidin-1-yl)pentan-2-yl)-N,3-di-methylbenzamide | 98 mg, 55% |
| $^1$H NMR and HRMS | Mixture of rotamers: (600 MHz, DMSO-d6) δ 0.70-0.77, 0.81-0 93, 0.95-1.50, 2.24, 2.33-2.41, 2.45-2.65, 2.67-2.76, 3.25-3.54, 4.06-4.19, 4.42-4.51, 5.20-5.27, 7.13-7.35. Total no of protons: 25. HRMS (M + H)$^+$: calculated 309.1978; found 309.1996 | |
| 8.12 | N-((S)-1-((3S,4S)-3,4-Dihydroxypyrrolidin-1-yl)-3-methylbutan-2-yl)-4-fluoro-N,3-dimethylbenzamide | 59 mg, 50% |
| $^1$H NMR and HRMS | Mixture of rotamers: (600 MHz, DMSO-d6) δ 0.73-0.81, 0.88, 0.97, 1.64-1.83, 2.24-2.27, 2.3-2.37, 2.39-2.54, 2.6-2.82, 3.13-3.24, 3.83-3.9, 4.2-4.33, 4.85, 4.92, 7.09-7.24, 7.27-7.42. HRMS (M + H)$^+$: calculated 339.2084; found 339.2089 | |
| 8.13 | 4-Chloro-N-((S)-1-((3S,4S)-3,4-dihydroxy-pyrrolidin-1-yl)-3-methylbutan-2-yl)-N,3-dimethylbenzamide | 84 mg, 57% |
| $^1$H NMR and HRMS | Mixture of rotamers: (600 MHz, DMSO-d6) δ 0.71-0.77, 0.86, 0.95, 1.63-1.79, 2.28-2.35, 2.37-2.42, 2.43-2.51, 2.57-2.79, 3.08-3.15, 3.81-3.87, 4.2-4.3, 4.83, 4.91, 7.15-7.19, 7.28-7.32, 7.33-7.36, 7.37-7.44. HRMS (M + H)$^+$: calculated 355.1788; found 355.1795 | |
| 8.14 | 4-Chloro-N-((S)-1-((3S,4S)-3,4-dihydroxypyrrolidin-1-yl)-3-methylbutan-2-yl)-N-methylbenzamide | 84 mg, 59% |
| $^1$H NMR and HRMS | Mixture of rotamers: (600 MHz, DMSO-d6) δ 0.7-0.77, 0.85, 0.95, 1.63-1.79, 2.27-2.52, 2.57-2.62, 2.67-2.79, 3.04-3.1, 3.81-3.87, 4.2-4.3, 4.81, 4.92, 7.34-7.37, 7.4-7.51. HRMS (M + H)$^+$: calculated 341.1632; found 341.1641 | |
| 8.15 | 4-Chloro-N-((S)-1-((3S,4S)-3,4-dihydroxypyrrolidin-1-yl)-3-methylbutan-2-yl)-3-fluoro-N-methylbenzamide | 77 mg, 52% |
| $^1$H NMR and HRMS | Mixture of rotamers: (600 MHz, DMSO-d6) δ 0.72-0.79, 0.86, 0.95, 1.65-1.79, 2.27-2.34, 2.36-2.42, 2.44-2.52, 2.57-2.8, 3.05-3.11, 3.81-3.87, 4.19-4.27, 4.85, 4.90, 7.18-7.22, 7.35-7.38, 7.39-7.43, 7.45-7.48, 7.55-7.59, 7.6-7.64. HRMS (M + H)$^+$: calculated 359.1537; found 359.1544 | |

-continued

| Example | Name | Yield |
|---|---|---|
| 8.16 | 4-Chloro-N-((S)-1-((3R,4R)-3,4-dihydroxypyrrolidin-1-yl)-3-methylbutan-2-yl)-N,3-dimethylbenzamide | 3 mg, 3% |
| HRMS | HRMS (M + H)⁺: calculated 355.1788; found 355.1794 | |
| 8.17 | (S)-4-Fluoro-N-(1-(3-hydroxyazetidin-1-yl)butan-2-yl)-N,3-dimethylbenzamide | 293 mg, 88% |
| HRMS | HRMS (M + H)⁺: calculated 295.1822; found 295.1813 | |

Example 9.1

(S)—N-(1-Cyclopropyl-2-(3-cyclopropyl-3-hydroxyazetidin-1-yl)ethyl)-4-fluoro-N,3-dimethylbenzamide

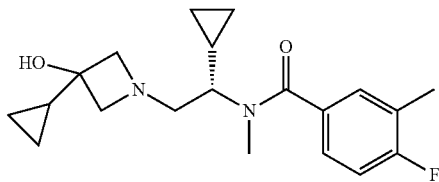 [SMILES: Cc1cc(C(=O)N(C)[C@H](CN2CC(O)(C3CC3)C2)C2CC2)ccc1F]

4-Fluoro-3-methylbenzoic acid (0.102 g, 0.66 mmol), TBTU (0.248 g, 0.77 mmol) and NMM (0.063 mL, 0.58 mmol) was mixed in DCM (10 mL). After 10 min at rt was (S)-3-cyclopropyl-1-(2-cyclopropyl-2-(methylamino)ethyl)azetidin-3-ol (Compound L2) (0.116 g, 0.55 mmol) added. The resultant mixture was stirred at rt for 48 h. To the mixture was 1.4 N KOH (5 mL) added. The organic phase was isolated, filtered through a phase separator and concentrated under reduced pressure. The residue was purified by preparative HPLC to give the title compound (96 mg, 50%). Mixture of rotamers: $^1$H NMR (600 MHz, DMSO-d6) δ 0.09-0.14, 0.22-0.70, 1.01, 1.18, 2.30, 2.52-2.55, 2.72-3.10, 3.20, 3.72, 5.12, 7.15-7.44. Total no of protons: 27. HRMS (M+H)⁺: calculated 347.2135. found 347.2124.

The compounds according to Examples 9.2-9.11 were prepared, from appropriate intermediates, by analogy with the method described for Example 9.1 hereinbefore.

| Example | Name | Yield |
|---|---|---|
| 9.2 | (S)-3-Chloro-N-(1-cyclopropyl-2-(3-cyclopropyl-3-hydroxyazetidin-1-yl)ethyl)-4-fluoro-N-methylbenzamide | 107 mg, 53% |
| $^1$H NMR and HRMS | Mixture of rotamers: (600 MHz, DMSO-d6) δ −0.03, 0.14-0.63, 0.92, 1.11, 2.59-3.22, 3.54-3.73, 5.09, 7.23-7.75. Total no of protons: 24. HRMS (M + H)⁺: calculated 367.1588; found 367.1594 | |
| 9.3 | (S)-N-(1-Cyclopropyl-2-(3-cyclopropyl-3-hydroxyazetidin-1-yl)ethyl)-3,4-difluoro-N-methylbenzamide | 104 mg, 54% |
| $^1$H NMR and HRMS | Mixture of rotamers: (600 MHz, DMSO-d6) δ 0.08, 0.25-0.74, 1.04, 1.20, 2.75-3.11, 3.15-3.35, 3.69, 5.18, 7.29, 7.45-7.78. Total no of protons: 23. HRMS (M + H)⁺: calculated 351.1884; found 351.1887 | |
| 9.4 | (S)-4-Cyano-N-(1-cyclopropyl-2-(3-cyclopropyl-3-hydroxyazetidin-1-yl)ethyl)-N-methylbenzamide | 99 mg, 53% |
| $^1$H NMR and | Mixture of rotamers: (600 MHz, DMSO-d6) δ −0.05-0.15, 0.19-0.73, 0.90-1.07, 1.10-1.25, 2.60-3.30, | |

| Example | Name | Yield |
|---|---|---|
| HRMS | 3.64-3.83, 5.13, 7.43-7.71, 7.87-8.04. Total no of protons: 25. HRMS (M + H)⁺: calculated 340.2025; found 340.2035 | |
| 9.5 | (S)-N-(1-Cyclopropyl-2-(3-cyclopropyl-3-hydroxyazetidin-1-yl)ethyl)-N,3,4-trimethylbenzamide | 116 mg, 62% |
| $^1$H NMR and HRMS | Mixture of rotamers: (600 MHz, DMSO-d6) δ −0.06, 0.11-0.62, 0.77-1.17, 2.21, 2.55-3.20, 3.64, 5.05, 6.94-7.19. Total no of protons: 30 HRMS (M + H)⁺: calculated 343.2386; found 343.2390 | |
| 9.6 | (S)-4-Bromo-N-(1-(3-hydroxy-3-methylazetidin-1-yl)-3-methyl-butan-2-yl)-N-methylbenzamide | 103 mg, 52% |
| $^1$H NMR and HRMS | Mixture of rotamers: (400 MHz, CD₃OD) δ 0.75-1.13, 1.46, 1.66-1.96, 2.56-2.64, 2.66-2.70, 2.71-3.16, 3.22-3.28, 3.33-3.38, 7.25-7.41, 7.43-7.74. Total no of protons: 24. HRMS (M + H)⁺: calculated 369.1177; found 369.1162 | |
| 9.7 | (S)-4-Chloro-N-(1-(3-hydroxy-3-methylazetidin-1-yl)-3-methyl-butan-2-yl)-N-methylbenzamide | 84 mg, 48% |
| $^1$H NMR and HRMS | Mixture of rotamers: (400 MHz, CD₃OD) δ 0.73-1.12, 1.46, 1.68-1.95, 2.58-2.64, 2.66-2.70, 2.71-3.17, 3.22-3.29, 3.32-3.40, 7.30-7.66. Total no of protons: 24. HRMS (M + H)⁺: calculated 325.1683; found 325.1692 | |
| 9.8 | (S)-4-Fluoro-N-(1-(3-hydroxy-3-methylazetidin-1-yl)-3-methyl-butan-2-yl)-N-methyl-3-(trifluoromethyl)benzamide | 103 mg, 51% |
| $^1$H NMR and HRMS | Mixture of rotamers: (400 MHz, CD₃OD) δ 0.65-1.17, 1.46, 1.68-1.96, 2.55-2.64, 2.67-3.20, 3.21-3.28, 3.33-3.41, 4.26, 7.28-7.60, 7.67-8.00, 8.03-8.23. Total no of protons: 24. HRMS (M + H)⁺: calculated 377.1852; found 377.1874 | |
| 9.9 | (S)-N-(1-Cyclopropyl-2-(3-hydroxyazetidin-1-yl)ethyl)-3,4-difluoro-N-methylbenzamide | 31 mg, 17% |
| $^1$H NMR and HRMS | Mixture of rotamers: (600 MHz, DMSO-d6) δ −0.18-0.76, 0.89-1.10, 2.65-3.03, 3.45-3.79, 4.19, 5.31, 7.15-7.39, 7.40-7.65. Total no of protons: 20. HRMS (M + H)⁺: calculated 311.1571; found 311.1557 | |
| 9.10 | N-[(1S)-2-(azetidin-1-yl)-1-cyclopropylethyl]-N,3,4-trimethylbenzamide | 3 mg, 2% |
| $^1$H NMR and HRMS | Mixture of rotamers: (600 MHz, CDCl₃) δ 0.07, 0.43, 0.58, 0.68, 0.84, 0.98, 2.03, 2.30, 2.57, 2.65, 2.77, 2.91, 3.01, 3.10, 3.25, 3.86, 7.14. Ratio major:minor: 1:0.8. Total no of protons: 26. HRMS (M + H)⁺: calculated 287.2123; found 287.2108 | |
| 9.11 | (S)-N-(2-(Azetidin-1-yl)-1-cyclopropylethyl)-3,4-difluoro-N-methylbenzamide | 6 mg, 4% |
| $^1$H NMR and HRMS | Mixture of rotamers: (400 MHz, CDCl₃) δ 0.16-0.33, 0.35-0.50, 0.51-0.64, 0.66-0.83, 1.46-1.75, 1.77-2.16, 2.37-2.71, 2.89-3.07, 3.20-3.48, 3.49-3.61, 3.68, 3.81-3.95, 4.29, 7.05-7.32. Total no of protons: 20. HRMS (M + H)⁺: calculated 295.1622; found 295.1611 | |

Example 10.1

(3S)-1-((S)-2-(2-Chloro-4-fluoro-N-methylbenzamido)-3-methylbutyl)-3-hydroxypyrrolidinium 2,3-dihydroxysuccinate

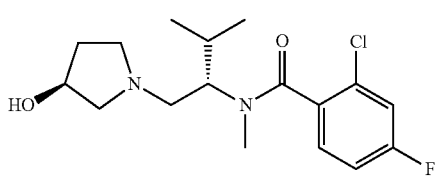 [SMILES: CC(C)[C@@H](CN1CC[C@H](O)C1)N(C)C(=O)c1ccc(F)cc1Cl]

To a solution of (S)-1-((S)-3-methyl-2-(methylamino)butyl)pyrrolidin-3-ol dihydrochloride (0.30 g, 1.16 mmol), which is commercially available, in DMF (2 mL) was DIPEA (0.809 mL, 4.63 mmol) and 2-chloro-4-fluorobenzoyl chloride (0.223 g, 1.16 mmol) added. The resultant mixture was stirred at rt overnight. To the mixture was added NH₃ in MeOH (1 mL, 2N). The reaction was concentrated under reduced pressure and the residue purified by preparative HPLC to give the neutral form of the title compound (280 mg, 58%). The product was dissolved in MeCN (5 mL) and a solution of DL-tartaric acid (61 mg, 0.41 mmol) in water (5 mL) was added. The resulting mixture was freeze dried in vacuo to give the title compound (280 mg, 58%). Mixture of rotamers: ¹H NMR (400 MHz, CD₃OD) δ 0.85-0.93, 1.05, 1.11, 1.93, 2.25, 2.77, 3.14, 3.32-3.51, 4.37, 4.50, 4.66, 7.12-7.28, 7.35. Ratio major:minor:1:0.05. Total no of protons: 23 (excluding the tartaric acid peak). HRMS (M+H)⁺: calculated 343.1588. found 343.1593.

The compound according to Example 10.2 was prepared, from appropriate intermediates, by analogy with the method described for Example 10.1 hereinbefore.

| Example | Name | Yield |
| --- | --- | --- |
| 10.2 | 4-Chloro-N-((S)-1-((S)-3-hydroxypyrrolidin-1-yl)-3-methylbutan-2-yl)-N-methylbenzamide hemi tartrate | 345 mg, 75% |
| ¹H NMR, HRMS and XRPD | Mixture of rotamers: (400 MHz, CD₃OD) δ 0.89, 0.93, 1.02, 1.10, 1.65-1.83, 1.86-2.03, 2.05-2.14, 2.26, 2.86, 2.93, 3.23, 3.31, 3.37-3.55, 4.35, 4.52, 4.63, 7.50. Ratio major:minor: 1:0.15. Total no of protons: 24 (excluding the tartaric acid peak). HRMS (M + H)⁺: calculated 325.1683; found 325.1669. The compound was found to be amorphous by XRPD. | |

Example 11

(S)—N-(1-(Azetidin-1-yl)-3-methylbutan-2-yl)-4-chloro-N-ethylbenzamide

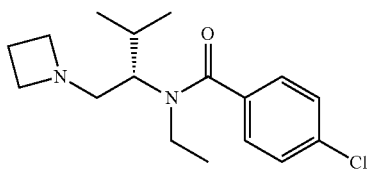 [SMILES: CCN(C(=O)c1ccc(Cl)cc1)[C@H](CN1CCC1)C(C)C]

4-Chlorobenzoic acid (0.030 mL, 0.29 mmol), TBTU (113 mg, 0.35 mmol) and DIPEA (0.303 mL, 1.74 mmol) was stirred in DMF (2 mL). (S)-1-(azetidin-1-yl)-N-ethyl-3-methylbutan-2-amine (Compound V) (50 mg, 0.29 mmol) was added and the resultant mixture was stirred at rt overnight. The reaction mixture was diluted with DCM (10 mL) and NaHCO₃ (saturated, 10 mL). The organic phase was isolated, filtered through a phase separator and concentrated under reduced pressure. The residue was purified by preparative HPLC to give the title compound (2.2 mg, 2%). Mixture of rotamers: ¹H NMR (600 MHz, DMSO-d6) δ 0.63-1.32, 1.60-1.76, 1.82-1.98, 2.0-3.5 (omitted signals), 7.27-7.51. HRMS (M+H)⁺: calculated 309.1725. found 309.1734.

Example 12.1

(S)-4-Fluoro-N,3-dimethyl-N-(3-methyl-1-(pyrrolidin-1-yl)butan-2-yl)benzamide-dihydroxysuccinate

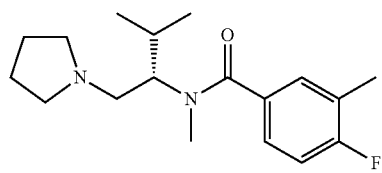 [SMILES: Cc1cc(C(=O)N(C)[C@H](CN2CCCC2)C(C)C)ccc1F]

NMM (2.80 mL, 25.5 mmol) was added to a slurry of (S)—N,3-dimethyl-1-(pyrrolidin-1-yl)butan-2-amine dihydrochloride (2.0 g, 8.22 mmol) (for synthesis, see e.g. Synthetic Communications (1994), 24 (10), 1475-81) in DMF (20 mL). The mixture was cooled to 0° C. and 4-fluoro-3-methylbenzoyl chloride (1.845 g, 10.69 mmol) was added. The resultant mixture was stirred at rt for 1 h. Additional NMM (1.36 mL, 12.3 mmol) was added and the resulting mixture was stirred for 2 h. The reaction mixture was diluted with NaHCO₃ (saturated, 100 mL) and DCM (100 mL). The organic phase was isolated, filtered through a phase separator and concentrated under reduced pressure. The residue was purified by preparative HPLC to give 1.29 g, 51% of neutral form of the title compound. The material was dissolved in MeCN (10 mL) and a solution of DL-tartaric acid (0.63 g, 4.2 mmol) in water (5 mL) was added. The resulting mixture was freeze dried in vacuo to give the title product (1.93 g, 51%). Mixture of rotamers: ¹H NMR (400 MHz, CD₃OD) δ 0.76-1.20, 1.72-2.15, 2.22-2.65, 2.73-2.98, 3.07-3.28, 3.32-3.64, 4.31, 4.52-4.72, 7.01-7.47. Ratio major:minor:6:1. Total no of protons: 27 (excluding the tartaric acid peak). HRMS (M+H)⁺: calculated 307.2186. found 307.2163. XRPD pattern d (Å) 20.1 (vs), 13.1 (str), 11.6 (str), 10.0 (str), 9.6 (str), 8.0 (str), 6.9 (str), 6.7 (str), 6.2 (str), 5.3 (str), 4.96 (str), 4.82 (str), 4.60 (str).

The compound according to Example 12.2 was prepared, from appropriate intermediates, by analogy with the method described for Example 12.1 hereinbefore.

| Example | Name | Yield |
| --- | --- | --- |
| 12.2 | (S)-1-(2-(N,3-Dimethylbenzamido)-3-methyl-butyl)pyrrolidinium 2,3-dihydroxysuccinate | 258 mg, 69% |
| ¹H NMR and HRMS | Mixture of rotamers: (400 MHz, DMSO-d6) 0.56-1.22, 1.43-1.93, 2.08-2.39, 2.65-2.91, 3.00-3.35, 4.29-4.56, 7.05-7.16, 7.16-7.38. Ratio major:minor: 65:31: 4. HRMS (M + H)⁺: calculated 289.2280; found 289.2266 | |

Example 13.1

(S)-3-Chloro-N-(1-cyclopropyl-2-(pyrrolidin-1-yl)ethyl)-4-fluoro-N-methylbenzamide

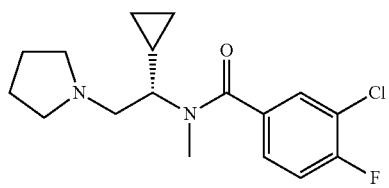 [SMILES: CN(C(=O)c1ccc(F)c(Cl)c1)[C@H](CN1CCCC1)C1CC1]

3-Chloro-4-fluorobenzoic acid (0.156 g, 0.89 mmol), TBTU (0.334 g, 1.04 mmol) and NMM (0.204 mL, 1.86 mmol) was mixed in DCM (10 mL). After 10 min at rt was (S)-1-cyclopropyl-N-methyl-2-(pyrrolidin-1-yl)ethanamine (Compound M3) (0.125 g, 0.74 mmol) added. The resultant mixture was stirred at rt for 48 h. To the mixture was 1.4 N KOH (5 mL) added. The organic phase was isolated, filtered through a phase separator and concentrated under reduced pressure. The residue was purified by preparative HPLC to give the title compound (130 mg, 54%). Mixture of rotamers: $^1$H NMR (600 MHz, DMSO-d6) δ 0.03, 0.16-0.62, 0.95, 1.50-1.74, 2.14-2.41, 2.47-2.51, 2.65-3.06, 3.84, 7.29, 7.46. Total no of protons: 22. HRMS (M+H)$^+$: calculated 325.1483. found 325.1475.

The compounds according to Example 13.2-13.4 were prepared, from appropriate intermediates, by analogy with the method described for Example 13.1 hereinbefore.

| Example | Name | Yield |
|---|---|---|
| 13.2 | (S)-N-(1-Cyclopropyl-2-(pyrrolidin-1-yl)ethyl)-N,3,4-trimethyl-benzamide | 88 mg, 39% |
| $^1$H NMR and HRMS | Mixture of rotamers: (400 MHz, CDCl$_3$) δ 0.02-0.25, 0.47, 0.65, 0.89, 1.73, 2.17-3.20, 7.11, 7.17. HRMS (M + H)$^+$: calculated 301.2280; found 301.227 | |
| 13.3 | (R)-3-Chloro-N-methyl-N-(4-methyl-1-(pyrrolidin-1-yl)pentan-3-yl)benzamide | 42 mg, 34% |
| HRMS | HRMS (M + H)$^+$: calculated 323.1890; found 323.1901 | |
| 13.4 | (R)-4-Fluoro-N,3-dimethyl-N-(4-methyl-1-(pyrrolidin-1-yl)pentan-3-yl)benzamide | 64 mg, 52% |
| HRMS | HRMS (M + H)$^+$: calculated 321.2342; found 321.2348 | |

Example 14

N-((2R,3R)-3-Tert-butoxy-1-(pyrrolidin-1-yl)butan-2-yl)-4-fluoro-N,3-dimethylbenzamide

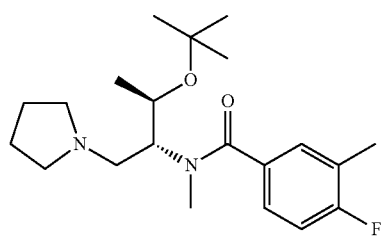 [SMILES: Cc1cc(C(=O)N(C)[C@H](CN2CCCC2)[C@@H](C)OC(C)(C)C)ccc1F]

4-Fluoro-3-methylbenzoic acid (101 mg, 0.66 mmol), TBTU (232 mg, 0.72 mmol) and DIPEA (0.172 mL, 0.99 mmol) was stirred in DCM (2 mL) for 1 h. (2R,3R)-3-tert-butoxy-N-methyl-1-(pyrrolidin-1-yl)butan-2-amine (Compound M7) (150 mg, 0.66 mmol) was added and the resultant mixture was stirred at rt overnight. The reaction mixture was washed with NaHCO$_3$ (8% aq., 2 mL), filtered through a phase separator and concentrated under reduced pressure. The residue was purified by preparative HPLC to give the title compound (43 mg, 18%). Mixture of rotamers: $^1$H NMR (600 MHz, DMSO-d6) δ 0.94, 1.05-1.15, 1.55-1.72, 2.20, 2.21-2.28, 2.31-2.45, 2.60-2.66, 2.77, 2.83, 2.90, 3.27, 3.44-3.50, 3.70-3.77, 3.87-3.93, 4.51-4.58, 7.08-7.22, 7.23-7.28, 7.37. HRMS (M+H)$^+$: calculated 365.2604. found 365.2592.

Example 15.1

(S)-4-Bromo-N-ethyl-N-(3-methyl-1-(pyrrolidin-1-yl)butan-2-yl)benzamide

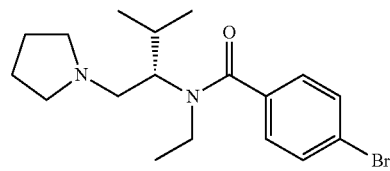 [SMILES: CCN(C(=O)c1ccc(Br)cc1)[C@H](CN1CCCC1)C(C)C]

To a solution of (S)—N-ethyl-3-methyl-1-(pyrrolidin-1-yl)butan-2-amine (0.1 g, 0.54 mmol) (for synthesis, see e.g. EP254545) in DCM (2 mL) was TEA (0.075 mL, 0.54 mmol) and 4-bromobenzoyl chloride (0.119 g, 0.54 mmol) added. The resultant mixture was stirred at rt overnight. The mixture was washed with H$_2$O (2 mL), filtered through a phase separator and concentrated under reduced pressure. The residue was purified by preparative HPLC to give the title compound (29 mg, 15%). Mixture of rotamers: $^1$H NMR (400 MHz, CD$_3$OD) δ 0.77-1.13, 1.30, 1.66-2.06, 2.26-2.59, 2.62-2.91, 3.00-3.29, 3.43-3.69, 7.27-7.42, 7.52-7.70. Total no of protons: 27. HRMS (M+H)$^+$: calculated 367.1385. found 367.1384.

The compounds according to Examples 15.2-15.5 were prepared, from appropriate intermediates, by analogy with the method described for Example 15.1 hereinbefore.

| Example | Name | Yield |
|---|---|---|
| 15.2 | (S)-N-Ethyl-4-fluoro-3-methyl-N-(3-methyl-1-(pyrrolidin-1-yl)butan-2-yl)benzamide | 54 mg, 31% |
| $^1$H NMR and HRMS | Mixture of rotamers: (400 MHz, CD$_3$OD) δ 0.72-1.15, 1.30, 1.61-2.07, 2.11-2.59, 2.60-2.93, 2.98-3.29, 3.33-3.42, 3.46-3.68, 7.00-7.17, 7.20-7.36. Total no of protons: 29. HRMS (M + H)$^+$: calculated 321.2342; found 321.2365 | |
| 15.3 | (S)-4-Chloro-N-ethyl-N-(3-methyl-1-(pyrrolidin-1-yl)butan-2-yl)benzamide | 69 mg, 40% |
| $^1$H NMR and HRMS | Mixture of rotamers: (400 MHz, CD$_3$OD) δ 0.75-1.14, 1.21-1.42, 1.64-2.07, 2.27-2.60, 2.67-2.93, 2.98-3.11, 3.17-3.29, 3.52-3.64, 7.26-7.59. Total no of protons: 27. HRMS (M + H)$^+$: calculated 323.1890; found 323.1902 | |
| 15.4 | (S)-4-Chloro-N-(2-methoxyethyl)-N-(3-methyl-1-(pyrrolidin-1-yl)butan-2-yl)benzamide | 39 mg, 24% |
| $^1$H NMR and HRMS | Mixture of rotamers: (400 MHz, CD$_3$OD) δ 0.73-1.14, 1.60-2.10, 2.25-2.78, 2.83-3.01, 3.06-3.22, 3.32-3.49, 3.51-3.86, 7.22-7.61. Ratio major:minor: 1.3:1. Total no of protons: 29. HRMS (M + H)$^+$: calculated 353.1996; found 353.1974 | |

| Example | Name | Yield |
|---|---|---|
| 15.5 | (S)-4-Bromo-N-(2-methoxyethyl)-N-(3-methyl-1-(pyrrolidin-1-yl)butan-2-yl)benzamide | 50 mg, 27% |
| $^1$H NMR and HRMS | Mixture of rotamers: (400 MHz, CD$_3$OD) δ 0.63-1.18, 1.62-2.12, 2.25-2.78, 2.81-3.25, 3.32-3.50, 3.56-3.82, 7.26-7.43, 7.56-7.67. Ratio major:minor: 1.3:1. Total no of protons: 29. HRMS (M + H)$^+$: calculated 397.1490; found 397.1476 | |

Example 16.1

(S)-3-Chloro-N-(1-(3,3-difluoropiperidin-1-yl)-3-methylbutan-2-yl)-4-fluoro-N-methylbenzamide

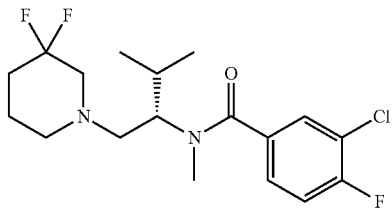 [SMILES: CC(C)[C@@H](CN1CCCC(F)(F)C1)N(C)C(=O)c1ccc(F)c(Cl)c1]

3-Chloro-4-fluorobenzoic acid (0.087 g, 0.50 mmol), TBTU (0.175 g, 0.54 mmol) and NMM (0.125 mL, 1.13 mmol) was mixed in DMF (2 mL). After 10 min at rt was (S)-1-(3,3-difluoropiperidin-1-yl)-N,3-dimethylbutan-2-amine (Compound S2) (0.1 g, 0.45 mmol) and additional DMF (1 mL) added. The resultant mixture was stirred at rt overnight. The mixture was concentrated and the residue dissolved in DCM (5 mL). The organic phase was washed with NaHCO$_3$ (saturated, 5 mL), filtered through a phase separator and concentrated under reduced pressure. The residue was purified by preparative HPLC to give the title compound (80 mg, 47%). HRMS (M+H)$^+$: calculated 377.1607. found 377.1613.

The compounds according to Examples 16.2-16.60 were prepared, from appropriate intermediates, by analogy with the method described for Example 16.1 hereinbefore.

| Example | Name | Yield |
|---|---|---|
| 16.2 | (S)-N-(1-(3,3-Difluoropiperidin-1-yl)-3-methylbutan-2-yl)-4-fluoro-N-methyl-3-(trifluoromethyl)benzamide | 79 mg, 43% |
| HRMS | HRMS (M + H)$^+$: calculated 411.1871; found 411.1840 | |
| 16.3 | (S)-N-(1-(3,3-Difluoropiperidin-1-yl)-3-methylbutan-2-yl)-N,3,4-trimethylbenzamide | 83 mg, 52% |
| HRMS | HRMS (M + H)$^+$: calculated 353.2404; found 353.2394 | |
| 16.4 | (S)-N-(1-(3,3-Difluoropiperidin-1-yl)-3-methylbutan-2-yl)-3-methoxy-N,4-dimethylbenzamide | 70 mg, 42% |
| HRMS | HRMS (M + H)$^+$: calculated 369.2354; found 369.2341 | |
| 16.5 | (S)-4-Bromo-N-(1-(3,3-difluoropiperidin-1-yl)-3-methylbutan-2-yl)-N-methylbenzamide | 77 mg, 42% |
| $^1$H NMR and HRMS | Mixture of rotamers: (600 MHz, DMSO-d6) δ 0.58-1.08, 1.41-1.99, 2.08-2.45, 2.49-2.65, 2.68-2.96, 4.18-4.56, 7.13-7.42, 7.50-7.77. Total no of protons: 24. HRMS (M + H)$^+$: calculated 403.1196; found 403.1212 | |
| 16.6 | 4-Chloro-N-methyl-N-(2-methyl-1-(pyrrolidin-1-yl)propan-2-yl)benzamide | 8 mg, 9% |
| $^1$H NMR and HRMS | Mixture of rotamers: (600 MHz, DMSO-d6, (CH$_3$)$_2$SO$^\#$) 1.37, 1.63, 2.14-2.70 (omitted signals), 2.80, 2.94, 3.3-3.4 (omitted signals), 7.32, 7.45. HRMS (M + H)$^+$: calculated 295.1577; found 295.1556 | |
| 16.7 | 4-Bromo-N-methyl-N-(2-methyl-1-(pyrrolidin-1-yl)propan-2-yl)benzamide | 26 mg, 23% |
| $^1$H NMR and HRMS | Mixture of rotamers: (600 MHz, DMSO-d6, (CH$_3$)$_2$SO$^\#$) δ 1.37, 1.63, 2.14-2.70 (omitted signals), 2.80, 2.94, 3.3-3.4 (omitted signals), 7.25, 7.59. HRMS (M + H)$^+$: calculated 339.1072; found 339.1086 | |
| 16.8 | (S)-3-Fluoro-N-methyl-N-(3-methyl-1-(pyrrolidin-1-yl)butan-2-yl)-5-(trifluoromethyl)benzamide | 4.3 mg, 6.0% |
| $^1$H NMR and HRMS | Mixture of rotamers: (600 MHz, DMSO-d6, (CH$_3$)$_2$SO$^\#$) δ 0.75-0.79, 0.83-0.8, 0.92-0.96, 1.57-1.81, 2.01-3.60 (omitted signals), 4.22-4.35, 7.38-7.55, 7.73-7.78. HRMS (M + H)$^+$: calcd 361.1903, found 361.1902 | |
| 16.9 | (S)-2,3,5-Trifluoro-N-methyl-N-(3-methyl-1-(pyrrolidin-1-yl)butan-2-yl)benzamide | 6.0 mg, 9.1% |
| $^1$H NMR and HRMS | Mixture of rotamers: (600 MHz, DMSO-d6, (CH$_3$)$_2$SO$^\#$) δ 0.69-0.83, 0.85, 0.95, 1.64, 1.72-1.81, 2.01-3.47 (omitted signals), 4.24-4.35, 6.89-7.08, 7.56-7.62. Ratio major:minor 3:1. HRMS (M + H)$^+$: calcd 329.1841, found 329.1828 | |
| 16.10 | (S)-N-Methyl-N-(3-methyl-1-(pyrrolidin-1-yl)butan-2-yl)-3-(tri-fluoromethyl)benzamide | 13.4 mg, 19.6% |
| $^1$H NMR and HRMS | Mixture of rotamers: (600 MHz, DMSO-d6, (CH$_3$)$_2$SO$^\#$) δ 0.76, 0.81, 0.87, 0.96, 1.63, 2.01-3.45 (omitted signals), 4.25-4.35, 7.53-7.69, 7.74-7.80. Ratio: 1:1. HRMS (M + H)$^+$: calcd 343.1997, found 343.1991 | |
| 16.11 | (S)-4-Fluoro-3-methoxy-N-methyl-N-(3-methyl-1-(pyrrolidin-1-yl)butan-2-yl)benzamide | 22 mg, 34% |
| $^1$H NMR and HRMS | Mixture of rotamers: (600 MHz, DMSO-d6, (CH$_3$)$_2$SO$^\#$) δ 0.74-0.80, 0.83, 0.94, 1.59-1.79, 2.02-3.45 (omitted signals), 3.83, 4.34, 7.06-7.13, 7.13-7.22. Ratio: 1:1. HRMS (M + H)$^+$: calcd 323.2135, found 323.2137 | |
| 16.12 | (S)-3,5-Difluoro-N-methyl-N-(3-methyl-1-(pyrrolidin-1-yl)butan-2-yl)benzamide | 3.2 mg, 5.1% |
| $^1$H NMR and HRMS | Mixture of rotamers: (600 MHz, DMSO-d6, (CH$_3$)$_2$SO$^\#$) δ 0.73-0.80, 0.85, 0.94, 1.60-1.80, 1.98-3.49 (omitted signals), 4.21-4.35, 6.92-6.97, 7.04-7.09, 7.26-7.33. Ratio: 1:1. HRMS (M + H)$^+$: calcd 311.1935, found 311.1926 | |
| 16.13 | (S)-3-Fluoro-N,2-dimethyl-N-(3-methyl-1-(pyrrolidin-1-yl)butan-2-yl)benzamide | 12 mg, 19% |
| $^1$H NMR and HRMS | Mixture of rotamers: (600 MHz, DMSO-d6, (CH$_3$)$_2$SO$^\#$) δ 0.87, 0.96, 1.58-1.79, 1.95-3.47 (omitted signals), 4.32-4.45, 6.76-6.94, 7.11-7.16, 7.21-7.30. Ratio major:minor 9:1. HRMS (M + H)$^+$: calcd 307.2186, found 307.2185 | |
| 16.14 | (S)-N,4-Dimethyl-N-(3-methyl-1-(pyrrolidin-1-yl)butan-2-yl)benzamide | 15 mg, 26% |
| $^1$H NMR and HRMS | Mixture of rotamers: (600 MHz, DMSO-d6, (CH$_3$)$_2$SO$^\#$) δ 0.76, 0.80, 0.84, 0.95, 1.62, 2.02-3.45 (omitted signals), 4.33, 7.12-7.23. Ratio major:minor 5:4. HRMS (M + H)$^+$: calcd 289.2280, found 289.2273 | |
| 16.15 | (S)-N-Methyl-N-(3-methyl-1-(pyrrolidin-1-yl)butan-2-yl)-4-(tri-fluoromethoxy)benzamide | 16 mg, 23% |
| $^1$H NMR and HRMS | Mixture of rotamers: (600 MHz, DMSO-d6, (CH$_3$)$_2$SO$^\#$) δ 0.78, 0.82, 0.85, 0.95, 1.63, 2.01-3.48 (omitted signals), 4.24-4.36, 7.37-7.46. Ratio major:minor 3:2. HRMS (M + H)$^+$: calcd 359.1946, found 359.1944 | |
| 16.16 | (S)-N-Methyl-N-(3-methyl-1-(pyrrolidin-1-yl)butan-2-yl)-3-(tri-fluoromethoxy)benzamide | 10 mg, 14% |
| $^1$H NMR and | Mixture of rotamers: (600 MHz, DMSO-d6, (CH$_3$)$_2$SO$^\#$) δ 0.75, 0.80, 0.85, 0.96, 1.58-1.80, | |

-continued

| Example | Name | Yield |
|---|---|---|
| HRMS | 2.01-3.89 (omitted signals), 4.22-4.36, 7.17-7.20, 7.28-7.36, 7.37-7.42, 7.52-7.59. Ratio: 1:1. HRMS (M + H)⁺: calcd 359.1946, found 359.1938 | |
| 16.17 | (S)-3-Chloro-2-fluoro-N-methyl-N-(3-methyl-1-(pyrrolidin-1-yl)butan-2-yl)benzamide | 20 mg, 31% |
| ¹H NMR and HRMS | Mixture of rotamers: (600 MHz, DMSO-d6, (CH₃)₂SO#) δ 0.70-0.83, 0.85, 0.95, 1.54-1.81, 2.01-3.48 (omitted signals), 4.26-4.36, 7.13-7.33, 7.57-7.64. Ratio major:minor 4:1. HRMS (M + H)⁺: calcd 327.1639, found 327.1647 | |
| 16.18 | (S)-2-Fluoro-N-methyl-N-(3-methyl-1-(pyrrolidin-1-yl)butan-2-yl)benzamide | 18 mg, 30% |
| ¹H NMR and HRMS | Mixture of rotamers: (600 MHz, DMSO-d6, (CH₃)₂SO#) δ 0.70-0.81, 0.85, 0.95, 1.55-1.80, 2.01-3.48 (omitted signals), 4.28-4.39, 7.16-7.27, 7.39-7.46. Ratio major:minor 3:1. HRMS (M + H)⁺: calcd 293.2029, found 293.2030 | |
| 16.19 | (S)-2-Fluoro-N-methyl-N-(3-methyl-1-(pyrrolidin-1-yl)butan-2-yl)-6-(trifluoromethyl)benzamide | 11 mg, 15% |
| ¹H NMR and HRMS | Mixture of rotamers: (600 MHz, DMSO-d6, (CH₃)₂SO#) δ 0.85, 0.88, 0.94-0.98, 1.02, 1.13, 1.60-1.86, 2.02-3.44 (omitted signals), 4.30-4.39, 7.60-7.69. Ratio major:minor 5:4. HRMS (M + H)⁺: calcd 361.1903, found 361.1881 | |
| 16.20 | (S)-N-Methyl-N-(3-methyl-1-(pyrrolidin-1-yl)butan-2-yl)-2-(trifluoromethyl)benzamide | 17 mg, 25% |
| ¹H NMR and HRMS | Mixture of rotamers: (600 MHz, DMSO-d6, (CH₃)₂SO#) δ 0.84, 0.92, 0.93-0.98, 1.60-1.85, 2.02-3.45 (omitted signals), 4.25-4.37, 7.21-7.32, 7.57-7.61, 7.69-7.79. Ratio major:minor 2:1. HRMS (M + H)⁺: calcd 343.1997, found 343.1988 | |
| 16.21 | (S)-3,4,5-Trifluoro-N-methyl-N-(3-methyl-1-(pyrrolidin-1-yl)butan-2-yl)benzamide | 10 mg, 15% |
| ¹H NMR and HRMS | Mixture of rotamers: (600 MHz, DMSO-d6, (CH₃)₂SO#) δ 0.73, 0.78, 0.84, 0.94, 1.59-1.79, 2.01-3.49 (omitted signals), 4.19-4.35, 7.21, 7.35. Ratio: 1:1. HRMS (M + H)⁺: calcd 329.1841, found 329.1855 | |
| 16.22 | (S)-2,5-Difluoro-N-methyl-N-(3-methyl-1-(pyrrolidin-1-yl)butan-2-yl)benzamide | 10 mg, 16% |
| ¹H NMR and HRMS | Mixture of rotamers: (600 MHz, DMSO-d6, (CH₃)₂SO#) δ 0.71-0.82, 0.85, 0.95, 1.59-1.81, 2.00-3.47 (omitted signals), 4.26-4.36, 6.98-7.19, 7.25-7.36. Ratio major:minor 3:1. HRMS (M + H)⁺: calcd 311.1935, found 311.1934 | |
| 16.23 | (S)-4-Fluoro-N-methyl-N-(3-methyl-1-(pyrrolidin-1-yl)butan-2-yl)-2-(trifluoromethyl)benzamide | 15 mg, 21% |
| ¹H NMR and HRMS | Mixture of rotamers: (600 MHz, DMSO-d6, (CH₃)₂SO#) δ 0.82, 0.88-0.92, 0.93-0.98, 1.59-1.85, 2.02-3.46 (omitted signals), 4.22-4.36, 7.24-7.40, 7.55-7.74. Ratio major:minor 2:1. HRMS (M + H)⁺: calcd 361.1903, found 361.1900 | |
| 16.24 | 2,6-Difluoro-N-methyl-N-[(1S)-2-methyl-1-(pyrrolidin-1-ylmethyl)propyl]benzamide | 18 mg, 28% |
| ¹H NMR and HRMS | Mixture of rotamers: (600 MHz, DMSO-d6, (CH₃)₂SO#) δ 0.81, 0.85, 0., 1.52-1.58, 1.58-1.69, 1.69-1.83, 2.07-3.53, 4.27-4.39, 7.11-7.18, 7.43-7.51. Ratio major:minor 9:1. HRMS (M + H)⁺: calcd 311.1935, found 311.1936 | |
| 16.25 | 4-Chloro-N,3-dimethyl-N-[(1S)-2-methyl-1-(piperidin-1-ylmethyl)propyl]benzamide | 2.4 mg, 3.6% |
| HRMS | HRMS (M + H)⁺: calcd 337.2047, found 337.2046 | |
| 16.26 | 2-Chloro-4-fluoro-N-methyl-N-[(1S)-2-methyl-1-(piperidin-1-yl-methyl)propyl]benzamide | 1.2 mg, 1.8% |
| HRMS | HRMS (M + H)⁺: calcd 341.1796, found 341.1797 | |
| 16.27 | 4-Bromo-N-methyl-N-[(1S)-2-methyl-1-(piperidin-1-ylmethyl)-propyl]benzamide | 2.2 mg, 3.0% |
| HRMS | HRMS (M + H)⁺: calcd 367.1385, found 367.1391 | |
| 16.28 | 3,4-Dichloro-N-methyl-N-[(1S)-2-methyl-1-(piperidin-1-ylmethyl)propyl]benzamide | 2.1 mg, 2.9% |
| HRMS | HRMS (M + H)⁺: calcd 357.1500, found 357.1506 | |
| 16.29 | N,3-Dimethyl-N-[(1S)-2-methyl-1-(piperidin-1-ylmethyl)-propyl]benzamide | 1.3 mg, 2.1% |
| HRMS | HRMS (M + H)⁺: calcd 303.2436, found 303.2434 | |
| 16.30 | 2,4-Dichloro-N-methyl-N-[(1S)-2-methyl-1-(piperidin-1-ylmethyl)propyl]benzamide | 2.4 mg, 3.4% |
| HRMS | HRMS (M + H)⁺: calcd 357.1500, found 357.1503 | |
| 16.31 | 4-Chloro-2-fluoro-N-methyl-N-[(1S)-2-methyl-1-(piperidin-1-yl-methyl)propyl]benzamide | 2.1 mg, 3.1% |
| HRMS | HRMS (M + H)⁺: calcd 341.1796, found 341.1810 | |
| 16.32 | N-Methyl-N-[(1S)-2-methyl-1-(piperidin-1-ylmethyl)propyl]-3-(trifluoromethyl)benzamide | 0.5 mg, 0.7% |
| HRMS | HRMS (M + H)⁺: calcd 357.2154, found 357.2151 | |
| 16.33 | 3-Chloro-4-fluoro-N-methyl-N-[(1S)-2-methyl-1-(piperidin-1-ylmethyl)propyl]benzamide | 2.0 mg, 2.9% |
| HRMS | HRMS (M + H)⁺: calcd 341.1796, found 341.1800 | |
| 16.34 | 4-Chloro-N-methyl-N-[(1S)-2-methyl-1-(piperidin-1-ylmethyl)-propyl]benzamide | 1.6 mg, 2.5% |
| HRMS | HRMS (M + H)⁺: calcd 323.1890, found 323.1887 | |
| 16.35 | (S)-3-Bromo-N-methyl-N-(3-methyl-1-(piperidin-1-yl)butan-2-yl)benzamide | 2.3 mg, 3.1% |
| HRMS | HRMS (M + H)⁺: calcd 367.1385, found 367.1376 | |
| 16.36 | (S)-4-Bromo-3-fluoro-N-methyl-N-(3-methyl-1-(piperidin-1-yl)butan-2-yl)benzamide | 2.2 mg, 2.9% |
| HRMS | HRMS (M + H)⁺: calcd 385.1291, found 385.302 | |
| 16.37 | (S)-3-Chloro-N-methyl-N-(3-methyl-1-(piperidin-1-yl)butan-2-yl)benzamide | 2.3 mg, 3.6% |
| HRMS | HRMS (M + H)⁺: calcd 323.1890, found 323.1886 | |
| 16.38 | (S)-3-Fluoro-N,2-dimethyl-N-(3-methyl-1-(piperidin-1-yl)butan-2-yl)benzamide | 1.5 mg, 2.3% |
| HRMS | HRMS (M + H)⁺: calcd 321.2342, found 321.2355 | |
| 16.39 | 3-Chloro-2-fluoro-N-[(1S)-1-{[(3S)-3-hydroxypyrrolidin-1-yl]-methyl}-2-methylpropyl)-N-methylbenzamide | 31 mg, 45% |
| ¹H NMR and HRMS | Mixture of rotamers: (600 MHz, DMSO-d6, (CH₃)₂SO#) δ 0.69-0.82, 0.85, 0.95, 1.45-1.52, 1.63-1.80, 1.90-2.00, 2.10-3.43 (omitted signals), 4.11-4.17, 4.25-4.34, 4.63-4.71, 7.17-7.30, 7.42-7.51, 7.58-7.65. Ratio major:minor 4:1. HRMS (M + H)⁺: calcd 343.1588, found 343.1572 | |
| 16.40 | 4-Fluoro-N-[(1S)-1-{[(3S)-3-hydroxypyrrolidin-1-yl]methyl}-2-methylpropyl]-N,3-dimethylbenzamide | 24 mg, 37% |
| ¹H NMR and HRMS | Mixture of rotamers: (600 MHz, DMSO-d6, (CH₃)₂SO#) δ 0.76, 0.80, 0.84, 0.94, 1.44-1.52, 1.64-1.77, 1.89-1.99, 2.18-3.48 (omitted signals), 4.09-4.17, 4.20-4.32, 4.66, 7.10-7.17, 7.18-7.25, 7.32. Ratio major:minor 3:2. HRMS (M + H)⁺: calcd 323.2135, found 323.2122 | |
| 16.41 | N-[(1S)-1-{[(3S)-3-Hydroxypyrrolidin-1-yl]methyl}-2-methyl-propyl]-N-methyl-4-(trifluoromethoxy)benzamide | 31 mg, 42% |
| ¹H NMR and HRMS | Mixture of rotamers: (600 MHz, DMSO-d6, (CH₃)₂SO#) δ 0.76, 0.79, 0.85, 0.95, 1.43-1.52, 1.64-1.79, 1.87-1.99, 2.16-3.37 (omitted signals), 4.06-4.17, 4.22-4.32, 4.62-4.68, 7.35-7.44, 7.49. Ratio: 1:1 HRMS (M + H)⁺: calcd 375.1895, found 375.1890 | |
| 16.42 | N-[(1S)-1-{[(3S)-3-Hydroxypyrrolidin-1-yl]methyl}-2-methyl-propyl]-N-methyl-3-(trifluoromethoxy)benzamide | 18 mg, 24% |
| ¹H NMR and HRMS | Mixture of rotamers: (600 MHz, DMSO-d6, (CH₃)₂SO#) δ 0.75, 0.78, 0.85, 0.95, 1.44-1.53, 1.65-1.80, 1.86-1.98, 2.16-2.28, 2.30-3.41 (omitted signals), 4.07-4.16, 4.21-4.31, 4.66, 7.21, 7.32, 7.34-7.42, 7.50-7.58. | |

| Example | Name | Yield |
|---|---|---|
| | Ratio: 1:1. HRMS (M + H)⁺: calcd 375.1895, found 375.1890 | |
| 16.43 | N-[(1S)-1-{[(3S)-3-Hydroxypyrrolidin-1-yl]methyl}-2-methyl-propyl]-N,4-dimethylbenzamide | 20 mg, 32% |
| ¹H NMR and HRMS | Mixture of rotamers: (600 MHz, DMSO-d6, (CH₃)₂SO#) δ 0.75, 0.78, 0.84, 0.94, 1.42-1.52, 1.63-1.78, 1.86-1.99, 2.13-2.22, 2.23-3.51 (omitted signals), 4.07-4.17, 4.23-4.32, 4.63, 4.64-4.67, 7.14-7.22, 7.24. Ratio major:minor 3:2. HRMS (M + H)⁺: calcd 305.2229, found 305.2220 | |
| 16.44 | 3-Fluoro-N-[(1S)-1-{[(3S)-3-hydroxypyrrolidin-1-yl]methyl}-2-methylpropyl]-N-methyl-5-(trifluoromethyl)benzamide | 26 mg, 35% |
| ¹H NMR and HRMS | Mixture of rotamers: (600 MHz, DMSO-d6, (CH₃)₂SO#) δ 0.76, 0.87, 0.95, 1.45-1.54, 1.66-1.81, 1.88-1.99, 2.17-3.46 (omitted signals), 4.09-4.17, 4.19-4.29, 4.67, 4.70, 7.43, 7.47-7.52, 7.56-7.63, 7.70-7.78. Ratio: 1:1. HRMS (M + H)⁺: calcd 377.1852, found 377.1858 | |
| 16.45 | 3-Fluoro-N-((S)-1-((S)-3-hydroxypyrrolidin-1-yl)-3-methylbutan-2-yl)-N,2-dimethylbenzamide | 10.2 mg, 15.9% |
| ¹H NMR and HRMS | Mixture of rotamers: (600 MHz, DMSO-d6, (CH₃)₂SO#) δ 0.65-0.69, 0.71-0.76, 0.81-0.84, 0.86, 0.88-0.92, 0.96, 1.41-1.55, 1.67-1.78, 1.85-1.94, 2.08-3.48 (omitted signals), 4.06-4.20, 4.27-4.42, 4.57-4.71, 6.85-6.90, 6.90-6.94, 7.10-7.16, 7.18-7.21, 7.22-7.28, 7.30-7.33. HRMS (M + H)⁺: calcd 323.2135, found 323.2128 | |
| 16.46 | 4-Fluoro-N-((S)-1-((S)-3-hydroxypyrrolidin-1-yl)-3-methylbutan-2-yl)-N-methyl-2-(trifluoromethyl)benzamide | 23.3 mg, 30.7% |
| ¹H NMR and HRMS | Mixture of rotamers: (600 MHz, DMSO-d6, (CH₃)₂SO#) δ 0.65-0.68, 0.75-0.78, 0.82, 0.87-0.92, 0.94, 1.41-1.54, 1.68-1.94, 1.96-2.03, 2.06-3.51 (omitted signals), 4.09-4.30, 4.56-4.60, 4.67-4.72, 7.35-7.44, 7.55-7.60, 7.67-7.72. HRMS (M + H)⁺: calcd 377.1852, found 377.1840 | |
| 16.47 | (S)-2,4-Dichloro-N-methyl-N-(3-methyl-1-(pyrrolidin-1-yl)butan-2-yl)benzamide | 180 mg, 67% |
| ¹H NMR and HRMS | Mixture of rotamers: (600 MHz, DMSO-d6, (CH₃)₂SO#)) δ 0.77, 0.87, 0.95, 1.53-1.81, 2.14-3.32 (omitted signals), 4.25-4.37, 7.07, 7.21-7.30, 7.43-7.54, 7.63-7.72. HRMS (M + H)⁺: calcd 343.1344; found 343.1333 | |
| 16.48 | (S)-3-Chloro-N-methyl-N-(3-methyl-1-(pyrrolidin-1-yl)butan-2-yl)benzamide | 8 mg, 13% |
| ¹H NMR and HRMS | Mixture of rotamers: (600 MHz, DMSO-d6, (CH₃)₂SO#)) δ 0.77, 0.85, 0.95, 1.60-1.79, 2.21-3.48 (omitted signals), 4.23-4.32, 7.21, 7.24-7.27, 7.36, 7.40-7.49. Ratio 1:1. HRMS (M + H)⁺: calcd 309.1733; found 309.1741 | |
| 16.49 | (S)-4-Isopropyl-N-methyl-N-(3-methyl-1-(pyrrolidin-1-yl)butan-2-yl)benzamide | 4 mg, 6% |
| ¹H NMR and HRMS | Mixture of rotamers: (600 MHz, DMSO-d6, (CH₃)₂SO#) δ 0.77, 0.80, 0.84, 0.95, 1.18, 1.58-1.78, 2.16-3.46 (omitted signals), 4.27-4.34, 7.18, 7.24, 7.26. Ratio major:minor: 3:2. HRMS (M + H)⁺: calcd 317.2593; found 317.2591 | |
| 16.50 | (S)-4-Chloro-N,3-dimethyl-N-(3-methyl-1-(pyrrolidin-1-yl)butan-2-yl)benzamide | 6 mg, 9% |
| ¹H NMR and HRMS | Mixture of rotamers: (600 MHz, DMSO-d6, (CH₃)₂SO#) δ 0.78, 0.84, 0.95, 1.59-1.79, 2.18-3.47 (omitted signals), 4.25-4.33, 7.08, 7.15, 7.23, 7.29, 7.43. Ratio major:minor: 3:2. HRMS (M + H)⁺: calcd 323.1890; found 323.1890 | |
| 16.51 | (S)-3,4-Dichloro-N-methyl-N-(3-methyl-1-(pyrrolidin-1-yl)butan-2-yl)benzamide | 11 mg, 16% |
| ¹H NMR and HRMS | Mixture of rotamers: (600 MHz, DMSO-d6, (CH₃)₂SO#) δ 0.77, 0.85, 0.94, 1.59-1.79, 2.22-3.47 (omitted signals), 4.22-4.31, 7.25, 7.30, 7.48, 7.59, 7.68. Ratio 1:1. HRMS (M + H)⁺: calcd 343.1344; found 343.1353 | |
| 16.52 | (S)-4-Bromo-3-fluoro-N-methyl-N-(3-methyl-1-(pyrrolidin-1-yl)butan-2-yl)benzamide | 14 mg, 19% |
| ¹H NMR and HRMS | Mixture of rotamers: (600 MHz, DMSO-d6, (CH₃)₂SO#) δ 0.76, 0.85, 0.94, 1.61-1.79, 2.25-3.48 (omitted signals), 4.19-4.29, 7.13, 7.20, 7.26, 7.38, 7.60. Ratio 1:1. HRMS (M + H)⁺: calcd 371.1134; found 371.1144 | |
| 16.53 | (S)-4-Chloro-2-fluoro-N-methyl-N-(3-methyl-1-(pyrrolidin-1-yl)butan-2-yl)benzamide | 152 mg, 53% |
| ¹H NMR and HRMS | Mixture of rotamers: (600 MHz, DMSO-d6, (CH₃)₂SO#) δ 0.71-0.88, 0.95, 1.56-1.80, 2.15-3.32 (omitted signals), 4.26-4.36, 7.22, 7.31-7.37, 7.47-7.54. Ratio major:minor: 7:3. HRMS (M + H)⁺: calcd 327.1639; found 327.1634 | |
| 16.54 | (S)-2-(Difluoromethoxy)-N-methyl-N-(3-methyl-1-(pyrrolidin-1-yl)butan-2-yl)benzamide | 4 mg, 6% |
| ¹H NMR and HRMS | Mixture of rotamers: (600 MHz, DMSO-d6, (CH₃)₂SO#) δ 0.75, 0.86, 0.95, 1.51-1.76, 2.19-3.49 (omitted signals), 4.30-4.38, 7.07-7.13, 7.15-7.26, 7.26-7.39, 7.39-7.46. HRMS (M + H)⁺: calcd 341.2040; found 341.2047 | |
| 16.55 A | (S)-3-Chloro-4-fluoro-N-methyl-N-(3-methyl-1-(pyrrolidin-1-yl)butan-2-yl)benzamide | 180 mg, 63% |
| ¹H NMR, HRMS and XRPD | Mixture of rotamers: (600 MHz, DMSO-d6, (CH₃)₂SO#) δ 0.76, 0.85, 0.95, 1.57-1.81, 2.23-2.43, 2.42-2.56 (omitted signals), 2.62, 2.69, 2.75, 2.81, 3.14, 4.20-4.32, 7.25-7.31, 7.31-7.37, 7.42-7.49, 7.58. Ratio 1:1. HRMS (M + H)⁺: calcd 327.1639; found 327.1650. | |
| | Example 16.55 B: (S)-1-(2-(3-Chloro-4-fluoro-N-methylbenzamido)-3-methylbutyl)pyrrolidinium chloride | |
| | To a mixture of (S)-3-chloro-4-fluoro-N-methyl-N-(3-methyl-1-(pyrrolidin-1-yl)butan-2-yl)benzamide (410 mg, 1.25 mmol) in DCM was HCl (1.25N in MeOH) and Et₂O added. The resultant mixture was concentrated under reduced pressure and the residue dissolved in DCM. Et₂O was added and the precipitated solid was collected to give the title compound (430 mg, 94%). | |
| | XRPD pattern d (Å) 10.2 (str), 8.6 (str), 6.0 (vs), 5.6 (vs), 5.4 (med), 4.97 (str), 4.64 (str), 4.27 (str), 3.85 (str), 3.51 (vs), 3.05 (med). | |
| 16.56 | (R)-3,4-Dichloro-N-methyl-N-(3-methyl-1-(pyrrolidin-1-yl)butan-2-yl)benzamide | 46 mg, 66% |
| ¹H NMR and HRMS | Mixture of rotamers: (600 MHz, DMSO-d6, (CH₃)₂SO#) δ 0.77, 0.85, 0.95, 1.58-1.80, 2.24-3.37 (omitted signals), 4.21-4.31, 7.24, 7.30, 7.47, 7.59, 7.68. Ratio 1:1. HRMS (M + H)⁺: calcd 343.1344; found 343.1334 | |
| 16.57 | (R)-4-Bromo-N-methyl-N-(3-methyl-1-(pyrrolidin-1-yl)butan-2-yl)benzamide | 48 mg, 68% |
| ¹H NMR and HRMS | Mixture of rotamers: (600 MHz, DMSO-d6, (CH₃)₂SO#) δ 0.76-0.88, 0.95, 1.58-1.80, 2.17-3.39 (omitted signals), 4.24-4.34, 7.20, 7.27, 7.60. Ratio major:minor: 3:2. HRMS (M + H)⁺: calcd 353.1228; found 353.1231 | |
| 16.58 | (R)-2,4-Dichloro-N-methyl-N-(3-methyl-1-(pyrrolidin-1-yl)butan-2-yl)benzamide | 46 mg, 68% |
| ¹H NMR and HRMS | Mixture of rotamers: (600 MHz, DMSO-d6, (CH₃)₂SO#) δ 0.74-0.81, 0.87, 0.95, 1.53-1.81, 2.12-3.40 (omitted signals), 4.25-4.36, 7.07, 7.22-7.30, 7.43-7.54, 7.63-7.72. HRMS (M + H)⁺: calcd 343.1344; found 343.1343 | |
| 16.59 | (R)-4-Chloro-2-fluoro-N-methyl-N-(3-methyl-1-(pyrrolidin-1-yl)butan-2-yl)benzamide | 45 mg, 69% |
| ¹H NMR and HRMS | Mixture of rotamers: (600 MHz, DMSO-d6, (CH₃)₂SO#) δ 0.72-0.88, 0.94, 1.56-1.80, 2.16-3.39 (omitted signals), 4.26-4.37, 7.22, 7.31-7.39, 7.47-7.55. Ratio major:minor: 4:1. HRMS (M + H)⁺: calcd 327.1639; found 327.1630 | |
| 16.60 | (R)-4-Bromo-3-fluoro-N-methyl-N-(3-methyl-1-(pyrrolidin-1-yl)butan-2-yl)benzamide | 51 mg, 68% |
| ¹H NMR and | Mixture of rotamers: (600 MHz, DMSO-d6, (CH₃)₂SO#) δ 0.77, 0.85, 0.94, 1.58-1.81, 2.27- | |

| Example | Name | Yield |
|---|---|---|
| HRMS | 3.38 (omitted signals), 4.18-4.30, 7.12, 7.20, 7.26, 7.38, 7.61. Ratio 1:1. HRMS (M + H)⁺: calcd 371.1134; found 371.1141 | |

Example 17.1

(S)-4-Bromo-N-methyl-N-(1-(pyrrolidin-1-yl)butan-2-yl)benzamide

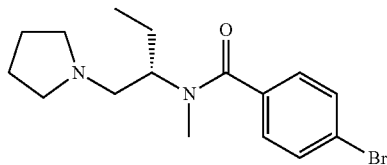 [SMILES: CC[C@@H](CN1CCCC1)N(C)C(=O)c1ccc(Br)cc1]

To a solution of (S)—N-methyl-1-(pyrrolidin-1-yl)butan-2-amine (Compound M5) (75 mg, 0.48 mmol) in DCM (1.5 mL) was NMM (0.058 mL, 0.53 mmol) and 4-bromobenzoyl chloride (137 mg, 0.62 mmol) added. The resultant mixture was stirred at rt overnight. The mixture was diluted with DCM (5 mL), washed with NaHCO₃ (saturated, 5 mL), filtered through a phase separator and concentrated under reduced pressure. The residue was purified by preparative HPLC to give the title compound (100 mg, 62%). Mixture of rotamers: ¹H NMR (400 MHz, CD₃OD) δ 0.92, 1.33-1.66, 1.66-1.97, 2.55, 2.94, 3.64, 4.70-4.83, 7.21-7.49, 7.49-7.76. Ratio major:minor:3:2. Total no of protons: 23.

HRMS (M+H)⁺: calculated 339.1072. found 339.1061.

The compounds according to Examples 17.2-17.7 were prepared, from appropriate intermediates, by analogy with the method described for Example 17.1 hereinbefore.

| Example | Name | Yield |
|---|---|---|
| 17.2 | (S)-3,4-Dichloro-N-methyl-N-(1-(pyrrolidin-1-yl)butan-2-yl)- benzamide | 95 mg, 60% |
| ¹H NMR and HRMS | Mixture of rotamers: (400 MHz, CD₃OD) δ 0.64-1.19, 1.40-1.98, 2.31-2.98, 3.3-3.42, 4.75, 7.12-7.53, 7.53-7.74. Ratio major:minor: 7:3. Total no of protons: 22. HRMS (M + H)⁺: calculated 329.1187; found 329.1195 | |
| 17.3 | 4-Fluoro-N-((S)-1-((R)-3-hydroxypyrrolidin-1-yl)-3-methylbutan-2-yl)-N,3-dimethylbenzamide | 143 mg, 83% |
| ¹H NMR and HRMS | Mixture of rotamers: (400 MHz, CD₃OD) δ 0.63-1.24, 1.59-1.95, 2.03-2.18, 2.23-2.64, 2.66-3.01, 4.20-4.57, 6.98-7.47. Total no of protons: 26. HRMS (M + H)⁺: calculated 323.2135; found 323.2134 | |
| 17.4 | 4-Chloro-N-((S)-1-((R)-3-hydroxypyrrolidin-1-yl)-3-methylbutan-2-yl)-N-methylbenzamide | 107 mg, 61% |
| ¹H NMR and HRMS | Mixture of rotamers: (400 MHz, CD₃OD) δ 0.49-1.41, 1.56-1.94, 1.98-2.64, 2.67-2.84, 2.86-3.04, 4.25-4.56, 7.13-7.68. Total no of protons: 24. HRMS (M + H)⁺: calculated 325.1683; found 325.1657 | |
| 17.5 | 4-Bromo-N-((S)-1-((R)-3-hydroxypyrrolidin-1-yl)-3-methylbutan-2-yl)-N-methylbenzamide | 120 mg, 61% |
| ¹H NMR and HRMS | Mixture of rotamers: (400 MHz, CD₃OD) δ 0.47-1.42, 1.50-1.93, 2.00-2.22, 2.25-2.64, 2.66-3.02, 4.18-4.60, 7.17-7.80. Total no of protons: 24. HRMS (M + H)⁺: calculated 369.1177; found 369.1178 | |
| 17.6 | 3-Chloro-4-fluoro-N-((S)-1-((R)-3-hydroxypyrrolidin-1-yl)-3-methylbutan-2-yl)-N-methylbenzamide | 122 mg, 66% |
| ¹H NMR and HRMS | Mixture of rotamers: (400 MHz, CD₃OD) δ 0.50-1.27, 1.57-1.94, 2.02-2.22, 2.35-2.62, 2.67-3.03, 4.17-4.58, 7.09-7.80. Total no of protons: 24. HRMS (M + H)⁺: calculated 343.1588; found 343.1590 | |
| 17.7 | 4-Fluoro-N-((S)-1-((R)-3-hydroxypyrrolidin-1-yl)-3-methylbutan-2-yl)-N-methyl-3-(trifluoromethyl)benzamide | 51 mg, 25% |
| ¹H NMR and HRMS | Mixture of rotamers: (400 MHz, CD₃OD) δ 0.59-1.38, 1.57-1.95, 1.97-2.23, 2.30-2.63, 2.67-3.08, 4.17-4.68, 7.27-7.52, 7.60-8.11. Total no of protons: 23. HRMS (M + H)⁺: calculated 377.1852; found 377.1844 | |

Example 18

(S)-1-(2-(4-Chloro-N-methylbenzamido)-3-methylbutyl)pyrrolidinium chloride

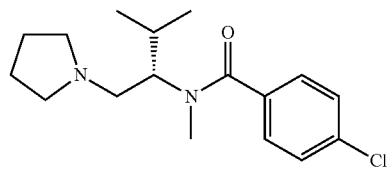 [SMILES: CC(C)[C@@H](CN1CCCC1)N(C)C(=O)c1ccc(Cl)cc1]

4-Chlorobenzoic acid (0.470 g, 3 mmol), TBTU (0.963 g, 3 mmol) and NMM (0.330 mL, 3 mmol) was mixed in DMF (10 mL). After 10 min at rt was a solution of (S)—N,3-dimethyl-1-(pyrrolidin-1-yl)butan-2-amine (0.426 mg, 2.50 mmol) (for synthesis, see e.g. Synthetic Communications (1994), 24 (10), 1475-81) and NMM (0.430 mL, 3.9 mmol) in DMF (5 mL) added. The resultant mixture was stirred at rt for 16 h. The reaction mixture was washed with Na₂CO₃ (1M, 2 mL) and concentrated under reduced pressure. The residue was purified by preparative HPLC to give an oily residue. The residue was dissolved in EtOH (5 mL). HCl (1.25 N EtOH solution, 10 mL) and H₂O (5 mL) were added and the mixture freezing-dried to give the title compound (600 mg, 58%). Mixture of rotamers: ¹H NMR (600 MHz, CD₃OD) δ 1.00, 1.10, 1.86-1.98, 2.11, 2.89, 3.18, 3.41, 3.63-3.79, 3.87, 4.68, 7.46, 7.60. HRMS (M+H)⁺: calculated 309.1733. found 309.1750. XRPD pattern d (Å) 8.4 (med), 7.7 (med), 7.4 (med), 5.0 (vs), 4.31 (str), 4.13 (str), 3.84 (str), 3.46 (str), 3.39 (med), 3.17 (med), 3.00 (med), 2.83 (med).

Example 19

(S)-1-(2-(4-bromo-N-methylbenzamido)-3-methylbutyl)pyrrolidinium 3-carboxy-2,3-dihydroxypropanoate

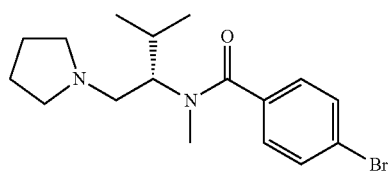 [SMILES: CC(C)[C@@H](CN1CCCC1)N(C)C(=O)c1ccc(Br)cc1]

At 0° C. was NMM (3 mL, 27.29 mmol) added to a mixture of (S)—N,3-dimethyl-1-(pyrrolidin-1-yl)butan-2-amine dihydrochloride (1.18 g, 4.85 mmol) (for synthesis, see e.g. Synthetic Communications (1994), 24 (10), 1475-81) in DMF (12 mL). After 10 min was 4-bromobenzoyl chloride (1.4 g, 6.38 mmol) and DCM added (6 mL). The resultant mixture was stirred at rt for 48 h. The mixture was concentrated and the residue was purified by preparative HPLC to give the title compound (1.45 g, 85%). The title compound was dissolved in MeCN (10 mL) and a solution of DL-tartaric acid (569 mg, 3.79 mmol) in water (20 mL) was added. The resulting mixture was freeze dried in vacuo to give the title product (1.85 g, 76%). Mixture of rotamers: $^1$H NMR (600 MHz, DMSO-d6) δ 0.61-1.10, 1.52-1.95, 2.17-2.41, 2.56-2.84, 2.84-3.43, 3.89-4.19, 4.45, 7.15-7.44, 7.52-7.75. Total no of protons: 27. HRMS (M+H)$^+$: calculated 353.1228. found 353.1247. The compound was found to be amorphous by XRPD.

Example 20

(S)-4-Chloro-N-cyclopentyl-N-(3-methyl-1-(pyrrolidin-1-yl)butan-2-yl)benzamide

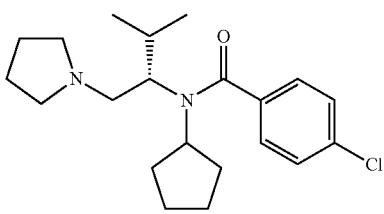 [SMILES: CC(C)[C@@H](CN1CCCC1)N(C(=O)c1ccc(Cl)cc1)C1CCCC1]

Cyclopent-3-enone (57.9 mg, 0.70 mmol) was added to a mixture of (S)-3-methyl-1-(pyrrolidin-1-yl)butan-2-amine (109 mg, 0.70 mmol), which is commercially available, in THF (1.7 mL). After 10 min was a solution of sodium cyanoborohydride (58 mg, 0.92 mmol) in THF (0.9 mL) added. The resultant mixture was stirred at rt for 3 h. Acetic acid (0.3 mL, 5.24 mmol) and MeOH (2 mL) was added and the mixture stirred at rt overnight. The reaction mixture was concentrated and the residue dissolved in DMF (2.5 mL). DIPEA (0.5 mL, 2.86 mmol) and a solution of 4-chlorobenzoyl chloride (2.2 mL, 1.01 mmol) in DCM (2 mL) was added. The resultant mixture was stirred at rt overnight. H$_2$O (0.5 mL) and MeOH (5 mL) were added and the mixture was stirred for 10 min. The solvent was removed under reduced pressure and the residue mixed in NaOH (1 N aq., 10 mL). The water layer was extracted with DCM (3×10 mL) and the combined organic layer were washed with brine (10 mL), filtered through a phase separator and concentrated under reduced pressure. The residue was purified by preparative HPLC to give the title compound (17 mg, 7%).

Mixture of rotamers: $^1$H NMR (600 MHz, DMSO-d6) δ 0.78, 0.90, 1.38-1.87, 2.03-2.28, 2.69, 3.05, 3.55, 7.24, 7.42. HRMS (M+H)$^+$: calculated 363.2203. found 363.2216.

Example 21

(S)—N-(1-(3,3-Difluoropyrrolidin-1-yl)-3-methylbutan-2-yl)-N,3,4-trimethylbenzamide

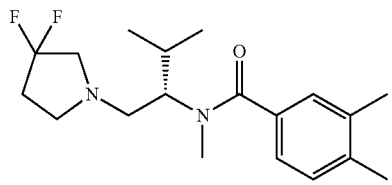 [SMILES: Cc1ccc(C(=O)N(C)[C@H](CN2CCC(F)(F)C2)C(C)C)cc1C]

To a mixture of (S)—N-(1-(3,3-difluoropyrrolidin-1-yl)-3-methylbutan-2-yl)-3,4-dimethylbenzamide (Compound P) (167 mg, 0.51 mmol) in THF (1 mL) was sodium hydride (0.024 mL, 0.51 mmol) added. After 30 min was MeI (0.032 mL, 0.51 mmol) added and the resultant mixture was stirred at rt overnight. Additional sodium hydride (0.013 mL, 0.51 mmol) and MeI (0.032 mL, 0.51 mmol) was added and the resulting mixture stirred for 2 h. The reaction was quenched with MeOH (0.5 mL). The solvent was removed under reduced pressure and the residue dissolved in DCM (5 mL). The organic phase was washed with NaHCO$_3$ (saturated, 5 mL), filtered through a phase separator and concentrated under reduced pressure. The residue was purified by preparative HPLC to give the title compound (47 mg, 27%). HRMS (M+H)$^+$: calculated 339.2248. found 339.2277.

Example 22

(S)-4-Fluoro-N-(1-(3-hydroxyazetidin-1-yl)-2,3-dimethylbutan-2-yl)-N,3-dimethylbenzamide

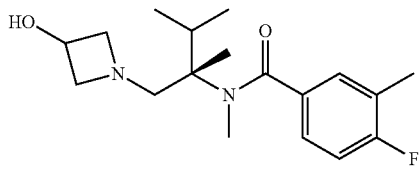 [SMILES: Cc1cc(C(=O)N(C)[C@](C)(CN2CC(O)C2)C(C)C)ccc1F]

HATU (0.408 g, 1.07 mmol) was added to a mixture of 4-fluoro-3-methylbenzoic acid (5.34 ml, 1.07 mmol) and DIPEA (2 mL, 11.45 mmol) in DMF (10 mL). After 10 min was (S)-1-(2,3-dimethyl-2-(methylamino)butyl)azetidin-3-ol (Compound Y) (0.1 g, 0.54 mmol) in DCM added. The resultant mixture was stirred at rt over night. The mixture was concentrated and the residue dissolved in DCM. The organic phase was washed with NaHCO$_3$ (saturated) and brine. The filtrate was dried (Na$_2$SO$_4$) and concentrated under reduced pressure. MeOH (10 mL) and KOH (2.221 ml, 3.22 mmol) was added and the resultant mixture was stirred at rt for 3 days. The solvent was removed and the residue was purified by preparative HPLC to give the title compound (1.1 mg, 0.5%). Mixture of rotamers: $^1$H NMR (400 MHz, CDCl$_3$) δ

0.91, 1.01, 2.29, 2.34-2.43, 2.81, 2.96, 3.03-3.56, 3.65-3.79, 3.79-3.96, 4.00-4.12, 4.28, 4.43-4.57, 6.92-7.06, 7.16-7.25. Total no of protons: 27. HRMS (M+H)⁺: calculated 323.2135. found 323.2113.

Example 23

(S)—N-(1-(3-Hydroxyazetidin-1-yl)pentan-2-yl)-N,3,4-trimethylbenzamide

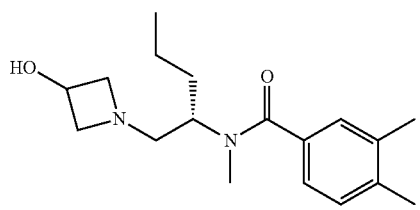 [SMILES: CCC[C@@H](CN1CC(O)C1)N(C)C(=O)c1ccc(C)c(C)c1]

3,4-Dimethylbenzoic acid (0.174 g, 1.16 mmol), TBTU (0.373 g, 1.16 mmol) and DIPEA (0.303 mL, 1.74 mmol) was stirred in DCM (2 mL) for 40 min before (S)-1-(2-(methylamino)pentyl)azetidin-3-ol (Compound J4) (0.1 g, 0.58 mmol) was added. The resultant mixture was stirred at rt overnight. The solvent was removed under reduced pressure and the residue dissolved in a mixture of MeOH (3 mL) and NaOH (aq. 1 mL, 1M). The resultant mixture was stirred at rt for 90 min before the MeOH was removed on a vacuum centrifuge. The crude product was extracted with DCM and concentrated under reduced pressure. To the residue was DMSO (1 mL), DCM (3 mL) and KOH (1M solution, 3 mL) added. The organic phase was filtered through a phase separator and concentrated under reduced pressure. The residue was purified by preparative HPLC. The product containing fractions was concentrated, water (5 mL) and DCM (5 mL) was added and the pH was adjusted to 12 using KOH (1M solution). The organic layer was filtered through a phase separator and the solvent was removed under reduced pressure to give the title compound (48 mg, 27%). Mixture of rotamers: (600 MHz, DMSO-d6) δ 0.69-0.78, 0.85-0.93, 0.94-1.06, 1.08-1.50, 2.19-2.28, 2.32-2.41, 2.44-2.56, 2.56-2.65, 2.66-2.76, 3.27-3.38, 3.43-3.55, 4.03-4.20, 4.44-4.52, 5.17-5.26, 6.97-7.21. Total no of protons: 28. HRMS (M+H)⁺: calculated 305.2229. found 305.2214.

Example 24

(S)-4-Fluoro-N-(1-(4-hydroxypiperidin-1-yl)-3-methylbutan-2-yl)-N,3-dimethylbenzamide

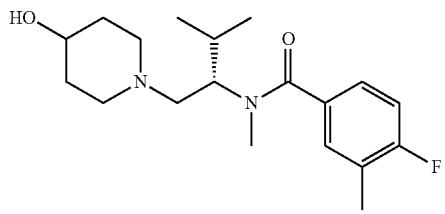 [SMILES: Cc1cc(C(=O)N(C)[C@H](CN2CCC(O)CC2)C(C)C)ccc1F]

Piperidin-4-ol (0.048 g, 0.48 mmol) and acetic acid (0.032 mL, 0.56 mmol) was added to (S)-4-fluoro-N,3-dimethyl-N-(3-methyl-1-oxobutan-2-yl)benzamide (Compound A2.1) (0.1 g, 0.40 mmol) in DCM (3 mL). The resultant mixture was stirred at rt for 30 min before sodium triacetoxyhydroborate (0.101 g, 0.48 mmol) was added. The stirring was continued at rt for 3 h. NaOH (1 N aq.) was added to the mixture. The organic phase was filtered through a phase separator and concentrated under reduced pressure. The residue was purified by preparative HPLC. The product containing fractions was concentrated and the residue was purified a second time by preparative HPLC using Chiralpak AD 5 μm 20×250 mm column and Heptan/EtOH/TEA 80/20/0.1, as mobile phase to give the title compound (29 mg, 22%). Enantiomeric excess: 99.9%. Mixture of rotamers: (600 MHz, CD₃OD) δ 0.82-1.08, 1.43-1.63, 1.71-2.06, 2.12-2.51, 2.54-2.81, 2.89, 2.97-3.09, 3.27-3.46, 3.51-3.65, 4.40-4.59, 7.06-7.14, 7.22-7.37. Total no of protons: 28. HRMS (M+H)⁺: calculated 337.2291. found 337.2268.

Example 25

(R)-4-Fluoro-N-(1-(4-hydroxypiperidin-1-yl)-3-methylbutan-2-yl)-N,3-dimethylbenzamide

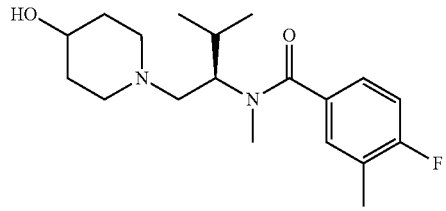 [SMILES: Cc1cc(C(=O)N(C)[C@@H](CN2CCC(O)CC2)C(C)C)ccc1F]

The slower eluting compound in Example 24 was collected and evaporated to yield the title compound (1.5 mg, 1.5%). Enantiomeric excess: 92.3%. Mixture of rotamers: (600 MHz, CD₃OD) Mixture of rotamers: ¹H NMR (600 MHz, CD₃OD) δ 0.82-1.06, 1.44-1.63, 1.71-2.05, 2.11-2.49, 2.54-2.79, 2.89, 2.98-3.07, 3.25-3.43, 3.51-3.64, 4.42-4.56, 7.07-7.14, 7.21-7.38. Total no of protons: 28. HRMS (M+H)⁺: calculated 337.2291. found 337.2290.

Example 26

(S)—N-(1-(4-Cyanopiperidin-1-yl)-3-methylbutan-2-yl)-4-fluoro-N,3-dimethylbenzamide

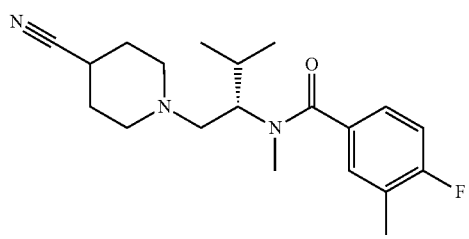 [SMILES: Cc1cc(C(=O)N(C)[C@H](CN2CCC(C#N)CC2)C(C)C)ccc1F]

TEA (0.552 mL, 3.98 mmol) was added to a mixture of piperidine-4-carbonitrile (0.132 g, 1.19 mmol) in EtOH (2 mL) and DCM (3 mL). To the mixture was added (S)-4-fluoro-N,3-dimethyl-N-(3-methyl-1-oxobutan-2-yl)benzamide (Compound A2.1) (0.2 g, 0.80 mmol). The resultant mixture was stirred at rt for 15 min before sodium triacetoxyhydroborate (0.337 g, 1.59 mmol) was added. The stirring was continued at rt over night. Sodium tetrahydroborate (0.015 g, 0.40 mmol) was added and the mixture was stirred for 1 h. The solvents were removed on a vacuum centrifuge.

The residue was diluted with DCM and washed with NaOH (aq., 1M). The organic phase was filtered through a phase separator and concentrated under reduced pressure. The residue was purified by preparative HPLC. The product containing fractions was concentrated and the residue was purified a second time by preparative HPLC using Chiralpak IC 5 μm 20×250 mm column and Heptan/EtOH/TEA 60/40/0.1, as mobile phase to give the title compound (11 mg, 4%). Enantiomeric excess: 98.2%. Mixture of rotamers: (400 MHz, CD$_3$OD) δ 0.85-1.08, 1.69-2.02, 2.12-2.96, 3.37-3.50, 4.41-4.59, 7.07-7.16, 7.19-7.36.

Total no of protons: 28. HRMS (M+H)$^+$: calculated 346.2295. found 346.2289.

Example 27

(S)-4-Chloro-N-(1-(4-hydroxypiperidin-1-yl)-3-methylbutan-2-yl)-N-methylbenzamide

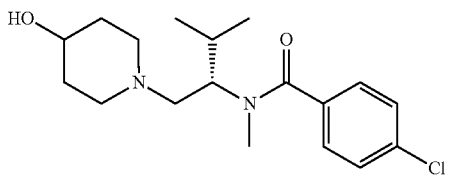 [SMILES: CC(C)[C@@H](CN1CCC(O)CC1)N(C)C(=O)c1ccc(Cl)cc1]

(S)-4-Chloro-N-methyl-N-(3-methyl-1-oxobutan-2-yl)benzamide (Compound A2.2) (0.12 g, 0.47 mmol) dissolved in DCM was added to piperidin-4-ol (72 mg, 0.71 mmol) and acetic acid (0.135 mL, 2.36 mmol) in MeOH (2 mL). Sodium cyanotrihydroborate (0.059 g, 0.95 mmol) was added and the resultant mixture was stirred at rt over night. The solvent was removed and the residue diluted with DCM. The organic phase was washed with LiOH (aq., 3 mL, 1M), filtered through a phase separator and concentrated under reduced pressure. The residue was purified by preparative HPLC. The product containing fractions was concentrated and the residue was purified a second time by preparative HPLC using Chiralpak IC 5 μm 20×250 mm column and Heptan/EtOH/TEA 60/40/0.1, as mobile phase to give the title compound (4 mg, 2.5%). Enantiomeric excess: 99.8%. Mixture of rotamers: (600 MHz, CD$_3$OD) δ 0.87, 0.92, 0.96, 1.03, 1.42-1.62, 1.71-1.90, 1.92-2.03, 2.14-2.21, 2.26-2.38, 2.42-2.50, 2.55-2.79, 2.88-2.93, 3.01, 3.28-3.38, 3.52-3.64, 4.43-4.56, 7.37-7.41, 7.43-7.52.

Total no of protons: 26. HRMS (M+H)$^+$: calculated 339.1839. found 339.1807.

Example 28

(S)-3,4-Difluoro-N-(1-(3-(methoxymethyl)azetidin-1-yl)-3-methylbutan-2-yl)-N-methylbenzamide

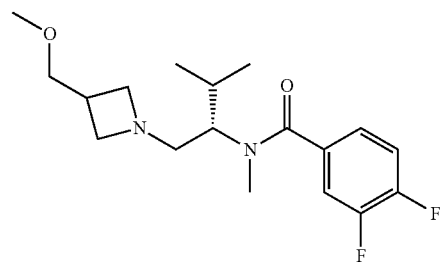 [SMILES: COCC1CN(C[C@H](C(C)C)N(C)C(=O)c2ccc(F)c(F)c2)C1]

(S)-3,4-Difluoro-N-methyl-N-(3-methyl-1-oxobutan-2-yl)benzamide (Compound A2.3) (0.25 g, 0.98 mmol) in MeOH (1.5 mL) was added to 3-(methoxymethyl)azetidine hydrochloride (0.202 g, 1.47 mmol) and TEA (0.679 mL, 4.90 mmol) in MeOH (1.5 mL). Sodium cyanotrihydroborate (0.103 mL, 1.96 mmol) was added and the resultant mixture was stirred at rt over night. The solvent was removed and the residue diluted with DCM. The organic phase was washed with LiOH (aq., 3 mL, 1M), filtered through a phase separator and concentrated under reduced pressure. The residue was purified by preparative HPLC. The product containing fractions was concentrated and the residue was purified a second time by preparative HPLC using Chiralpak AD 5 μm 20×250 mm column and Heptan/EtOH/TEA 80/20/0.1, as mobile phase to give the title compound (69 mg, 21%). Enantiomeric excess: 99.9%. Mixture of rotamers: (400 MHz, CD$_3$OD) δ 0.77-0.86, 0.93, 1.06, 1.70-1.90, 2.57-2.88, 2.94-3.09, 3.22-3.36, 3.40-3.57, 4.18-4.36, 7.23-7.52, 7.63-7.74. Total no of protons: 26. HRMS (M+H)$^+$: calculated 341.2040. found 341.2051.

Example 29.1

3,4-Difluoro-N-((2S,3S)-1-(3-hydroxyazetidin-1-yl)-3-methylpentan-2-yl)-N-methylbenzamide

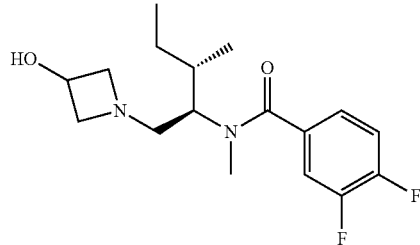 [SMILES: CC[C@H](C)[C@H](CN1CC(O)C1)N(C)C(=O)c1ccc(F)c(F)c1]

DIPEA (0.224 mL, 1.29 mmol) was added to 3,4-difluorobenzoic acid (0.068 g, 0.43 mmol) and TBTU (0.138 g, 0.43 mmol) in DCM (2 mL). The mixture was stirred at rt for 30 min. 1-((2S,3S)-3-Methyl-2-(methylamino)pentyl)azetidin-3-ol (Compound G2.1) (0.1 g, 0.43 mmol) in DCM (1 mL) was added and the resultant mixture was stirred at rt overnight. The mixture was washed with NaHCO$_3$, filtered through a phase separator and concentrated under reduced pressure. The residue was purified by preparative HPLC to give the title compound (95 mg, 68%). Mixture of rotamers: $^1$H NMR (600 MHz, DMSO-d6) δ 0.61-0.74, 0.75-0.92, 0.97-1.09, 1.20-1.63, 2.33-2.45, 2.48-2.83, 3.11-3.23, 3.32-3.38, 3.39-3.53, 4.04-4.23, 5.14-5.31, 7.10-7.22, 7.28-7.41, 7.42-7.56, 7.56-7.70. Total number of protons: 24. HRMS (M+H)$^+$: calculated 327.1884. found 327.1878. The compounds according to Examples 29.2-29.9 were prepared, from appropriate intermediates, by analogy with the method described for Example 29.1 hereinbefore.

| Example | Name | Yield |
| --- | --- | --- |
| 29.2 | 4-Chloro-N-((2S,3S)-1-(3-hydroxyazetidin-1-yl)-3-methylpentan-2-yl)-N-methylbenzamide | 105 mg, 75% |
| $^1$H NMR and HRMS | Mixture of rotamers: $^1$H NMR (600 MHz, DMSO-d6) δ 0.60-0.76, 0.76-0.93, 0.97-1.09, 1.24-1.47, 1.49-1.62, 2.32-2.43, 2.49-2.78, 3.09-3.19, 3.37-3.54, 4.02-4.26, 5.15-5.27, 7.26-7.34, 7.41-7.54. Total number of protons: 25. HRMS (M + H)$^+$: calculated 325.1683; found 325.1673 | |

-continued

| Example | Name | Yield |
|---|---|---|
| 29.3 | 4-Ethyl-N-((2S,3S)-1-(3-hydroxyazetidin-1-yl)-3-methylpentan-2-yl)-N-methylbenzamide | 98 mg, 71% |
| $^1$H NMR and HRMS | Mixture of rotamers: $^1$H NMR (600 MHz, DMSO-d6) δ 0.63-0.76, 0.78-0.85, 0.85-0.92, 0.96-1.08, 1.12-1.19, 1.25-1.45, 1.47-1.62, 2.32-2.53, 2.54-2.76, 3.21-3.29, 3.39-3.53, 4.06-4.26, 5.12-5.26, 7.15-7.28, 7.29-7.38. Total number of protons: 30. HRMS (M + H)$^+$: calculated 319.2386; found 319.2372 | |
| 29.4 | N-((2S,3S)-1-(3-Hydroxyazetidin-1-yl)-3-methylpentan-2-yl)-N-methylbenzamide | 103 mg, 83% |
| $^1$H NMR and HRMS | Mixture of rotamers: $^1$H NMR (600 MHz, DMSO-d6) δ 0.62-0.79, 0.80-0.86, 0.85-0.92, 0.99-1.08, 1.25-1.46, 1.51-1.62, 2.33-2.53, 2.56-2.77, 3.14-3.24, 3.38-3.55, 4.06-4.28, 5.14-5.25, 7.21-7.29, 7.32-7.47. Total number of protons: 26. HRMS (M + H)$^+$: calculated 291.2072; found 291.2072 | |
| 29.5 | 4-Cyano-N-((2S,3S)-1-(3-hydroxyazetidin-1-yl)-3-methylpentan-2-yl)-N-methylbenzamide | 66 mg, 49% |
| $^1$H NMR and HRMS | Mixture of rotamers: $^1$H NMR (600 MHz, DMSO-d6) δ 0.62-0.77, 0.79-0.93, 0.97-1.09, 1.26-1.48, 1.51-1.62, 2.33-2.60, 2.61-2.78, 2.98-3.07, 2.97-3.09, 3.22-3.29, 3.38-3.53, 4.07-4.26, 5.16-5.27, 7.41-7.50, 7.55-7.63, 7.80-7.95. Total number of protons: 25. HRMS (M + H)$^+$: calculated 316.2025; found 316.2022 | |
| 29.6 | N-((2S,3S)-1-(3-Hydroxyazetidin-1-yl)-3-methylpentan-2-yl)-4-methoxy-N-methylbenzamide | 99 mg, 72% |
| $^1$H NMR and HRMS | Mixture of rotamers: $^1$H NMR (600 MHz, DMSO-d6) δ 0.62-0.75, 0.76-0.91, 0.97-1.07, 1.24-1.46, 1.49-1.60, 2.33-2.44, 2.49-2.55, 2.56-2.77, 3.20-3.38, 3.39-3.53, 3.70-3.79, 4.05-4.26, 5.13-5.25, 6.87-7.01, 7.19-7.30, 7.39-7.50. Total number of protons: 28. HRMS (M + H)$^+$: calculated 321.2178; found 321.2172 | |
| 29.7 | 4-Cyano-2-fluoro-N-((2S,3S)-1-(3-hydroxyazetidin-1-yl)-3-methylpentan-2-yl)-N-methylbenzamide | 38 mg, 26% |
| $^1$H NMR and HRMS | Mixture of rotamers: $^1$H NMR (600 MHz, DMSO-d6) δ 0.63-0.85, 0.85-0.92, 0.93-1.09, 1.13-1.67, 2.25-2.44, 2.48-2.60, 2.60-2.79, 2.82-2.94, 3.37-3.54, 4.00-4.29, 5.09-5.31, 7.38-7.52, 7.65-7.80, 7.84-8.01. Total number of protons: 24. HRMS (M + H)$^+$: calculated 334.1931; found 334.1949 | |
| 29.8 | N-((2S,3S)-1-(3-Hydroxyazetidin-1-yl)-3-methylpentan-2-yl)-2-methoxy-N,5-dimethylbenzamide | 66 mg, 46% |
| $^1$H NMR and HRMS | Mixture of rotamers: $^1$H NMR (600 MHz, DMSO-d6) δ 0.62-0.90, 0.92-1.08, 1.23-1.42, 1.43-1.67, 1.98-2.25, 2.26-2.80, 2.88-3.02, 3.09-3.26, 3.33-3.58, 3.59-3.77, 3.98-4.19, 4.19-4.33, 5.11-5.25, 6.74-6.95, 7.01-7.19. Total number of protons: 30. HRMS (M + H)$^+$: calculated 335.2335; found 335.2311 | |
| 29.9 | 5-Chloro-N((2S,3S)-1-(3-hydroxyazetidin-1-yl)-3-methylpentan-2-yl)-2-methoxy-N-methylbenzamide | 110 mg, 72% |
| $^1$H NMR and HRMS | Mixture of rotamers: $^1$H NMR (600 MHz, DMSO-d6) δ 0.63-0.92, 0.94-1.09, 1.25-1.68, 2.25-2.81, 2.88, 3.11-3.27, 3.37-3.57, 3.64-3.84, 3.99-4.18, 4.17-4.30, 5.14-5.29, 6.97-7.12, 7.29-7.45. Total number of protons: 27. HRMS (M + H)$^+$: calculated 355.1788; found 355.1789 | |

Example 30

4-Chloro-N-((2R,3R)-1-(3-hydroxyazetidin-1-yl)-3-methoxybutan-2-yl)-N-methylbenzamide

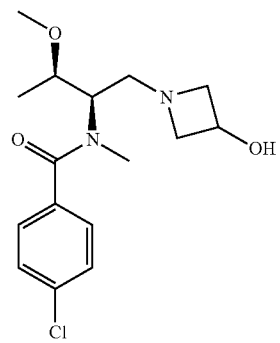 [SMILES: CO[C@H](C)[C@@H](CN1CC(O)C1)N(C)C(=O)c1ccc(Cl)cc1]

To 4-chlorobenzoic acid (65.7 mg, 0.42 mmol) and DIPEA (0.365 mL, 2.10 mmol) in DCM (0.7 mL) was TBTU (148 mg, 0.46 mmol) added 1-((2R,3R)-3-Methoxy-2-(methylamino)butyl)azetidin-3-ol (Compound B2.2) (79 mg, 0.42 mmol) in DCM (0.7 mL) was added and the resultant mixture stirred at rt for 2 h. NaHCO$_3$ was added and the stirring continued for 30 min. The layers were separated and the organic phase concentrated under reduced pressure. The residue was dissolved in THF/MeOH/water (3:1:1) and a small amount of NaOH (3.8M) was added. The resultant mixture was stirred for 30 min. The mixture was diluted with water and the organic solvent was removed. The water layer was extracted with DCM. The combined organic layers were filtered through a phase separator and concentrated. The residue was purified by preparative HPLC to give the title compound (39 mg, 28%). Mixture of rotamers: $^1$H NMR (600 MHz, DMSO-d6) δ 0.92, 1.08, 2.34-2.40, 2.52-2.59, 2.63, 2.69, 2.70-2.76, 2.77, 3.18-3.23, 3.34-3.39, 3.44-3.48, 3.48-3.54, 4.04-4.10, 4.11-4.16, 4.40, 5.16-5.24, 7.31, 7.40, 7.43-7.50. Total of protons in spectrum: 22. Ratio major:minor:3:2. HRMS (M+H)$^+$: calculated 327.1475. found 327.1476.

Example 31.1

(S)-4-Chloro-N-(1-(3-ethoxyazetidin-1-yl)pentan-2-yl)-N-methylbenzamide

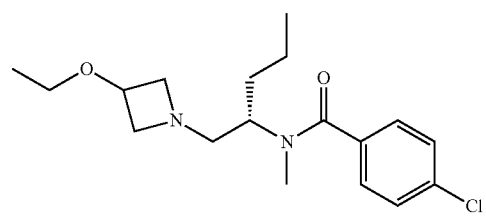 [SMILES: CCC[C@@H](CN1CC(OCC)C1)N(C)C(=O)c1ccc(Cl)cc1]

To (S)-4-chloro-N-(1-(3-hydroxyazetidin-1-yl)pentan-2-yl)-N-methylbenzamide (Example 8.2 A) (85 mg, 0.27 mmol) in dry THF (3 mL) was NaH (60% in mineral oil) (16.41 mg, 0.41 mmol) added carefully. The mixture was stirred at rt for 30 minutes then iodoethane (0.023 mL, 0.29 mmol) was added in one portion. The mixture was left standing at rt on. NaHCO$_3$ and DCM were added and the two layers were separated using a phase separator. The organic phase was concentrated and the residue was purified by preparative HPLC to give the title compound (36 mg, 39%). Mixture of rotamers: $^1$H NMR (600 MHz, DMSO-d6) δ 0.71, 0.86, 0.93-1.08, 1.08-1.32, 1.33-1.49, 2.36, 2.49-2.53, 2.54-2.61, 2.66, 2.70, 2.72-2.80, 3.19-3.32, 3.48, 3.96, 7.32, 7.38, 7.47. HRMS (M+H)$^+$: calculated 339.1839. found 339.1840.

The compounds according to Example 31.2-31.4 were prepared, from appropriate intermediates, by analogy with the method described for Example 31.1 hereinbefore.

| Example | Name | Yield |
|---|---|---|
| 31.2 | (S)-4-Chloro-N-(1-(3-methoxyazetidin-1-yl)pentan-2-yl)-N-methylbenzamide | 15 mg, 14% |
| $^1$H NMR and HRMS | $^1$H NMR (600 MHz, DMSO-d6) δ 0.71-0.77, 0.86-0.92, 0.96-1.06, 1.10-1.50, 2.35-2.43, 2.46-2.63, 2.68-2.75, 2.77-2.83, 3.10-3.14, 3.28-3.42, 3.46-3.52, 3.86-3.96, 4.45-4.52, 7.33-7.36, 7.39-7.42, 7.47-7.51. Total no of protons: 25 HRMS (M + H)$^+$: calculated 325.1683; found 325.1674 | |
| 31.3 | 4-chloro-N-{(2S)-1-[3-(cyanomethoxy)azetidin-1-yl]pentan-2-yl}-N-methylbenzamide | 34.2 mg, 30.4% |
| $^1$H NMR and HRMS | $^1$H NMR (400 MHz, DMSO) δ 0.59 (t, 1H), 0.74 (t, 1H), 0.80-1.43 (m, 3H), 2.20-2.56 (m, 10H), 2.58 (s, 1H), 2.63-2.83 (m, 1H), 3.13-3.33 (m, 3H), 3.40 (q, 1H), 3.96-4.13 (m, 1H), 4.29 (dd, 1H), 7.16-7.31 (m, 1H), 7.35 (d, 1H). HRMS (M + H)$^+$: calculated 350.164; found 350.1645. | |
| 31.4 | 4-chloro-N-methyl-N-{(2S)-1-[3-(propan-2-yloxy)azetidin-1-yl]pentan-2-yl}benzamide | (12 mg, 10%) |
| $^1$H NMR and HRMS | $^1$H NMR (600 MHz, DMSO-d6) δ 0.72, 0.87, 0.94-1.07, 1.07-1.33, 1.33-1.48, 2.30-2.43, 2.53-2.67, 2.67-2.79, 3.36, 3.50, 3.91-4.09, 7.32, 7.39, 7.47. Total of protons in spectrum: 29. HRMS (M + H)$^+$: calculated 353.1996; found 353.2004. | |

Example 32.1

(R)— and (S)—N-(1-Cyclopentyl-2-(3-hydroxyazetidin-1-yl)ethyl)-3,4-difluoro-N-methylbenzamide

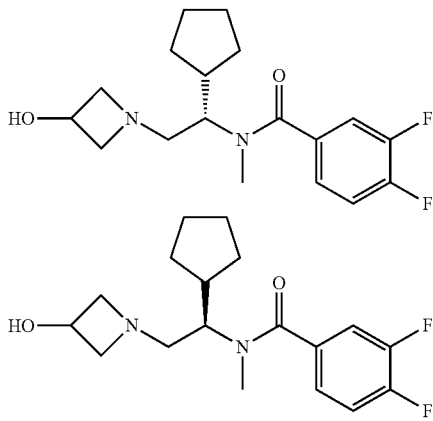

TBTU (0.534 g, 1.66 mmol) was added to 1-(2-cyclopentyl-2-(methylamino)ethyl)azetidin-3-ol dihydrochloride (dihydrochloride of Compound L2.1) (0.22 g, 0.81 mmol), 3,4-difluorobenzoic acid (0.283 g, 1.79 mmol) and DIPEA (2.5 mL, 14.31 mmol) in DCM (20 mL) at rt. The mixture was stirred for 3 h. The mixture was concentrated under reduced pressure. To the residue was added KOH (6 mL, 6.00 mmol), water (6 mL) and MeOH (20 mL). The resultant mixture was stirred at rt for 5 min. Part of the solvent was removed and the remaining mixture was diluted with water and extracted with DCM. The combined DCM layers were washed with brine, KHSO$_4$ (0.1M) and NaHCO$_3$ (saturated), dried (MgSO$_4$) and concentrated under reduce pressure. The residue was purified by preparative HPLC. The product containing fractions were concentrated in vacuo. The enantiomers were separated by chiral preparative HPLC using Chiralpak AD 5 μm 20×250 mm column and Heptan/EtOH/TEA 80/20/0.1, as mobile phase. The enantiomers are given in order of elution:

Isomer 1: (90 mg, 33%), ee: 99.9%. Mixture of rotamers: (600 MHz, CDCl$_3$) δ 0.74-1.98, 2.33-2.61, 2.60-3.02, 3.25-3.90, 4.20-4.53, 6.98-7.22, 7.22-7.39, 7.55. Total no of protons: 24. HRMS (M+H)$^+$: calculated 339.1884. found 339.1901.

Isomer 2: (90 mg, 33%), ee: 98.8%. Mixture of rotamers: (600 MHz, CDCl$_3$) δ 0.73-2.05, 2.31-3.02, 3.05-3.80, 4.10-4.69, 6.99-7.23, 7.22-7.44, 7.55. Total no of protons: 24. HRMS (M+H)$^+$: calculated 339.1884. found 339.1862.

The compounds according to Examples 32.2-32.7 were prepared, from appropriate intermediates, by analogy with the method described for Example 32.1 hereinbefore.

| Example | Name | Yield/ee |
|---|---|---|
| 32.2 | (R)- and (S)-N-[1-cyclopentyl-2-(3-hydroxyazetidin-1-yl)ethyl]-4-methoxy-N-methylbenzamide | Isomer 1: 35.6 mg, 99.9% ee Isomer 2: 35.7 mg, 99.9% ee |
| $^1$H NMR and HRMS | Isomer 1: $^1$H NMR (400 MHz, CDCl$_3$) δ 0.70-1.03, 1.05-2.01, 2.28-2.88, 3.28-3.63, 3.69, 4.09-4.52, 6.76, 7.22, 7.41. HRMS (M + H)$^+$: calculated 333.2178; found 333.218. Isomer 2: $^1$H NMR (400 MHz, CDCl$_3$) δ 0.73-1.04, 1.05-2.08, 2.26-2.90, 3.27-3.61, 3.69, 4.25, 6.75, 7.22, 7.41. HRMS (M + H)$^+$: calculated 333.2178; found 333.2187. | |
| 32.3 | (R)- and (S)-4-chloro-N-[1-cyclopentyl-2-(3-hydroxyazetidin-1-yl)ethyl]-N-methylbenzamide | Isomer 1: 29.2 mg, 99.9% Isomer 2: 31.5 mg, 99.9% ee |
| $^1$H NMR and HRMS | Isomer 1: $^1$H NMR (400 MHz, CDCl$_3$) δ 0.68-0.86, 0.86-1.01, 1.05-1.91, 1.92-2.27, 2.30-2.49, 2.51-2.90, 3.25, 3.35, 3.45-3.62, 4.08-4.51, 7.16-7.31, 7.39. HRMS (M + H)$^+$: calculated 337.1683; found 337.1684. Isomer 2: $^1$H NMR (400 MHz, CDCl$_3$) δ 0.69-0.85, 0.86-1.02, 1.03-1.92, 2.26-2.51, 2.51-2.89, 3.14-3.42, 3.43-3.65, 4.05-4.55, 7.16-7.28, 7.39. HRMS (M + H)$^+$: calculated 337.1683; found 337.1679. | |
| 32.4 | (R)- and (S)-N-[1-cyclopentyl-2-(3-hydroxyazetidin-1-yl)ethyl]-4-fluoro-N,3-dimethylbenzamide | Isomer 1: 29.9 mg, >99.9% ee Isomer 2: 32.2 mg, 97.7% ee |
| 1H NMR and HRMS | Isomer 1: $^1$H NMR (400 MHz, CDCl$_3$) δ 0.63-1.91, 2.16, 2.24-2.88, 3.18-3.40, 3.41-3.66, 4.09-4.51, 6.87, 6.97-7.11, 7.20-7.32. HRMS (M + H)$^+$: calculated 335.2135; found 335.2147. Isomer 2: $^1$H NMR (400 MHz, CDCl$_3$) δ 0.57-2.01, 2.15, 2.24-2.90, 3.30, 3.42-3.64, 4.04-4.51, 6.86, 7.00-7.11, 7.26. HRMS (M + H)$^+$: calculated 335.2135; found 335.2141. | |
| 32.5 | (R)- and (S)-4-cyano-N-[1-cyclopentyl-2-(3-hydroxyazetidin-1-yl)ethyl]-N-methylbenzamide | Isomer 1: 19.5 mg, >99.9% ee Isomer 2: 20.1 mg, 99.2% ee |

| Example | Name | Yield/ee |
|---|---|---|
| | ¹H NMR Isomer 1: ¹H NMR (400 MHz, CDCl₃) δ 0.67-0.97, 0.97-1.93, 2.22-2.51, 2.51-2.92, 3.11, 3.26-3.39, 3.44-3.66, 4.12-4.42, 7.27-7.46, 7.56. HRMS (M + H)⁺: calculated 328.2025; found 328.2026. Isomer 2: ¹H NMR (400 MHz, CDCl₃) δ 0.65-0.99, 1.05-1.92, 2.25-2.50, 2.53-2.68, 2.69-2.92, 3.12, 3.33, 3.46-3.65, 4.18-4.42, 7.13, 7.37, 7.51-7.63. HRMS (M + H)⁺: calculated 328.2025; found 328.2018. | |
| 32.6 | (R)- and (S)-2-chloro-N-[1-cyclopentyl-2-(3-hydroxyazetidin-1-yl)ethyl]-4-fluoro-N-methylbenzamide | Isomer 1: 14 mg, 98% ee Isomer 2: 14 mg, 99.4% ee |
| | ¹H NMR Isomer 1: ¹H NMR (400 MHz, CDCl₃) δ 0.60-2.28 (m), 2.28-3.26 (m), 3.29-3.68 (m), 4.06-4.57 (m), 6.81-7.24 (m), 7.55-7.70 (m). HRMS (M + H)⁺: calculated 355.1588; found 355.1604 Isomer 2: ¹H NMR (400 MHz, CDCl₃) δ 0.63-2.02 (m), 2.03-3.25 (m), 3.30-3.84 (m), 3.98-4.65 (m), 6.76-7.26 (m), 7.58-7.69 (m) HRMS (M + H)⁺: calculated 355.1588; found 355.1588 | |
| 32.7 | (R)- and (S)-3-chloro-N-[1-cyclopentyl-2-(3-hydroxyazetidin-1-yl)ethyl]-4-fluoro-N-methylbenzamide | 37.5 mg, >99.9% ee 28.1 mg, 97.6% ee |
| | ¹H NMR Isomer 1: ¹H NMR (400 MHz, CDCl₃) δ 0.71-1.00, 1.03-1.95, 2.00-2.89, 3.22, 3.39, 3.46-3.66, 4.10-4.44, 6.93-7.10, 7.10-7.22, 7.26-7.45, 7.66. HRMS (M + H)⁺: calculated 355.1588; found 355.1592 Isomer 2: ¹H NMR (400 MHz, CDCl₃) δ 0.71-0.98, 1.02-1.94, 2.39, 2.54-2.89, 3.22, 3.39, 3.48-3.69, 4.27, 6.88-7.09, 7.10-7.23, 7.25-7.44, 7.66. HRMS (M + H)⁺: calculated 355.1588; found 355.1594 | |

Example 33.1

(S)-4-chloro-N-(1-(3-hydroxyazetidin-1-yl)hexan-2-yl)-N-methylbenzamide

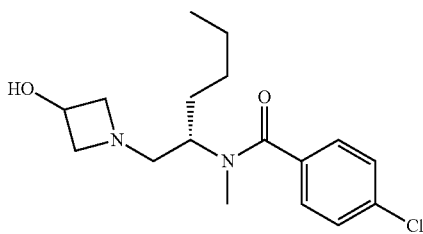 [SMILES: CCCC[C@@H](CN1CC(O)C1)N(C)C(=O)c1ccc(Cl)cc1]

DIPEA (0.275 mL, 1.58 mmol) was added to a stirred suspension of 4-chlorobenzoic acid (0.082 g, 0.53 mmol) and TBTU (0.169 g, 0.53 mmol) in DCM (1 mL) at rt. The suspension was stirred for 5 min. A solution of (S)-1-(2-(methylamino)hexyl)azetidin-3-ol (Compound G2.2) (0.11 g, 0.53 mmol) in DCM (1 mL) was added and the reaction was stirred at rt overnight. The reaction mixture was washed with an 8% aq. sol. of NaHCO₃ (2 mL). The organic layer was dried through a phase separator and the solvent was removed in vacuo. Purification by preparative HPLC afforded the title compound (51 mg, 30%). Mixture of rotamers: ¹H NMR (600 MHz, DMSO-d6) δ 0.75-0.80, 0.82-0.87, 0.91-0.99, 1.02-1.46, 2.31-2.39, 2.44-2.62, 2.65-2.73, 3.16-3.53, 3.99-4.17, 4.36-4.48, 5.23, 7.30-7.33, 7.35-7.39, 7.45-7.49. Total number of protons in spectrum: 25. HRMS (M+H)⁺: calculated 325.1683. found 325.169

The compounds according to Examples 33.2-33.10 were prepared, from appropriate intermediates, by analogy with the method described for Example 33.1 hereinbefore.

| Example | Name | Yield |
|---|---|---|
| 33.2 | 3,4-Difluoro-N-[(2S)-1-(3-hydroxyazetidin-1-yl)hexan-2-yl]-N-methylbenzamide | 75 mg, 44% |
| | ¹H NMR and HRMS Mixture of rotamers: 1H NMR (600 MHz, DMSO-d6) δ 0.74-0.88, 0.90-1.51, 2.30-2.42, 2.45-2.76 , 3.19-3.53, 4.03-4.18, 4.34-4.45, 5.17-5.30, 7.11-7.28, 7.32-7.54. HRMS (M + H)⁺: calculated 327.1884; found 327.1885 | |
| 33.3 | 4-Cyano-2-fluoro-N-[(2S)-1-(3-hydroxyazetidin-1-yl)hexan-2-yl]-N-methylbenzamide | 93 mg, 53% |
| | ¹H NMR and HRMS Mixture of rotamers: 1H NMR (600 MHz, DMSO-d6) δ 0.74-0.88, 0.93-1.52, 2.32-2.79, 3.00-3.60, 3.99-4.17, 4.41-4.51, 5.19-5.31, 7.42-8.00. HRMS (M + H)⁺: calculated 334.1931; found 334.1928 | |
| 33.4 | 4-Cyano-N-[(2S)-1-(3-hydroxyazetidin-1-yl)hexan-2-yl]-N-methylbenzamide | 78 mg, 47% |
| | ¹H NMR and HRMS Mixture of rotamers: ¹H NMR (600 MHz, DMSO-d6) δ 0.76-0.87, 0.90-1.47, 2.30-2.39, 2.44-2.79, 3.18-3.54, 4.03-4.17, 4.39-4.48, 5.23, 7.42-7.56, 7.84-7.94. HRMS (M + H)⁺: calculated 316.2025; found 316.2025 | |
| 33.5 | N-[(2S)-1-(3-Hydroxyazetidin-1-yl)hexan-2-yl]-N-methylbenzamide | 68 mg, 45% |
| | ¹H NMR and HRMS Mixture of rotamers: ¹H NMR (600 MHz, DMSO-d6) δ 0.72-0.88, 0.91-1.47, 2.32-2.74, 3.19-3.53, 4.02-4.17, 4.41-4.50, 5.16-5.25, 7.23-7.46. HRMS (M + H)⁺: calculated 291.2072; found 291.2075 | |
| 33.6 | 4-Hydroxy-N-[(2S)-1-(3-hydroxyazetidin-1-yl)hexan-2-yl]-N-methylbenzamide | 39 mg, 24% |
| | ¹H NMR and HRMS Mixture of rotamers: ¹H NMR (600 MHz, DMSO-d6) δ 0.70-1.55, 2.13-2.79, 3.09-3.63, 4.00-4.17, 4.33-4.45, 5.11-5.35, 6.68-6.79, 7.11-7.23. HRMS (M + H)⁺: calculated 307.2021; found 307.2027 | |
| 33.7 | 4-Fluoro-N-[(2S)-1-(3-hydroxyazetidin-1-yl)hexan-2-yl]-N-methylbenzamide | 77 mg, 47.5% |
| | ¹H NMR and HRMS Mixture of rotamers: ¹H NMR (600 MHz, DMSO-d6) δ 0.73-0.87, 0.90-0.99, 1.02-1.47, 2.31-2.73, 3.20-3.54, 4.03-4.17, 4.38-4.48, 5.22, 7.12-7.27, 7.32-7.45. HRMS (M + H)⁺: calculated 309.1978; found 309.1980 | |
| 33.8 | 3-Chloro-4-fluoro-N-[(2S)-1-(3-hydroxyazetidin-1-yl)hexan-2-yl]-N-methylbenzamide | 82 mg, 45.5% |
| | ¹H NMR and HRMS Mixture of rotamers: ¹H NMR (600 MHz, DMSO-d6) δ 0.73-0.88, 0.90-0.99, 1.02-1.48, 2.30-2.40, 2.44-2.75, 3.21-3.52, 4.05-4.17, 4.34-4.44, 5.19-5.29, 7.30-7.35, 7.37-7.41, 7.43-7.49, 7.50-7.54, 7.61-7.65. HRMS (M + H)⁺: calculated 343.1588; found 343.1592 | |
| 33.9 | 2,5-Difluoro-N-[(2S)-1-(3-hydroxyazetidin-1-yl)hexan-2-yl]-N-methylbenzamide | 76 mg, 44% |
| | ¹H NMR and HRMS Mixture of rotamers: ¹H NMR (600 MHz, DMSO-d6) δ 0.72-0.86, 0.93-1.62, 2.30-2.82, 3.33, 4.01-4.17, 4.38-4.48, 5.17-5.30, 7.10-7.40. HRMS (M + H)⁺: calculated 327.1884; found 327.1882 | |
| 33.10 | 3-(Difluoromethyl)-N-[(2S)-1-(3-hydroxyazetidin-1-yl)hexan-2-yl]-N-methylbenzamide | 92 mg, 51% |
| | ¹H NMR and HRMS Mixture of rotamers: ¹H NMR (600 MHz, DMSO-d6) δ 0.73-0.89, 0.92-1.01, 1.03-1.48, 2.29-2.41, 2.42-2.64, 2.65-2.77, 3.18-3.37, 3.44-3.54, 4.03-4.17, 4.40-4.52, 5.18-5.26, 6.93-6.98, 7.01-7.09, 7.11-7.18, 7.43- 7.65. HRMS (M + H)⁺: calculated 341.204; found 341.2037 | |

Example 34.1

4-Chloro-N-[(2S)-1-(3-hydroxyazetidin-1-yl)pentan-2-yl]-N-(propan-2-yl)benzamide

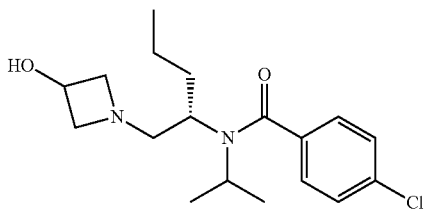 [SMILES: CCC[C@@H](CN1CC(O)C1)N(C(=O)c1ccc(Cl)cc1)C(C)C]

To a mixture of 4-chlorobenzoic acid (0.067 g, 0.43 mmol) and TBTU (0.137 g, 0.43 mmol) in DCM (2 mL) was added N-ethyl-N-isopropylpropan-2-amine (0.222 mL, 1.28 mmol). The suspension was stirred at rt for 30 min. A solution of (S)-1-(2-(isopropylamino)pentyl)azetidin-3-ol (Compound O2.1) (0.142 g, 0.43 mmol) in DCM (1 mL) was added and the reaction mixture was stirred at rt overnight. The reaction was washed with saturated NaHCO$_3$ solution (2 ml). The organic phase was concentrated using a vacuum centrifuge. The residue was dissolved in MeOH (2 ml) and 1M NaOH (aq., 0.5 ml) was added. The mixture was stirred at rt for 1.5 h. Acetic acid (110 mg) was added and the mixture was concentrated. The residue was dissolved in DCM (3.5 ml) and washed with saturated NaHCO$_3$ solution (2 ml). The organic phase was concentrated using a vacuum centrifuge and the residue purified by preparative HPLC affording the title compound (20 mg, 14%). Mixture of rotamers: $^1$H NMR (600 MHz, DMSO-d6) δ 0.62-0.78, 0.76-0.93, 0.93-1.14, 1.14-1.54, 1.67-1.93, 2.24-2.40, 2.41-2.77, 2.76-2.97, 2.96-3.15, 3.16-3.45, 3.45-3.75, 3.96-4.20, 5.12-5.31, 7.17-7.35, 7.38-7.52. Number of protons: 27. HRMS (M+H)$^+$: calculated 339.1839. found 339.1866

The compound according to Examples 34.2 was prepared, from appropriate intermediates, by analogy with the method described for Example 34.1 hereinbefore.

| Example | Name | Yield |
|---|---|---|
| 34.2 | 3,4-Difluoro-N-[(2S)-1-(3-hydroxyazetidin-1-yl)pentan-2-yl]-N- (propan-2-yl)benzamide | 14 mg, 10% |
| $^1$H NMR and HRMS | Mixture of rotamers: $^1$H NMR (600 MHz, DMSO-d6) δ 0.59-0.77, 0.80-0.92, 0.95-1.13, 1.13-1.53, 1.67-1.94, 2.30-2.39, 2.42-2.61, 2.61-2.76, 2.88, 2.99-3.16, 3.16-3.33, 3.36-3.75, 4.00-4.22, 5.12-5.31, 7.04-7.17, 7.30-7.56. Number of protons: 26. HRMS (M + H)$^+$: calculated 341.2041; found 341.2041 | |

Example 35.1

4-Chloro-N-[(1R)-1-cyclobutyl-2-(3-hydroxyazetidin-1-yl)ethyl]-N-methylbenzamide

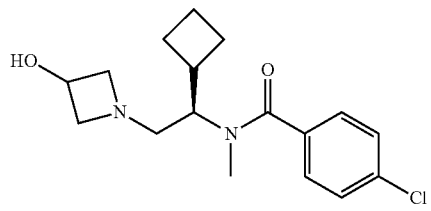 [SMILES: CN(C(=O)c1ccc(Cl)cc1)[C@@H](CN1CC(O)C1)C1CCC1]

DIPEA (0.275 mL, 1.57 mmol) was added to a suspension of 4-chlorobenzoic acid (82 mg, 0.52 mmol) and TBTU (168 mg, 0.52 mmol) in DCM (1 mL) at rt. The reaction mixture was stirred for 45 min before a solution of (R)-1-(2-cyclobutyl-2-(methylamino)ethyl)azetidin-3-ol (Compound G2.6) (184 mg, 0.52 mmol) in NMP (1.000 mL) was added. The reaction mixture was stirred at rt over the weekend. The reaction mixture was washed with NaHCO$_3$ (8% aq.2 mL). The organic layer was passed through a phase separator and the solvent was removed in vacuo. The residue was purified by preparative HPLC to give the title compound (88 mg, 52%). $^1$H NMR (600 MHz, DMSO-d6) δ 1.38-1.52, 1.55-1.62, 1.64-1.95, 2.00-2.06, 2.21-2.25, 2.27-2.33, 2.36-2.43, 2.55-2.62, 2.64-2.68, 2.70-2.72, 2.73-2.79, 3.23-3.26, 3.40-3.44, 3.54-3.57, 4.11-4.18, 4.43-4.51, 5.20-5.27, 7.29-7.35, 7.47-7.54. HRMS (M+H)$^+$: calculated 323.1526. found 323.1535

The compounds according to Examples 35.2-35.14 were prepared, from appropriate intermediates, by analogy with the method described for Example 35.1 hereinbefore.

| Example | Name | Yield |
|---|---|---|
| 35.2 | 4-Cyano-N-[(1R)-1-cyclobutyl-2-(3-hydroxy-azetidin-1-yl)ethyl]-N-methylbenzamide | 73 mg, 44% |
| $^1$H NMR and HRMS | $^1$H NMR (600 MHz, DMSO-d6) δ 1.35-1.63, 1.68-1.97, 2.00-2.07, 2.20-2.29, 2.36-2.49, 2.55-2.58, 2.64-2.71, 2.72-2.74, 3.17-3.28, 3.41-3.54, 4.11-4.17, 4.43-4.51, 5.21-5.26, 7.45-7.47, 7.60-7.63, 7.89-7.95. HRMS (M + H)$^+$: calculated 314.1868; found 314.1876 | |
| 35.3 | N-[(1R)-1-Cyclobutyl-2-(3-hydroxyazetidin-1-yl)ethyl]-4-(difluoromethoxy)-N-methylbenzamide | 80 mg, 43% |
| $^1$H NMR and HRMS | $^1$H NMR (600 MHz, DMSO-d6) δ 1.35-1.94, 1.99-2.04, 2.17-2.41, 2.55-2.78, 3.16-3.26, 3.38-3.65, 4.08-4.15, 4.36-4.52, 5.19-5.27, 7.08-7.42, 7.49-7.52. HRMS (M + H)$^+$: calculated 355.1833; found 355.1836 | |
| 35.4 | N-[(1R)-1-Cyclobutyl-2-(3-hydroxyazetidin-1-yl)ethyl]-4-fluoro-N,3-dimethylbenzamide | 77.7 mg, 46% |
| $^1$H NMR and HRMS | $^1$H NMR (600 MHz, DMSO-d6) δ 1.34-1.59, 1.62-1.92, 1.98-2.04, 2.11-2.28, 2.31-2.43, 2.51-2.59, 2.64-2.75, 3.20-3.24, 3.35-3.41, 3.46-3.60, 4.08-4.14, 4.40-4.50, 5.19-5.24, 7.07-7.23, 7.27-7.42. HRMS (M + H)$^+$: calculated 321.1978; found 321.1988 | |
| 35.5 | N-[(1R)-1-Cyclobutyl-2-(3-hydroxyazetidin-1-yl)ethyl]-4-fluoro-N-methylbenzamide | 81 mg, 50% |
| $^1$H NMR and | $^1$H NMR (600 MHz, DMSO-d6) δ 1.31-1.60, 1.65-2.05, 2.17-2.41, 2.51-2.75, 3.20-3.25, 3.36- | |

-continued

| Example | Name | Yield |
|---|---|---|
| HRMS | 3.50, 4.11, 4.44, 5.19, 7.19-7.35, 7.49. HRMS (M + H)+: calculated 307.1822; found 307.1829 | |
| 35.6 | 2-Chloro-N-[(1R)-1-cyclobutyl-2-(3-hydroxy-azetidin-1-yl)ethyl]-4-fluoro-N-methylbenzamide | 30 mg, 17% |
| 1H NMR and HRMS | 1H NMR (600 MHz, DMSO-d6) δ 1.35-2.06, 2.20-2.42, 2.55-2.77, 2.99-3.24, 3.44-3.54, 3.55-3.74, 4.01-4.19, 4.38-4.56, 4.66, 5.16-5.28, 7.21-7.43, 7.47-7.58, 7.60-7.63. HRMS (M + H)+: calculated 341.1432; found 341.1436 | |
| 35.7 | N-[(1R)-1-Cyclobutyl-2-(3-hydroxyazetidin-1-yl)ethyl]-3,4-difluoro-N-methylbenzamide | 2 mg, 2.4% |
| HRMS | HRMS (M + H)+: calculated 325.1728; found 325.1722 | |
| 35.8 | N-[(1R)-1-Cyclobutyl-2-(3-hydroxyazetidin-1-yl)ethyl]-3-(difluoromethyl)-N-methylbenzamide | 2.8 mg, 3.5% |
| HRMS | HRMS (M + H)+: calculated 339.1884; found 339.1890 | |
| 35.9 | 3-Cyano-N-[(1R)-1-cyclobutyl-2-(3-hydroxy-azetidin-1-yl)ethyl]-4-fluoro-N-methylbenzamide | 64 mg, 37% |
| 1H NMR and HRMS | 1H NMR (600 MHz, DMSO-d6) δ 1.37-1.46, 1.52-1.59, 1.61-2.04, 2.19-2.27, 2.31-2.46, 2.55-2.62, 2.63-2.77, 3.21-3.25, 3.41-3.52, 4.06-4.19, 4.37-4.49, 5.16-5.30, 7.53-7.65, 7.66-7.73, 7.84-7.91, 8.04-8.10. HRMS (M + H)+: calculated 332.1774; found 332.1781 | |
| 35.10 | N-[(1R)-1-Cyclobutyl-2-(3-hydroxyazetidin-1-yl)ethyl]-2,4-difluoro-N-methylbenzamide | 73 mg, 43% |
| 1H NMR and HRMS | 1H NMR (600 MHz, DMSO-d6) δ 1.35-2.09, 2.14-2.46, 2.61-2.73, 3.09-3.23, 3.35-3.51, 4.05-4.16, 4.36-4.56, 5.16-5.23, 7.11-7.20, 7.28-7.54. HRMS (M + H)+: calculated 325.1728; found 325.173 | |
| 35.11 | 3-Chloro-N-[(1R)-1-cyclobutyl-2-(3-hydroxy-azetidin-1-yl)ethyl]-2-fluoro-N-methylbenzamide | 58 mg, 33% |
| 1H NMR and HRMS | 1H NMR (600 MHz, DMSO-d6) δ 1.43-2.04 (m), 2.16-2.38 (m), 2.61-2.77 (m), 3.07-3.22 (m), 3.44-3.67 (m), 4.04-4.16 (m), 4.35-4.56 (m), 5.15-5.25 (m), 7.16-7.33 (m), 7.47-7.66 (m). HRMS (M + H)+: calculated 341.1432; found 341.1439 | |
| 35.12 | N-[(1R)-1-Cyclobutyl-2-(3-hydroxyazetidin-1-yl)ethyl]-2-fluoro- 4-methoxy-N-methylbenzamide | 72 mg, 41% |
| 1H NMR and HRMS | 1H NMR (600 MHz, DMSO-d6) δ 1.33-2.02, 2.15-2.47, 2.56-2.71, 3.15-3.26, 3.37-3.42, 3.45-3.50, 3.70-3.81, 4.03-4.14, 4.38-4.54, 5.19, 6.65-6.92, 7.11-7.20, 7.27-7.38. HRMS (M + H)+: calculated 337.1927; found 337.1928 | |
| 35.13 | N-[(1R)-1-Cyclobutyl-2-(3-hydroxyazetidin-1-yl)ethyl]-3-fluoro- 4-methoxy-N-methylbenzamide | 89 mg, 50% |
| 1H NMR and HRMS | 1H NMR (600 MHz, DMSO-d6) δ 1.36-1.47, 1.51-1.59, 1.62-1.94, 1.97-2.05, 2.20-2.27, 2.30-2.44, 2.56-2.73, 3.39-3.53, 3.76-3.88, 4.09-4.14, 4.37-4.45, 5.16-5.26, 7.07-7.39. HRMS (M + H)+: calculated 337.1927; found 337.1935 | |
| 35.14 | N-[(1R)-1-Cyclobutyl-2-(3-hydroxyazetidin-1-yl)ethyl]-N- methylbenzamide | 68 mg, 45% |
| 1H NMR and HRMS | 1H NMR (600 MHz, DMSO-d6) δ 1.33-1.40, 1.47-1.61, 1.68-1.96, 2.00-2.06, 2.25, 2.33-2.41, 2.46, 2.58, 2.65, 2.67-2.75, 3.24, 3.40-3.44, 3.52, 4.10-4.16, 4.49, 5.23, 7.25-7.28, 7.40-7.46. HRMS (M + H)+: calculated 289.1916; found 289.1921 | |

Example 36.1

4-cyano-N-[(1S)-1-cyclohexyl-2-(3-hydroxyazetidin-1-yl)ethyl]-N-methylbenzamide

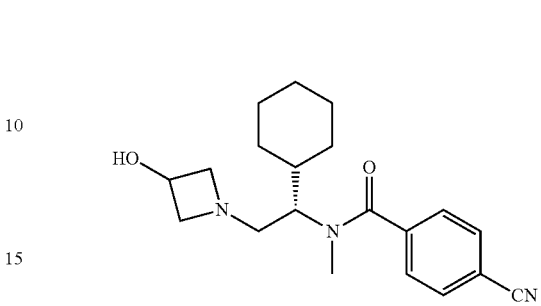

4-cyanobenzoic acid (65.0 mg, 0.44 mmol) in DCM (2 mL) was treated with DIPEA (0.231 mL, 1.32 mmol) and TBTU (142 mg, 0.44 mmol) and the suspension was stirred for 10 min. A 125 mg/mL solution of (S)-1-(2-cyclohexyl-2-(methylamino)ethyl)azetidin-3-ol (Compound G2.3) (125 mg, 0.44 mmol) in DCM (1 mL) was added and the reaction was stirred at ambient temperature overnight. The reaction was washed with 8% aq. sol. of NaHCO3 and concentrated. The residue was dissolved in DMSO (0.4 mL) and filtered through a syringe filter. The residue was purified by HPLC to give the title compound (73.6 mg, 49%). Mixture of rotamers. 1H NMR (600 MHz, DMSO-d6) δ 0.53-0.70, 0.89-1.81, 2.43-2.59, 2.64-2.78, 3.03, 3.28-3.31, 3.43-3.54, 4.11-4.30, 5.23, 5.26, 7.48, 7.61, 7.87-7.94. HRMS (M+H)+: calculated 342.2181. found 342.2193

The compounds according to Examples 36.2-36.8 were prepared, from appropriate intermediates, by analogy with the method described for Example 36.1 hereinbefore

| Example | Name | Yield |
|---|---|---|
| 36.2 | 4-Chloro-N-[(1S)-1-cyclohexyl-2-(3-hydroxy-azetidin-1-yl)ethyl]-N-methylbenzamide | 76 mg, 49% |
| 1H NMR and HRMS | Mixture of rotamers: 1H NMR (600 MHz, DMSO-d6) δ 0.58-0.69, 0.90-1.05, 1.07-1.25, 1.33-1.81, 2.44-2.58, 2.61, 2.65, 2.69-2.76, 3.15, 3.42-3.48, 3.48-3.53, 4.11-4.29, 5.22, 5.25, 7.31-7.34, 7.45-7.51. HRMS (M + H)+: calculated 351.184; found 351.1856 | |
| 36.3 | 3-Cyano-N-[(1S)-1-cyclohexyl-2-(3-hydroxy-azetidin-1-yl)ethyl]-N-methylbenzamide | 76 mg, 50% |
| 1H NMR and HRMS | Mixture of rotamers: 1H NMR (600 MHz, DMSO-d6) δ 0.56-0.66, 0.99, 1.06-1.26, 1.35-1.82, 2.44-2.53, 2.54-2.60, 2.61, 2.64-2.72, 2.72-2.78, 3.05, 3.44-3.54, 4.11-4.32, 5.22, 5.29, 7.62-7.68, 7.75-7.80, 7.87-7.92, 7.93-7.96. HRMS (M + H)+: calculated 342.218; found 342.2196 | |
| 36.4 | 4-Cyano-N-[(1S)-1-cyclohexyl-2-(3-hydroxy-azetidin-1-yl)ethyl]-2-fluoro-N-methylbenzamide | 50 mg, 31.5% |
| 1H NMR and HRMS | Mixture of rotamers: 1H NMR (600 MHz, DMSO-d6) δ 0.53-0.74, 0.86-1.26, 1.35-1.80, 2.45-2.53, 2.57, 2.64-2.67, 2.74, 2.78, 2.84-2.90, 3.41-3.54, 4.08-4.32, 5.24, 7.46-7.50, 7.72-7.80, 7.92-8.00. HRMS (M + H)+: calculated 360.209; found 360.2105 | |
| 36.5 | 4-(2-Cyanopropan-2-yl)-N-[(1S)-1-cyclohexyl-2-(3-hydroxyazetidin-1-yl)ethyl]-N-methylbenzamide | 99.7 mg, 59% |
| 1H NMR and HRMS | Mixture of rotamers: 1H NMR (600 MHz, DMSO-d6) δ 0.54-0.72, 0.91-1.06, 1.06-1.33, 1.30-1.68, 1.69-1.73, 1.75-1.82, 2.45-2.53, 2.58, 2.61-2.63, 2.64-2.77, 3.19-3.25, 3.29-3.37, 3.44-3.49, 3.49- | |

-continued

| Example | Name | Yield |
|---|---|---|
| | 3.54, 4.11-4.32, 5.22, 5.25, 7.35-7.39, 7.50-7.53, 7.54-7.60. HRMS (M + H)⁺: calculated 384.265; found 384.2674 | |
| 36.6 | 3-Cyano-N-[(1S)-1-cyclohexyl-2-(3-hydroxy-azetidin-1-yl)ethyl]-5-fluoro-N-methylbenzamide | 53 mg, 33% |
| $^1$H NMR and HRMS | Mixture of rotamers: $^1$H NMR (600 MHz, DMSO-d6) δ 0.54-0.70, 0.88-1.25, 1.35-1.81, 2.44-2.48, 2.51-2.58, 2.59-2.64, 2.64-2.71, 2.72-2.79, 3.05, 3.28-3.38, 3.45-3.53, 4.13-4.23, 5.23, 5.31, 7.52-7.58, 7.67, 7.76, 7.84, 7.90-7.96. HRMS (M + H)⁺: calculated 360.209; found 360.2105 | |
| 36.7 | N-[(1S)-1-Cyclohexyl-2-(3-hydroxyazetidin-1-yl)ethyl]-4-fluoro-N-methylbenzamide | 93 mg, 63% |
| $^1$H NMR and HRMS | Mixture of rotamers: $^1$H NMR (600 MHz, DMSO-d6) δ 0.57-0.68 (m), 0.88-1.24 (m), 1.33-1.82 (m), 2.44-2.59 (m), 2.61 (s), 2.63-2.76 (m), 3.20 (td), 3.29-3.36 (m), 3.42-3.48 (m), 3.48-3.53 (m), 4.11-4.31 (m), 5.22 (d), 5.25 (d), 7.22-7.28 (m), 7.34-7.39 (m), 7.49-7.54 (m). HRMS (M + H)⁺: calculated 335.214; found 335.215 | |
| 36.8 | N-[(1S)-1-Cyclohexyl-2-(3-hydroxyazetidin-1-yl)ethyl]-N-methylbenzamide | 87 mg, |
| $^1$H NMR and HRMS | Mixture of rotamers: $^1$H NMR (600 MHz, DMSO-d6) δ 0.53-0.71, 0.90-1.25, 1.33-1.42, 1.42-1.82, 2.45-2.56, 2.59-2.77, 3.21, 3.29-3.34, 3.43-3.54, 4.10-4.36, 5.22, 5.24, 7.26-7.46. HRMS (M + H)⁺: calculated 317.223; found 317.2244 | |

Example 37

4-Chloro-N-[(2R)-1-(3-hydroxyazetidin-1-yl)pentan-2-yl]-N-methylbenzamide

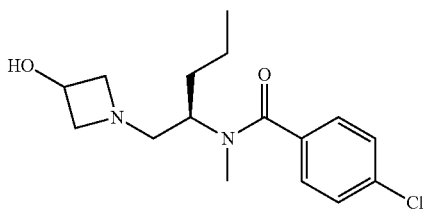 [SMILES: CCC[C@H](CN1CC(O)C1)N(C)C(=O)c1ccc(Cl)cc1]

4-chlorobenzoic acid (0.527 g, 3.37 mmol) and DIPEA (1.176 mL, 6.73 mmol) were mixed in DCM (20 mL) at 0° C. After stirring for 10 min, TBTU (1.103 g, 3.43 mmol) was added to the reaction mixture. The mixture was stirred at 0° C. for 20 min. The above mixture was added in three portions to a solution of (R)-1-(2-(methylamino)pentyl)-azetidin-3-ol (Compound G2.5) (0.58 g, 3.37 mmol) in DCM (20 mL) within 10 min at 0° C. The mixture was stirred at 0° C. for 2.5 h, then warmed to rt and the mixture was stirred overnight. The mixture was concentrated to dryness. To the residue was added aq KOH (30 mL, 15.00 mmol) and methanol (15 mL)/THF (15 mL). The reaction mixture was stirred at rt for 2.5 h. The mixture was concentrated and extracted with DCM (30 mL×2). The DCM layers were combined, evaporated in vacuo to an oil residue. The crude was purified by preparative HPLC to afford the title compound (0.766 g, 73.2%). Mixture of rotamers:

$^1$H NMR (400 MHz, CD$_3$OD) δ 0.87, 0.99, 1.11-1.70, 2.49, 2.64-3.04, 3.40-3.66, 3.67-3.81, 4.34, 4.63-4.79, 7.30-7.70. Total number of protons: 22 (proton from hydroxyl group missing). HRMS (M+H)⁺: calculated 311.153. found 311.1529

Example 38.1

3,4-Difluoro-N-[(2S)-1-(3-hydroxyazetidin-1-yl)-4-methylpentan-2-yl]-N-methylbenzamide

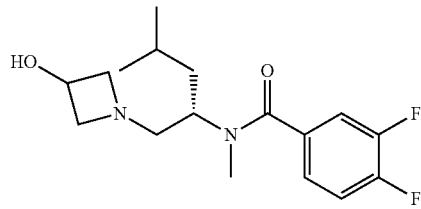 [SMILES: CC(C)C[C@@H](CN1CC(O)C1)N(C)C(=O)c1ccc(F)c(F)c1]

DIPEA (0.252 mL, 1.45 mmol) was added to a stirred suspension of 3,4-difluorobenzoic acid (76 mg, 0.48 mmol) and TBTU (155 mg, 0.48 mmol) in DCM (2 mL) at rt. The suspension was stirred for 3 min. A solution of (S)-1-(4-methyl-2-(methylamino)pentyl)azetidin-3-ol (Compound G2.4) (100 mg, 0.48 mmol) in DCM (1 mL) was added and the reaction was stirred at rt overnight. The reaction was washed with an 8% aq. solution of NaHCO$_3$ (1.5 mL). The organic layer was concentrated and purified by preparative HPLC affording the title compound (102 mg, 65%). Mixture of rotamers:

$^1$H NMR (600 MHz, DMSO-d6) δ 0.56, 0.75, 0.82-0.92, 1.14-1.25, 1.29-1.41, 1.44-1.58, 2.35, 2.44, 2.52-2.57, 2.62, 2.65-2.75, 3.34, 3.44-3.54, 4.11-4.18, 4.50-4.58, 5.25, 5.28, 7.16-7.21, 7.29-7.35, 7.39-7.45, 7.46-7.56, 7.59-7.66. HRMS (M+H)⁺: calculated 327.1884. found 327.1881.

The compounds according to Examples 38.2-38.8 were prepared, from appropriate intermediates, by analogy with the method described for Example 38.1 hereinbefore.

| Example | Name | Yield |
|---|---|---|
| 38.2 | 4-Chloro-N-[(2S)-1-(3-hydroxyazetidin-1-yl)-4-methylpentan-2-yl]-N-methylbenzamide | 88 mg, 56% |
| $^1$H NMR and HRMS | Mixture of rotamers: $^1$H NMR (600 MHz, DMSO) δ 0.56, 0.75, 0.83-0.93, 1.17-1.25, 1.29-1.39, 1.44-1.56, 2.35, 2.43, 2.51-2.53, 2.61, 2.65, 2.69-2.76, 3.30-3.38, 3.42-3.54, 4.10-4.19, 4.52-4.61, 5.21-5.30, 7.31-7.37, 7.43-7.53. HRMS (M + H)⁺: calculated 325.168; found 325.1707 | |
| 38.3 | 4-Ethyl-N-[(2S)-1-(3-hydroxyazetidin-1-yl)-4-methylpentan-2-yl]-N-methylbenzamide | 97 mg, 63% |
| $^1$H NMR and HRMS | Mixture of rotamers: $^1$H NMR (600 MHz, DMSO) δ 0.54, 0.75, 0.90, 1.15-1.25, 1.28-1.39, 1.44-1.57, 2.36, 2.44, 2.48-2.53, 2.59-2.66, 2.69-2.75, 3.30-3.38, 3.48-3.58, 4.08-4.19, 4.53-4.62, 5.24, 7.21-7.28, 7.33. HRMS (M + H)⁺: calculated 319.239; found 319.2357 | |
| 38.4 | 3-(Difluoromethyl)-N-[(2S)-1-(3-hydroxyazetidin-1-yl)-4-methylpentan-2-yl]-N-methylbenzamide | 103 mg, 63% |
| $^1$H NMR and HRMS | Mixture of rotamers: $^1$H NMR (600 MHz, DMSO) δ 0.55, 0.74, 0.80-0.94, 1.17-1.26, 1.29-1.41, 1.43-1.58, 2.34-2.44, 2.48-2.58, 2.59-2.66, 2.70-2.77, 3.29-3.45, 3.53, 4.09-4.19, 4.55-4.65, 5.25, 6.99, 7.08, 7.18, 7.47-7.52, 7.56-7.67. HRMS (M + H)⁺: calculated 341.204; found 341.2024 | |
| 38.5 | 4-Fluoro-N-[(2S)-1-(3-hydroxyazetidin-1-yl)-4-methylpentan-2-yl]-3-methoxy-N-methylbenzamide | 109 mg, 67% |
| $^1$H NMR and | Mixture of rotamers: $^1$H NMR (600 MHz, DMSO) δ 1.31, 1.42, 1.52, 1.56, 1.60-1.75, 1.93-2.44, 3.12-3.46, | |

-continued

| Example | Name | Yield |
|---|---|---|
| HRMS | 3.48-3.56, 3.89-4.21, 4.27-4.38, 4.48-4.64, 4.83-5.00, 5.27-5.66, 5.99-6.07, 7.45-7.65, 7.67-8.09. HRMS (M + H)⁺: calculated 339.208; found 339.2089 | |
| 38.6 | 4-Cyano-2-fluoro-N-[(2S)-1-(3-hydroxyazetidin-1-yl)-4-methylpentan-2-yl]-N-methylbenzamide | 94 mg, 58% |
| ¹H NMR and HRMS | Mixture of rotamers: ¹H NMR (600 MHz, DMSO-d6) δ 0.61, 0.75, 0.80-0.94, 1.17-1.54, 2.34-2.75, 2.79, 3.05-3.42, 3.48-3.56, 4.03-4.20, 4.53-4.62, 5.22-5.31, 7.48-7.58, 7.68-7.85, 7.93-8.05. HRMS (M + H)⁺: calculated 334.1931; found 334.1962 | |
| 38.7 | 4-Chloro-N-[(2S)-1-(3-hydroxyazetidin-1-yl)-4-methylpentan-2-yl]-2-methoxy-N-methylbenzamide | 112 mg, 65% |
| ¹H NMR and HRMS | 1H NMR (600 MHz, dmso) δ 0.52, 0.62, 0.72, 0.76, 0.80-0.93, 1.11-1.64, 2.30-2.66, 2.73, 3.33, 3.46-3.58, 3.68-3.86, 4.04-4.19, 4.42-4.85, 5.20-5.27, 6.98-7.20, 7.26. HRMS (M + H)⁺: calculated 355.1788; found 355.1809 | |
| 38.8 | N-[(2S)-1-(3-Hydroxyazetidin-1-yl)-4-methylpentan-2-yl]-N-methyl-4-(methylsulfanyl)benzamide Mixture of rotamers: 1H NMR (600 MHz, DMSO-d6) δ 0.56 (d), 0.76 (d), 0.82-0.93 (m), 1.16-1.25 (m), 1.27-1.40 (m), 1.43-1.57 (m), 2.33-2.39 (m), 2.41-2.56 (m), 2.62-2.76 (m), 3.30-3.39 (m), 3.48-3.59 (m), 4.09-4.19 (m), 4.52-4.61 (m), 5.21-5.27 (m), 7.23-7.31 (m), 7.38 (d). Some signals overlap with solvent/water. HRMS (M + H)⁺: calculated 337.1950; found 337.1962 | 105 mg, 65% |

Example 39.1

(S)-2-chloro-N-(1-cyclobutyl-2-(3-hydroxyazetidin-1-yl)ethyl)-4-fluoro-N-methylbenzamide

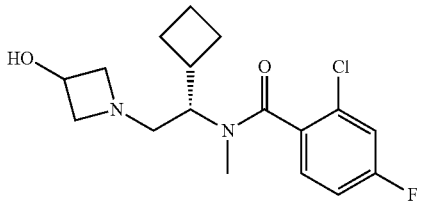 [SMILES: CN(C(=O)c1ccc(F)cc1Cl)[C@H](CN1CC(O)C1)C1CCC1]

DIPEA (0.183 mL, 1.05 mmol) was added to a stirred suspension of 2-chloro-4-fluorobenzoic acid (55 mg, 0.31 mmol) and TBTU (0.101 g, 0.31 mmol) in DCM (1 mL) at rt. The suspension was stirred for 5 min before it was cooled on an ice-bath. A solution of (S)-1-(2-cyclobutyl-2-(methylamino)ethyl)azetidin-3-ol (Compound Z2.1) (0.07 g, 0.35 mmol) in DCM (1 mL) was added over 3 min. The ice-bath was removed and the reaction was stirred at rt for 2 h. The reaction mixture was washed with NaHCO₃ (8% aq., 3 mL), filtered through a phase separator and concentrated under reduced pressure. The residue was purified by preparative HPLC to give the title compound (54 mg, 45%). Mixture of rotamers: ¹H NMR (600 MHz, DMSO-d6) δ 1.41-2.1, 2.22-2.85, 3.06-3.59, 4.02-4.23, 4.46-4.60, 5.17-5.35, 7.23-7.72. HRMS (M+H)⁺: calculated 341.1432. found 341.1442.

Example 39.2

(S)-4-Cyano-N-(1-cyclobutyl-2-(3-hydroxyazetidin-1-yl)ethyl)-N-methylbenzamide

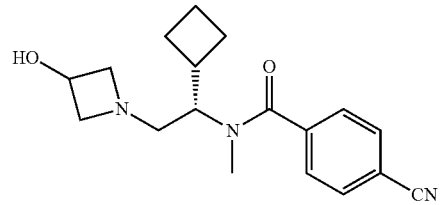 [SMILES: CN(C(=O)c1ccc(C#N)cc1)[C@H](CN1CC(O)C1)C1CCC1]

DIPEA (2.504 mL, 14.38 mmol) was added to a stirred suspension of 4-cyanobenzoic acid (0.670 g, 4.55 mmol) and TBTU (1.462 g, 4.55 mmol) in DCM (10 mL) at rt. The suspension was stirred for 5 min before it was cooled on an ice-bath. A solution of (S)-1-(2-cyclobutyl-2-(methylamino)ethyl)azetidin-3-ol (Compound Z2.1) (0.960 g, 4.79 mmol) in DCM (10 mL) was added over 5 min. The ice-bath was removed after 10 min and the reaction was stirred at rt for 3 h. The reaction mixture was diluted with DCM (20 mL), washed with NaHCO₃ (8% aq., 35 mL), filtered through a phase separator and concentrated under reduced pressure. The residue was purified by preparative HPLC. The selected fractions were concentrated and NaHCO₃ (saturated, 40 mL) was added. The water layer was extracted with DCM (3×75 mL) and the combined organic layers were filtered through a phase separator and concentrated under reduced pressure to give the title compound (0.925 g, 62%). Mixture of rotamers: ¹H NMR (400 MHz, DMSO-d6) δ 1.32-1.62, 1.65-1.97, 1.97-2.08, 2.17-2.28, 2.32-2.60, 2.62-2.74, 3.16-3.27, 3.39-3.45, 3.46-3.52, 4.07-4.18, 4.40-4.52, 5.19-5.24, 7.42-7.46, 7.57-7.62, 7.87-7.95.

HRMS (M+H)⁺: calculated 314.1868. found 314.1870

The compounds according to Examples 39.3-39.16 were prepared, from appropriate intermediates, by analogy with the method described for Example 39.1 hereinbefore.

| Example | Name | Yield |
|---|---|---|
| 39.3 | (S)-N-(1-Cyclobutyl-2-(3-hydroxyazetidin-1-yl)ethyl)-3,4-difluoro-N-methylbenzamide | 82 mg, 72% |
| ¹H NMR and HRMS | Mixture of rotamers: (600 MHz, DMSO-d6) δ 1.39-2.09, 2.16-2.78, 3.26-3.56, 4.10-4.22, 4.40-4.54, 5.20-5.42, 7.13-7.22, 7.30-7.67. HRMS (M + H)⁺: calculated 325.1728; found 325.1752 | |
| 39.4 | (S)-N-(1-Cyclobutyl-2-(3-hydroxyazetidin-1-yl)ethyl)-2,4-difluoro-N-methylbenzamide | 74 mg, 65% |
| ¹H NMR and HRMS | Mixture of rotamers: (600 MHz, DMSO-d6) δ 1.42-2.1, 2.21-2.8, 3.12-3.75, 4.07-4.22, 4.41-4.56, 5.28, 6.98-7.58. HRMS (M + H)⁺: calculated 325.1683; found 325.1680 | |
| 39.5 | (S)-N-(1-Cyclobutyl-2-(3-hydroxyazetidin-1-yl)ethyl)-2-fluoro-4-methoxy-N-methylbenzamide | 60 mg, 51% |
| ¹H NMR and HRMS | Mixture of rotamers: (600 MHz, DMSO-d6) δ 1.44-2.08, 2.22-2.77, 3.18-3.87, 4.06-4.21, 4.41-4.58, 5.28, 6.67-6.96, 7.14-7.25, 7.3-7.43. HRMS (M + H)⁺: calculated 337.1927; found 337.1944 | |
| 39.6 | (S)-N-(1-Cyclobutyl-2-(3-hydroxyazetidin-1-yl)ethyl)-3-fluoro-4-methoxy-N-methylbenzamide | 79 mg, 67% |
| ¹H NMR and | Mixture of rotamers: (600 MHz, DMSO-d6) δ 1.35-1.5, 1.54-2.06, 2.22-2.77, 3.27-3.6, 3.79- | |

-continued

| Example | Name | Yield |
|---|---|---|
| | HRMS 3.98, 4.09-4.22, 4.38-4.51, 5.24-5.36, 7.05-7.48. HRMS (M + H)+: calculated 337.1927; found 337.1939 | |
| 39.7 | (S)-N-(1-Cyclobutyl-2-(3-hydroxyazetidin-1-yl)ethyl)-N-methylbenzamide | 70 mg, 70% |
| | $^1$H NMR Mixture of rotamers: (600 MHz, DMSO-d6) δ 1.32-1.42, 1.48-1.62, 1.69-2.09, 2.22-2.81, 3.22-3.28, 3.36-3.58, 4.08-4.21, 4.45-4.57, 5.28, 7.24-7.51. HRMS (M + H)+: calculated 289.1916; found 289.1927 | |
| 39.8 | (S)-N-(1-Cyclobutyl-2-(3-hydroxyazetidin-1-yl)ethyl)-N-methyl-4-(trifluoromethyl)benzamide | 69 mg, 55% |
| | $^1$H NMR Mixture of rotamers: (600 MHz, DMSO-d6) δ 1.37-1.46, 1.49-2.08, 2.2-2.77, 3.18-3.58, 4.1-4.21, 4.45-4.57, 5.30, 7.43-7.78, 7.78-7.9. HRMS (M + H)+: calculated 357.1790; found 357.1795 | |
| 39.9 | (S)-N-(1-Cyclobutyl-2-(3-hydroxyazetidin-1-yl)ethyl)-4-methoxy-N,3-dimethylbenzamide | 63 mg, 54% |
| | $^1$H NMR Mixture of rotamers: (600 MHz, DMSO-d6) δ 1.36-1.53, 1.56-1.98, 2.01-2.78, 3.27-3.61, 3.71-3.89, 4.1-4.19, 4.43-4.55, 5.22-5.33, 6.92-7.05, 7.07-7.19, 7.25-7.37. HRMS (M + H)+: calculated 333.2178; found 333.2195 | |
| 39.10 | (S)-N-(1-Cyclobutyl-2-(3-hydroxyazetidin-1-yl)ethyl)-2-fluoro-N,5-dimethylbenzamide | 78 mg, 70% |
| | $^1$H NMR Mixture of rotamers: (600 MHz, DMSO-d6) δ 1.38-1.5, 1.54-2.09, 2.15-2.79, 3.11-3.73, 4.08-4.2, 4.46-4.79, 5.2-5.41, 7.02-7.34. HRMS (M + H)+: calculated 321.1978; found 321.1988 | |
| 39.11 | (S)-4-Chloro-3-fluoro-N-(1-(3-hydroxyazetidin-1-yl)butan-2-yl)-N-methylbenzamide | 1.30 g, 76% |
| | $^1$H NMR Mixture of rotamers: (500 MHz, CD$_3$OD) δ 0.82, 0.96, 1.43-1.67, 2.39-2.55, 2.65-3.04, 3.43-3.59, 3.67-3.81, 4.24-4.45, 4.52-4.67, 7.24-7.37, 7.38-7.51, 7.55-7.67. HRMS (M + H)+: calculated 315.1275; found 315.1284 | |
| 39.12 | (S)-4-Chloro-N-(1-(3-hydroxyazetidin-1-yl)butan-2-yl)-N-methylbenzamide | 275 mg, 83% |
| | $^1$H NMR Mixture of rotamers: (400 MHz, CD$_3$OD) δ 0.82, 0.95, 1.47-1.62 2.41-2.52, 2.62-2.99, 3.28-3.54, 3.65-3.76, 4.22-4.39, 4.53-4.64, 7.41-7.53. HRMS (M + H)+: calculated 297.1370; found 297.1369 | |
| 39.13 | (S)-N-(1-Cyclobutyl-2-(3-hydroxyazetidin-1-yl)ethyl)-4-fluoro-N-methylbenzamide | 72 mg, 67% |
| | $^1$H NMR Mixture of rotamers: (600 MHz, DMSO-d6) δ 1.34-2.08, 2.2-2.8, 3.21-3.58, 4.09-4.21, 4.42-4.55, 5.21-5.31, 7.08-7.43, 7.47-7.58. HRMS (M + H)+: calculated 307.1822; found 307.1825 | |
| 39.14 | (S)-4-Chloro-N-(1-cyclobutyl-2-(3-hydroxyazetidin-1-yl)ethyl)-N-methylbenzamide | 69 mg, 61% |
| | $^1$H NMR Mixture of rotamers: (600 MHz, DMSO-d6) δ 1.36-2.1, 2.21-2.77, 3.2-3.57, 4.1-4.2, 4.43-4.53, 5.23-5.28, 7.31-7.35, 7.45-7.58. HRMS (M + H)+: calculated 323.1526; found 323.1539 | |
| 39.15 | (S)-N-(1-Cyclobutyl-2-(3-hydroxyazetidin-1-yl)ethyl)-3-(difluoromethyl)-N-methylbenzamide | 62 mg, 52% |
| | $^1$H NMR Mixture of rotamers: (400 MHz, CD$_3$OD) 1.42-2.98, 3.47-3.84, 4.23-4.42, 4.64-4.78, 6.58-6.87, 6.93-7.04, 7.4-7.79. HRMS (M + H)+: calculated 339.1884; found 339.1900 | |
| 39.16 | (S)-N-(1-Cyclobutyl-2-(3-hydroxyazetidin-1-yl)ethyl)-4-fluoro-N,3-dimethylbenzamide | 61 mg, 55% |
| | $^1$H NMR Mixture of rotamers: (600 MHz, DMSO-d6) 1.37-1.53, 1.56-1.98, 2.01-2.08, 2.16-2.76, 3.24-3.56, 4.11-4.2, 4.41-4.55, 5.22-5.32, 7.13-7.44. HRMS (M + H)+: calculated 321.1978; found 321.1983 | |

Example 40.1

(S)-4-Chloro-N-(1-(3-hydroxyazetidin-1-yl)propan-2-yl)-N-methylbenzamide

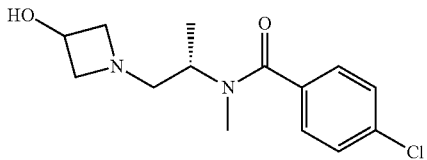 [SMILES: C[C@@H](CN1CC(O)C1)N(C)C(=O)c1ccc(Cl)cc1]

DIPEA (0.200 mL, 1.15 mmol) was added to a stirred suspension of 4-chlorobenzoic acid (0.06 g, 0.38 mmol) and TBTU (0.123 g, 0.38 mmol) in DCM (2 mL) at rt. The suspension was stirred for 5 min before it was cooled on an ice-bath. A solution of (S)-1-(2-(methylamino)propyl)azetidin-3-ol (Compound M11) (0.06 g, 0.42 mmol) in THF (1.5 mL) was added over 10 min. The ice-bath was removed and the reaction was stirred at rt over night. DCM (3 mL) was added and the mixture was washed with NaHCO$_3$ (8% aq., 3 mL), filtered through a phase separator and concentrated under reduced pressure. The residue was dissolved in MeOH (2 mL) and NaOH (aq., 2M) was added. The resulting mixture was stirred at rt for 3 h, then concentrated under reduced pressure. DCM (5 mL) and NaHCO$_3$, (aq., 8%, 5 mL) was added. The organic phase was collected and the solvents were removed under reduced pressure. The residue was purified by preparative HPLC to give the title compound (17 mg, 16%). Mixture of rotamers: $^1$H NMR (600 MHz, DMSO-d6) δ 0.99-1.12, 2.18-2.23, 2.33-2.79, 3.15-3.56, 4.03-4.18, 4.44-4.54, 5.16-5.28, 7.32-7.55. Some signals overlap with solvent. HRMS (M+H)+: calculated 283.1213. found 283.1219.

The compounds according to Examples 40.2-40.12 were prepared, from appropriate intermediates, by analogy with the method described for Example 40.1 hereinbefore.

| Example | Name | Yield |
|---|---|---|
| 40.2 | (S)-N-(1-(3-Hydroxyazetidin-1-yl)propan-2-yl)-N,3,4-trimethylbenzamide | 13 mg, 11% |
| | $^1$H NMR Mixture of rotamers: (600 MHz, DMSO-d6) δ 0.99-1.09, 2.15-2.26, 2.34-2.40, 2.46-2.77, 3.18-3.61, 4.03-4.18, 4.44-4.51, 5.19-5.30, 7.04, 7.09-7.11, 7.16. HRMS (M + H)+: calculated 277.1916; found 277.1926 | |
| 40.3 | (S)-4-Chloro-3-fluoro-N-(1-(3-hydroxyazetidin-1-yl)propan-2-yl)-N-methylbenzamide | 12 mg, 10% |
| | $^1$H NMR Mixture of rotamers: (600 MHz, DMSO-d6) δ 1.01-1.10, 2.19-2.26, 2.33-2.39, 2.46-2.80, 3.18-3.57, 4.04-4.19, 4.42-4.51, 5.22-5.30, 7.19-7.26, 7.40-7.49, 7.62-7.68. HRMS (M + H)+: calculated 301.1119; found 301.1119 | |
| 40.4 | (S)-4-Chloro-N-(1-(3-hydroxyazetidin-1-yl)propan-2-yl)-N,3-dimethylbenzamide | 7 mg, 6% |
| | $^1$H NMR Mixture of rotamers: (600 MHz, DMSO-d6) δ 1.02-1.09, 2.18-2.39, 2.45-2.78, 3.17-3.56, 4.03-4.19, 4.43-4.52, 5.19-5.31, 7.15-7.21, 7.33, 7.45. HRMS (M + H)+: calculated 297.1370; found 297.1381 | |

Example 41

(S)-4-Bromo-N-(1-(3-hydroxyazetidin-1-yl)propan-2-yl)-N-methylbenzamide

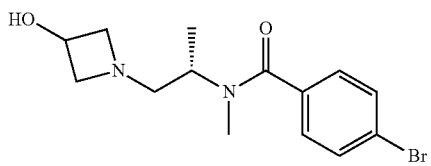 [SMILES: C[C@@H](CN1CC(O)C1)N(C)C(=O)c1ccc(Br)cc1]

DIPEA (0.217 mL, 1.25 mmol) was added to a stirred suspension of 4-bromobenzoic acid (0.075 g, 0.37 mmol) and TBTU (0.120 g, 0.37 mmol) in DCM (2 mL) at rt. The suspension was stirred for 20 min before it was cooled on an ice-bath. A solution of (S)-1-(2-(methylamino)propyl)azetidin-3-ol (Compound M11) (0.06 g, 0.42 mmol) in THF (1.5 mL) was added over 10 min. The ice-bath was removed and the reaction was stirred at rt over night. DCM (3 mL) was added and the mixture was washed with NaHCO$_3$ (8% aq., 3 mL). The aqueous layer was extracted with DCM (2×3 mL). The combined organic layers were filtered through a phase separator and concentrated under reduced pressure. The residue was purified by preparative HPLC to give the title compound (23 mg, 17%). Mixture of rotamers: $^1$H NMR (600 MHz, DMSO-d6) δ 1.01-1.11, 2.17-2.24, 2.33-2.38, 2.45-2.77, 3.15-3.56, 4.03-4.20, 4.44-4.53, 5.18-5.28, 7.27-7.34, 7.59-7.66. Some signals overlap with solvent. HRMS (M+H)$^+$: calculated 327.0708. found 327.0722.

Example 42

(S)-4-Bromo-N-(1-(3-hydroxyazetidin-1-yl)butan-2-yl)-N-methylbenzamide

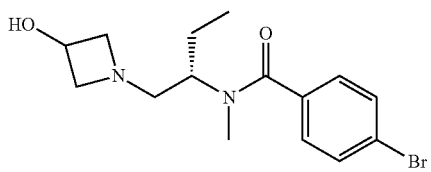 [SMILES: CC[C@@H](CN1CC(O)C1)N(C)C(=O)c1ccc(Br)cc1]

DIPEA (0.52 mL, 3.0 mmol) was added to a stirred suspension of 4-bromobenzoic acid (462 mg, 3.0 mmol) and TBTU (963 mg, 3.0 mmol) in THF (15 mL) at rt. After 10 min was (S)-1-(2-(methylamino)butyl)azetidin-3-ol (Compound M12) (475 mg, 3.0 mmol) added, followed by addition of DIPEA (0.52 mL, 3.0 mmol). The reaction was stirred at rt for 4 h. The mixture was concentrated under reduced pressure and the residue dissolved in DCM (60 mL). The organic phase was washed with NaHCO$_3$ (aq., 60 mL). The aqueous layer was extracted with DCM (15 mL). The combined organic layers were washed with NaHCO$_3$ (8% aq., 60 mL), dried (Na$_2$SO$_4$) and concentrated under reduced pressure. The residue was purified by preparative HPLC to give the title compound (577 mg, 56%). Mixture of rotamers: $^1$H NMR (500 MHz, DMSO-d6) δ 0.82, 1.43-1.54, 2.43, 2.54-2.62, 2.70-2.80, 3.39-3.51, 4.18, 4.88, 7.33, 7.63. Total number of protons: 20. There is one additional very broad proton signal between 4.2 and 3.1 ppm. HRMS (M+H)$^+$: calculated 341.0865. found 341.0870.

Example 43.1

4-Chloro-N—((S)-1-((2S,3R)-3-hydroxy-2-methylazetidin-1-yl)pentan-2-yl)-N-methylbenzamide and 4-chloro-N—((S)-1-((2R,3S)-3-hydroxy-2-methylazetidin-1-yl)pentan-2-yl)-N-methylbenzamide

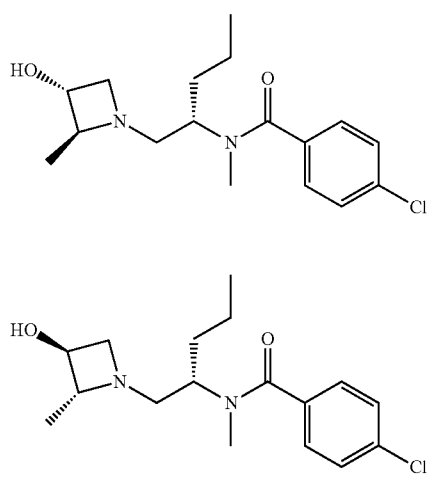

DIPEA (0.198 mL, 1.14 mmol), 4-chlorobenzoic acid (0.107 g, 0.68 mmol) and TBTU (0.292 g, 0.91 mmol) were added to a stirred solution of a 1:1 mixture of (2S,3R)-2-methyl-1-((S)-2-(methylamino)pentyl)azetidin-3-ol and (2R,3S)-2-methyl-1-((S)-2-(methylamino)pentyl)azetidin-3-ol (Compound V2.1) (0.200 g, 63% purity, 0.68 mmol) in DCM (5 mL). The resulting mixture was stirred over night. DCM (5 mL) and 8% NaHCO$_3$ (10 mL) were added, and the phases were separated on a phase separator. The organic layer was concentrated, the residue dissolved in THF (20 mL) and 1M NaOH (10 mL) was added. The resulting mixture was stirred over the weekend at rt. Phases were separated and the organic layer was concentrated. The residue was purified by preparative HPLC to yield the isomers. The diastereomers are given in order of elution:

Isomer 1: (76 mg, 35%) Mixture of rotamers: $^1$H NMR (400 MHz, CD$_3$OD) δ 0.87, 0.98, 1.05, 1.12-1.64, 2.26-2.39, 2.43, 2.63, 2.68-2.98, 3.54, 3.65-3.76, 3.80, 4.74, 7.38-7.52. Ratio major:minor:6:5. Total no of protons: 24. HRMS (M+H)$^+$: calculated 325.1683. found 325.1685.

Isomer 2: (76 mg, 35%) Mixture of rotamers: $^1$H NMR (400 MHz, CD$_3$OD) δ 0.81, 0.98, 1.02-1.65, 2.46, 2.53, 2.60-2.77, 2.79, 2.84-2.98, 3.50, 3.61-3.84, 4.68, 7.38-7.57. Ratio major:minor:1:1. Total no of protons: 24. HRMS (M+H)$^+$: calculated 325.1683. found 325.1691.

The compounds according to Examples 43.2-43.6 were prepared, from appropriate intermediates, by analogy with the method described for Example 43.1 hereinbefore. The isomers in Example 43.6 were separated by HPLC on a CelluCoat column (250×50 mm), using heptane/IPA/TEA 90:10:0.1 as mobile phase.

| Example | Name | Yield |
|---|---|---|
| 43.2 | 4-Fluoro-N-((S)-1-((2R*,3S*)-3-hydroxy-2-methylazetidin-1-yl)pentan-2-yl)-N-methylbenzamide, isomer 2 | 61 mg, 24% |
| ¹H NMR and HRMS | Mixture of rotamers: (400 MHz, CD₃OD) δ 0.80, 0.98, 1.01-1.64, 2.46, 2.52, 2.61-2.76, 2.79, 2.84-2.97, 3.49, 3.64-3.84, 4.67, 7.14-7.23, 7.46, 7.58. Ratio major:minor: 1:1. Total no of protons: 24. HRMS (M + H)⁺: 309.1978; found 309.1986 | |
| 43.3 | 3,4-Difluoro-N-((S)-1-((2R*,3S*)-3-hydroxy-2-methylazetidin-1-yl)pentan-2-yl)-N-methylbenzamide, isomer 2 | 73 mg, 33% |
| ¹H NMR and HRMS | Mixture of rotamers: (400 MHz, CD₃OD) δ 0.80, 0.98, 1.01-1.62, 2.48, 2.56, 2.63, 2.68-2.77, 2.79, 2.87, 2.88-2.98, 3.54, 3.66-3.84, 4.66, 7.22-7.29, 7.30-7.44, 7.69. Ratio major:minor: 1:1. Total no of protons: 23. HRMS (M + H)⁺: calculated 327.1884; found 327.1878 | |
| 43.4 | 4-Chloro-N-((S)-1-((2S,3S)-3-hydroxy-2-methylazetidin-1-yl)pentan-2-yl)-N-methylbenzamide and 4-chloro-N-((S)-1-((2R,3R)-3-hydroxy-2-methylazetidin-1-yl)pentan-2-yl)-N-methylbenzamide | Isomer 1: 33 mg, 13% Isomer 2: 19 mg, 7% |
| ¹H NMR and HRMS | Isomer 1: Mixture of rotamers: 400 MHz, CD₃OD) δ 0.85, 0.93-1.02, 1.09-1.62, 2.33-2.42, 2.67-2.75, 2.82, 2.87, 2.98, 3.07, 3.15-3.40 (partially obscured by solvent peak), 3.48, 4.23, 4.29, 4.67, 7.41-7.50. Ratio major:minor: 1:1. Total no of protons: 24. HRMS (M + H)⁺: calculated 325.1683; found 325.1678. Isomer 2: Mixture of rotamers: ¹H NMR (400 MHz, CD₃OD) δ 0.81, 0.97, 1.01-1.62, 2.50, 2.55-2.65, 2.70, 2.77, 2.86, 3.01, 3.10, 3.24-3.34 (partially obscured by solvent peak), 3.39, 3.61, 4.26, 4.32, 4.62, 7.40-7.49, 7.54-7.60. Ratio major:minor: 1:1. Total no of protons: 24. HRMS (M + H)⁺: calculated 325.1683; found 325.1701. | |
| 43.5 | 3,4-Difluoro-N-((S)-1-((2S,3S)-3-hydroxy-2-methylazetidin-1-yl)pentan-2-yl)-N-methylbenzamide and 3,4-Difluoro-N-((S)-1-((2R,3R)-3-hydroxy-2-methylazetidin-1-yl)pentan-2-yl)-N-methylbenzamide | Isomer 1: 76 mg, 30% Isomer 2: 64 mg, 25% |
| ¹H NMR and HRMS | Isomer 1: Mixture of rotamers: (400 MHz, CD₃OD) δ 0.85, 0.97, 1.02, 1.09-1.62, 2.31-2.43, 2.68-2.90, 3.01, 3.08, 3.17, 3.22-3.40 (partially obscured by solvent peak), 3.49, 4.25, 4.29, 4.65, 7.25-7.51. Ratio major:minor: 8:7. Total no of protons: 23. HRMS (M + H)⁺: calculated 327.1884; found 327.1885 Isomer 2: Mixture of rotamers: (400 MHz, CD₃OD) δ 0.80, 0.97, 1.00-1.61, 2.49-2.76, 2.78, 2.85, 3.04, 3.14, 3.25-3.44 (partially obscured by solvent peak), 3.65, 4.27, 4.33, 4.61, 7.23-7.48, 7.73. Ratio major:minor: 1:1. Total no of protons: 23. HRMS (M + H)⁺: calculated 327.1884; found 327.1897 | |
| 43.6 | 4-Fluoro-N-((S)-1-((2S,3S)-3-hydroxy-2-methylazetidin-1-yl)pentan-2-yl)-N-methylbenzamide and 4-fluoro-N-((S)-1-((2R,3R)-3-hydroxy-2-methylazetidin-1-yl)pentan-2-yl)-N-methylbenzamide | Isomer 1: 54 mg, 22% Isomer 2: 60 mg, 25% |
| ¹H NMR and HRMS | Isomer 1: Mixture of rotamers: (400 MHz, CD₃OD) δ 0.84, 0.94-1.02, 1.08-1.62, 2.34-2.43, 2.72, 2.74, 2.83, 2.87, 2.99, 3.07, 3.16-3.42 (partially obscured by the solvent peak), 3.51, 4.22, 4.30, 4.67, 7.15-7.23, 7.47-7.54. Ratio major:minor: 8:7. Total no of protons: 24. HRMS (M + H)⁺: calculated 309.1978; found 309.1980. Isomer 2: Mixture of rotamers: (400 MHz, CD₃OD) δ 0.80, 0.97, 1.00-1.63, 2.51, 2.58-2.67, 2.72, 2.78, 2.86, 3.01, 3.10, 3.27-3.36 (partially obscured by the solvent peak), 3.43, 3.64, 4.25, 4.33, 4.63, 7.14-7.23, 7.48, 7.62. Ratio major:minor: 8:7. Total no of protons: 24. HRMS (M + H)⁺: calculated 309.1978; found 309.1991 | |

Example 44

(S)-4-Chloro-N-(1-(4-hydroxypiperidin-1-yl)pentan-2-yl)-N-methylbenzamide

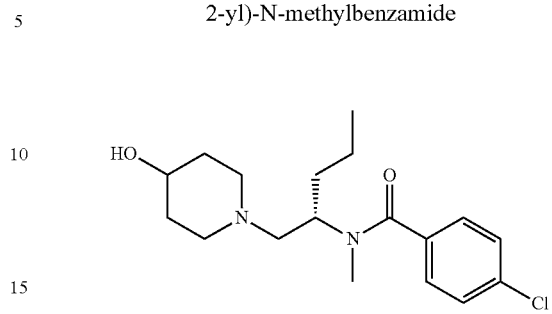

4-Chlorobenzoyl chloride (1.683 mL, 13.12 mmol) was added to a solution of (S)-1-(2-(methylamino)pentyl)piperidin-4-ol (Compound J6) (2.629 g, 13.12 mmol) and TEA (3.66 mL, 26.25 mmol) in DCM (25 mL) at 0° C. A white slurry was formed. The reaction was stirred for 45 min at 0° C. and was then allowed to attain rt. The reaction was stirred overnight and was then quenched by addition of NaHCO₃ (8% aq., 25 mL). The aqueous phase was extracted with DCM. The organic phases were pooled, dried (MgSO₄), filtered and evaporated under reduced pressure. The crude product was chromatographed to give the title product (3.13 g, 70.3%) as a colourless glue. ¹H NMR (400 MHz, CD₃OD) 0.87, 0.99, 1.17-1.33, 1.35-1.63, 1.71-1.90, 1.95-2.15, 2.15-2.36, 2.43-2.51, 2.52-2.68, 2.71-2.80, 2.89, 2.99-3.08, 3.51-3.64, 3.68-3.77, 4.87-4.97, 7.08-7.24, 7.37-7.51. HRMS (M+H)⁺: calculated 339.1839. found 339.1827.

Example 45

(S)-4-Chloro-N-(1-(4-methoxypiperidin-1-yl)pentan-2-yl)-N-methylbenzamide

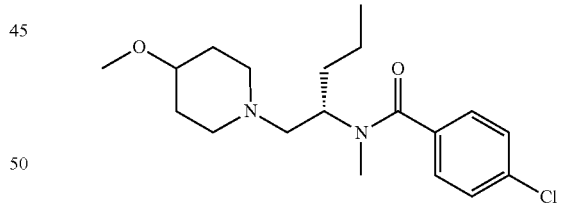

NaH (21.24 mg, 0.89 mmol) was added to a solution of (S)-4-chloro-N-(1-(4-hydroxypiperidin-1-yl)pentan-2-yl)-N-methylbenzamide (Example 44) (200 mg, 0.59 mmol) in dry THF (10 mL) at room temperature under N₂. After 5 min was MeI (0.037 mL, 0.59 mmol) added. The reaction was stirred overnight and was then quenched by addition of NH₃ saturated H₂O (2 mL). The resulting solution was evaporated and the remainder was dissolved in EtOAc and poured on an SCX-2 column (5 g). The column was washed with MeOH and the product was eluted by NH₃ saturated MeOH. The crude product was purified by preparative HPLC to yield the title product (106 mg, 51.0%). ¹H NMR (600 MHz, DMSO-d6) δ 0.78, 0.91, 1.05-1.51, 1.70-1.84, 1.91-2.03, 2.09-2.13, 2.17-2.23, 2.33-2.39, 2.41-2.54, 2.58-2.64, 2.76, 2.82, 3.12, 3.19-3.22, 3.53-3.59, 4.71-4.79, 7.31-7.35, 7.36-7.40, 7.47-7.53. HRMS (M+H)+: calculated 353.1996. found 353.2006.

Example 46.1

4-Cyano-N-((S)-1-((S)-3-hydroxypyrrolidin-1-yl)pentan-2-yl)-N-methylbenzamide

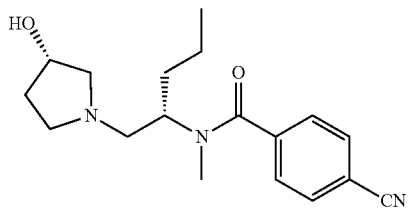 [SMILES: CCC[C@@H](CN1CC[C@H](O)C1)N(C)C(=O)c1ccc(C#N)cc1]

4-Cyanobenzoyl chloride (0.800 g, 4.83 mmol) was added to a solution of (S)-1-((S)-2-(methylamino)pentyl)pyrrolidin-3-ol (Compound J7) (1 g, 5.37 mmol) and TEA (1.496 mL, 10.74 mmol) in DCM (25 mL) at 0° C. The reaction was stirred for 30 min and was then allowed to attain rt. After 1.5 h the reaction was quenched with $K_2CO_3$ (1 M aq., 25 mL) and the aqueous phase was extracted with DCM. The organic phases were pooled, dried ($MgSO_4$), filtered and evaporated. The residue was dissolved in EtOAc and poured on an SCX-2 column (10 g). The column was washed with EtOAc and MeOH, The product was eluted with $NH_3$ saturated MeOH. The crude product (1.200 g, 70.9%) was obtained as a yellow oil. A fraction of the crude material was purified by preparative HPLC to yield 31 mg of the title product with a purity of 99.5%. $^1$H NMR (400 MHz, $CD_3OD$) δ 0.85-1.09, 1.14-1.75, 2.03-2.23, 2.29-2.61, 2.66-2.76, 2.82-3.00, 4.24-4.39, 5.49, 7.57-7.65, 7.80-7.85. HRMS (M+H)+: calculated 316.2025. found 316.2038.

The compounds according to Example 46.2 was prepared, from appropriate intermediates, by analogy with the method described for Example 46.1 hereinbefore.

| Example | Name | Yield |
|---|---|---|
| 46.2 | 4-Chloro-N-((S)-1-((S)-3-hydroxypyrrolidin-1-yl)pentan-2-yl)-N-methylbenzamide | 1.24 g, 71% crude yield |
| $^1$H NMR and HRMS | $^1$H NMR (400 MHz, $CD_3OD$) δ 0.87, 0.99, 1.14-1.75, 2.02-2.20, 2.29-2.39, 2.42-2.60, 2.64-2.71, 2.76, 2.82-2.98, 3.66-3.75, 4.23-4.38, 7.38-7.50. HRMS (M + H)+: calculated 325.1683; found 325.1653 | |

Example 47

Additional Compounds

The following compounds were prepared in similar manners as described for the preparation of the compounds above.

| Name | HRMS (M + H)+ |
|---|---|
| (S)-3-Cyano-N-methyl-N-(3-methyl-1-(pyrrolidin-1-yl)butan-2-yl)benzamide | Calc. 375.2059, found 375.2063 |
| 2-Fluoro-N-methyl-N-[(1S)-2-methyl-1-(pyrrolidin-1-ylmethyl)propyl]-5-(trifluoromethyl)benzamide | Calc. 300.2076, found 300.2081 |
| (S)-4-Fluoro-N-methyl-N-(3-methyl-1-(piperidin-1-yl)butan-2-yl)-2-(trifluoromethyl)benzamide | Calc. 375.2059, found 375.2063 |
| 2-Fluoro-N-methyl-N-[(1S)-2-methyl-1-(pyrrolidin-1-ylmethyl)propyl]-5-(trifluoromethyl)benzamide | Calc. 375.2059, found 375.2059 |
| (S)-N-Methyl-N-(3-methyl-1-(piperidin-1-yl)butan-2-yl)-3-(trifluoromethoxy)benzamide | Calc. 373.2103, found 373.2115 |
| (S)-4-Fluoro-N,3-dimethyl-N-(3-methyl-1-(piperidin-1-yl)butan-2-yl)benzamide | Calc. 321.2342, found 321.234 |
| (S)-4-(Difluoromethoxy)-N-methyl-N-(3-methyl-1-(pyrrolidin-1-yl)butan-2-yl)benzamide | Calc. 341.204, found 341.2032 |
| (S)-4-Cyano-N-(1-(4-methoxypiperidin-1-yl)-3-methylbutan-2-yl)-N-methylbenzamide | Calc. 344.2338, found 344.2331 |
| (S)-3,4-Difluoro-N-(1-(4-methoxypiperidin-1-yl)-3-methylbutan-2-yl)-N-methylbenzamide | Calc. 355.2197, found 355.2201 |
| (S)-N-(3,3-Dimethyl-1-(pyrrolidin-1-yl)butan-2-yl)-4-fluoro-N,3-dimethylbenzamide | Calc. 321.2342, found 321.2333 |
| (S)-4-Chloro-N-(3,3-dimethyl-1-(pyrrolidin-1-yl)butan-2-yl)-N-methylbenzamide | Calc. 323.189, found 323.1898 |
| (S)-N-(1-(Azetidin-1-yl)pentan-2-yl)-4-fluoro-N,2-dimethylbenzamide | Calc. 293.2029, found 293.2023 |
| (R)-3-Bromo-N-methyl-N-(3-methyl-1-(pyrrolidin-1-yl)butan-2-yl)benzamide | Calc. 353.1228, found 353.1222 |
| (R)-N-Methyl-N-(3-methyl-1-(pyrrolidin-1-yl)butan-2-yl)-4-(trifluoromethoxy)benzamide | Calc. 359.1946, found 359.1945 |
| (S)-3-Bromo-N-methyl-N-(3-methyl-1-(pyrrolidin-1-yl)butan-2-yl)benzamide | Calc. 353.1228, found 353.1226 |
| N,2-Dimethyl-N-[(1S)-2-methyl-1-(pyrrolidin-1-ylmethyl)propyl]benzamide | Calc. 289.228, found 289.2278 |
| (S)-N-(1-(4,4-difluoropiperidin-1-yl)-3-methylbutan-2-yl)-N,3,4-trimethylbenzamide | Calc. 353.2404, found 353.2385 |
| (S)-4-Chloro-N-(1-(4,4-difluoropiperidin-1-yl)-3-methylbutan-2-yl)-N-methylbenzamide | Calc. 359.1702, found 359.1696 |
| (S)-4-Bromo-N-(1-(4,4-difluoropiperidin-1-yl)-3-methylbutan-2-yl)-N-methylbenzamide | Calc. 403.1196, found 403.1196 |
| (R)-3-Chloro-4-fluoro-N-methyl-N-(4-methyl-1-(pyrrolidin-1-yl)pentan-3-yl)benzamide | Calc. 341.1796, found 341.1797 |
| (R)-N,3,4-Trimethyl-N-(4-methyl-1-(pyrrolidin-1-yl)pentan-3-yl)benzamide | Calc. 317.2593, found 317.2598 |
| (R)-4-Chloro-N,2-dimethyl-N-(4-methyl-1-(pyrrolidin-1-yl)pentan-3-yl)benzamide | Calc. 337.2047, found 337.2036 |
| (R)-3,4-Difluoro-N-methyl-N-(4-methyl-1-(pyrrolidin-1-yl)pentan-3-yl)benzamide | Calc. 325.2091, found 325.2099 |
| (R)-2-Chloro-4-fluoro-N-methyl-N-(4-methyl-1-(pyrrolidin-1-yl)pentan-3-yl)benzamide | Calc. 341.1796, found 341.1819 |
| (R)-4-Bromo-N-methyl-N-(4-methyl-1-(pyrrolidin-1-yl)pentan-3-yl)benzamide | Calc. 367.1385, found 367.139 |
| (S)-4-Cyano-N-(1-cyclopropyl-2-(pyrrolidin-1-yl)ethyl)-N-methylbenzamide | |
| (S)-N-(1-Cyclopropyl-2-(pyrrolidin-1-yl)ethyl)-4-fluoro-N-methylbenzamide | Calc. 291.1873, found 291.1862 |
| (S)-4-Cyano-N-(1-(3,3-difluoropiperidin-1-yl)-3-methylbutan-2-yl)-N-methylbenzamide | Calc. 350.2044, found 350.2049 |
| (S)-N-(1-(3,3-Difluoropiperidin-1-yl)-3-methylbutan-2-yl)-N,3-dimethylbenzamide | Calc. 339.2248, found 339.2238 |
| (S)-N-(1-(3,3-Difluoropiperidin-1-yl)-3-methylbutan-2-yl)-4-fluoro-N,3-dimethylbenzamide | Calc. 357.2154, found 357.2145 |
| (S)-4-Chloro-N-(1-(3,3-difluoropiperidin-1-yl)-3-methylbutan-2-yl)-N-methylbenzamide | Calc. 359.1702, found 359.1702 |
| (S)-3,4-Difluoro-N-(1-(3-fluoroazetidin-1-yl)-3-methylbutan-2-yl)-N-methylbenzamide | Calc. 315.1684, found 315.1683 |
| (S)-N-(1-(3-Fluoroazetidin-1-yl)-3-methylbutan-2-yl)-N,3,4-trimethylbenzamide | Calc. 307.2186, found 307.2157 |
| (S)-N-(1-(3-Fluoroazetidin-1-yl)-3-methylbutan-2-yl)-3-methoxy-N,4-dimethylbenzamide | Calc. 323.2135, found 323.2136 |
| (R)-2,4-Dichloro-N-methyl-N-(4-methyl-1-(pyrrolidin-1-yl)pentan-3-yl)benzamide | Calc. 357.15, found 357.1511 |
| (R)-N,3-Dimethyl-N-(4-methyl-1-(pyrrolidin-1-yl)pentan-3-yl)benzamide | Calc. 303.2436, found 303.2443 |
| (R)-4-Chloro-N-methyl-N-(4-methyl-1-(pyrrolidin-1-yl)pentan-3-yl)benzamide | Calc. 323.189, found 323.1874 |
| (S)-4-Fluoro-N,3-dimethyl-N-(1-(pyrrolidin-1-yl)butan-2-yl)benzamide | Calc. 293.2029, found 293.2036 |
| (S)-N-(1-(Azetidin-1-yl)-3-methylbutan-2-yl)-4-bromo-N-ethylbenzamide | Calc. 353.1228, found 353.1202 |
| (S)-4-Fluoro-N-(2-methoxyethyl)-3-methyl-N-(3-methyl-1-(pyrrolidin-1-yl)butan-2-yl)benzamide | Calc. 351.2448, found 351.2429 |

-continued

| Name | HRMS (M + H)+ |
|---|---|
| (R)-4-Fluoro-N-(1-(3-hydroxyazetidin-1-yl)-3-methylbutan-2-yl)-N,3-dimethylbenzamide | Calc. 309.1978, found 309.1976 |
| (S)-N-(1-(3-Hydroxy-3-methylazetidin-1-yl)-3-methylbutan-2-yl)-N,3-dimethylbenzamide | Calc. 305.2229, found 305.2238 |
| (S)-3-Chloro-4-fluoro-N-(1-(3-hydroxy-3-methylazetidin-1-yl)-3-methylbutan-2-yl)-N-methylbenzamide | Calc. 343.1588, found 343.1606 |
| (S)-4-Fluoro-N-(1-(3-hydroxy-3-methylazetidin-1-yl)-3-methylbutan-2-yl)-N,3-dimethylbenzamide | Calc. 323.2135, found 323.2114 |
| (S)-N-(2-(Azetidin-1-yl)-1-cyclopropylethyl)-3-chloro-4-fluoro-N-methylbenzamide | Calc. 311.1326, found 311.1316 |
| N-((S)-1-((S)-2-(Methoxymethyl)pyrrolidin-1-yl)-3-methylbutan-2-yl)-N,4-dimethylbenzamide | Calc. 333.2542, found 333.2542 |
| (S)-4-Chloro-N-isopropyl-N-(3-methyl-1-(pyrrolidin-1-yl)butan-2-yl)benzamide | Calc. 337.2047, found 337.2032 |
| (S)-N-(1-(Azetidin-1-yl)-3-methylbutan-2-yl)-4-fluoro-N,2-dimethylbenzamide | Calc. 293.2029, found 293.203 |
| (S)-N-(1-(Azetidin-1-yl)-3-methylbutan-2-yl)-4-cyano-2-fluoro-N-methylbenzamide | Calc. 304.1825, found 304.1819 |
| (S)-N-(1-(Azetidin-1-yl)-3-methylbutan-2-yl)-3-methoxy-N-methylbenzamide | Calc. 291.2072, found 291.2072 |
| (S)-N-(1-(Azetidin-1-yl)-3-methylbutan-2-yl)-3,4-difluoro-N-methylbenzamide | Calc. 297.1778, found 297.1787 |
| (S)-N-(1-(Azetidin-1-yl)-3-methylbutan-2-yl)-3-chloro-5-fluoro-N-methylbenzamide | Calc. 313.1483, found 313.147 |
| 3-fluoro-N-methyl-N-[(1S)-2-methyl-1-(pyrrolidin-1-ylmethyl)propyl]benzamide | Calc. 293.2029, found 293.2033 |
| 4-Chloro-N-{(1S)-1-[(2,5-dimethylpyrrolidin-1-yl)methyl]-2-methylpropyl}-N-methylbenzamide | Calc. 337.2047, found 337.2052 |
| 5-Fluoro-N,2-dimethyl-N-[(1S)-2-methyl-1-(pyrrolidin-1-ylmethyl)propyl]benzamide | Calc. 307.2186, found 307.2178 |
| (S)-4-Chloro-N-methyl-N-(1-(pyrrolidin-1-yl)butan-2-yl)benzamide | |
| N-[(2S)-1-(3-Hydroxyazetidin-1-yl)pentan-2-yl]-N-(propan-2-yl)benzamide | Calc. 305.2229; found 305.2239 |
| 4-Cyano-N-[(2S)-1-(3-hydroxyazetidin-1-yl)pentan-2-yl]-N-(propan-2-yl)benzamide | Calc. 330.2181; found 330.2195 |
| 4-Cyano-N-[(1S)-1-cyclobutyl-2-(3-hydroxyazetidin-1-yl)ethyl]-2-fluoro-N-methylbenzamide | Calc. 332.1774; found 332.178 |
| 4-Chloro-N-((S)-1-((3R,4R)-3,4-dihydroxypyrrolidin-1-yl)-3-methylbutan-2-yl)-3-fluoro-N-methylbenzamide | Calc. 359.1537; found 359.1555 |
| 4-Fluoro-N-((S)-1-((2S*,3R*)-3-hydroxy-2-methylazetidin-1-yl)pentan-2-yl)-N-methylbenzamide | Calc. 309.1978; found 309.1982 |
| 3,4-Difluoro-N-((2R,3R)-1-(3-hydroxyazetidin-1-yl)-3-methoxybutan-2-yl)-N-methylbenzamide | Calc. 329.1677; found 329.1675 |
| (S)-N-(1-(3-Hydroxyazetidin-1-yl)-4-methylpentan-2-yl)-2-methoxy-N,5-dimethylbenzamide | Calc. 335.2335; found 335.2319 |
| 3,4-Difluoro-N-((S)-1-((R)-2-(hydroxymethyl)azetidin-1-yl)-3-methylbutan-2-yl)-N-methylbenzamide | Calc. 327.1884; found 327.1888 |

Pharmacological Activity, In Vitro

Human KCNJ3 encoding Kir3.1 (Genbank acc. No. NM_002239) was inserted between EcoRI and NotI in the pIRESneo3 vector (Clontech Laboratories, Inc. CA, USA). Human KCNJ5 encoding Kir3.4 (Genbank Acc. No. BC069482) was inserted between EcoR1 and Not1 in the pIRESpuro3 vector (Clontech Laboratories, Inc. CA, USA). A Kozak sequence (GCCACC) was introduced before the start codon ATG of both constructs. Chinese Hamster Ovary K1, CHO-FLP/IN, cells (Invitrogen Corporation, Paisley, UK) were transfected simultaneously using Lipofectamine 2000 reagent (Invitrogen Corporation, Paisley, UK). Geneticin 600 µg/mL (Invitrogen Corporation, Paisley, UK) and puromycin 3 µg/mL (BD Bioscience) were added to the cell culture medium 3 days after transfection. Two weeks after transfection, colonies had appeared and were manually picked and sorted to one cell per well in a 96-well plate. Cells were then tested for Kir3.1 and Kir3.4 expression using membrane potential assay, Western Blot and Immunocytochemistry. The resulting clone was transfected with human CHRM2 construct encoding Muscarinic 2 receptor (Genbank acc. No. NM_001006630) using the FLP/IN technology (Invitrogen Corporation, Paisley, UK) and resulted in a stable CHO-FLP/IN-hKCNJ3/KCNJ5/CHRM2 cell line. The cell line was resorted by flow cytometry and resulting clones were assayed electrophysiologically using IonWorks (Molecular Devices) and later validated on the Q-Patch (Sophion A/S).

The stable cell line was cultured in DMEM/F12 with Glutamax 1 (Invitrogen Corporation, Paisley, UK), supplemented with foetal bovine serum 10%, puromycin 3 µg/mL, hygromycin 300 µg/mL and geneticin 600 µg/mL (Invitrogen Corporation, Paisley, UK). Care was taken not to seed cells at too low density and cells were passaged at approximately 70-80% confluency. Cells used for patch-clamp experiments were prepared by washing using PBS (—Mg, —$Ca^{2+}$), 2 times, detached using Accutase (Sigma). For Q-Patch measurements, storage medium was prepared fresh by adding 1.25 mL of 1M Hepes (GibcoBRL) to 50 mL CHO-SFM II medium (GibcoBRL) and detached cells were diluted to 2 million cells/mL in this medium. Frozen (Cryopreserved) cells were used for Atomic Absorption Screening (AAS) and plated poly-D-lysine 384-well plates (Greiner) at a density of 11,000-13,000 cells/well, the day before assay.

The blocking effects of compounds on the human cardiac ion channel proteins hKir3.1/Kir3.4 were assessed in CHO-K1 cells stably expressing the channel proteins using Atomic Absorption Screening (AAS). Cells were washed and then loaded with 25 µL Rb-loading buffer for three hours at 37° C. After that, the cells were washed again and 25 µL of diluted compound was transferred to the cell plate, incubated for 5 min in RT, and then 250 µL of Carbachol/high K+ (10 µM carbachol and 20 mM KCl final concentration) buffer added to stimulate the cells and open the Kir3.1/Kir3.4 channel. After 10 min stimulation, 600 µL of the supernatant was transferred to a new microplate, 45 µL washing buffer added to the supernatant and the level of Rb in the supernatant was then measured using an Aurora ICR 8000. Compounds were studied at concentrations ranging from 0.003 to 67 µmol/L (dilutions by three, 10-pt CR) or from 0.037 to 27 µmol/L (dilutions by three, 7-pt CR).

Currents were recorded at room temperature (RT, 22° C.) by using the whole-cell configuration of the patch-clamp technique and Q-Patch (Sophion). The inward currents of hKir3.1/Kir3.4, in transfected cells together with human muscarinic receptor 2 (hM2), were activated by the addition of 10 µM carbachol and by increasing the extracellular potassium concentration to 50 mM. The hKir3.1/Kir3.4 currents were clamped at −90 mV, incubated with compound for 90-120 s and stimulated by carbachol/high $K^+$ and the current level was measured at the end of the sweep. Compounds were studied at concentrations ranging from 0.12 to 30 µmol/L (dilutions by three, 6-pt CR).

Stock solutions of compounds were prepared in DMSO 10 mM and stored at RT. Buffers used for AAS contained (in mM): HEPES 20, NaCl 150, $MgCl_2$ 1.0, $CaCl_2$ 2.0 and $NaH_2PO_4$ 0.8 and Glucose 10 (wash 1) or KCl 5 and Glucose 5 (wash 2) or KCl 5 (dilution buffer). The High $K^+$ channel opener buffer contained (in mM): HEPES 20, NaCl 130, $MgCl_2$ 1.0, $CaCl_2$ 2.0 and $NaH_2PO_4$ 0.8 together with KCl 20. Solutions used for Q-Patch (extracellular) in mM: NaCl 145, KCl 4, $CaCl_2$ 2.0, $MgCl_2$ 1.0, HEPES 10 and glucose 10. The high $K^+$ extra cellular solution used for Q-Patch in mM: NaCl 96.7, KCl 50.7, $CaCl_2$ 2.0, $MgCl_2$ 1.0, HEPES 10 and glucose 10 while the intra cellular solution used was (in mM): KCl 120, $CaCl_2$ 5.374, $MgCl_2$ 1.75, EGTA 10, KOH 3.125, HEPES 10, $Na_2ATP$ 4.

Results are given as mean $IC_{50}$ of >4 replicates (10-pt CR, AAS) or >3 replicates (7-pt CR, AAS). Some of the data in Table 1 are mean values of two or more runs. Data was analyzed using H-base calculation method "EC50 main method" (sample based) for AAS experiments.

The title compounds of the Examples 1.1-46.2 were tested in the biological test described above, and these compounds were found to exhibit an $IC_{50}$ of <20 μM.

TABLE 1

| Example | IKACh $IC_{50}$ 10-pt CR, AAS [μM] | IKACh $IC_{50}$ 7-pt CR, AAS [μM] |
|---|---|---|
| 1.1 | 2.3 | |
| 1.2 | 3.6 | |
| 1.3 | 3.1 | |
| 1.4 | 3.7 | |
| 1.5 | 12 | |
| 1.6 | 6.7 | |
| 1.7 | 5.0 | |
| 1.8 | 11 | |
| 1.9 | 3.6 | |
| 1.10 | 6.9 | |
| 1.11 | 1.2 | |
| 1.12 | 2.9 | |
| 1.13 | 12 | |
| 1.14 | 6.6 | |
| 1.15 | 2.3 | |
| 1.16 | 17 | |
| 1.17 | 4.2 | 2.8 |
| 2.1 | 11 | |
| 2.2 | 14 | |
| 2.3 | 1.6 | |
| 2.4 | 1.8 | |
| 2.5 | 2.7 | |
| 2.6 | 2.0 | |
| 3.1 | 7.4 | |
| 3.2 | 20 | |
| 3.3 | 7.2 | |
| 3.4 | 2.2 | |
| 3.5 | 7.2 | |
| 3.6 | 3.2 | |
| 3.7 | 1.3 | |
| 3.8 | 4.8 | |
| 3.9 | 3 | |
| 3.10 | 14 | |
| 3.11 | 7.2 | |
| 3.12 | 2.5 | |
| 3.13 | 3.6 | |
| 3.14 | 5.7 | |
| 3.15 | 3.8 | |
| 3.16 | 13 | |
| 3.17 | 9.3 | |
| 3.18 | 1.9 | |
| 3.19 | 6.0 | |
| 3.20 | 8.4 | |
| 4.1 | 5.9 | |
| 4.2 | 2.8 | |
| 4.3 | 6.8 | |
| 4.4 | 0.59 | |
| 5.1 | 6 | |
| 5.2 | 1.8 | |
| 6.1 | 1.5 | |
| 6.2 | 2.6 | |
| 6.3 | 2.5 | |
| 7.1 | 1.3 | |
| 7.2 | 1.8 | |
| 7.3 | 1.9 | |
| 7.4 | 9.8 | |
| 7.5 | 1.8 | |
| 8.1 | 1.7 | |
| 8.2 | 0.88 | |
| 8.3 | 0.8 | |
| 8.4 | 0.2 | |
| 8.5 | 0.58 | |
| 8.6 | 8.5 | |
| 8.7 | 1.7 | |
| 8.8 | 2.4 | |
| 8.9 | 8.6 | |
| 8.10 | 4.3 | |
| 8.11 | 0.84 | |
| 8.12 | 4.3 | |
| 8.13 | 1.9 | |
| 8.14 | 5.8 | |
| 8.15 | 4.5 | |
| 8.16 | 16 | |
| 8.17 | 2.0 | |
| 9.1 | 2.6 | |
| 9.2 | 1.2 | |
| 9.3 | 3.1 | |
| 9.4 | 14 | |
| 9.5 | 1.3 | |
| 9.6 | 2.8 | |
| 9.7 | 8.6 | |
| 9.8 | 5.3 | |
| 9.9 | 11 | |
| 9.10 | 2.1 | |
| 9.11 | 12 | |
| 10.1 | 6.1 | 3.7 |
| 10.2 | 5.1 | 2.0 |
| 11 | 5.6 | |
| 12.1 | 15 | 1.4 |
| 12.2 | 16 | 5.8 |
| 13.1 | 2.5 | |
| 13.2 | 3.9 | |
| 13.3 | 19 | |
| 13.4 | 19 | |
| 14 | 16 | |
| 15.1 | 11 | |
| 15.2 | 18 | |
| 15.3 | 7.4 | |
| 15.4 | 5.7 | |
| 15.5 | 2.3 | |
| 16.1 | 17 | |
| 16.2 | 15 | |
| 16.3 | 11 | |
| 16.4 | 18 | |
| 16.5 | 11 | |
| 16.6 | 20 | |
| 16.7 | 14 | |
| 16.8 | | 8.0 |
| 16.9 | 14 | 3.9 |
| 16.10 | | 2.6 |
| 16.11 | | 11 |
| 16.12 | 15 | 23 |
| 16.13 | 14 | 5.3 |
| 16.14 | | 6.7 |
| 16.15 | | 2.5 |
| 16.16 | | 2.6 |
| 16.17 | | 1.2 |
| 16.18 | | 11 |
| 16.19 | | 14 |
| 16.20 | | 14 |
| 16.21 | | 12 |
| 16.22 | | 18 |
| 16.23 | | 6.7 |
| 16.24 | 9.8 | >27 |
| 16.25 | | 2.8 |
| 16.26 | | 4.8 |
| 16.27 | | 4.0 |
| 16.28 | | 0.84 |
| 16.29 | 9.3 | 8.8 |
| 16.30 | | 1.7 |
| 16.31 | | 2.4 |
| 16.32 | | 4.0 |
| 16.33 | | 6.7 |
| 16.34 | | 4.3 |
| 16.35 | | 12 |
| 16.36 | | 11 |
| 16.37 | 15 | 14 |
| 16.38 | | 17 |
| 16.39 | | 3.9 |

TABLE 1-continued

| Example | IKACh IC$_{50}$ 10-pt CR, AAS [μM] | IKACh IC$_{50}$ 7-pt CR, AAS [μM] |
|---|---|---|
| 16.40 | | 3.2 |
| 16.41 | | 6.8 |
| 16.42 | | 3.9 |
| 16.43 | | 5.5 |
| 16.44 | | 8.4 |
| 16.45 | | 16 |
| 16.46 | | 19 |
| 16.47 | | 0.56 |
| 16.48 | | 4.2 |
| 16.49 | 9.7 | 7.1 |
| 16.50 | | 0.42 |
| 16.51 | | 0.46 |
| 16.52 | | 3.2 |
| 16.53 | | 0.9 |
| 16.54 | 9.1 | 6.0 |
| 16.55 | 1.9 | 1.4 |
| 16.56 | | 3.6 |
| 16.57 | 8.8 | 11 |
| 16.58 | | 5.8 |
| 16.59 | | 18 |
| 16.60 | | 16 |
| 17.1 | 12 | |
| 17.2 | 1.4 | |
| 17.3 | 11 | |
| 17.4 | 17 | |
| 17.5 | 2.7 | |
| 17.6 | 12 | |
| 17.7 | 3.6 | |
| 18 | 6.8 | 1.2 |
| 19 | 4.6 | 0.82 |
| 20 | 11 | |
| 21 | 19 | |
| 22 | 19 | |
| 23 | 0.44 | |
| 24 | 4.0 | |
| 25 | 17 | |
| 26 | 7.0 | |
| 27 | 1.1 | |
| 28 | 19 | |
| 29.1 | 9.3 | |
| 29.2 | 0.16 | |
| 29.3 | 0.22 | |
| 29.4 | 12 | |
| 29.5 | 12 | |
| 29.6 | 1.6 | |
| 29.7 | 3.5 | |
| 29.8 | 11 | |
| 29.9 | 16 | |
| 30 | 6.3 | |
| 31.1 | 0.43 | |
| 31.2 | 5.9 | |
| 31.3 | 1.7 | |
| 31.4 | 0.33 | |
| 32.1, isomer 1 and 2 | 0.26; 2.3 | |
| 32.2, isomer 1 and 2 | 0.58; 15 | |
| 32.3, isomer 1 and 2 | 0.055; 0.30 | |
| 32.4, isomer 1 and 2 | 0.034; 0.98 | |
| 32.5, isomer 1 and 2 | 0.34; 7.5 | |
| 32.6, isomer 1 and 2 | 1.1; 2.3 | |
| 32.7, isomer 1 and 2 | 0.075; 0.16 | |
| 33.1 | 0.12 | |
| 33.2 | 0.32 | |
| 33.3 | 0.84 | |
| 33.4 | 1.1 | |
| 33.5 | 1.0 | |
| 33.6 | 11 | |
| 33.7 | 0.55 | |
| 33.8 | 0.16 | |
| 33.9 | 4.3 | |
| 33.10 | 1.1 | |
| 34.1 | 3.3 | |
| 34.2 | 11 | |
| 35.1 | 3.4 | |
| 35.2 | 14 | |
| 35.3 | 8.7 | |
| 35.4 | 0.66 | |
| 35.5 | 11 | |
| 35.6 | 4.6 | |
| 35.7 | 3.9 | |
| 35.8 | 8.0 | |
| 35.9 | 4.6 | |
| 35.10 | 15 | |
| 35.11 | 4.8 | |
| 35.12 | 16 | |
| 35.13 | 11 | |
| 35.14 | 13 | |
| 36.1 | 0.41 | |
| 36.2 | 0.049 | |
| 36.3 | 0.92 | |
| 36.4 | 0.33 | |
| 36.5 | 1.9 | |
| 36.6 | 1.9 | |
| 36.7 | 1.4 | |
| 36.8 | 1.1 | |
| 37 | 9.7 | |
| 38.1 | 1.3 | |
| 38.2 | 0.11 | |
| 38.3 | 2.1 | |
| 38.4 | 0.77 | |
| 38.5 | 4.2 | |
| 38.6 | 3.4 | |
| 38.7 | 0.47 | |
| 38.8 | 0.83 | |
| 39.1 | 1.1 | |
| 39.2 | 0.49 | |
| 39.3 | 0.41 | |
| 39.4 | 7.8 | |
| 39.5 | 1.1 | |
| 39.6 | 0.48 | |
| 39.7 | 1.4 | |
| 39.8 | 0.23 | |
| 39.9 | 0.34 | |
| 39.10 | 0.81 | |
| 39.11 | 1.6 | |
| 39.12 | 3.9 | |
| 39.13 | 0.16 | |
| 39.14 | 0.072 | |
| 39.15 | 0.25 | |
| 39.16 | 0.078 | |
| 40.1 | 9.7 | |
| 40.2 | 8.5 | |
| 40.3 | 9.4 | |
| 40.4 | 6.1 | |
| 41 | 7.3 | |
| 42 | 4.0 | |
| 43.1, isomer 1 and 2 | 1.3; 3.0 | |
| 43.2 | 9.1 | |
| 43.3 | 2.7 | |
| 43.4, isomer 1 and 2 | 1.7; 0.72 | |
| 43.5, isomer 1 and 2 | 8.4; 2.7 | |
| 43.6, isomer 1 and 2 | 9.5; 9.0 | |
| 44 | 0.81 | |
| 45 | 0.68 | |
| 46.1 | 8.0 | |
| 46.2 | 5.5 | |

It has been shown that compounds according to the invention possess promising potency as IKACh blockers and the compounds are thus believed to be useful for treatment of cardiac arrhythmias.

It may be noted that the following compounds were found to have an $IC_{50}$ of >67 μM in the above described 10-pt CR assay or $IC_{50}$>27 μM in the above described 7-pt CR assay:

3-Chloro-N-methyl-N-(1-methyl-2-pyrrolidin-1-ylethyl)benzamide
(S)-N-(1-(3,3-Difluoropiperidin-1-yl)-3-methylbutan-2-yl)-3,4-difluoro-N-methylbenzamide
(S)-4-Cyano-2-fluoro-N-(1-(3-fluoroazetidin-1-yl)-3-methylbutan-2-yl)-N-methylbenzamide
(S)-N-(1-(3-Fluoroazetidin-1-yl)-3-methylbutan-2-yl)-3-methoxy-N-methylbenzamide
(S)-N-(1-(4,4-Difluoropiperidin-1-yl)-3-methylbutan-2-yl)-4-fluoro-N,3-dimethylbenzamide
(S)-N-(1-(3,3-Difluoropyrrolidin-1-yl)-3-methylbutan-2-yl)-4-fluoro-N,3-dimethylbenzamide
(S)-4-Bromo-N-(1-(3,3-difluoropyrrolidin-1-yl)-3-methylbutan-2-yl)-N-methylbenzamide
(R)-N-(1-(Azetidin-1-yl)-3-methylbutan-2-yl)-4-bromo-N-methylbenzamide
4-Chloro-2-fluoro-N-methyl-N-[(1R)-2-methyl-1-(2-pyrrolidin-1-ylethyl)propyl]benzamide
N-Methyl-N-[(1R)-2-methyl-1-(2-pyrrolidin-1-ylethyl)propyl]benzamide
2-Chloro-N-methyl-N-[(1R)-2-methyl-1-(2-pyrrolidin-1-ylethyl)propyl]benzamide
(S)-N-(3,3-Dimethyl-1-(pyrrolidin-1-yl)butan-2-yl)-4-fluoro-N,2-dimethylbenzamide
(S)-N-(1-(3-Hydroxy-3-methylazetidin-1-yl)-3-methylbutan-2-yl)-N-methylbenzamide
(S)-3,4-Difluoro-N-(1-(3-hydroxy-3-methylazetidin-1-yl)-3-methylbutan-2-yl)-N-methylbenzamide
(S)-4-Fluoro-N-(1-(3-hydroxy-3-methylazetidin-1-yl)-3-methylbutan-2-yl)-N-methylbenzamide
N-Methyl-N-[(1S)-2-methyl-1-(pyrrolidin-1-ylmethyl)propyl]benzamide
(S)-4-Chloro-N-(1-(3,3-difluoropyrrolidin-1-yl)-3-methylbutan-2-yl)-N-methylbenzamide
3-Chloro-4-fluoro-N-methyl-N-[(1R)-2-methyl-1-(pyrrolidin-1-ylmethyl)propyl]benzamide
N-Methyl-N-[(1R)-2-methyl-1-(pyrrolidin-1-ylmethyl)propyl]-2-(trifluoromethoxy)benzamide
3-Cyano-N-methyl-N-[(1R)-2-methyl-1-(pyrrolidin-1-ylmethyl)propyl]benzamide
2,3,5-Trifluoro-N-methyl-N-[(1S)-2-methyl-1-(piperidin-1-ylmethyl)propyl]benzamide
(S)-N-(1-(Azetidin-1-yl)-3-methylbutan-2-yl)-3-fluoro-4-methoxy-N-methylbenzamide
(S)-N-(1-(Azetidin-1-yl)-3-methylbutan-2-yl)-4-cyano-N-methylbenzamide
N-Methyl-N-[(1S)-2-methyl-1-(piperidin-1-ylmethyl)propyl]-4-(trifluoromethoxy)benzamide
3-Cyano-N-methyl-N-[(1S)-2-methyl-1-(piperidin-1-ylmethyl)propyl]benzamide
2,3,5-Trifluoro-N-[(1S)-1-{[(3S)-3-hydroxypyrrolidin-1-yl]methyl}-2-methylpropyl]-N-methylbenzamide
2-Fluoro-N-[(1S)-1-{[(3S)-3-hydroxypyrrolidin-1-yl]methyl}-2-methylpropyl]-N-methyl-5-(trifluoromethyl)benzamide
N-[(1S)-1-{[(3S)-3-Hydroxypyrrolidin-1-yl]methyl}-2-methylpropyl]-N,3-dimethylbenzamide
3-Cyano-N-[(1S)-1-{[(3S)-3-hydroxypyrrolidin-1-yl]methyl}-2-methylpropyl]-N-methylbenzamide
4-Fluoro-N-methyl-N-[(1S)-2-methyl-1-(pyrrolidin-1-ylmethyl)propyl]benzamide
4-Bromo-N-methyl-N-[(1S)-1-methyl-2-pyrrolidin-1-ylethyl]benzamide
4-Fluoro-N,3-dimethyl-N-(2-methyl-1-(pyrrolidin-1-yl)propan-2-yl)benzamide
4-Fluoro-N-[(1S)-1-[(3-hydroxyazetidin-1-yl)methyl]-2-methyl-propyl]-3-(hydroxymethyl)-N-methyl-benzamide
N-[(1S)-2-(Azetidin-1-yl)-1-cyclopropyl-ethyl]-4-cyano-N-methyl-benzamide
N-[(1S)-1-[(3,3-Difluoro-1-piperidyl)methyl]-2-methyl-propyl]-3-methoxy-N-methyl-benzamide
(S)-3,4-Difluoro-N-(1-(3-fluoro-3-(hydroxymethyl)azetidin-1-yl)-3-methylbutan-2-yl)-N-methylbenzamide
3,4-Difluoro-N-((S)-1-((2S,3R)-3-hydroxy-2-methylazetidin-1-yl)pentan-2-yl)-N-methylbenzamide
4-Cyano-N-((S)-1-((3S,4S)-3,4-dihydroxypyrrolidin-1-yl)-3-methylbutan-2-yl)-N-methylbenzamide
N-((S)-1-((3R,4R)-3,4-Dihydroxypyrrolidin-1-yl)-3-methylbutan-2-yl)-4-fluoro-N,3-dimethylbenzamide
4-Chloro-N-((S)-1-((3R,4R)-3,4-dihydroxypyrrolidin-1-yl)-3-methylbutan-2-yl)-N-methylbenzamide
4-Cyano-N-((S)-1-((3R,4R)-3,4-dihydroxypyrrolidin-1-yl)-3-methylbutan-2-yl)-N-methylbenzamide Inhibition of the human ether-a-go-go-related gene (hERG)-encoded $K^+$ channel was determined using hERG-expressing Chinese hamster ovary K1 (CHO) cells on a IonWorks™ HT assay platform as described by M. H. Bridgland-Taylor et al. J. of Pharmacological and Toxicological Methods (2006); 54:189-199. The results for some compounds according to the invention are presented in Table 2.

TABLE 2

| Example | hERG $IC_{50}$ [μM] |
|---|---|
| 1.2 | 20 |
| 1.4 | >33 |
| 1.17 | >100 |
| 4.1 | >33 |
| 4.4 | >33 |
| 5.1 | 76 |
| 5.2 | 34 |
| 6.1 | >100 |
| 6.2 | >53 |
| 7.1 | >33 |
| 7.2 | >33 |
| 7.3 | >33 |
| 8.1 | >100 |
| 8.2 | >57 |
| 8.6 | >33 |
| 10.2 | >33 |
| 12.1 | >100 |
| 12.2 | >33 |
| 16.55 | >31 |
| 18 | >30 |
| 19 | 17 |
| 29.7 | >33 |
| 33.4 | 18 |
| 33.7 | 79 |
| 38.1 | >33 |
| 38.2 | >33 |
| 38.6 | >33 |
| 39.2 | 80 |
| 39.12 | >33 |
| 39.14 | >33 |
| 39.16 | >33 |

Pharmacological Activity In Vivo Rabbit

Efficacy in an in vivo pharmacodynamic (PD) model was demonstrated using a model in anaesthetized rabbits subjected to vagal stimulation. Rabbits were anaesthetized using ketalar and domitor (2.5 and 0.07 mg/kg, respectively) as an i.v. bolus followed by a maintenance i.v. infusion (11 and 0.33 mg/kg/h, respectively) and ventilated with room air. Two percutaneous polyethylene catheter (Venflon 0.8 mm, Viggo, Helsingborg, Sweden) for administration of anaesthetics and drug infusions, respectively, were inserted into marginal veins on the right and left ear. A polyethylene catheter (Intramedic PE 160 Clay Adams, Becton Dickinson, Sparks, Md., USA) was inserted into the left carotid artery and advanced to the level of the aortic arch for blood pressure recording (by means of a pressure transducer, Peter von Berg Medizintechnik Gmbh, Kirchseeon/Englharting, Germany) and for blood sampling. For recording of right atrial electrogram and for atrial pacing, a 4F quadripolar electrophysiological recording catheters (Electrophysiology catheter-Deflectable tip, Biosense Webster Inc, Johnson & Johnson, Diamond Bar, Calif., USA) was advanced into the right jugular vein and positioned high up in the right atrium (HRA). Electrodes were advanced via introducers (4F Fast-Cath haemostasis introducer, ST. Jude Medical, DAIG Division, Inc. Minnetonka, Minn., USA) correctly positioned through fluoroscopic guidance. The effective refractory period in the right atrium (RAERP) was determined at a stimulation current strength approximately 20% above the threshold for pacing the atria. A custom-made PC-based (AstraZeneca R&D, Mölndal, Sweden) programmable stimulator and constant current pulse generator (WPI Stimulus Isolator, World Precision Instruments, Sarasota, Fla., USA) were used for stimulation at one or two predefined basic cycle lengths (S1) of for example 200 and 300 ms. A premature extra stimulus (S2) was introduced after every 10$^{th}$ paced basic beat with increments of 2 ms until capture. The RAERP was defined as the longest S1 S2 interval at which S2 failed to capture. For vagal stimulation, both vagal nerves were ligated and cut in the cervical region and propranolol (0.5 mg/kg) was administrated as an i.v. infusion to decrease sympathetic influence. Electrodes were inserted in the middle of the right vagal nerve to stimulate the efferent vagi. The RAERP was determined without or with vagal stimulation at 50% of maximal vagal response. Subsequent infusion of compound aimed to increase the RAERP with 20 ms during the first dose of two consecutive doses. The drug infusion was followed by a washout period of approximately 30-60 min. QT prolongation was recorded from surface electrocardiography (ECG). The effect on RAERP was measured several times during infusion and washout and blood samples were taken at each measurements. Effect and plasma concentration data was analysed accounting for a concentration-effect-time delay and the unbound plasma concentration (Ceu) increasing the RAERP by 20 ms was calculated.

The results for some compounds according to the invention are presented in Table 3.

TABLE 3

| Example | $C_{eu}$ 20 ms [µM] |
|---|---|
| 1.2 | 0.40 |
| 1.4 | 0.60 |
| 1.17 | 1.40 |
| 4.1 | 0.74 |
| 4.4 | 0.75 |
| 5.1 | 1.00 |
| 5.2 | 0.60 |
| 6.1 | 0.54 |
| 6.2 | 0.40 |
| 7.1 | 5.40 |
| 7.2 | 1.00 |
| 7.3 | 2.10 |
| 8.1 | 0.87 |
| 8.2 | 0.34 |
| 8.6 | 2.50 |
| 10.2 | 1.40 |
| 12.1 | 0.68 |
| 12.2 | 2.20 |
| 16.55 | 0.60 |
| 18 | 0.70 |
| 19 | 0.34 |
| 29.7 | 0.79 |
| 33.4 | 0.52 |
| 33.7 | 0.80 |
| 38.1 | 0.34 |
| 38.2 | 0.38 |
| 38.6 | 0.72 |
| 39.2 | 0.28 |
| 39.12 | 2.06 |
| 39.14 | 0.10 |
| 39.16 | 0.24 |

While the invention has been described in detail and with reference to specific embodiments thereof, it will be apparent for one skilled in the art that various changes and modifications can be made therein without departing from the spirit and scope thereof.

The invention claimed is:
1. A compound having the structure of Formula I:

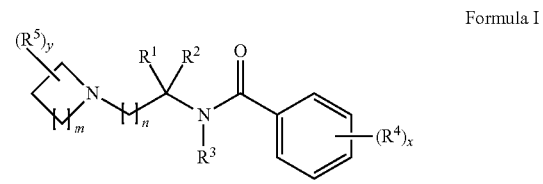

Formula I or a pharmaceutically acceptable salt thereof, wherein:
each $R^5$ is independently selected from fluoro, nitrile, hydroxy, oxo, $C_{1-5}$ alkyl, $C_{3-5}$ cycloalkyl, $C_{1-5}$ alkoxy or $C_{1-5}$ alkoxyalkyl, wherein:
any alkyl, cycloalkyl or alkoxy group is substituted by 0, 1 or 2 substituents independently selected from fluoro, nitrile or hydroxy,
$R^1$ is selected from $C_{1-6}$ alkyl, $C_{3-6}$ cycloalkyl or $C_{1-6}$ alkoxyalkyl, wherein:
any alkyl, cycloalkyl or alkoxy group is substituted by 0, 1 or 2 substituents independently selected from fluoro or nitrile,
$R^2$ is selected from hydrogen or $C_{1-3}$ alkyl;
$R^3$ is selected from $C_{1-6}$ alkyl, $C_{3-6}$ cycloalkyl or $C_{1-6}$ alkoxyalkyl, wherein:
any alkyl or cycloalkyl group is substituted by 0, 1 or 2 substituents independently selected from fluoro, nitrile or hydroxy;
each $R^4$ is independently selected from halo, nitrile, hydroxy, $C_{1-3}$ alkyl, $C_{1-3}$ alkoxy, $C_{1-3}$ alkoxyalkyl or $C_{1-3}$ alkylsulfide, wherein:
any alkyl or alkoxy group is substituted by 0, 1, 2 or 3 substituents independently selected from halo, nitrile or hydroxy;
m is selected from 1, 2 or 3;
n is selected from 1 or 2;
x is selected from 0, 1, 2, or 3; and
y is selected from 0, 1, 2 or 3.

2. A compound according to claim 1 or a pharmaceutically acceptable salt thereof, wherein:
$R^5$ is hydroxy;
$R^1$ is selected from $C_{1-6}$ alkyl, $C_{1-6}$ alkoxyalkyl or $C_{3-6}$ cycloalkyl;
$R^2$ is hydrogen;
$R_3$ is selected from $C_{1-6}$ alkyl, $C_{1-6}$ alkoxyalkyl or $C_{3-6}$ cycloalkyl;
each $R^4$ is independently selected from chloro, fluoro, bromo, nitrile, methyl, difluoromethyl, trifluoromethyl, methoxy, hydroxy, difluoromethoxy, trifluoromethoxy or methylsulfide;
m is 1;
n is 1;
x is selected from 1 or 2; and
y is selected from 0, 1 or 2.

3. A compound according to claim 1 having the structure of Formula Ic:

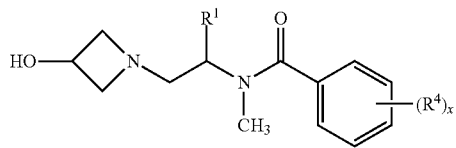

Formula Ic or a pharmaceutically acceptable salt thereof, wherein:
R$^1$ is selected from C$_{2-4}$ alkyl or C$_{3-6}$ cycloalkyl;
each R$^4$ is independently selected from chloro, fluoro, bromo, nitrile or methyl; and
x is selected from 1 or 2.

4. A compound according to claim 1 having the structure of Formula Id:

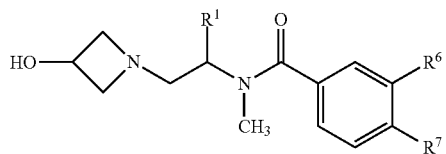

Formula Id or a pharmaceutically acceptable salt thereof, wherein:
R$_1$ is selected from ethyl, propyl, isopropyl, butyl, 1-methyl-propyl, 2-methyl-propyl, cyclopropyl, cyclobutyl, cyclopentyl or cyclohexyl;
R$^6$ is selected from hydrogen, chloro, fluoro or methyl; and
R$^7$ is selected from chloro, fluoro, bromo, nitrile or methyl.

5. A compound according to claim 4 which is selected from:
(S)-4-Bromo-N-(1-cyclopropyl-2-(3-hydroxyazetidin-1-yl)ethyl)-N-methylbenzamide;
(S)-4-Fluoro-N-(1-(3-hydroxyazetidin-1-yl)-3-methylbutan-2-yl)-N,3-dimethylbenzamide;
(S)-4-Chloro-N-(1-(3-hydroxyazetidin-1-yl)-3-methylbutan-2-yl)-N-methylbenzamide;
(S)-4-Bromo-N-(1-(3-hydroxyazetidin-1-yl)-3-methylbutan-2-yl)-N-methylbenzamide;
(S)—N-(1-Cyclopropyl-2-(3-hydroxyazetidin-1-yl)ethyl)-4-fluoro-N,3-dimethylbenzamide;
(S)-4-Chloro-N-(1-cyclopropyl-2-(3-hydroxyazetidin-1-yl)ethyl)-N-methylbenzamide;
(S)-3-Chloro-N-(1-cyclopropyl-2-(3-hydroxyazetidin-1-yl)ethyl)-4-fluoro-N-methylbenzamide;
(S)—N-(1-Cyclopropyl-2-(3-hydroxyazetidin-1-yl)ethyl)-4-fluoro-N-methylbenzamide;
(S)-3,4-Difluoro-N-(1-(3-hydroxyazetidin-1-yl)pentan-2-yl)-N-methylbenzamide;
(S)-4-Chloro-N-(1-(3-hydroxyazetidin-1-yl)pentan-2-yl)-N-methylbenzamide;
(S)-3-Chloro-4-fluoro-N-(1-(3-hydroxyazetidin-1-yl)pentan-2-yl)-N-methylbenzamide;
(S)-4-Chloro-N-(1-(3-hydroxyazetidin-1-yl)pentan-2-yl)-N,3-dimethylbenzamide;
(S)-4-Fluoro-N-(1-(3-hydroxyazetidin-1-yl)pentan-2-yl)-N-methylbenzamide;
(S)-4-Bromo-N-(1-(3-hydroxyazetidin-1-yl)pentan-2-yl)-N-methylbenzamide;
(S)-4-Cyano-N-(1-(3-hydroxyazetidin-1-yl)pentan-2-yl)-N-methylbenzamide;
(S)-4-Fluoro-N-(1-(3-hydroxyazetidin-1-yl)pentan-2-yl)-N,3-dimethylbenzamide;
(S)-4-Fluoro-N-(1-(3-hydroxyazetidin-1-yl)butan-2-yl)-N,3-dimethylbenzamide;
(S)—N-(1-Cyclopropyl-2-(3-hydroxyazetidin-1-yl)ethyl)-3,4-difluoro-N-methylbenzamide;
(S)—N-(1-(3-Hydroxyazetidin-1-yl)pentan-2-yl)-N,3,4-trimethylbenzamide;
3,4-Difluoro-N-((2S,3S)-1-(3-hydroxyazetidin-1-yl)-3-methylpentan-2-yl)-N-methylbenzamide;
4-Chloro-N-((2S,3S)-1-(3-hydroxyazetidin-1-yl)-3-methylpentan-2-yl)-N-methylbenzamide;
4-Cyano-N-((2S,3S)-1-(3-hydroxyazetidin-1-yl)-3-methylpentan-2-yl)-N-methylbenzamide;
(R)—N-(1-Cyclopentyl-2-(3-hydroxyazetidin-1-yl)ethyl)-3,4-difluoro-N-methylbenzamide;
(S)—N-(1-Cyclopentyl-2-(3-hydroxyazetidin-1-yl)ethyl)-3,4-difluoro-N-methylbenzamide;
(R)-4-Chloro-N-[1-cyclopentyl-2-(3-hydroxyazetidin-1-yl)ethyl]-N-methylbenzamide;
(S)-4-Chloro-N-[1-cyclopentyl-2-(3-hydroxyazetidin-1-yl)ethyl]-N-methylbenzamide;
(R)—N-[1-Cyclopentyl-2-(3-hydroxyazetidin-1-yl)ethyl]-4-fluoro-N,3-dimethylbenzamide;
(S)—N-[1-Cyclopentyl-2-(3-hydroxyazetidin-1-yl)ethyl]-4-fluoro-N,3-dimethylbenzamide;
(R)-4-Cyano-N-[1-cyclopentyl-2-(3-hydroxyazetidin-1-yl)ethyl]-N-methylbenzamide;
(S)-4-Cyano-N-[1-cyclopentyl-2-(3-hydroxyazetidin-1-yl)ethyl]-N-methylbenzamide;
(R)-3-Chloro-N-[1-cyclopentyl-2-(3-hydroxyazetidin-1-yl)ethyl]-4-fluoro-N-methylbenzamide;
(S)-3-Chloro-N-[1-cyclopentyl-2-(3-hydroxyazetidin-1-yl)ethyl]-4-fluoro-N-methylbenzamide;
(S)-4-Chloro-N-(1-(3-hydroxyazetidin-1-yl)hexan-2-yl)-N-methylbenzamide;
3,4-Difluoro-N-[(2S)-1-(3-hydroxyazetidin-1-yl)hexan-2-yl]-N-methylbenzamide;
4-Cyano-N-[(2S)-1-(3-hydroxyazetidin-1-yl)hexan-2-yl]-N-methylbenzamide;
4-Fluoro-N-[(2S)-1-(3-hydroxyazetidin-1-yl)hexan-2-yl]-N-methylbenzamide;
3-Chloro-4-fluoro-N-[(2S)-1-(3-hydroxyazetidin-1-yl)hexan-2-yl]-N-methylbenzamide;
4-Chloro-N-[(1R)-1-cyclobutyl-2-(3-hydroxyazetidin-1-yl)ethyl]-N-methylbenzamide;
4-Cyano-N-[(1R)-1-cyclobutyl-2-(3-hydroxyazetidin-1-yl)ethyl]-N-methylbenzamide;
N-[(1R)-1-Cyclobutyl-2-(3-hydroxyazetidin-1-yl)ethyl]-4-fluoro-N,3-dimethylbenzamide;
N-[(1R)-1-Cyclobutyl-2-(3-hydroxyazetidin-1-yl)ethyl]-4-fluoro-N-methylbenzamide;
N-[(1R)-1-Cyclobutyl-2-(3-hydroxyazetidin-1-yl)ethyl]-3,4-difluoro-N-methylbenzamide;
4-Cyano-N-[(1S)-1-cyclohexyl-2-(3-hydroxyazetidin-1-yl)ethyl]-N-methylbenzamide;
4-Chloro-N-[(1S)-1-cyclohexyl-2-(3-hydroxyazetidin-1-yl)ethyl]-N-methylbenzamide;
N-[(1S)-1-Cyclohexyl-2-(3-hydroxyazetidin-1-yl)ethyl]-4-fluoro-N-methylbenzamide; 4-Chloro-N-[(2R)-1-(3-hydroxyazetidin-1-yl)pentan-2-yl]-N-methylbenzamide;
3,4-Difluoro-N-[(2S)-1-(3-hydroxyazetidin-1-yl)-4-methylpentan-2-yl]-N-methylbenzamide;
4-Chloro-N-[(2S)-1-(3-hydroxyazetidin-1-yl)-4-methylpentan-2-yl]-N-methylbenzamide;

(S)-4-Cyano-N-(1-cyclobutyl-2-(3-hydroxyazetidin-1-yl)ethyl)-N-methylbenzamide;

(S)—N-(1-Cyclobutyl-2-(3-hydroxyazetidin-1-yl)ethyl)-3,4-difluoro-N-methylbenzamide;

(S)-4-Chloro-3-fluoro-N-(1-(3-hydroxyazetidin-1-yl)butan-2-yl)-N-methylbenzamide;

(S)-4-Chloro-N-(1-(3-hydroxyazetidin-1-yl)butan-2-yl)-N-methylbenzamide;

(S)—N-(1-Cyclobutyl-2-(3-hydroxyazetidin-1-yl)ethyl)-4-fluoro-N-methylbenzamide;

(S)-4-Chloro-N-(1-cyclobutyl-2-(3-hydroxyazetidin-1-yl)ethyl)-N-methylbenzamide;

(S)—N-(1-Cyclobutyl-2-(3-hydroxyazetidin-1-yl)ethyl)-4-fluoro-N,3-dimethylbenzamide; or (S)-4-Bromo-N-(1-(3-hydroxyazetidin-1-yl)butan-2-yl)-N-methylbenzamide; or a pharmaceutically acceptable salt of any of the foregoing compounds.

6. A pharmaceutical composition, wherein the composition comprises:
a compound or pharmaceutically acceptable salt according to claim 1, and
a pharmaceutically acceptable carrier.

7. A pharmaceutical composition according to claim 6, wherein the composition further comprises an additional ingredient, wherein the additional ingredient is therapeutically active.

\* \* \* \* \*